(12) United States Patent
Marnett et al.

(10) Patent No.: US 7,736,624 B2
(45) Date of Patent: Jun. 15, 2010

(54) METHODS AND COMPOSITIONS FOR DIAGNOSTIC AND THERAPEUTIC TARGETING OF COX-2

(76) Inventors: Lawrence J. Marnett, 1884 Laurel Ridge Dr., Nashville, TN (US) 37215; Md. Jashim Uddin, 3808 Waterford Cir., Nashville, TN (US) 37221; Brenda C. Crews, 410 Stable Dr., Franklin, TN (US) 37069

( * ) Notice: Subject to any disclaimer, the term of this patent is extended or adjusted under 35 U.S.C. 154(b) by 0 days.

(21) Appl. No.: 11/820,481

(22) Filed: Jun. 19, 2007

(65) Prior Publication Data

US 2007/0292352 A1   Dec. 20, 2007

Related U.S. Application Data

(60) Provisional application No. 60/814,854, filed on Jun. 19, 2006.

(51) Int. Cl.
*A61B 5/00* (2006.01)
*A61K 31/435* (2006.01)
*C07D 491/22* (2006.01)

(52) U.S. Cl. .................. 424/9.6; 514/279; 546/37
(58) Field of Classification Search .............. 424/9.6; 514/150, 165, 279, 229.5, 364, 370, 406, 514/414, 420
See application file for complete search history.

(56) References Cited

U.S. PATENT DOCUMENTS

| | | | |
|---|---|---|---|
| 3,161,654 | A | 12/1964 | Shen |
| 3,196,162 | A | 7/1965 | Lewis et al. |
| 3,285,908 | A | 11/1966 | Shen |
| 3,336,194 | A | 8/1967 | Shen |
| 3,470,203 | A | 9/1969 | Gal et al. |
| 3,654,349 | A | 4/1972 | Shen et al. |
| 3,725,548 | A | 4/1973 | Shen et al. |
| 4,229,447 | A | 10/1980 | Porter |
| 4,412,994 | A | 11/1983 | Sloan et al. |
| 4,851,426 | A | 7/1989 | Ladkani et al. |
| 5,016,652 | A | 5/1991 | Rose et al. |
| 5,032,588 | A | 7/1991 | Brooks et al. |
| 5,093,356 | A | 3/1992 | Yves et al. |
| 5,360,925 | A | 11/1994 | Chabrier de Lassauniere et al. |
| 5,436,265 | A | 7/1995 | Black et al. |
| 5,504,086 | A | 4/1996 | Ellinwood, Jr. et al. |
| 5,510,368 | A | 4/1996 | Lau et al. |
| 5,607,966 | A | 3/1997 | Hellberg et al. |
| 5,681,964 | A | 10/1997 | Ashton et al. |
| 5,811,425 | A | 9/1998 | Woods et al. |
| 5,811,438 | A | 9/1998 | Hellberg et al. |
| 5,861,419 | A | 1/1999 | Dube et al. |
| 5,922,742 | A | 7/1999 | Black et al. |
| 5,965,619 | A | 10/1999 | Rifat et al. |
| 6,045,773 | A | 4/2000 | Isakson et al. |
| 6,048,850 | A | 4/2000 | Young et al. |
| 6,207,700 | B1 | 3/2001 | Kalgutkar et al. |
| 6,277,878 | B1 | 8/2001 | Nakao et al. |
| 6,306,890 | B1 | 10/2001 | Kalgutkar et al. |
| 6,399,647 | B2 | 6/2002 | Kalgutkar et al. |
| 6,762,182 | B1 | 7/2004 | Kalgutkar et al. |
| 6,933,316 | B2 | 8/2005 | Hsieh et al. |
| 7,491,744 | B2 | 2/2009 | Marnett et al. |
| 2001/0034361 | A1 | 10/2001 | Kalgutkar et al. |
| 2003/1954244 | | 10/2003 | Hsieh et al. |
| 2005/0002859 | A1* | 1/2005 | Marnett et al. ............ 424/1.11 |
| 2005/0250839 | A1 | 11/2005 | Marnett et al. |
| 2009/0118290 | A1 | 5/2009 | Marnett et al. |

FOREIGN PATENT DOCUMENTS

| | | |
|---|---|---|
| CN | 1337851 A | 2/2002 |
| DE | 2735537 | 2/1979 |
| DE | 2926472 | 1/1981 |
| DE | 3145465 | 5/1983 |
| DE | 3235850 | 8/1983 |
| DE | 3206885 | 9/1983 |
| DE | 10163426 | 7/2003 |
| EP | 0051278 | 5/1982 |
| EP | 0080271 | 6/1983 |
| EP | 0144845 | 6/1985 |
| EP | 0327766 | 8/1989 |
| EP | 335164 | 10/1989 |
| EP | 335545 | 10/1989 |
| EP | 342682 | 11/1989 |

(Continued)

OTHER PUBLICATIONS

Timofeevski et al., Isoform-Selective Interaction of Cyclooxygenase-2 with Indomethacin Amides Studied by Real-Time Fluorescence, Inhibition Kinetics, and Site-Directed Mutagenesis, 2002, Biochemistry, 41, p. 9655.*

(Continued)

*Primary Examiner*—Kamal A Saeed
*Assistant Examiner*—Kristin Bianchi
(74) *Attorney, Agent, or Firm*—Jenkins, Wilson, Taylor & Hunt, P.A.

(57) ABSTRACT

The presently disclosed subject matter provides compositions that selectively bind cyclooxygenase-2 and comprise a therapeutic and/or diagnostic moiety. Also provided are methods for using the disclosed compositions for diagnosing (i.e., by imaging) a target cell and/or treating a disorder associated with a cyclooxygenase-2 biological activity.

21 Claims, 20 Drawing Sheets

FOREIGN PATENT DOCUMENTS

| | | |
|---|---|---|
| EP | 1148783 | 6/2006 |
| ES | 432545 | 11/1976 |
| FR | 2392008 | 12/1978 |
| JP | 54090174 | 7/1979 |
| JP | 58201763 | 11/1983 |
| JP | 59161358 | 9/1984 |
| JP | 60152462 | 8/1985 |
| JP | 61060649 | 3/1986 |
| JP | 63196598 | 8/1988 |
| JP | 63275593 | 11/1988 |
| NL | 8105139 | 6/1982 |
| WO | WO95/004030 | 2/1995 |
| WO | WO95/020567 | 8/1995 |
| WO | WO00/040087 | 7/2000 |
| WO | WO00/040088 | 7/2000 |
| WO | WO01/015686 | 3/2001 |
| WO | WO02/008188 | 1/2002 |
| WO | WO02/020478 | 3/2002 |
| WO | WO02/060438 | 8/2002 |
| WO | WO02/028831 | 11/2002 |
| WO | WO2004/020409 | 3/2004 |
| WO | WO2005/002293 | 1/2005 |
| WO | WO2005/112921 | 12/2005 |

OTHER PUBLICATIONS

Besselievre et al., *Structural Immunochemistry of Melatonin-BSA Binding, Model of Amino and Indole Groups Cross-Linking*. Biomedicine Express. vol. 33, No. 7 pp. 226-228 (1980).
Correspondence from foreign patent attorney regarding Chinese Patent Application No. 99816425.9 dated Jun. 21, 2004.
Correspondence from foreign patent attorney regarding Israel Patent Application No. 144,127 dated May 26, 2005.
Correspondence from foreign patent attorney regarding Israel Patent Application No. 144,127 dated Dec. 11, 2005.
Correspondence from foreign patent attorney regarding Notice of Allowance corresponding to Israel Patent Application No. 144,127 dated Jul. 5, 2006.
Decision to grant a European patent pursuant to article 97(2) EPC corresponding to European Patent Application No. 00957717.2-2117 dated Sep. 20, 2007.
Decision to grant a European patent pursuant to article 97(2) EPC corresponding to European Patent Application No. 99967416.1-2107 dated May 11, 2006.
Decision to grant a European patent pursuant to article 97(2) EPC corresponding to European Patent Application No. 99967417.9-1521 dated Apr. 26, 2007.
Del Rosario et al., *Synthesis of [C-11]indomethacin methyl ester for in vivo brain studies of cyclooxygenase 2*. Journal of Nuclear Medicine. vol. 37, No. 5 (1996) [Abstract].
European Search Report corresponding to European Patent Application No. 00957717.2-2123 dated Nov. 16, 2004.
European Search Report corresponding to European Patent Application No. 99967416.1-2107 dated Apr. 8, 2003.
Faust et al., *Mapping the Melatonin Receptor. 6. Melatonin Agonists and Antagonists Derived from 6H-Isoindolo[2,1-a]indoles, 5,6-Dihydroindolo[2,1-a]isoquinolines, and 6,7-Dihydro-5H-benzo[c]azepino[2,1-a]indoles. Journal of Medicinal Chemistry.* vol. 43 pp. 1050-1061 (2000).
Flaugh et al., *Synthesis and Evaluation of the Antiovulatory Activity of a Variety of Melatonin Analogues. Journal of Medicinal Chemistry.* vol. 22, No. 1 pp. 63-69 (1979).
Frohn et al., Structure —Activity Relationship of Melatonin Analogues. *Life Sciences.* vol. 27, No. 22 pp. 2043-2046 (1980).
Issued Patent corresponding to Chinese Patent No. ZL 99816425.9 dated Apr. 6, 2005.
Issued Patent corresponding to Israel Patent No. 144127 dated Nov. 3, 2007.
Issued Patent corresponding to Republic of China Invention Patent No. I286474 dated Sep. 11, 2007.
Kalgutkar et al., *Ester and Amide Derivatives of the Nonsteroidal Antiinflammatory Drug, Cyclooxygenase-2 Inhibitors. Journal of Medicinal Chemistry.* vol. 43, No. 15 pp. 2860-2870 (2000).
McMurray, R.W., and Hardy, K.J., *Cox-2 Inhibitors: Today and Tomorrow. The American Journal of the Medical Sciences.* vol. 323, No. 4 pp. 181-189 (2002).
Mor et al., *Melatonin Receptor Ligands: Synthesis of New Melatonin Derivatives and Comprehensive Comparative Molecular Field Analysis (CoMFA) Study. Journal of Medicinal Chemistry.* vol. 41, No. 20 pp. 3831-3844 (1998).
Notice of Acceptance corresponding to Australian Patent Application No. 23697/00 dated Mar. 19, 2004.
Notice of Acceptance corresponding to Australian Patent Application No. 23698/00 dated Apr. 1, 2003.
Notice of Acceptance corresponding to Australian Patent Application No. 69297/00 dated Mar. 9, 2004.
Notice of Allowance corresponding to U.S. Appl. No. 09/226,693 dated Oct. 24, 2000.
Notice of Allowance corresponding to U.S. Appl. No. 09/385,748 dated Jun. 5, 2001.
Notice of Allowance corresponding to U.S. Appl. No. 09/818,201 dated Jan. 15, 2002.
Notice of Allowance corresponding to U.S. Appl. No. 09/869,384 dated Nov. 6, 2003.
Notice of Decision of Granting Patent Right for Invention corresponding to Chinese Patent Application No. 99816425.9 dated Dec. 3, 2004.
Official Action corresponding to Australian Patent Application No. 23697/00 dated Nov. 15, 2002.
Official Action corresponding to Australian Patent Application No. 23697/00 dated Dec. 16, 2003.
Official Action corresponding to Australian Patent Application No. 23698/00 dated Nov. 15, 2002.
Official Action corresponding to Australian Patent Application No. 69297/00 dated Nov. 17, 2003.
Official Action corresponding to Chinese Patent Application No. 99816425.9 dated Aug. 20, 2003.
Official Action corresponding to European Patent Application No. 99 967 416.1-2107 dated May 27, 2004.
Official Action corresponding to European Patent Application No. 00957717.2-2117 dated Jul. 13, 2006.
Official Action corresponding to Republic of China (Taiwan) Patent Application No. 89117582 dated Dec. 20, 2003.
Official Action corresponding to Republic of China (Taiwan) Patent Application No. 89117582 dated Jul. 1, 2005.
Official Action corresponding to Republic of China (Taiwan) Patent Application No. 89117582 dated May 19, 2006.
Official Action corresponding to Republic of China (Taiwan) Patent Application No. 89117582 dated Jan. 26, 2007.
Official Action corresponding to U.S. Appl. No. 09/226,693 dated Mar. 27, 2000.
Official Action corresponding to U.S. Appl. No. 09/385,748 dated Aug. 7, 2000.
Official Action corresponding to U.S. Appl. No. 09/385,748 dated Nov. 13, 2000.
Official Action corresponding to U.S. Appl. No. 09/869,384 dated Nov. 22, 2002.
Official Action corresponding to U.S. Appl. No. 09/869,384 dated Apr. 8, 2003.
Supplementary European Search Report corresponding to European Patent Application No. 99967417.9 dated Jul. 25, 2003.
Chinery et al., *Prostaglandin $J_2$ and 15-Deoxy-$\Delta^{12,14}$-prostaglandin $J_2$ Induce Proliferation of Cyclooxygenase-depleted Colorectal Cancer Cells. Cancer Research.* vol. 59 pp. 2739-2746 (1999).
Decision of Granting Patent Right for Invention corresponding to Chinese Patent Application No. 00814912.7 dated May 30, 2008.
Fan et al., *Membrane effects of antiinflammatory agents. 1. Interaction of sulindace and its metabolites with phospholipid membrane, a magnetic resonance study. Journal of Medicinal Chemistry.* vol. 24, No. 10 pp. 1197-1202 (1981). [Abstract].
Grant of Canadian Patent Application No. 2,382,296 dated Nov. 17, 2009.

Heasley et al., *Induction of Cytosolic Phospholipase A₂ by Oncogenic Ras in Human Non-small Cell Lung Cancer.* The Journal of Biological Chemistry. vol. 272, No. 23 pp. 14501-14504 (1997).

Hong et al., *Relationship of Arachidonic Acid Metabolizing Enzyme Expression in Epithelial Cancer Cell Lines to the Growth Effect of Selective Biochemical Inhibitors.* Cancer Research. vol. 59 pp. 2223-2228 (1999).

Hwang et al., Expression of Cyclooxygenase-1 and Cyclooxygenase-2 in Human Breast Cancer. Journal of the National Cancer Institute. vol. 90, No. 6 pp. 455-460 (1998).

Kozak et al., Enantiospecific, Selective Cyclooxygenase-2 Inhibitors. Bioorganic & Medicinal Chemistry Letters. vol. 12 pp. 1315-1318 (2002).

Official Action corresponding to Chinese Patent Application No. 200580021387.8 dated Oct. 9, 2009.

Official Action corresponding to European Patent Application No. 99 967 417.9-1521 dated Apr. 6, 2004.

Official Action corresponding to European Patent Application No. 99 967 417.9-1521 dated Feb. 11, 2005.

Official Action corresponding to European Patent Application No. 99 967 417.9-1521 dated Nov. 8, 2005.

Official Action corresponding to European Patent Application No. 99 967 416.1-2107 dated Aug. 31, 2005.

Prusakiewicz et al., *Molecular basis of the time-dependent inhibition of cyclooxygenases by indomethacin.* Biochemistry. vol. 43, No. 49 pp. 15439-15445 (2004).

Sheng et al., Inhibition of Human Colon Cancer Cell Growth by Selective Inhibition of Cyclooxygenase-2. The Journal of Clinical Investigation. vol. 99, No. 9 pp. 2254-2259 (1997).

Supplementary European Search Report corresponding to International Patent Application No. 05778497.7-2123/1744747 dated Nov. 2, 2009.

Whitehouse et al., Esterification of acidic antiinflammatory drugs suppresses their gastrotoxicity without adversely affecting their antiinflammatory activity in rats. Journal of Pharmacy and Pharmacology. vol. 32, No. 11 pp. 795-796 (1980). [Abstract].

Yoneda et al., Expression of Angiogeneis-Related Genes and Progression of Human Ovarian Carcinomas in Nude Mice. Journal of the National Cancer Institute. vol. 90, No. 6 pp. 447-454 (1998).

Zimmermann et al., Cyclooxygenase-2 Expression in Human Esophageal Carcinoma. Cancer Research. vol. 59 pp. 198-204 (1999).

Allison et al., *Gastrointestinal Damage Asssociated with the Use of Nonsteroidal Antiinflammatoty Drugs.* The New England Journal of Medicine. vol. 327, No. 11 pp. 749-754 (1992).

Archibald et al., *Synthesis and Hypotensive Activity of Benzamidopiperidylethylindoles.* Journal of Medicinal Chemistry. vol. 14, No. 11 pp. 1054-1059 (1971).

Bahner et al., *Anticancer Compounds. Further Analogs of 1-(4-dimethylaminobenzylidene) indene.* Journal of Medicinal Chemistry. vol. 16, No. 4 pp. 421-425 (1973).

Barasoain et al., *Immunosuppressive Effects of Some Organic Compounds with Anti-Inflammatory Activity.* Proceedings of the International Congress of Chemotherapy. vol. 8. pp. 21-26 (1976) (Abstract).

Barasoain et al., *Indomethacin Esters Acting as Anti-Inflammatory and Immunosuppressive Drugs.* International Journal of Clinical Pharmacology Biopharm. vol. 16, No. 5 pp. 235-239 (1978) (Abstract).

Black et al., *From Indomethacin to a Selective COX-2 Inhibitor: Development of Indolalkanoic Acids as Potent and Selective COX-2 Inhibitors.* Bioorganic & Medicinal Chemistry Letters. vol. 6, No. 6 pp. 725-730 (1996).

Boltze et al., *Chemical Structure and Antiinflammatory Activity in the Group of Substituted Indole-3-Acetic Acids.* Arzneim-Forsch. vol. 30, No. 8A pp. 1314-1325 (1980) (English Abstract).

Bonina et al., *In Vitro and In Vivo Evaluation of Polyoxyethylene Indomethacin Esters as Dermal Prodrugs.* Journal of Controlled Release. vol. 34, No. 3 pp. 223-232 (1995) (Abstract).

Bonina et al., *Pharmacokinetic and pharmacodynamic profile of triethylene glycol indomethacin ester as a new oral prodrug.* Journal of Controlled Release. vol. 41, No. 3 pp. 187-193 (1996) (Abstract).

Chan et al., *Pharmacology of a Selective Cyclooxygenase-2 Inhibitor, L-745, 337: A Novel Nonsteroidal Anti-inflammatory Agent with an Ulcerogenic Sparing Effect in Rat and Nonhuman Primate Stomach.* The Journal of Pharmacology and Experimental Therapeutics. vol. 274, No. 3 pp. 1531-1537 (1995).

Correspondence from foreign patent attorney regarding Notice of Allowance corresponding to Israeli Patent Application No. 144,126 dated Aug. 9, 2007.

Correspondence from foreign patent attorney regarding Official Action corresponding to Chinese Patent Application No. 00814912.7 dated Mar. 11, 2004.

Correspondence from foreign patent attorney regarding Official Action corresponding to Chinese Patent Application No. 00814912.7 dated Aug. 11, 2004.

Correspondence from foreign patent attorney regarding Official Action corresponding to Chinese Patent Application No. 00814912.7 dated May 10, 2006.

Correspondence from foreign patent attorney regarding Official Action corresponding to Chinese Patent Application No. 99816452.6 dated Sep. 30, 2003.

Correspondence from foreign patent attorney regarding Official Action corresponding to Chinese Patent Application No. 99816452.6 dated Jul. 29, 2004.

Correspondence from foreign patent attorney regarding Official Action corresponding to Chinese Patent Application No. 99816452.6 dated Jan. 26, 2005.

Correspondence from foreign patent attorney regarding Official Action corresponding to Israeli Patent Application No. 144,126 dated Sep. 14, 2005.

Davaran et al., *Acrylic type polymers containing ibuprofen and indomethacin with disfunctional spacer group: synthesis and hydrolysis.* Journal of Controlled Release. vol. 47 pp. 41-49 (1997).

De Caprariis et al., *Synthesis and Pharmacological Evaluation of Oligoethylene Ester Derivatives as Indomethacin Oral Prodrugs.* Journal of Pharmaceutical Science. vol. 83, No. 11 pp. 1578-1581 (1994) (Abstract).

Devane et al., *Isolation and Structure of a Brain Constituent That Binds to the Cannabinoid Receptor.* Science. vol. 258 pp. 1946-1949 (1992).

Dewitt et al., *Primary structure of prostaglandin G/H synthase from sheep vesicular gland determined from the complementary DNA sequence.* PNAS. USA vol. 85 pp. 1412-1416 (1988).

Diago-Meseguer et al., *A New Reagent for Activating Carboxyl Groups; Preparation and Reactions of N,N-Bis [2-oxo-3-oxazolidinyl]phosphorodiamidic Chloride.* Communications. pp. 547-551 (1980).

Downing et al., *Enzyme Inhibition by Acetylenic Compounds.* Biochemical and Biophysical Research Communications. vol. 40, No. 1 pp. 218-223 (1970).

Downing et al., *Structural Requirements of Acetylenic Fatty Acids for Inhibition of Soybean Lipoxygenase and Prostaglandin Synthetase.* Biochimica et Biophysica Acta. vol. 280 pp. 343-347 (1972).

Fisnerova et al., *Esters of 1-(p-chlorobenzoyl)-5-methoxy-2-methyl-3-indolylacetic Acid.* Heterocycles. vol. 95 p. 667 (1981).

Fisnerova et al., *Pharmacologically Interesting Indomethacin Derivatives.* Heterocycles. vol. 88 p. 373 (1978).

Flynn et al., *Nonsteroidal Anti-inflammatory Drug Hydroxamic Acids. Dual Inhibitors of Both Cyclooxygenase and 5-lipoxygenase.* Journal of Medicinal Chemistry. vol. 33, No. 8 pp. 2070-2072 (1990).

Futaki et al., *NS-398, A new anti-inflammatory agent, selectively inhibits prostaglandin G/H synthase/cyclooxygenase (COX-2) activity in vitro.* Prostaglandins. vol. 47 pp. 55-59 (1994).

Gans et al., *Anti-Inflammatory and Safety Profile of DuP 697, a Novel Orally Effective Prostaglandin Synthesis Inhibitor.* The Journal of Pharmacology and Experimental Therapeutics. vol. 254, No. 1 pp. 180-187 (1990).

Graedon et al., *Pills Promise Relief Without Ulcers.* The News and Observer. p. 8D (Sep. 13, 1998) (Newspaper article).

Hla et al., *Human cyclooxygenase-2 cDNA.* PNAS USA. vol. 89 pp. 7384-7388 (1992).

Issued Patent corresponding to Israeli Patent No. 144126 dated Apr. 21, 2008.

Kalgutkar et al., *Amide Derivatives of Meclofenamic Acid as Selective Cyclooxygenase-2 Inhibitors.* Bioorganic and Medicinal Chemistry Letters. vol. 12 pp. 521-524 (2002).

Kalgutkar et al., *Aspirin-Like Molecules that Covalently Inactivate Cyclooxygenase-2.* Science. vol. 280 pp. 1268-1270 (1998).

Kalgutkar et al., *Biochemically based design of cyclooxygenase-2 (COX-2) inhibitors: Facile conversion of nonsteroidal antiinflammatory drugs to potent and highly selective COX-2 inhibitors.* PNAS. vol. 97, No. 2 pp. 925-930 (2000).

Kappe et al., *Non-steroidal Antiinflammatory Agents. V. Basic Esters of Indomethacin.* Journal für Praktische Chemie. vol. 332, No. 4 pp. 475-478 (1990) (Abstract).

Katori et al., *Induction of Prostaglandin H Synthase-2 in Rat Carrageenin-induced Pleurisy and Effect of a Selective Cox-2 Inhibitor.* Advances in Prostaglandin Thromboxane and Leukotriene Research. vol. 23 pp. 345-347 (1995).

Kennedy et al., *Cloning and Expression of Rat Prostaglandin Endoperoxide Synthase (Cyclooxygenase)-2 cDNA.* Biochemical and Biophysical Research Communications. vol. 197, No. 2 pp. 494-500 (1993).

Khanna et al., *1,2-Diarylimidazoles as Potent Cyclooxygenase-2 Selective, and Orally Active Antiinflammatory Agents.* Journal of Medicinal Chemistry. vol. 40, No. 11 pp. 1634-1647 (1997).

Khanna et al., *1,2-Diarylpyrroles as Potent, and Selective Inhibitors of Cyclooxygenase-2.* Journal of Medicinal Chemistry. vol. 40, No. 11 pp. 1619-1633 (1997).

Kolasa et al., *Nonsteroidal Anti-Inflammatory Drugs as Scaffolds for the Design of 5-Lipoxygenase Inhibitors.* Journal of Medicinal Chemistry. vol. 40 pp. 819-924 (1997).

Kujubu et al., *TIS10, a Phorbol Ester Tumor Promoter-inducible mRNA from Swiss 3T3 Cells, Encodes a Novel Prostaglandin Synthase/Cyclooxgenase Homologue.* The Journal of Biological Chemistry. vol. 266, No. 20 pp. 12866-12872 (1991).

Kumar, J.S.D., et al., *Synthesis of [11C]-TMI: A potential PET tracer for imaging COX-2 expression.* Abstracts of Papers, 228th ACS National Meeting; Philiadelphia, PA, United States, Aug. 22-26, 2004 (Abstract).

Kwapiszewski et al., *Synthesis of N[1-(p-chlorobenzoyl)-5-methoxy-2-methyl-3- indoleacetyl] Amino Acids and their Esters.* Acta. Pol. Pharm. vol. 39, No. 5-6 pp. 327-336 (1982) (Abstract).

Lee et al., *Selective Expression of Mitogen-inducible Cyclooxygenase in Macrophages Stimulated with Lipopolysaccharide.* The Journal of Biological Chemistry. vol. 267 pp. 25934-25938 (1992).

Li et al., *1,2-Diarylcyclopentenes as Selective Cyclooxgenase-2 Inhibitors and Orally Active Anti-inflammatory Agents.* Journal of Medicinal Chemistry. vol. 38, No. 22 pp. 4570-4578 (1995).

Li et al., *Cyclooxygenase-2 Inhibitors. Synthesis and Pharmacological Activities of 5- Methanesulfonamido-1-indanone Derivatives.* Journal of Medicinal Chemistry. vol. 38, No 25 pp. 4897-4905 (1995).

Li et al., *Novel Terphenyls as Selective Cyclooxygenase-2 Inhibitors and Orally Active Anti-inflammatory Agents.* Journal of Medicinal Chemistry. vol. 39, No. 9 pp. 1846-1856 (1996).

Linari et al., *Substituted Anilides of 1-(p-Chlorobenzoyl)-5-methoxy-2-methyl-indole-3-acetic Acid.* Arzneim-Foprsch. (Drug Research) vol. 23, No. 1 pp. 89-91 (1973).

Luong et al., *The Structure of Human Cyclooxygenase-2: Conservation and Flexibility of the NSAID Binding Site.* Nature Structural Biology. vol. 3 pp. 927-933 (1996).

Makovec et al., *Pharmacokinetics and metabolism of [14C]-proglumetacin after oral administration in the rat.* Arzneim-Forsch. vol. 37, No. 7 pp. 806-813 (1987) (Abstract).

Marnett et al., *Mechanism of the Stimulation of Prostaglandin H Synthase and Prostacyclin Synthase by the Antithrombotic and Antimetastatic Agent,* Nafazatrom. Molecular Pharmacology. vol. 26 pp. 328-335 (1984).

Masferrer et al., *Selective inhibition of inducible cyclooxygenase 2 in vivo is antiinflammatory and nonulcerogenic.* PNAS USA. vol. 91 pp. 3228-3232 (1994).

Mclean et al., *Synthesis and pharmacological evaluation of congugates of prednisolone and non-steroidal anti-inflammatory agents.* Steroids. vol. 54, No. 4 pp. 421-439 (1989) (Abstract).

McMurry, *Carboxylic Acid Derivatives.* Organic Chemistry. pp. 742-745 (1988).

Meade et al., *Differential Inhibition of Prostaglandin Endoperoxide Synthase (Cyclooxygenase) Isozymes by Aspirin and Other Nonsteroidal Anti-inflammatory Drugs.* The Journal of Biological Chemistry. vol. 238, No. 9 pp. 6610-6614 (1993).

Mulders, *Indole Acid Amides.* Heterocyclic Compounds. vol. 62 pp. 16198-16199 (1965).

Nakamura et al., *Studies on Antiinflammatory Agents II. Synthesis and Pharmacological Properties of 2'-(Phenylthio)methanesulfonanilides and Related Derivatives.* Chemical and Pharmaceutical Bulletin. vol. 41, No. 5 pp. 894-906 (1993).

Notice of Allowance corresponding to Canadian Patent Application No. 2,358,289 dated Mar. 16, 2009.

Notice of Allowance corresponding to Canadian Patent Application No. 2,382,296 dated Feb. 3, 2009.

Notice of Allowance corresponding to U.S. Appl. No. 11/114,921 dated Oct. 15, 2008.

Notification Concerning Transmittal of Copy of International Preliminary Report on Patentability (Chapter I of the Patent Cooperation Treaty) corresponding to International Application No. PCT/US2004/020455 dated Jan. 12, 2006.

Notification Concerning Transmittal of Copy of International Preliminary Report on Patentability (Chapter I of the Patent Cooperation Treaty) corresponding to International Application No. PCT/US2005/014328 dated Mar. 15, 2007.

Notification Concerning Transmittal of Copy of International Preliminary Report on Patentability (Chapter I of the Patent Cooperation Treaty) corresponding to International Application No. PCT/US2007/014315 dated Jan. 8, 2009.

Notification of Transmittal of the International Preliminary Examination Report corresponding to International Application No. PCT/US00/23153 dated Apr. 13, 2001.

Notification of Transmittal of the International Preliminary Examination Report corresponding to International Application No. PCT/US99/30219 dated Dec. 5, 2000.

Notification of Transmittal of the International Preliminary Examination Report corresponding to International Application No. PCT/US99/30220 dated Dec. 7, 2000.

Notification of Transmittal of the International Search Report and the Written Opinion of the International Searching Authority, or the Declaration corresponding to International Application No. PCT/USO4/20455 dated Feb. 22, 2005.

Notification of Transmittal of the International Search Report and the Written Opinion of the International Searching Authority, or the Declaration corresponding to International Application No. PCT/US05/14328 dated Jan. 31, 2007.

Notification of Transmittal of the International Search Report and the Written Opinion of the International Searching Authority, or the Declaration corresponding to International Application No. PCT/US07/14315 dated Aug. 14, 2008.

Notification of Transmittal of the International Search Report or the Declaration corresponding to International Application No. PCT/US00/23153 dated Oct. 26, 2000.

Notification of Transmittal of the International Search Report or the Declaration corresponding to International Application No. PCT/US99/30219 dated Apr. 5, 2000.

Notification of Transmittal of the International Search Report or the Declaration corresponding to International Application No. PCT/US99/30220 dated Apr. 4, 2000.

Odenwaller et al., *Preparation and Proteolytic Cleavage of Apoprostaglandin Endoperoxide Synthase.* Methods in Enzymology. vol. 187 pp. 479-485 (1990).

Official Action corresponding to Canadian Patent Application No. 2,358,241 dated Aug. 28, 2008.

Official Action corresponding to Canadian Patent Application No. 2,358,289 dated Apr. 15, 2008.

Official Action corresponding to Canadian Patent Application No. 2,358,289 dated Sep. 2, 2009.

Official Action corresponding to Canadian Patent Application No. 2,382,296 dated Sep. 17, 2007.

Official Action corresponding to Canadian Patent Application No. 2,382,296 dated Apr. 1, 2008.
Official Action corresponding to U.S. Appl. No. 10/877,303 dated Jul. 24, 2007.
Official Action corresponding to U.S. Appl. No. 10/877,303 dated Apr. 3, 2008.
Official Action corresponding to U.S. Appl. No. 10/877,303 dated Oct. 16, 2008.
Official Action corresponding to U.S. Appl. No. 11/114,921 dated Aug. 17, 2007.
Official Action corresponding to U.S. Appl. No. 11/114,921 dated Mar. 6, 2008.
Official Action corresponding to U.S. Appl. No. 11/114,921 dated Jun. 24, 2008.
Official Action corresponding to U.S. Appl. No. 12/319,262 dated Oct. 22, 2009.
Ogiso et al., *Pharmacokinetics of indomethacin ester prodrugs: gastrointestinal and hepatic toxicity and hydrolytic capacity of various tissues in rats.* Biological and Pharmaceutical Bulletin. vol. 19 No. 9 pp. 1178-1183 (1996) (Abstract).
O'Sullivan et al., *Lipopolysaccharide-induced expression of prostaglandin H synthase-2 in alveolar macrophages is inhibited by dexamethasone but not by aspirin.* Biochemical and Biophysical Research Communications. vol. 191, No. 3 pp. 1294-1300 (1993).
Otis et al., *Synthesis and Pharmacological Evaluation of Amide Derivatives of Non-steroidal Anti-Inflammatory Drugs.* Inflammopharmacology. vol. 1, No. 3 pp. 201-212.
Pal et al., *7-Oxabicycloheptylprostanoic Acids: Potent, Time-Dependent Cyclooxygenase Inhibitors that Induce a Conformational Change in the Prostaglandin Endoperoxide Synthase Protein.* Journal of Medicinal Chemistry. vol. 35, No. 12 pp. 2340-2342 (1992).
Penning et al., *Synthesis and Biological Evaluation of the 1,5-Diarylpyrazole Class of Cyclooxygenase-2 Inhibitors: Indentification of 4[5(4-Methylphenyl)-3- (trifluoromethyl)-1H-pyrazolyl]benzenesulfonamide (SC-58635, Celecoxib).* Journal of Medicinal Chemistry. vol. 40 pp. 1347-1365 (1997).
Phelan et al., *Improved Delivery Through Biological Membranes. XXXVII. Synthesis and Stability of Novel Redox Derivatives of Naproxen and Indomethacin.* Pharmaceutical Research. vol. 6, No. 8 pp. 667-676 (1989).
Physician's Desk Reference, 41st Edition, pp. 1305-1310 (1987) INDOCIN® (Indomethacin, MSD).
Prasit et al., *L-745,337: A Selective Cyclooxygenase-2 Inhibitor.* Medicinal Chemistry Research. vol. 5 pp. 364-374 (1995).
Ramesha, *Human and Rat Cyclooxygenases are Pharmacologically Distinct.* Eicosanoids Other Bioactive Lipids in Cancer Inflammation and Radiation Injury. Chp. 10 pp. 67-71 (1997).
Reitz et al., *Novel 1,2-Diarylcyclopentenes are Selective, Potent, and Orally Active Cyclooxygenase Inhibitors.* Medicinal Chemistry Research. vol. 5, No. 3 pp. 351-363 (1995).
Riendeau et al., *Biochemical and pharmacological profile of a tetrasubstituted furanone as a highly selective COX-2 inhibitor.* British Journal of Pharmacology. vol. 121 pp. 105-117 (1997).
Rojo et al., *Variable Effects of Indomethacin and Four Related Compounds on Lymphocyte Blastogenesis and Cell-mediated Cytotoxicity.* International Journal of Clinical Pharmacology, Therapy, and Toxicology. vol. 19, No. 9 pp. 420-424 (1981) (Abstract).
Rojo et al., *Variation in the immunosuppressive activity by structural modifications of a series of non-steroidal antiinflammatory drugs (indomethacin esters).* Arch. Farmacol Toxicol. vol. 4 No. 3 pp. 287-292 (1978) (Abstract).
Rouzer et al., *Cyclooxygenase-1-dependent Prostaglandin Synthesis Modulates Tumor Necrosis Factor-α Secretion in Lipopolysaccharide-challenged Murine Resident Peritoneal Macrophages.* The Journal of Biological Chemistry. vol. 279, No. 33 pp. 34256-34268 (2004).

Roy et al., *A New Series of Selective COX-2 Inhibitors; 5,6-Diarylthiazolo[3,2- b][1,2,4]Triazoles.* Bioorganic & Medicinal Chemistry Letters. vol. 7, No. 1 pp. 57-62 (1997).
Sauvaire et al., *Pharmacological activity and toxicity of apyramide: comparison with non-steroidal anti-inflammatory agents.* Drugs Under Experimental and Clinical Research. vol. 13, No. 5 pp. 247-252 (1987) (Abstract).
Shaw, *The Synthesis of Tryptamines Related to Serotonin.* Journal of the American Chemical Society. vol. 77 pp. 4319-4324 (1955).
Smith et al., *Prostaglandin Endoperoxide H Synthases (Cyclooxygenases)-1 and -2.* The Journal of Biological Chemistry. vol. 271, No. 52 pp. 33157-33160 (1996).
Soai et al., *Mixed Solvents Containing Methanol as Useful Reaction Media for Unique Chemoselective Reductions with Lithium Borohydride.* Journal of Organic Chemistry. vol. 51, No. 21 pp. 4000-4005 (1986).
Svoboda et al., *Potential Anti-inflammatory Agents on the Basis of Indomethacin Esters.* Ceskoslovenska Farmacie. vol. 40, No. 2 pp. 71-74 (1991) (Abstract).
Tammara et al., *Synthesis and Evaluation of Morpholinoalkyl Ester Prodrugs of Indomethacin and Naproxen.* Pharmaceutical Research. vol. 10, No. 8 pp. 1191-1199 (1993).
Tanaka et al., *Pharmacological Studies of the New Antiinflammatory Agent 3- Formylamino-7-Methylsulfonylamino-6-Phenoxy-4H-1-Benzopyran-4-One.* Arzneim-Forsch/Drug Res. vol. 42(II), No. 7 pp. 935-944 (1992).
Therien et al., *Synthesis and Biological Evaluation of 5,6-Diatylimidazo[2.1-b]Thiazole as Selective COX-2 Inhibitors.* Bioorganic & Medicinal Chemistry Letters. vol. 7, No. 1 pp. 47-52 (1997).
Touhey et al., *Structure-Activity Relationship of Indomethicin Analogues for MRP-1, COX-1 and COX-2 Inhibition: Identification of Novel Chemotherapeutic Drug Resistance Modulators.* European Journal of Cancer. vol. 38, No. 12 pp. 1661-1670 (2002).
Tsuji et al., *Studies on Anti-inflammatory Agents. IV. Synthesis and Pharmacological Properties of 1,5-Diarylpyrazoles and Related Derivatives.* Chemical Pharmacology Bulletin. vol. 45, No. 6 pp. 987-995 (1997).
Ueda et al., *Design, synthesis and antiinflammatory activity of a new indomethacin ester, 2-[N-[3-{3-(piperidinomethy)phenoxy}propyl]carbamoylmethylthio]ethyl 1-(p-chlorobenzoyl)-5-methoxy-2-methyl-indole-3- acetate.* Chemical Pharmacology Bulletin. vol. 39, No. 3 pp. 679-684 (1991) (Abstract).
Vane et al., *Inducible isoforms of cyclooxygenase and nitric-oxide synthase in inflammation.* PNAS USA. vol. 91 pp. 2046-2050 (1994).
Wang et al., *A Selective Method for the Preparation of Primary Amides: Synthesis of Fmoc-L-4- Carboxamidophenylalanine and Other Compounds.* Tetrahedron Letters. vol. 40 pp. 2501-2504 (1999).
Wiesenberg-Boettcher et al., *The Pharmacological Profile of CGP 28238, a Novel Highly Potent Anti-inflammatory Compound.* Drugs Under Experimental and Clinical Research. vol. 15, No. 11-12 pp. 501-509 (1989) (Abstract).
Yamawaki et al., *Piperazinealkanol ester derivatives of indomethacin as dual inhibitors of 5-lipoxygenase and cyclooxgenase.* Chemical Pharmacology Bulletin. vol. 42, No. 4 pp. 963-971 (1994) (Abstract).
Yokoyama et al., *Cloning of Human Gene Encoding Prostaglandin Endoperoxide Synthase and Primary Structure of the Enzyme.* Biochemical and Biophysical Research Communications. vol. 165, No. 2 pp. 888-894 (1989).
Yu et al., *Synthesis of Prostaglandin E2 Ethanolamide from Anandamide by Cyclooxygenase-2.* The Journal of Biological Chemistry. vol. 272, No. 34 pp. 21181-21186 (1997).

* cited by examiner

Compound 27j

Compound 30c

Compound 27z

Compound 27aa

Compound 27ff

FIG. 9 Compound 27ii

Compound 27qq

METHODS AND COMPOSITIONS FOR DIAGNOSTIC AND THERAPEUTIC TARGETING OF COX-2

CROSS REFERENCE TO RELATED APPLICATION

The presently disclosed subject matter claims the benefit of U.S. Provisional Patent Application Ser. No. 60/814,854, filed Jun. 19, 2006; the disclosure of which is incorporated herein by reference in its entirety

GRANT STATEMENT

This work was supported by grant U54-CA 105296 from the United States National Institutes of Health. Accordingly, the United States Government has certain rights in the presently disclosed subject matter.

TECHNICAL FIELD

The presently disclosed subject matter generally relates to diagnostic and therapeutic agents that comprise COX-2-selective ligands. More particularly, the presently disclosed subject matter relates to derivatives of non-steroidal anti-inflammatory drugs that exhibit selective binding to cyclooxygenase-2 (COX-2) and that comprise functional groups allowing them to be used as diagnostic and/or therapeutic agents.

BACKGROUND

A limitation of current therapeutic and/or diagnostic methods is that it is often not possible to deliver the therapeutic and/or diagnostic agent selectively or specifically to the appropriate tissue or cell type. In the case of diagnostic imaging of cancer, for example, current methods for tumor-specific imaging are hindered by imaging agents that also accumulate in normal tissues. With respect to therapeutic targeting, specificity also plays an important role as some therapeutics (e.g., anti-cancer therapeutics) are toxic, and delivery to non-target cells (e.g. normal cells) is preferably avoided.

Additionally, continuing with respect to cancer, a lack of targeting ligands that are capable of binding to multiple tumor types necessitates the synthesis of a wide range of active agents in order to treat and/or diagnose different tumor types. Ideally, a targeting molecule should display specific targeting in the absence of substantial binding to normal tissues, and a capacity for targeting to a variety of tumor types and stages. Finally, early diagnosis of neoplastic changes can result in more effective treatment of cancer. Thus, there exists a long-felt need in the art for methods to achieve delivery of imaging agents to tumors early in the course of tumorigenesis.

Cyclooxygenase (COX) activity originates from two distinct and independently regulated enzymes, termed COX-1 and COX-2 (see DeWitt & Smith (1988) Proc Natl Acad Sci USA 85, 1412-1416; Yokoyama & Tanabe (1989) Biochem Biophys Res Commun 165, 888-894; Hla & Neilson (1992) Proc Natl Acad Sci USA 89, 7384-7388). COX-1 is a constitutive isoform and is mainly responsible for the synthesis of cytoprotective prostaglandin in the gastrointestinal tract and for the synthesis of thromboxane, which triggers aggregation of blood platelets (Allison et al. (1992) N Engl J Med 327, 749-754). COX-2, on the other hand, is inducible and short-lived. Its expression is stimulated in response to endotoxins, cytokines, and mitogens (Kujubu et al. (1991) J Biol Chem 266, 12866-12872; Lee et al. (1992) J Biol Chem 267, 25934-25938; O'Sullivan et al. (1993) Biochem Biophys Res Commun 191, 1294-1300).

Cyclooxygenase-2 (COX-2) catalyzes the committed step in the biosynthesis of prostaglandins, thromboxane, and prostacyclin (Smith et al. (2000) Annu Rev Biochem 69, 145-182). COX-2 is not expressed in most normal tissues, but is present in inflammatory lesions and tumors (Fu et al. (1990) J Biol Chem 265, 16737-16740; Eberhart et al. (1994) Gastroenterology 107, 1183-1188). Studies by Eberhart et al. and Kargman et al. by first demonstrated that COX-2 mRNA and protein are expressed in tumor cells from colon cancer patients but not in surrounding normal tissue (Eberhart et al. (1994) Gastroenterology 107, 1183-1188; Kargman et al. (1995) Cancer Res 55, 2556-2559). COX-2 expression appears to be an early event in colon tumorigenesis because it is detectable in colon polyps (Eberhart et al. (1994) Gastroenterology 107, 1183-1188). Approximately 55% of polyps demonstrate COX-2 expression compared to approximately 85% of colon adenocarcinomas. The concept that COX-2 is expressed in malignant tumors and their precursor lesions has been extended to a broader range of solid tumors including those of the esophagus (Kandil et al. (2001) Dig Dis Sci 46, 785-789), bladder (Ristimaki et al. (2001) Am J Pathol 158, 849-853), breast (Ristimaki et al. (2002) Cancer Res 62, 632-635), pancreas (Tucker et al. (1999) Cancer Res 59, 987-990), lung (Soslow et al. (2000) Cancer 89, 2637-2645), stomach (Ristimaki et al. (1997) Cancer Res 57, 1276-1280), liver (Rahman et al. (2001) Clin Cancer Res 7, 1325-1332), head and neck (Chan et al. (1999) Cancer Res 59, 991-994), cervix (Gaffney et al. (2001) Intl J Radiat Oncol Biol Phys 49, 1213-1217), endometrium (Jabbour et al. (2001) Br J Cancer 85, 1023-1031), and skin, including melanoma (Denkert et al. (2001) Cancer Res 61, 303-308).

The expression of COX-2 in tumors appears to have functional consequences. Prostaglandins have been demonstrated to stimulate cell proliferation (Marnett (1992) Cancer Res 52, 5575-5589), inhibit apoptosis (Tsujii & DuBois (1995) Cell 83, 493-501), increase cell motility (Sheng et al. (2001) J Biol Chem 276, 18075-18081), and enhance angiogenesis in animal models (Daniel et al. (1999) Cancer Res 59, 4574-4577; Masferrer et al. (2000) Cancer Res 60, 1306-1311). COX-2 expression is dramatically elevated in rodent models of colon cancer and crossing COX-2 knockout mice into the APC$^{Min}$ background (a mouse strain that is highly susceptible to the formation of spontaneous intestinal adenomas) reduces the number of intestinal tumors by ~85% compared to APC$^{Min}$ controls (DuBois et al. (1996) Gastroenterology 110, 1259-1262; Oshima et al. (1996) Cell 87, 803-809). COX-2 expression is detected in breast cancers from the subset of patients exhibiting Her-2/neu overexpression. Overexpression of COX-2 specifically targeted to the breast of multiparous rodents induces breast cancer. These findings suggest that COX-2 contributes to tumor progression so that its expression in tumor tissue plays an important functional role. In fact, high COX-2 expression in tumors is associated with poor clinical outcome (Tucker et al. (1999) Cancer Res 59, 987-990; Denkert et al. (2001) Cancer Res 61, 303-308; Kandil et al. (2001) Dig Dis Sci 46, 785-789; Ristimaki et al. (2002) Cancer Res 62, 632-635).

What are needed, therefore, are multifunctional compositions that can specifically bind to COX-2 in order to modulate a biological activity of COX-2, while concurrently delivering an active agent comprising a therapeutic and/or a diagnostic composition to a cell or tissue expressing COX-2, as well as methods for employing such compositions to image, diagnose, and/or treat disorders associated with abnormal proliferation of such cells and/or tissues.

To address this need, the presently disclosed subject matter provides methods and compositions for treating, diagnosing, and/or imaging COX-2-expressing cells including, but not limited to neoplastic cells and their normal and/or pre-neoplastic precursors.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides cyclooxygenase-2-selective therapeutic and/or diagnostic agents. In some embodiments, the cyclooxygenase-2-selective therapeutic and/or diagnostic agents comprise an active agent and a derivative of a non-steroidal anti-inflammatory drug (NSAID). In some embodiments, (a) the active agent and the derivative of the NSAID are linked to each other via a tether; and (b) the therapeutic and/or diagnostic agent selectively binds to COX-2. In some embodiments, the non-steroidal anti-inflammatory drug comprises a carboxylic acid moiety or has been modified to comprise a carboxylic acid moiety, and the derivative of the NSAID is a secondary amide or ester derivative of the carboxylic acid moiety. In some embodiments, the NSAID is selected from the group consisting of fenamic acids, indoles, phenylalkanoic acids, phenylacetic acids, coxibs, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11, 14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, celecoxib, pharmaceutically acceptable salts thereof, and combinations thereof. In some embodiments, the NSAID is selected from the group consisting of indomethacin, celecoxib, pharmaceutically acceptable salts thereof, and combinations thereof.

In some embodiments, the therapeutic and/or diagnostic agent comprises a structural formula selected from:

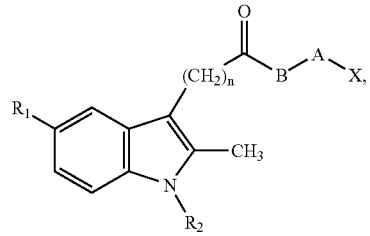

Formula I

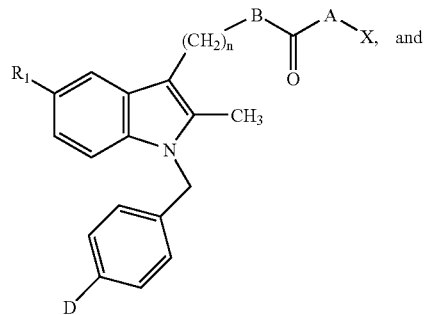

Formula II

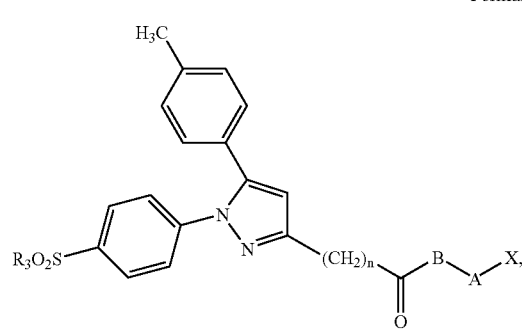

Formula III wherein:
$R_1 = C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions thereof, or $R_1$ is halo where halo is chloro, fluoro, bromo, or iodo;

$R_2 = C_1$ to $C_6$ alkyl, $C_4$ to $C_8$ aroyl, $C_4$ to $C_8$ aryl, $C_4$ to $C_8$ heterocyclic alkyl or aryl with O, N or S in the ring, $C_4$ to $C_8$ aryl-substituted $C_1$ to $C_6$ alkyl, alkyl-substituted or aryl-substituted $C_4$ to $C_8$ heterocyclic alkyl or aryl with O, N or S in the ring, alkyl-substituted $C_4$ to $C_8$ aroyl, or alkyl-substituted $C_4$ to $C_8$ aryl, or halo-substituted versions thereof or $R_1$ is halo where halo is chloro, bromo, or iodo;

$R_3 = C_1$ to $C_3$ alkyl or branched alkyl, $NH_2$, or a dipolar $N_3$ group;

X comprises an active agent;
A comprises a tether;
B is O or —NH;
D is halo, $C_1$ to $C_4$ alkyl, branched alkyl, or cycloalkyl; and
n is 0-4.

In some embodiments, the active agent comprises a chemotherapeutic. In some embodiments, the chemotherapeutic is selected from the group consisting of taxol, retinoic acid and derivatives thereof, doxorubicin, sulfathiazole, sulfadimethoxane, mitomycin C, retinoic acid or derivative thereof, camptothecin and derivatives thereof, podophyllotoxin, and mycophenolic acid. In some embodiments, the therapeutic agent is selected from the group consisting of:

Compound 27a
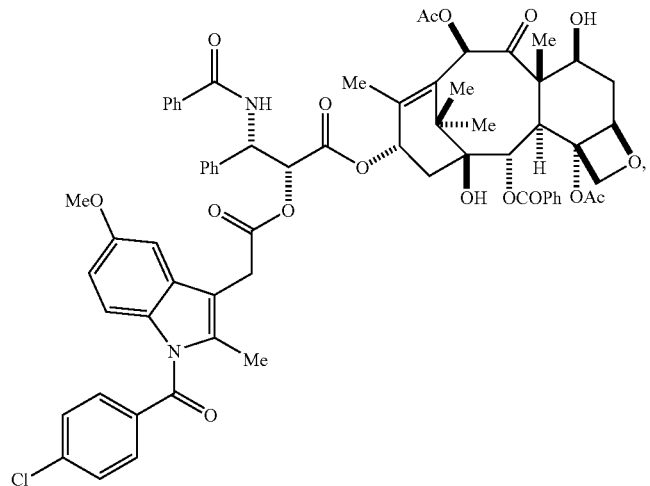
Compound 27c
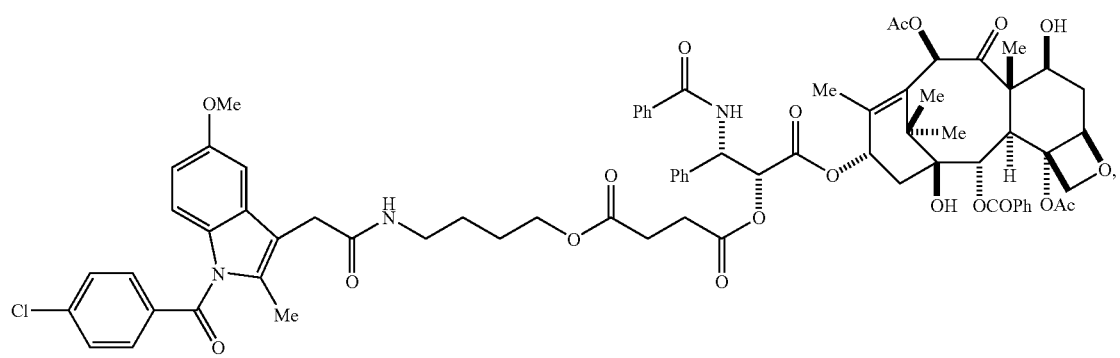
Compound 27d
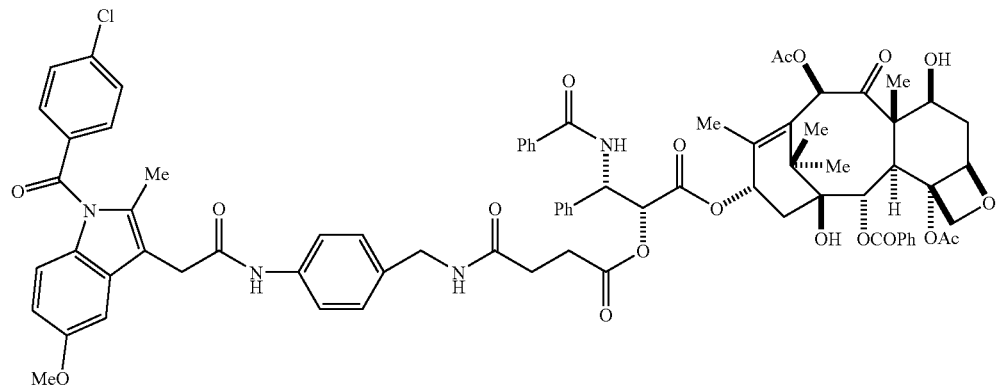
Compound 27g
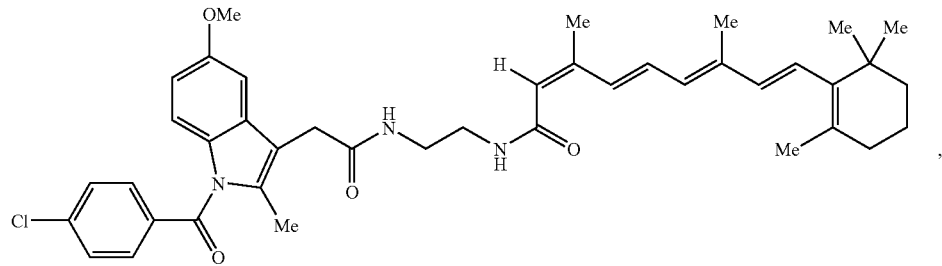

-continued
Compound 27h
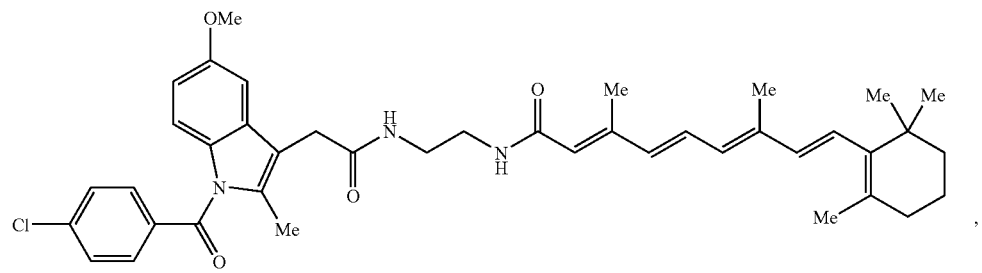,
Compound 27i
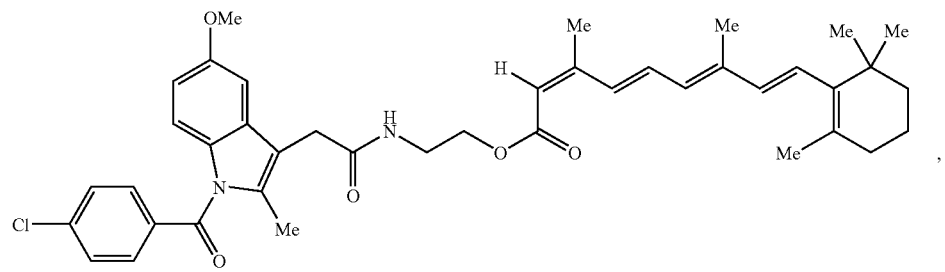,
Compound 27j
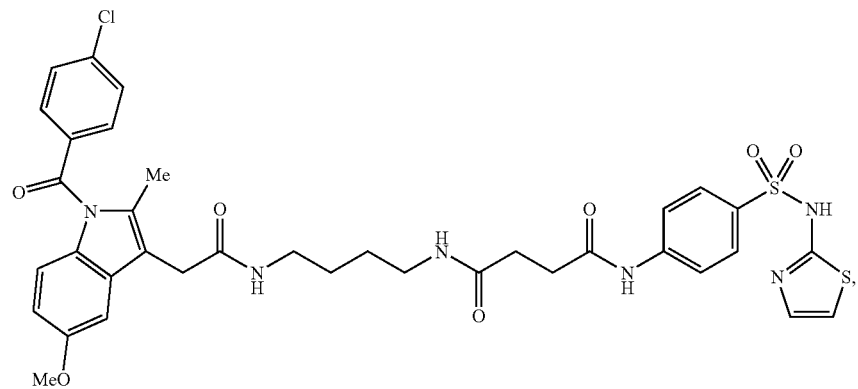,
Compound 27n
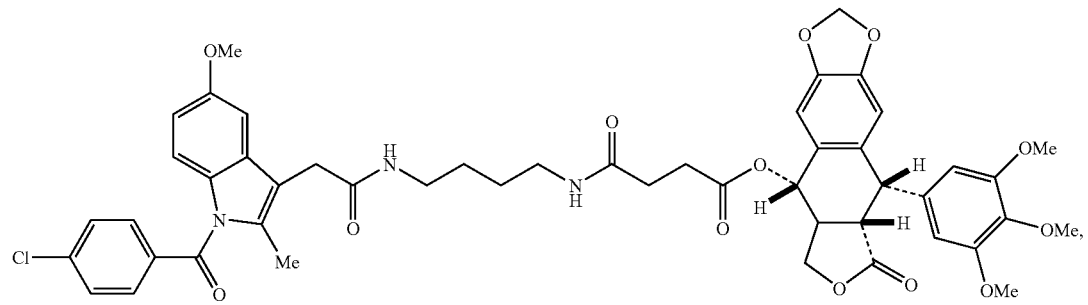,
Compound 27o
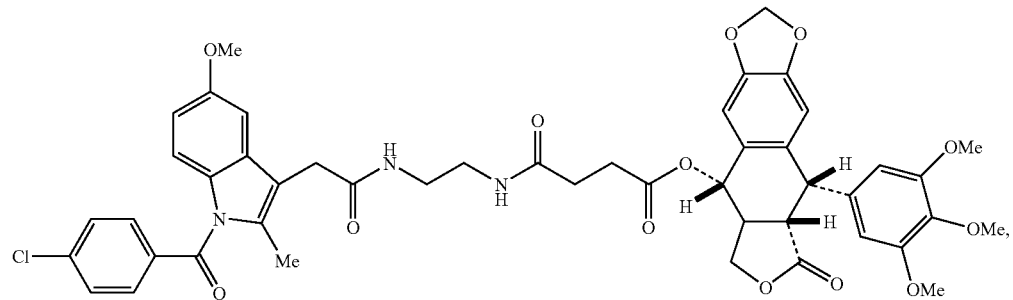

-continued
Compound 27p
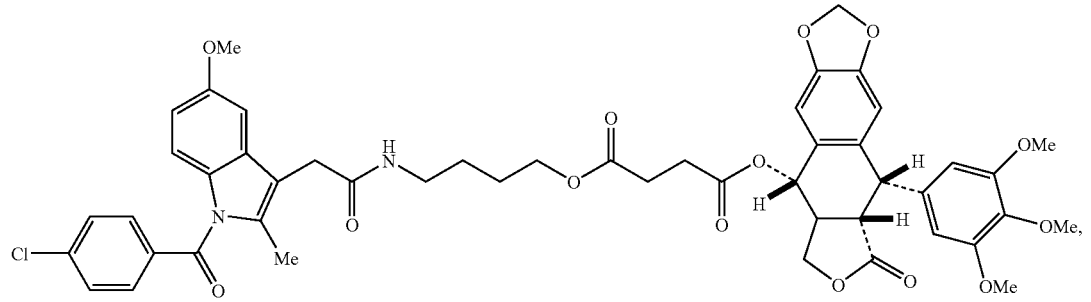
Compound 27q
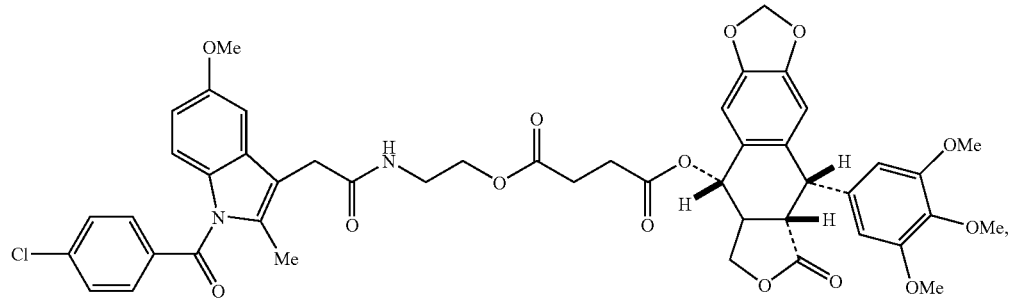
Compound 27r
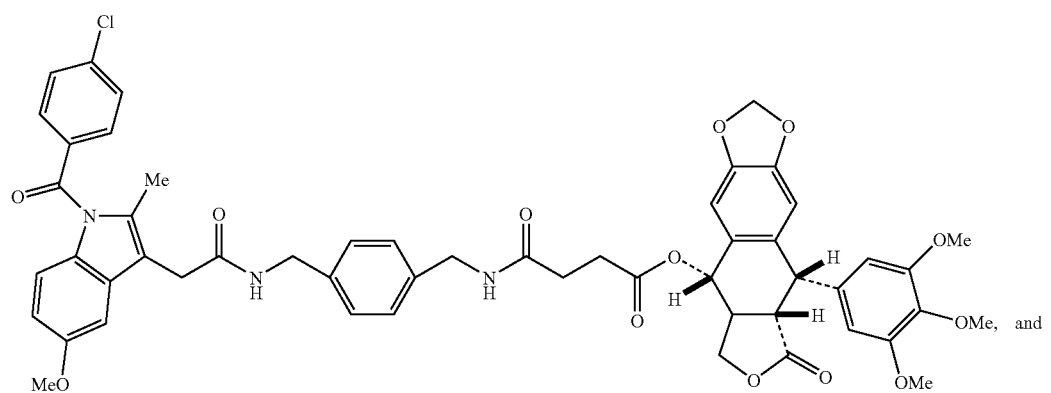
, and
Compound 27s
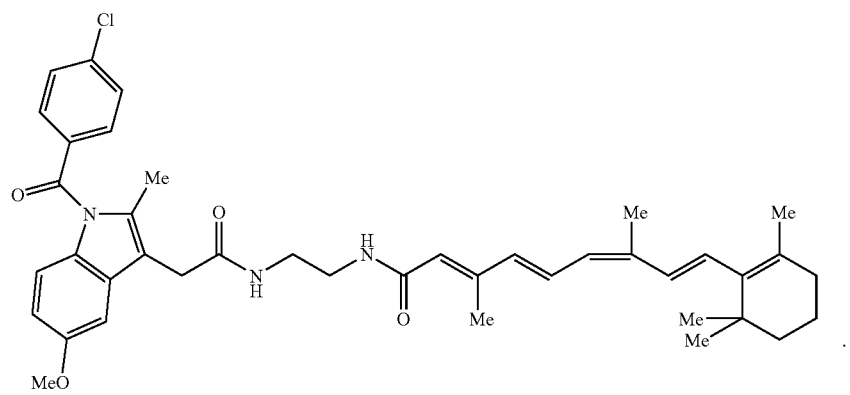
.

In some embodiments, the active agent comprises a detectable moiety. In some embodiments, the detectable moiety comprises a fluorescent molecule selected from the group consisting of a fluorophore, a cyanine dye, and near infrared (NIR) dye. In some embodiments, the fluorophore is selected from the group consisting of coumarin and derivatives thereof, dansyl chloride, dabsyl chloride, nitrobenzodiazolamine (NBD), cinnamic acid, fluorescein and derivatives thereof, rhodamine and derivatives thereof, Nile Blue, an Alexa Fluor and derivatives thereof, and combinations thereof. In some embodiments, the therapeutic and/or diagnostic agent is selected from the group consisting of:

Compound 27x

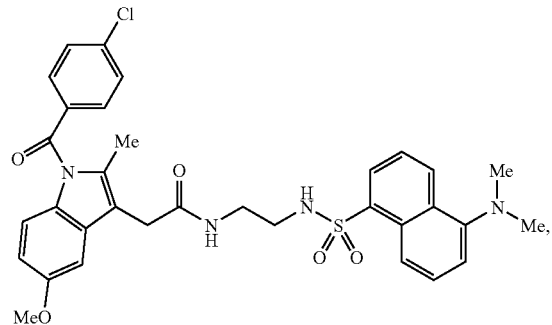

Compound 27y

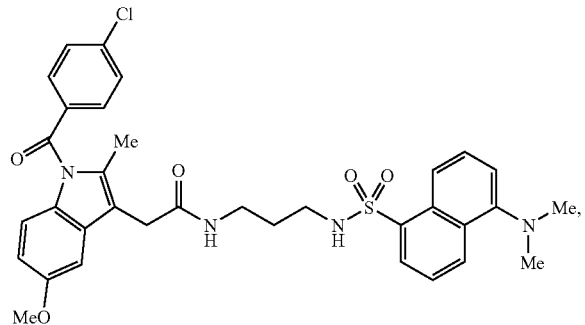

Compound 27z

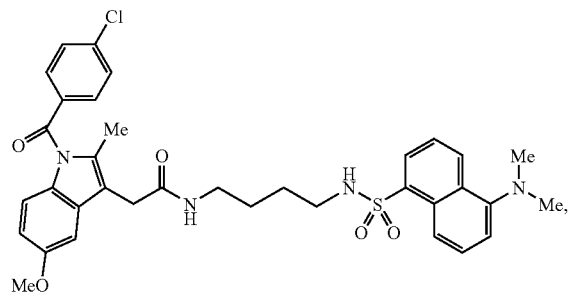

Compound 27aa

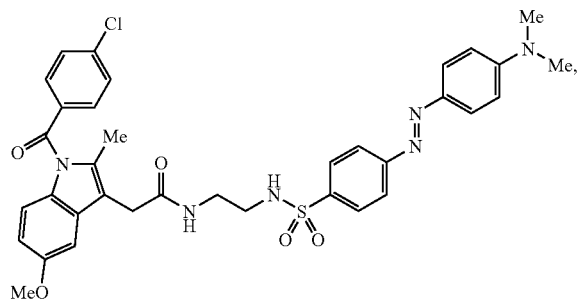

Compound 27cc

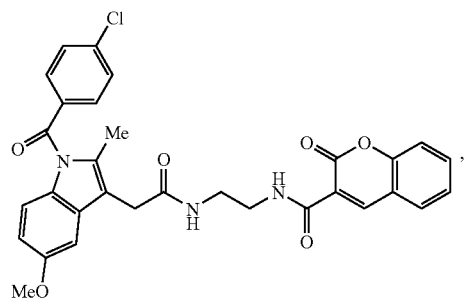

Compound 27ff

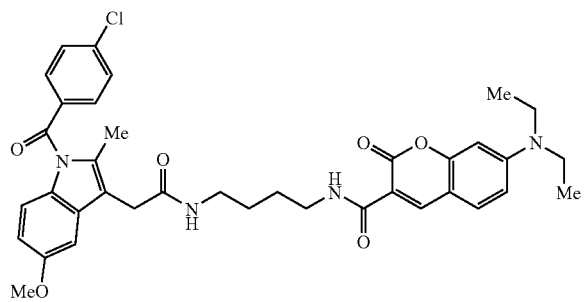

Compound 27gg

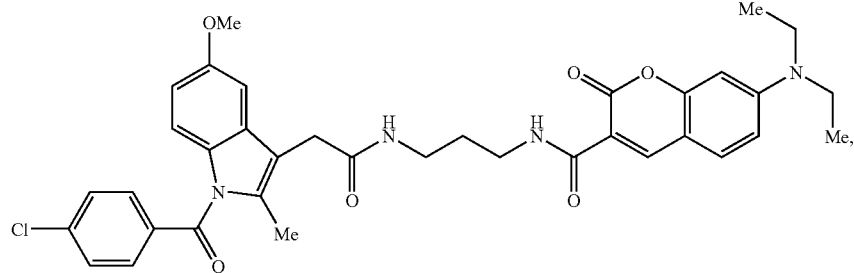

Compound 27ii
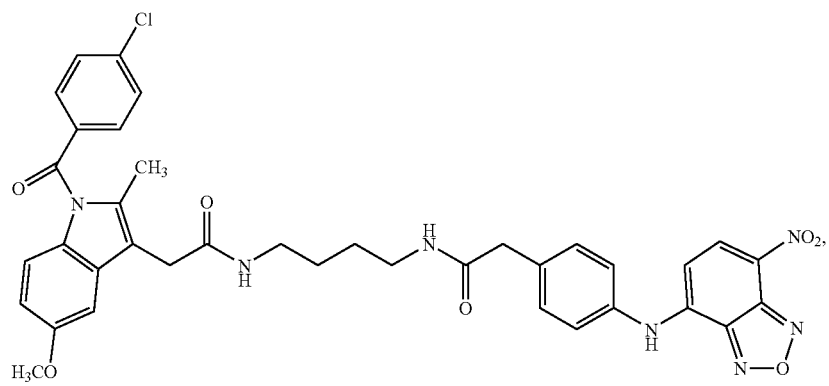
Compound 27qq
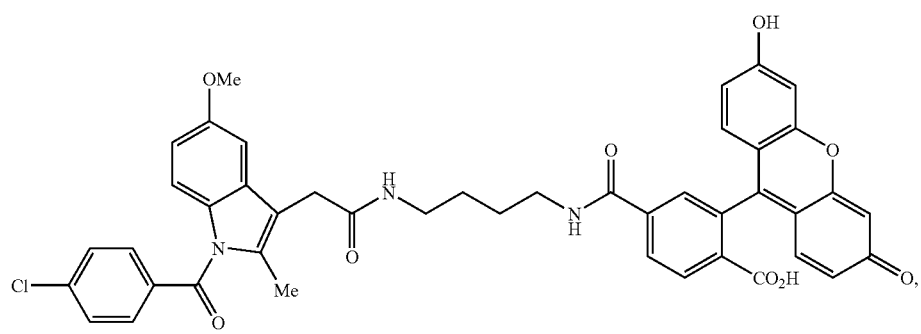
Compound 27uu
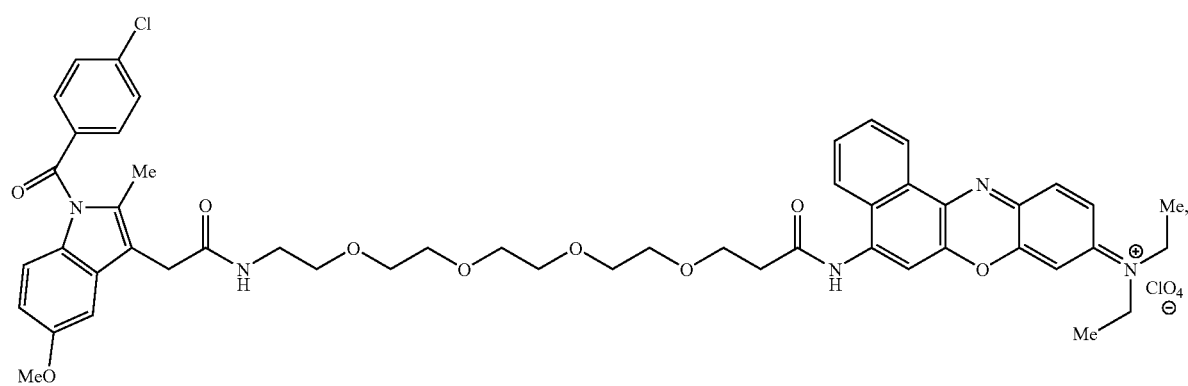
Compound 27vv
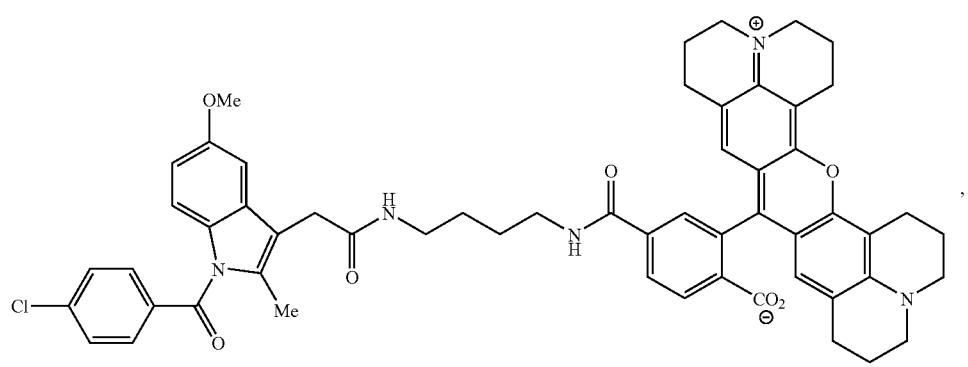

-continued
Compound 27eee
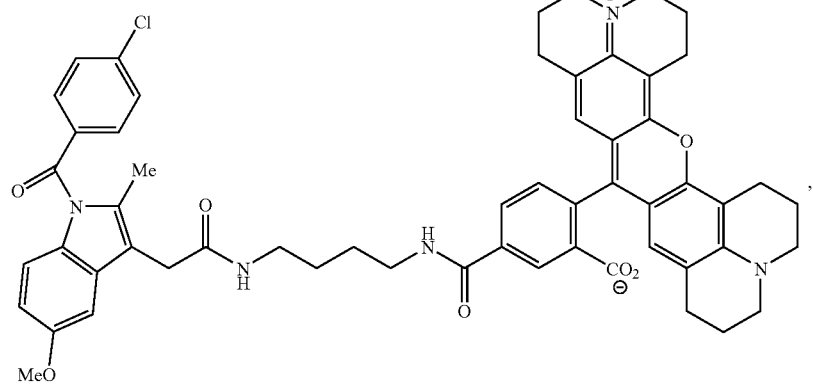
Compound 27iii
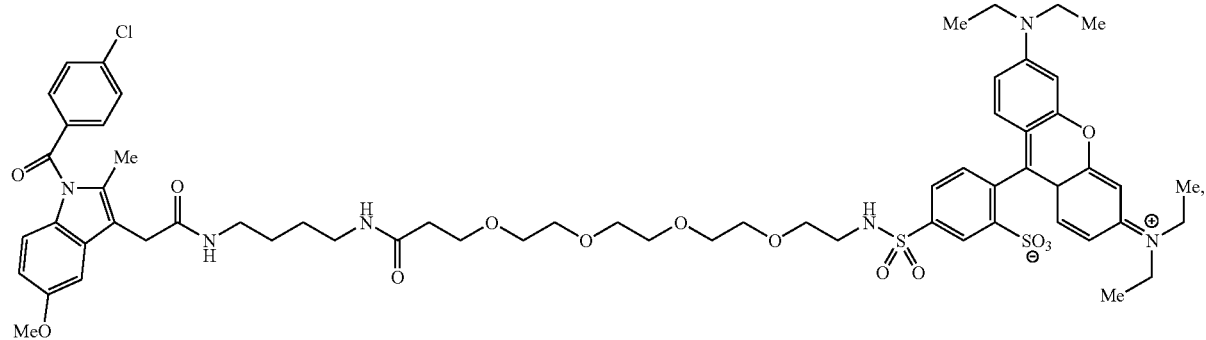
Compound 27qqq
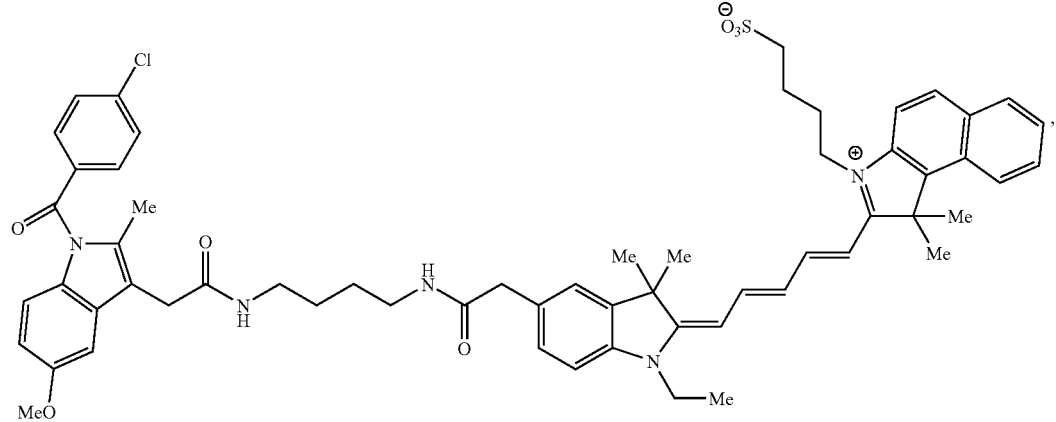

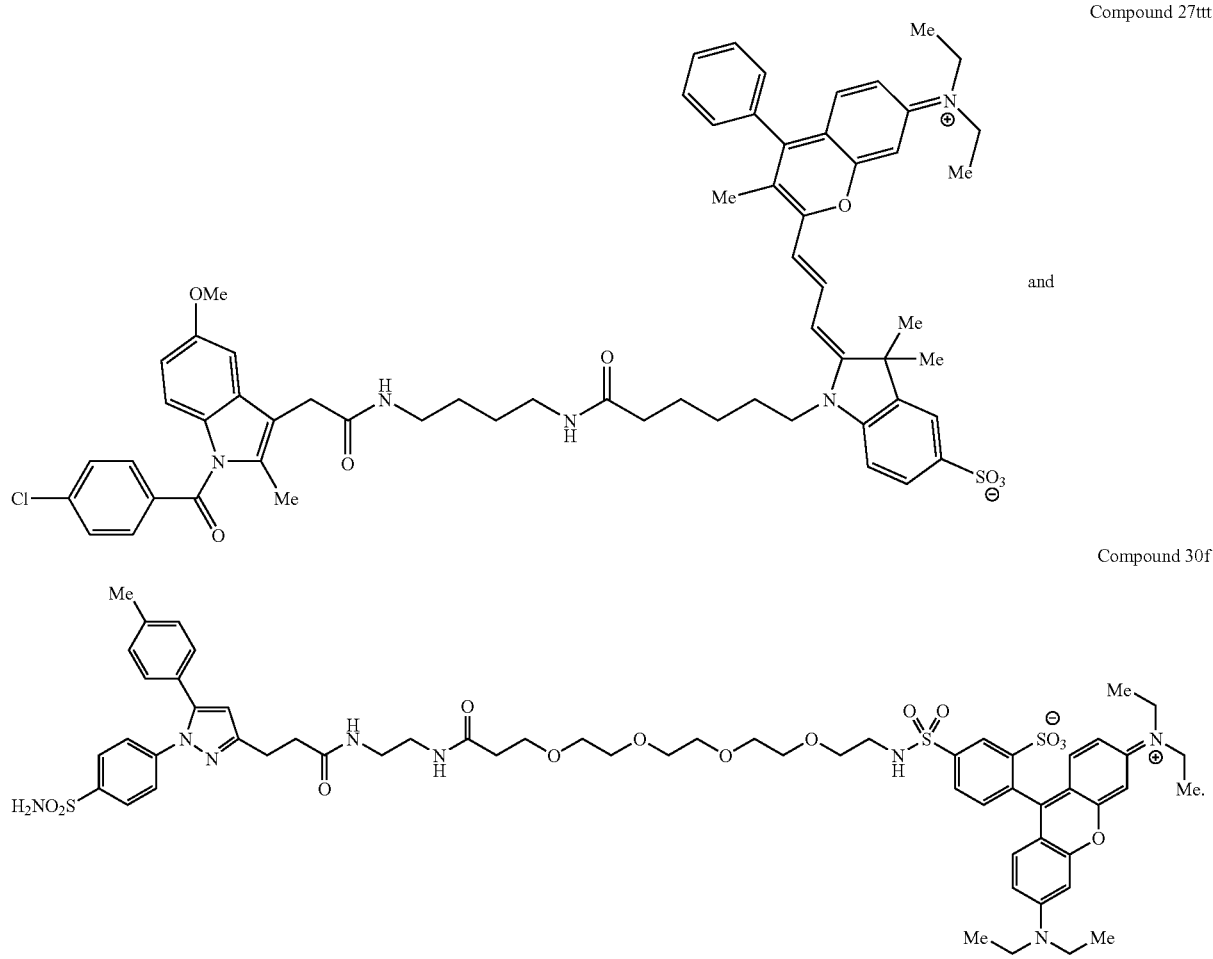

In some embodiments, the rhodamine and derivatives thereof are selected from the group consisting of 5-carboxy-X-rhodamine and 6-carboxy-X-rhodamine. In some embodiments, the cyanine dye is selected from the group consisting of Cy5, Cy5.5, and Cy7. In some embodiments, the NIR dye is selected from the group consisting of NIR641, NIR664, NIR700, and NIR782.

In some embodiments, the therapeutic and/or diagnostic agent comprises a tether. In some embodiments, the tether is selected from the group consisting of an alkylamide tether, a PEG tether, an alkylpiperazine tether, and a phenylene tether. In some embodiments, the alkylamide tether is selected from the group consisting of an alkyldiamide, an alkylamidosulfonamide, an alkylamidothiourea, and alkyldiamidosulfonamide, and an aminoalkyldiamide. In some embodiments, the PEG tether is selected from the group consisting of a PEG4amidoester, a PEG4diamide, and an alkyldiamidoPEG4sulfonamide. In some embodiments, the alkylpiperazine tether is selected from the group consisting of a diamidopiperazine, an alkyldiamidopiperazine, an alkylaminopiperazinylethyl acetamidoether, an alkylaminopiperazinylether ester, and a dialkyldiamidopiperazine.

The presently disclosed subject matter also provides methods for synthesizing a therapeutic and/or diagnostic agent. In some embodiments, the methods comprise (a) providing a non-steroidal anti-inflammatory drug (NSAID), or a derivative thereof, comprising a carboxylic acid moiety; (b) derivatizing the carboxylic acid moiety to a secondary amide or an ester; and (c) complexing an active agent to the secondary amide or the ester, wherein: (i) the active agent comprises a therapeutic moiety, a diagnostic moiety, or both a therapeutic moiety and a diagnostic moiety; (ii) the active agent is complexed to the derivative of the NSAID via a tether; and (iii) the therapeutic and/or diagnostic agent selectively binds to cyclooxygenase-2 (COX-2).

In some embodiments, the NSAID is selected from the group consisting of fenamic acids, indoles, phenylalkanoic acids, phenylacetic acids, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, meclofenamic acid, 5,8,11,14-eicosatetraynoic acid (ETYA), ketorolac, and pharmaceutically acceptable salts thereof, and combinations thereof. In some embodiments, the NSAID is indomethacin, a derivative thereof, or a pharmaceutically acceptable salt thereof.

In some embodiments of the synthetic methods, the therapeutic and/or diagnostic agent comprises a structural formula selected from Formula I, Formula II, and Formula III as defined hereinabove.

In some embodiments, the therapeutic moiety comprises a chemotherapeutic. In some embodiments, the chemotherapeutic is selected from the group consisting of taxol, retinoic acid and derivatives thereof, doxorubicin, sulfathiazole, sulfadimethoxane, mitomycin C, retinoic acid or derivative thereof, camptothecin and derivatives thereof, podophyllotoxin, and mycophenolic acid. In some embodiments, the therapeutic and/or diagnostic agent is selected from the group consisting of:

Compound 27a

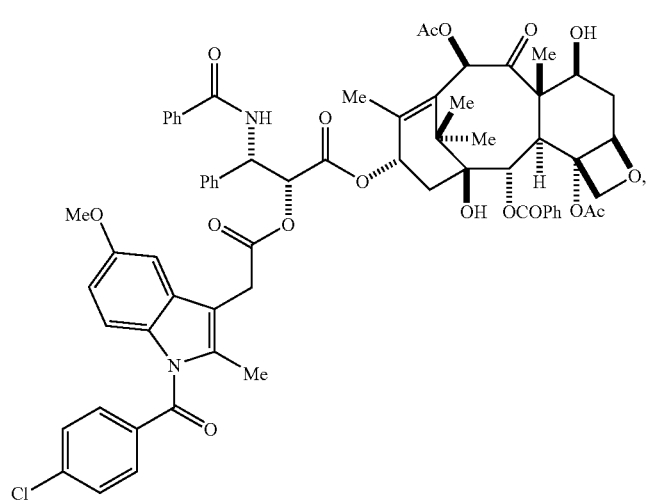

Compound 27c

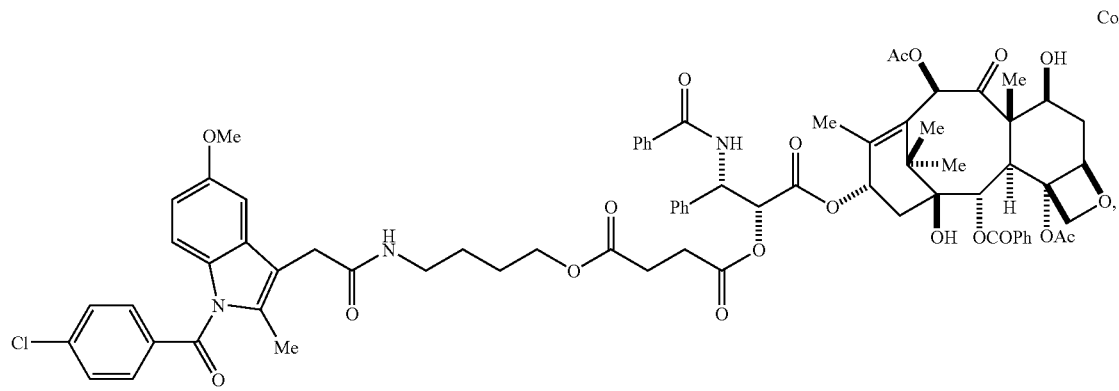

Compound 27d

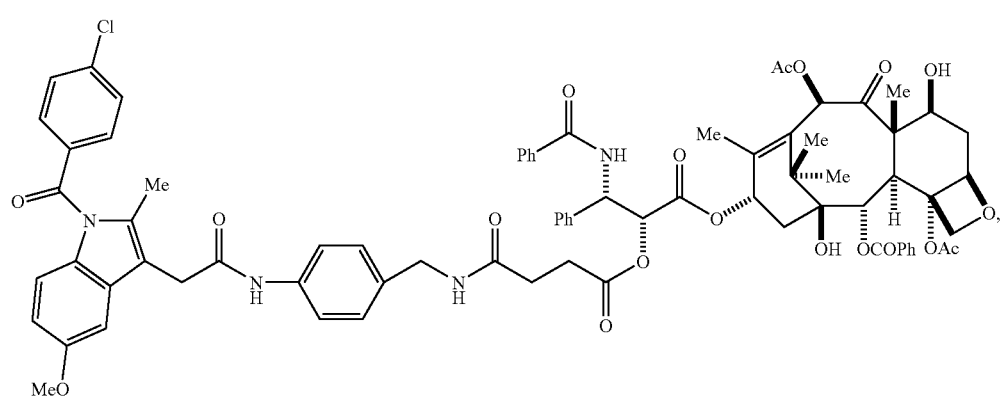

-continued
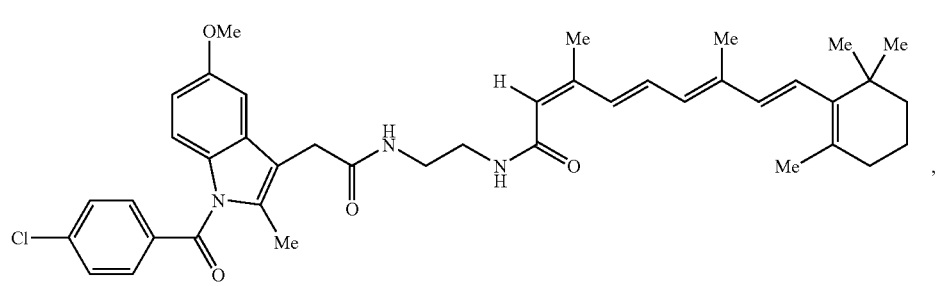
Compound 27g
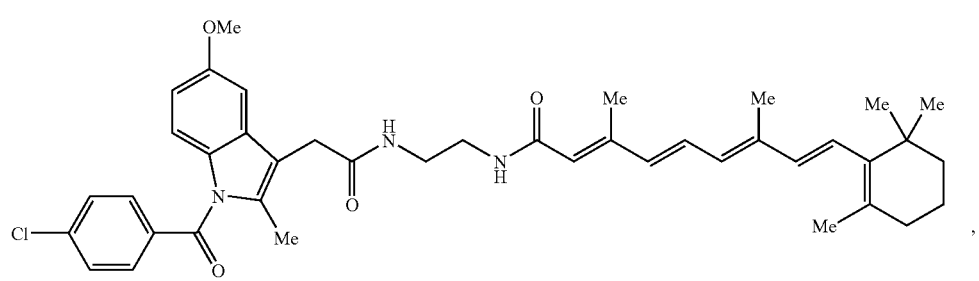
Compound 27h
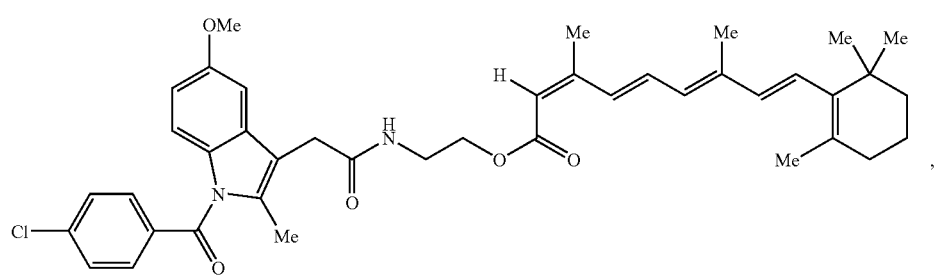
Compound 27i
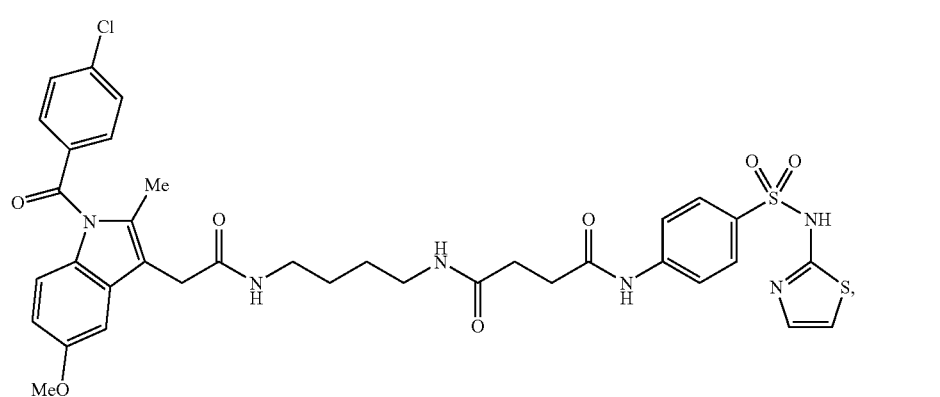
Compound 27j
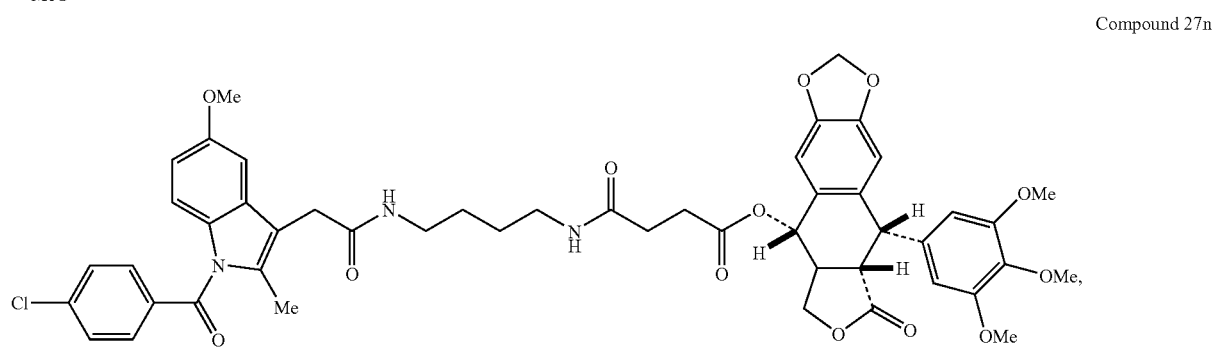
Compound 27n Compound 27o
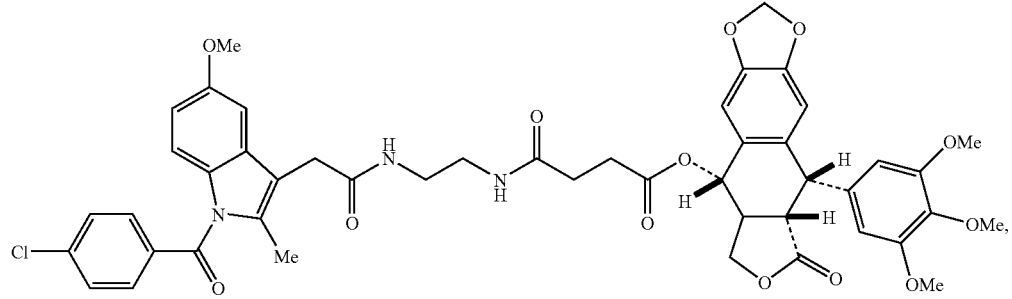
Compound 27p
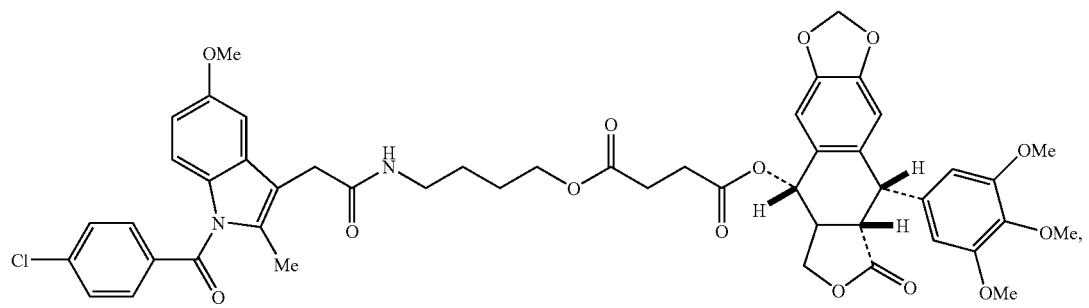
Compound 27q
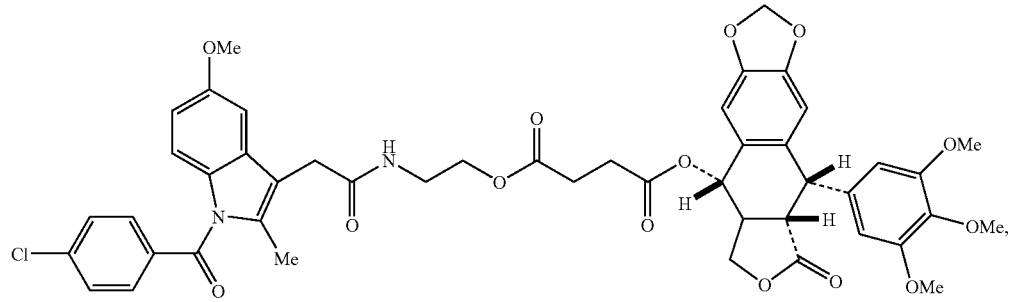
Compound 27r
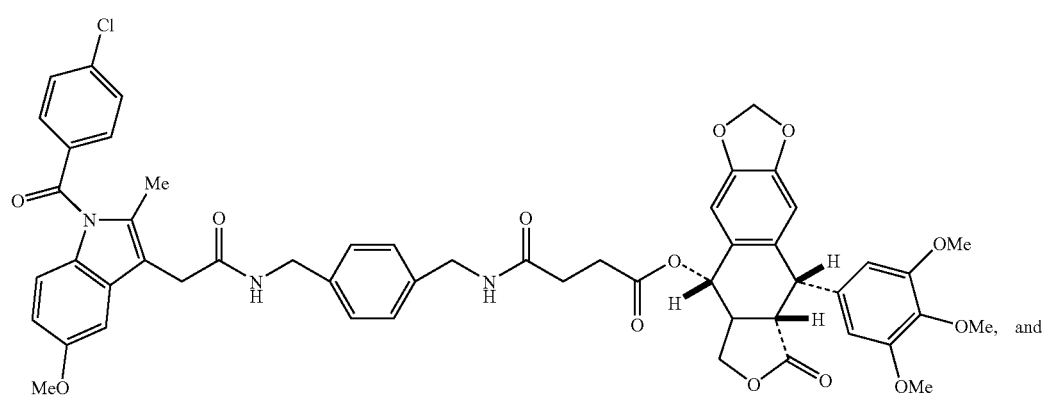
and -continued

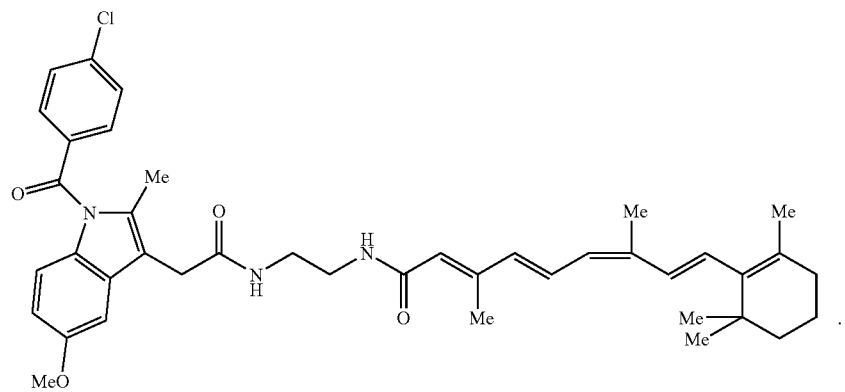

Compound 27s

In some embodiments, the diagnostic moiety comprises a detectable moiety. In some embodiments, the detectable moiety comprises a fluorescent molecule selected from the group consisting of a fluorophore, a cyanine dye, and a near infrared (NIR) dye. In some embodiments, the fluorophore is selected from the group consisting of coumarin and derivatives thereof, dansyl chloride, dabsyl chloride, nitrobenzodiazolamine (NBD), cinnamic acid, fluorescein and derivatives thereof, rhodamine and derivatives thereof, and Nile Blue. In some embodiments, the therapeutic and/or diagnostic agent is selected from the group consisting of:

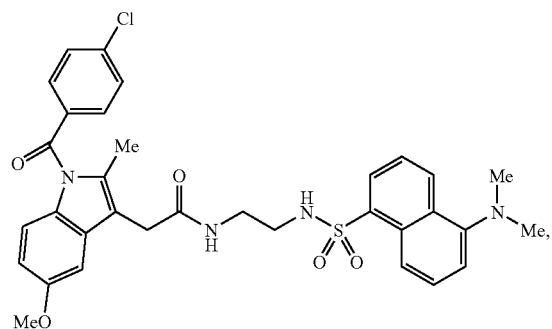

Compound 27x

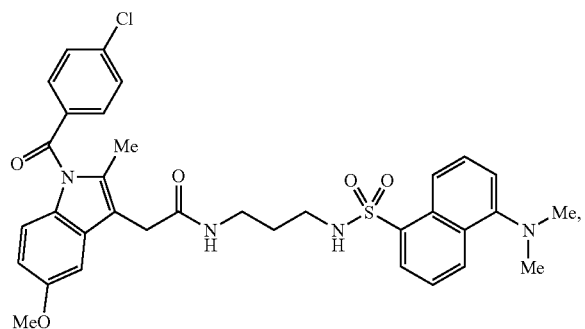

Compound 27y

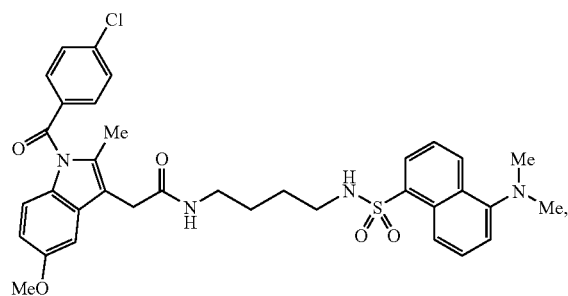

Compound 27z

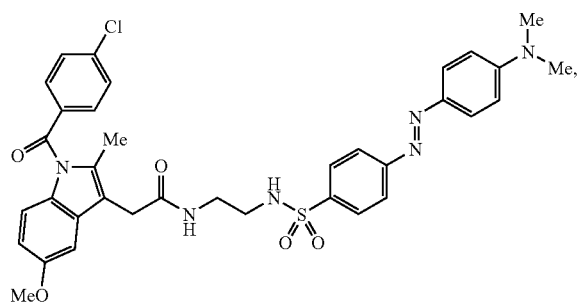

Compound 27aa

-continued
Compound 27cc
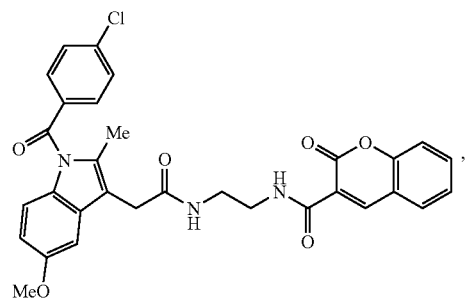
Compound 27ff
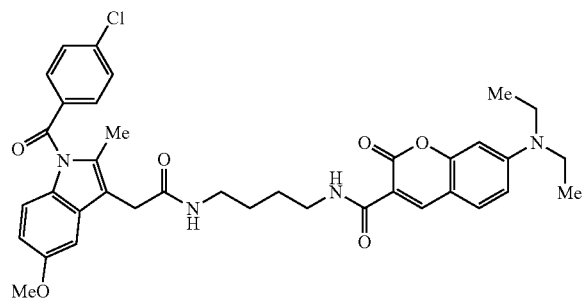
Compound 27gg
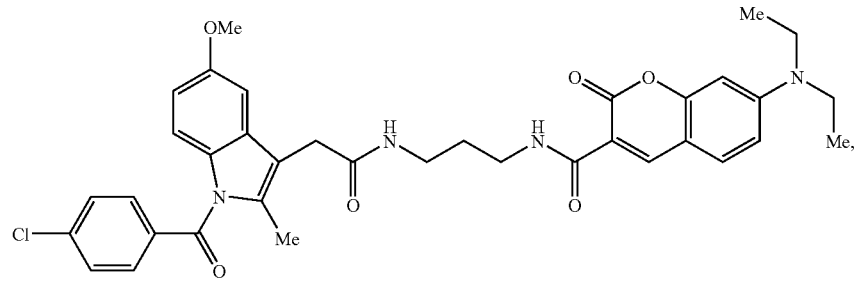
Compound 27ii
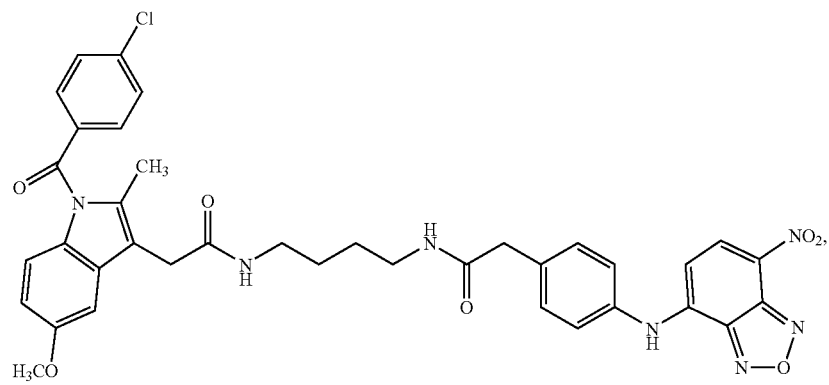
Compound 27qq
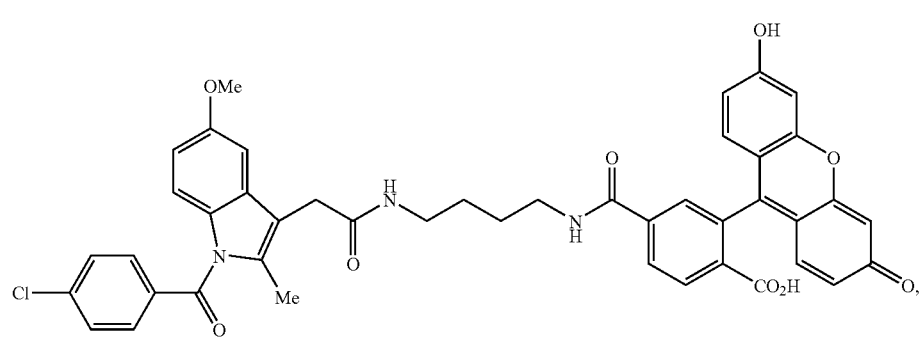

Compound 27uu
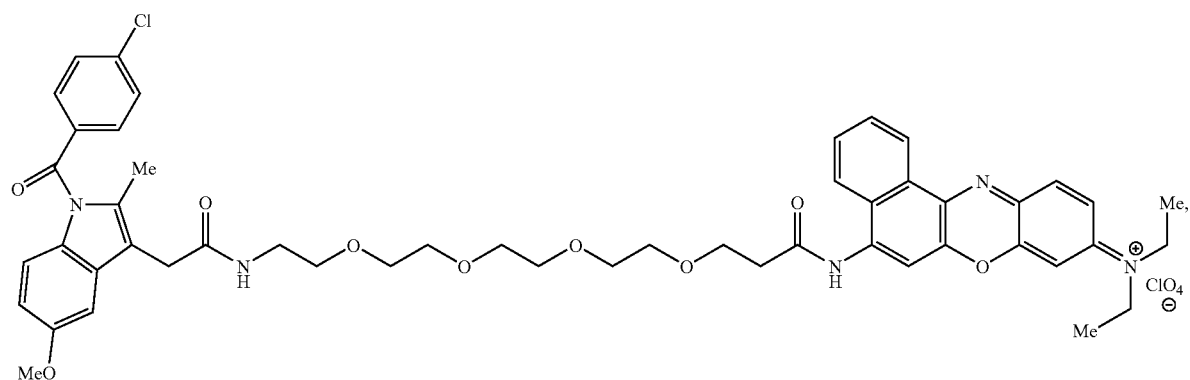
Compound 27vv
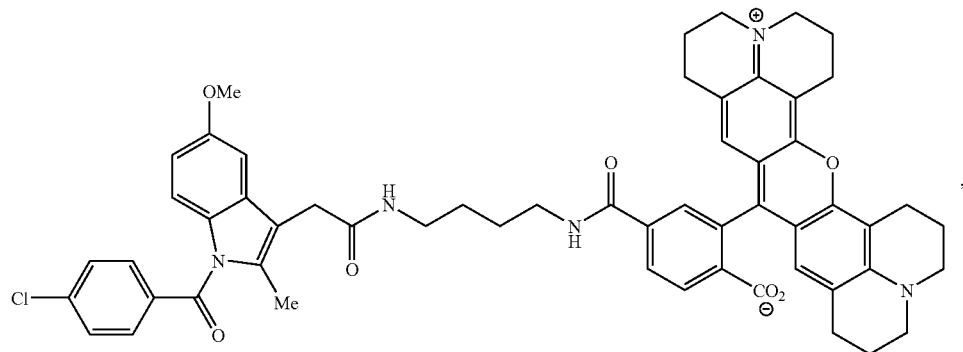
Compound 27eee
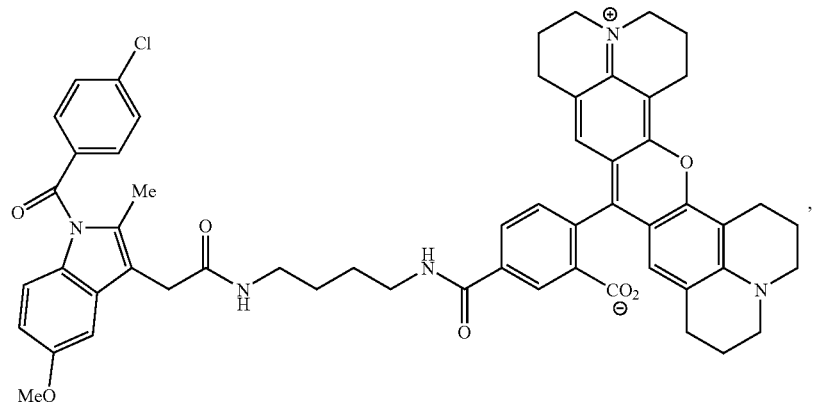
Compound 27iii
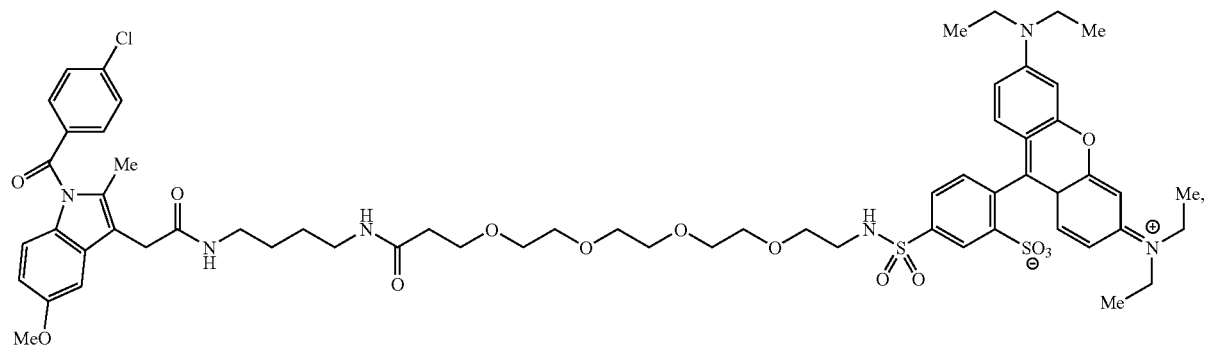

-continued
Compound 27qqq
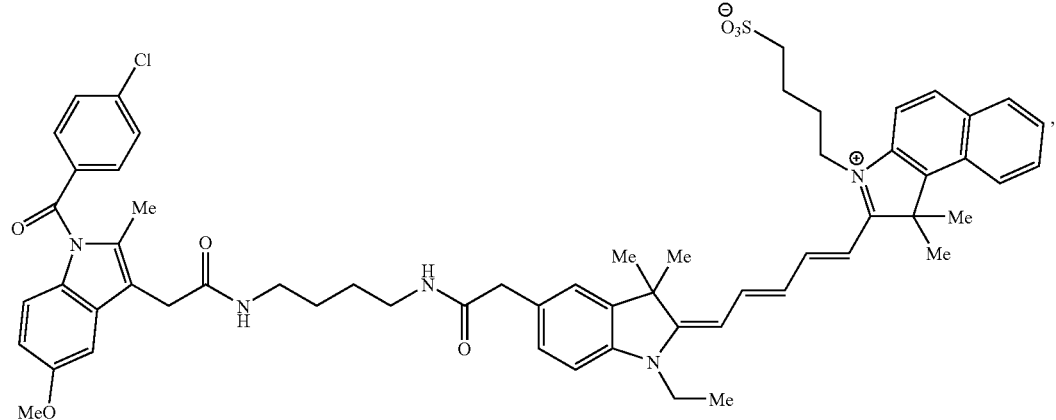
Compound 27ttt
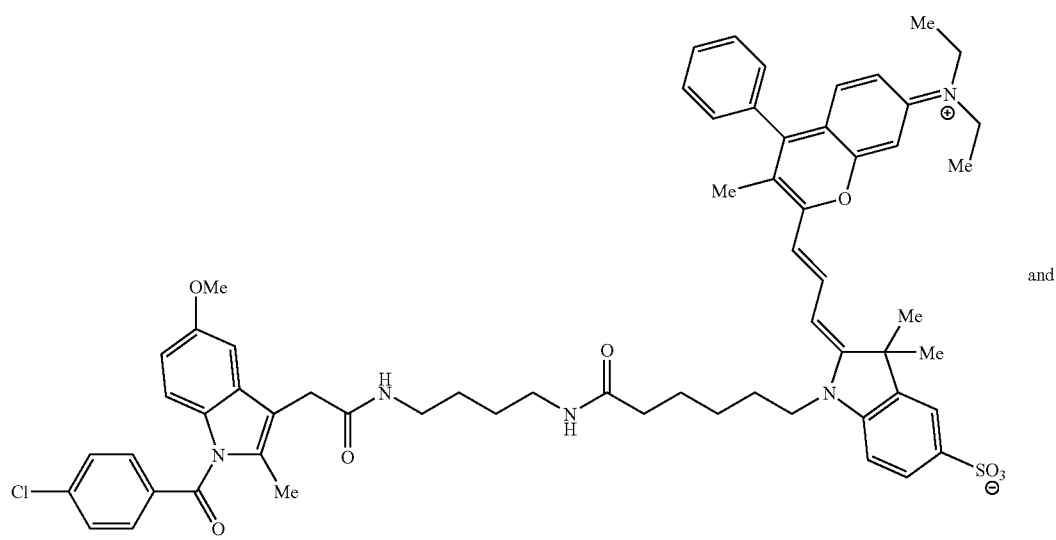
and
Compound 30f
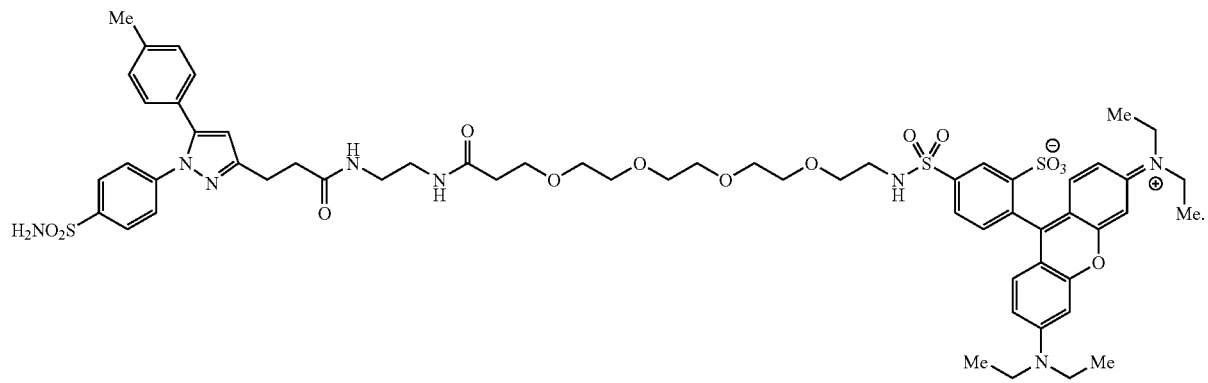

In some embodiments, the rhodamine and derivatives thereof are selected from the group consisting of 5-carboxy-X-rhodamine and 6-carboxy-X-rhodamine. In some embodiments, the cyanine dye is selected from the group consisting of Cy5, Cy5.5, and Cy7. In some embodiments, the NIR dye is selected from the group consisting of NIR641, NIR664, NIR700, and NIR782.

In some embodiments of the presently disclosed synthetic methods, the tether is selected from the group consisting of alkylamide tether, a PEG tether, an alkylpiperazine tether, and phenylene tether. In some embodiments, the alkylamide tether is selected from the group consisting of an alkyldiamide, an alkylamidosulfonamide, an alkylamidothiourea, and alkyldiamidosulfonamide, and an aminoalkyldiamide. In some embodiments, the PEG tether is selected from the group consisting of a PEG4amidoester, a PEG4diamide, and an alkyldiamidoPEG4sulfonamide. In some embodiments, the alkylpiperazine tether is selected from the group consisting of a diamidopiperazine, an alkyldiamidopiperazine, an alkylaminopiperazinylethyl acetamidoether, an alkylaminopiperazinylether ester, and a dialkyldiamidopiperazine.

The presently disclosed subject matter also provides methods for employing the compositions disclosed herein in therapeutic and/or diagnostic methods. In some embodiments, the presently disclosed subject matter provides methods for imaging a target cell in a subject. In some embodiments, the method comprises (a) administering to the subject a diagnostic agent as disclosed herein under conditions sufficient for contacting the diagnostic agent with the target cell, wherein the diagnostic agent comprises a detectable moiety covalently linked via a tether to a derivative of a non-steroidal anti-inflammatory drug (NSAID), and further wherein the diagnostic agent selectively binds to COX-2 expressed by the target cell; and (b) detecting the detectable moiety. In some embodiments, the target cell is present in a tissue selected from the group consisting of an inflammatory lesion, a tumor, a pre-neoplastic lesion, a neoplastic cell, a pre-neoplastic cell, and a cancer cell. In some embodiments, the pre-neoplastic lesion is selected from the group consisting of a colon polyp and Barrett's esophagus. In some embodiments, the tumor is selected from the group consisting of a primary tumor, a metastasized tumor, and a carcinoma. In some embodiments, the tumor is selected from the group consisting of a colon adenocarcinoma, an esophageal tumor, a bladder tumor, a breast tumor, a pancreatic tumor, a lung tumor, a gastric tumor, a hepatic tumor, a head and/or neck tumor, a cervical tumor, an endometrial tumor, and a skin tumor. In some embodiments, the administering is via a route selected from the group consisting of peroral, intravenous, intraperitoneal, inhalation, and intratumoral.

In some embodiments of the presently disclosed imaging methods, the non-steroidal anti-inflammatory drug comprises a carboxylic acid moiety or has been modified to comprise a carboxylic acid moiety, and the derivative of the NSAID is a secondary amide or ester derivative of the carboxylic acid moiety. In some embodiments, the NSAID is selected from the group consisting of fenamic acids, indoles, phenylalkanoic acids, phenylacetic acids, coxibs, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, celecoxib, pharmaceutically acceptable salts thereof, and combinations thereof. In some embodiments, the NSAID is selected from the group consisting of indomethacin, celecoxib, pharmaceutically acceptable salts thereof, and combinations thereof. In some embodiments, the therapeutic and/or diagnostic agent comprises a structural formula selected from Formula I, Formula II, and Formula III as defined hereinabove.

In some embodiments, the therapeutic and/or diagnostic agent is selected from the group consisting of:

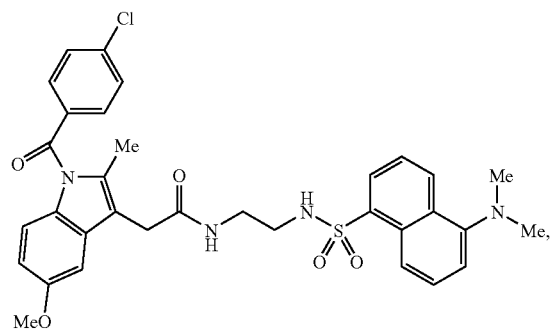

Compound 27x

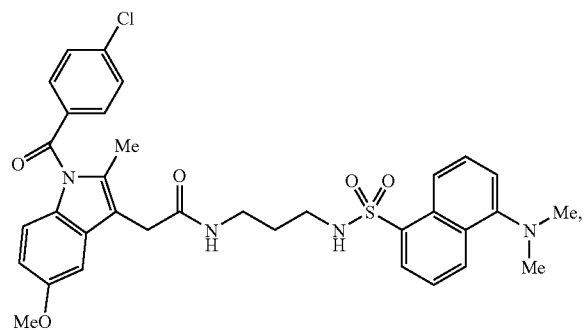

Compound 27y

-continued
Compound 27z
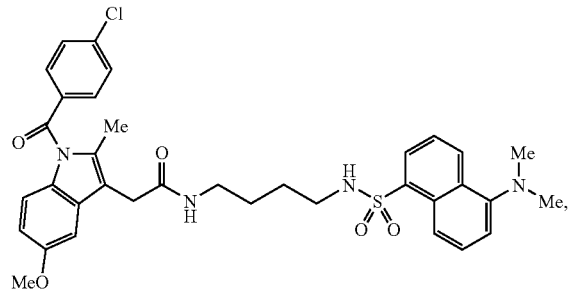
Compound 27aa
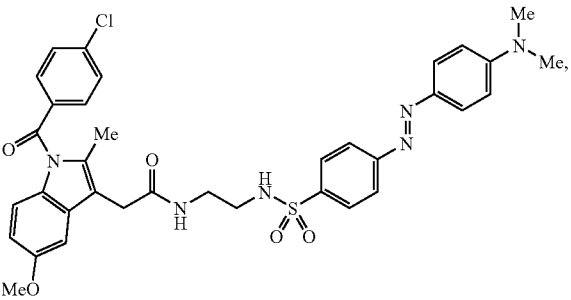
Compound 27cc
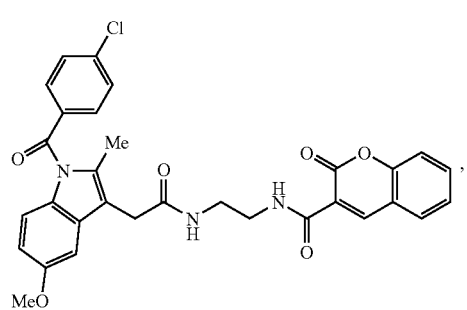
Compound 27ff
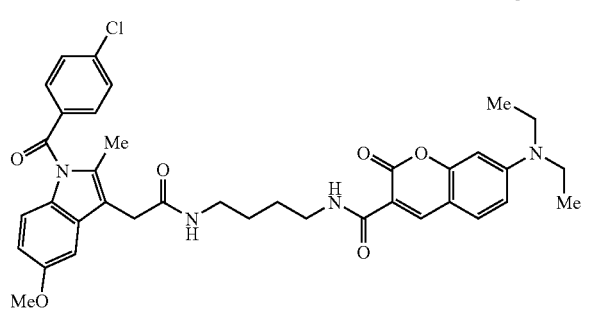
Compound 27gg
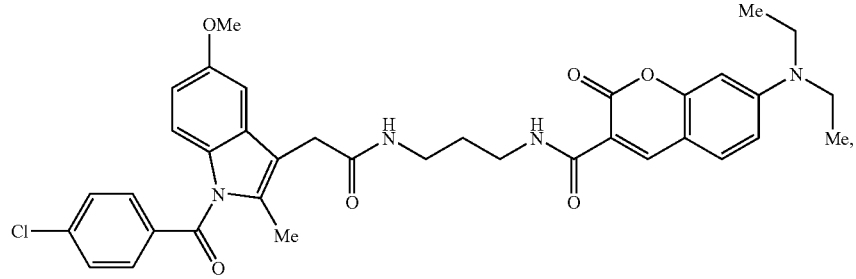
Compound 27ii
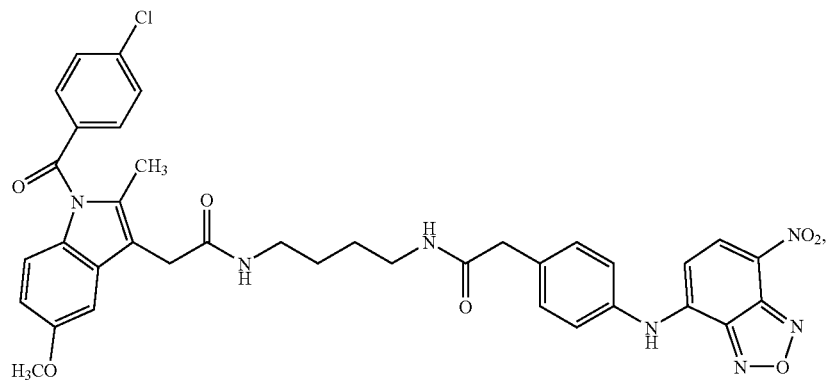
Compound 27qq
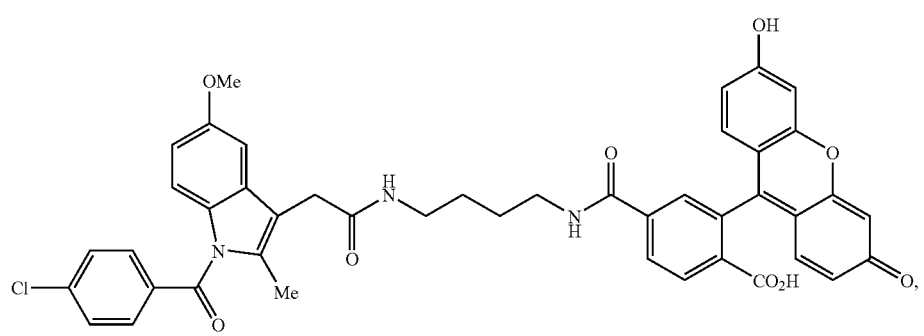

Compound 27uu
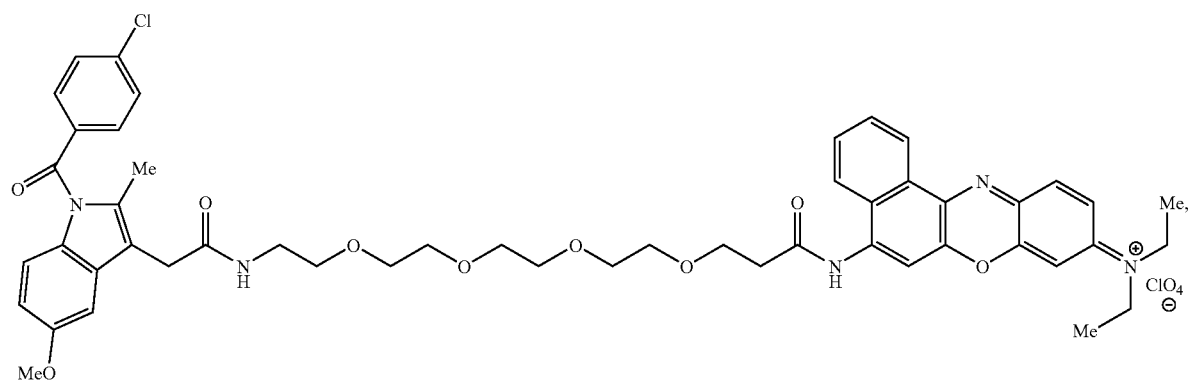
Compound 27vv
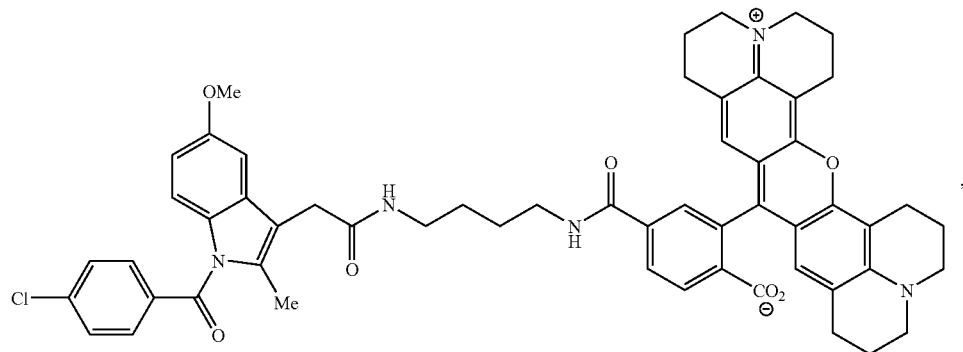
Compound 27eee
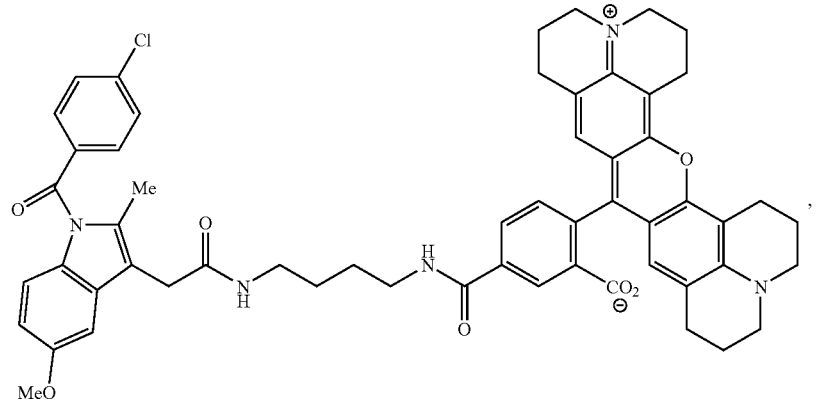
Compound 27iii
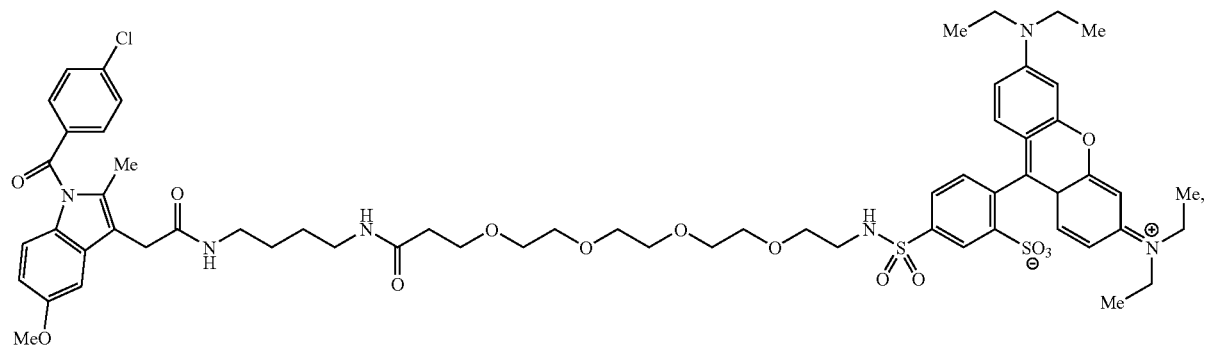

-continued

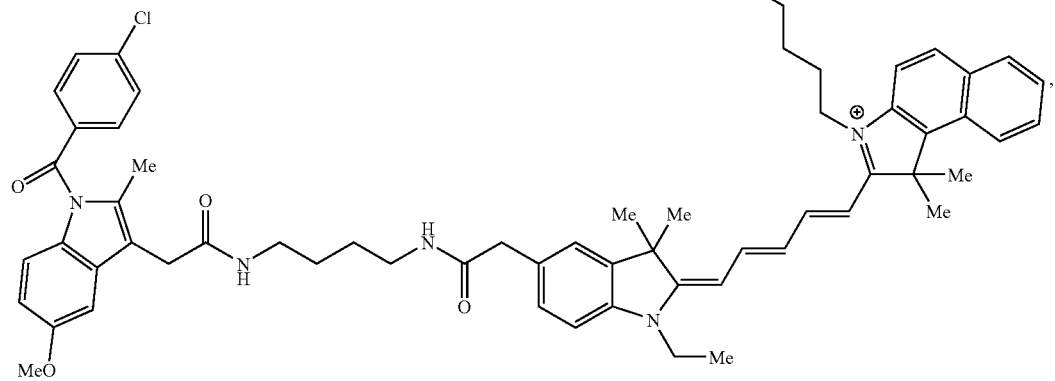

Compound 27qqq

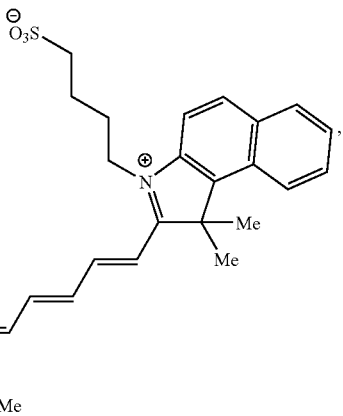

Compound 27ttt and

Compound 30f

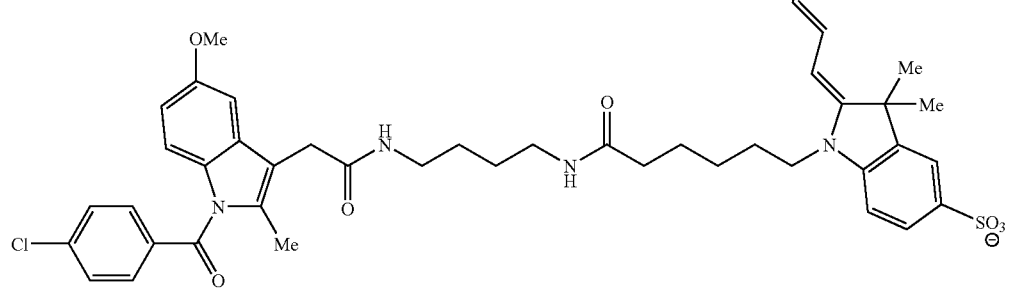

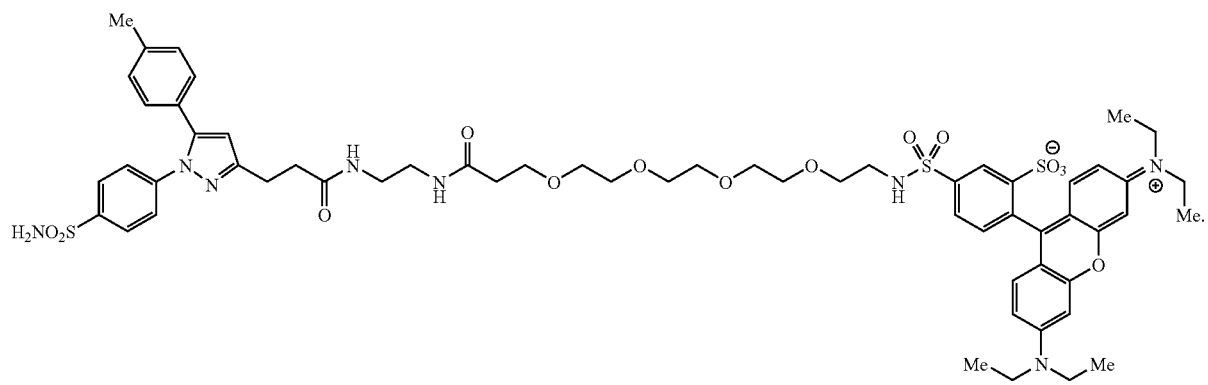

In some embodiments, the detectable moiety comprises a fluorescent molecule selected from the group consisting of a fluorophore, a cyanine dye, and a near infrared (NIR) dye. In some embodiments, the fluorophore is selected from the group consisting of coumarin and derivatives thereof, dansyl chloride, dabsyl chloride, nitrobenzodiazolamine (NBD), cinnamic acid, fluorescein and derivatives thereof, rhodamine and derivatives thereof, and Nile Blue. In some embodiments, the rhodamine and derivatives thereof are selected from the group consisting of 5-carboxy-X-rhodamine and 6-carboxy-X-rhodamine. In some embodiments, the cyanine dye is selected from the group consisting of Cy5, Cy5.5, and Cy7. In some embodiments, the NIR dye is selected from the group consisting of NIR641, NIR664, NIR700, and NIR782.

In some embodiments of the presently disclosed imaging methods, the tether is selected from the group consisting of alkylamide tether, a PEG tether, an alkylpiperazine tether, and phenylene tether. In some embodiments, the alkylamide tether is selected from the group consisting of an alkyldiamide, an alkylamidosulfonamide, an alkylamidothiourea, and alkyldiamidosulfonamide, and an aminoalkyldiamide. In some embodiments, the PEG tether is selected from the group consisting of a PEG4amidoester, a PEG4diamide, and an alkyldiamidoPEG4sulfonamide. In some embodiments, the alkylpiperazine tether is selected from the group consisting of a diamidopiperazine, an alkyldiamidopiperzine, an alkylaminopiperizinylethyl acetamidoether, an alkylaminopiperazinylether ester, and a dialkyldiamidopiperazine.

The presently disclosed subject matter also provides methods for treating a disorder associated with a cyclooxygenase-2 (COX-2) biological activity in a subject. In some embodiments, the methods comprise administering to the subject a therapeutically effective amount of a therapeutic agent comprising a therapeutic moiety and a derivative of a non-steroidal anti-inflammatory drug (NSAID), wherein (i) the therapeutic moiety and the derivative of a non-steroidal anti-inflammatory drug (NSAID) are covalently bound to each other via a tether; and (ii) the therapeutic agent selectively binds to COX-2. In some embodiments, the administering is via a route selected from the group consisting of peroral, intravenous, intraperitoneal, inhalation, and intratumoral. In some embodiments, the non-steroidal anti-inflammatory drug comprises a carboxylic acid moiety or has been modified to comprise a carboxylic acid moiety, and the carboxylic acid moiety is derivatized to the secondary amide or ester derivative.

In some embodiments of the presently disclosed treatment methods, the NSAID is selected from the group consisting of fenamic acids, indoles, phenylalkanoic acids, phenylacetic acids, coxibs, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, and pharmaceutically acceptable salts thereof, and combinations thereof. In some embodiments, the NSAID is selected from the group consisting of indomethacin, celecoxib, pharmaceutically acceptable salts thereof, and combinations thereof. In some embodiments, the secondary amide comprises a structural formula selected from Formula I, Formula II, and Formula III as defined hereinabove.

In some embodiments of the presently disclosed treatment methods, the active agent comprises a chemotherapeutic. In some embodiments, the chemotherapeutic is selected from the group consisting of taxol, retinoic acid and derivatives thereof, doxorubicin, sulfathiazole, sulfadimethoxane, mitomycin C, retinoic acid and derivatives thereof, camptothecin and derivatives thereof, podophyllotoxin, and mycophenolic acid. In some embodiments, the therapeutic agent is selected from the group consisting of:

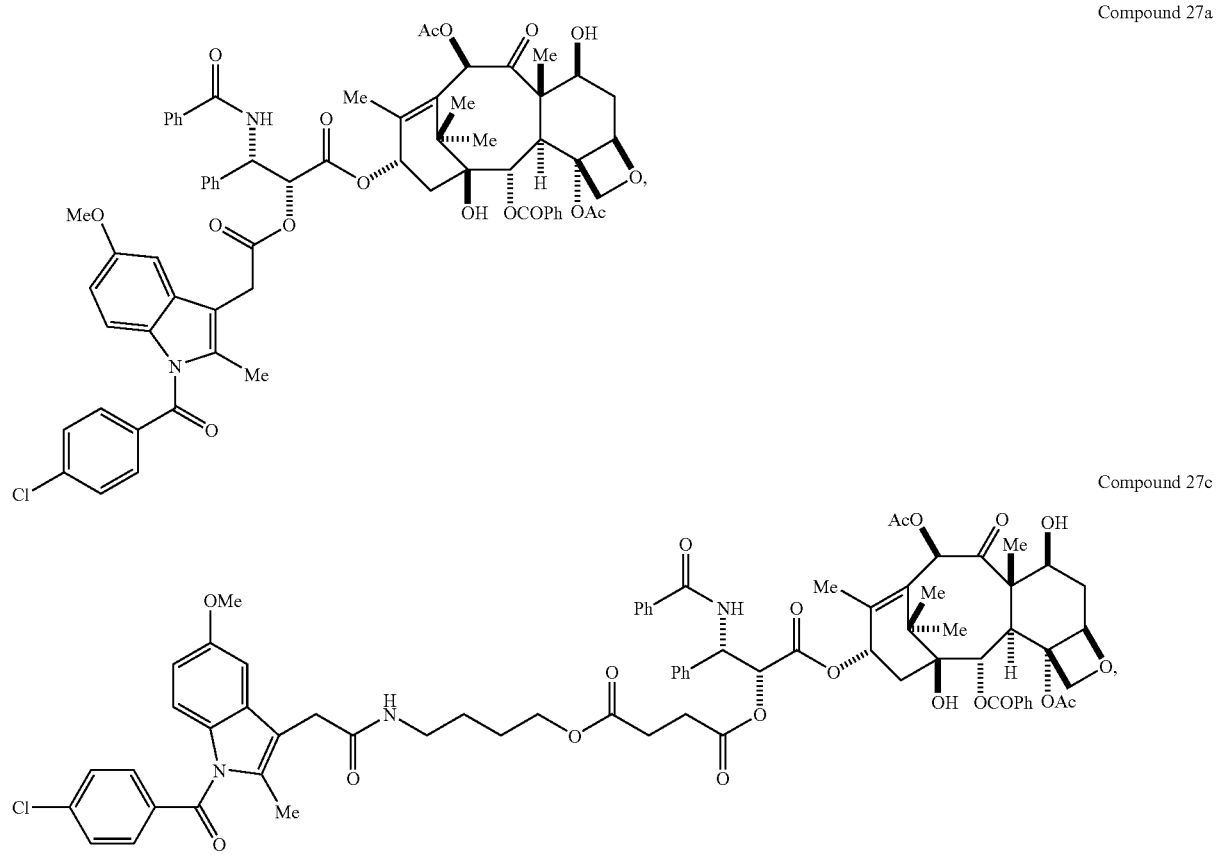

-continued
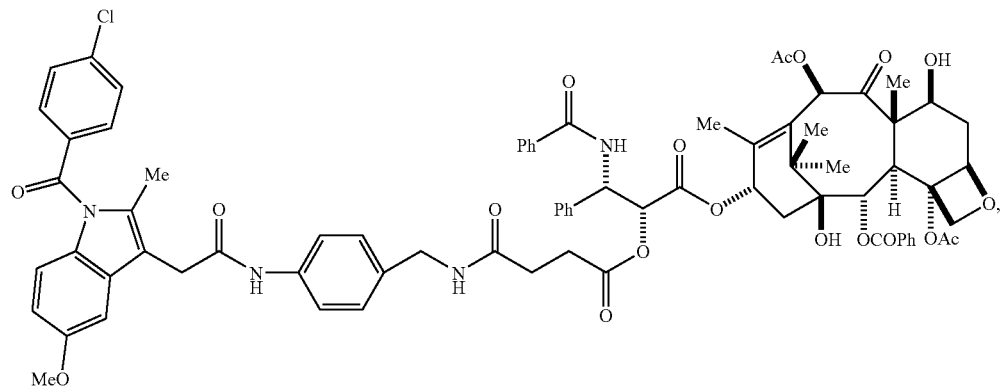
Compound 27d
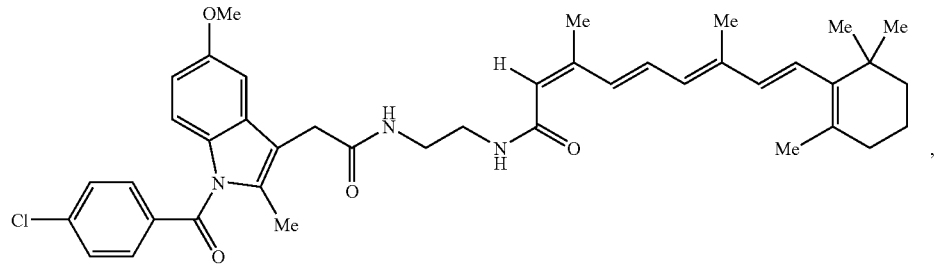
Compound 27g
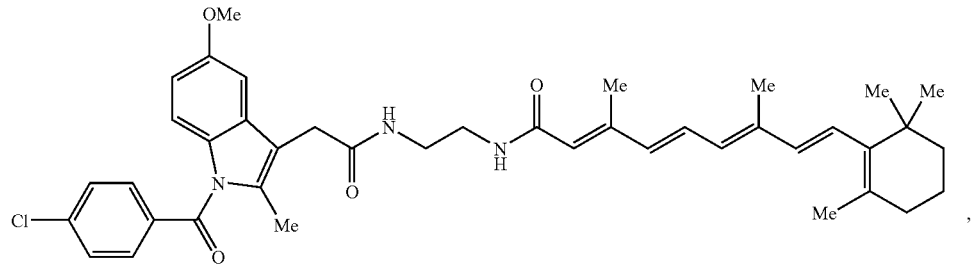
Compound 27h
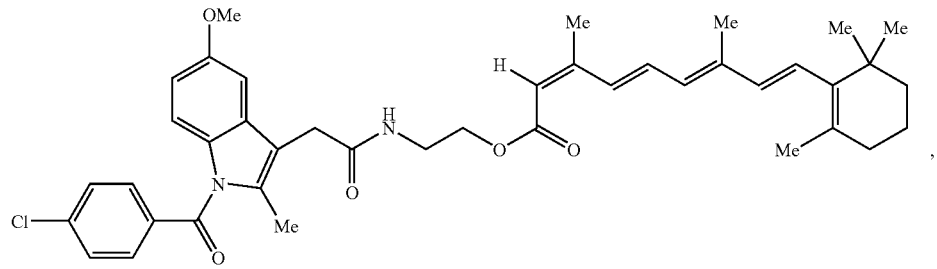
Compound 27i
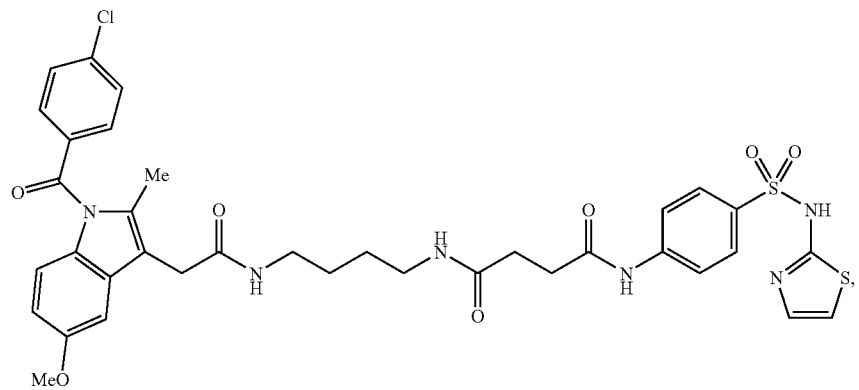
Compound 27j -continued
Compound 27n
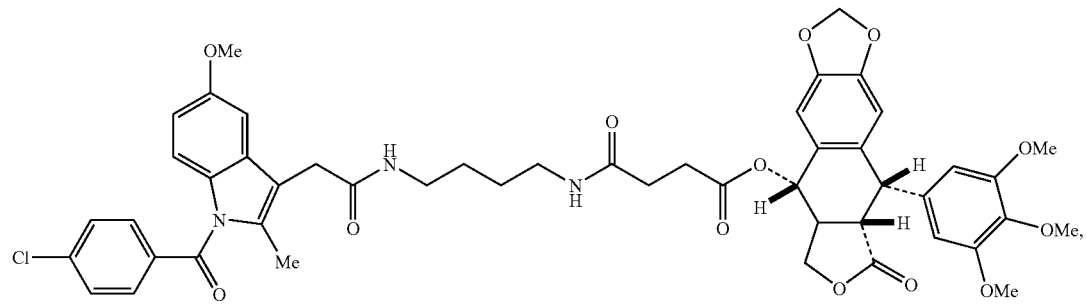
Compound 27o
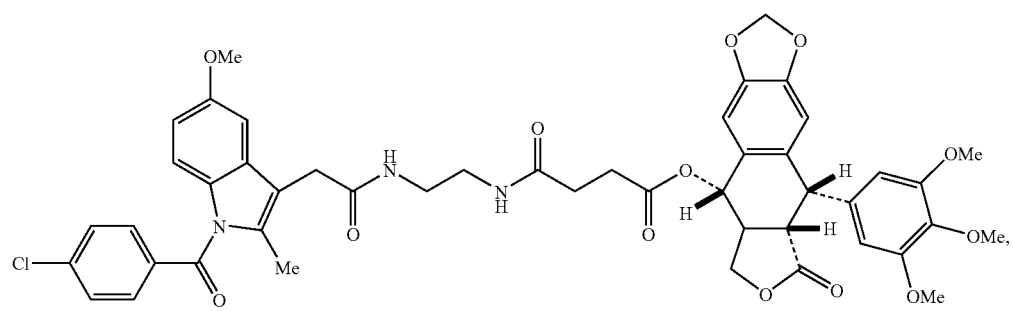
Compound 27p
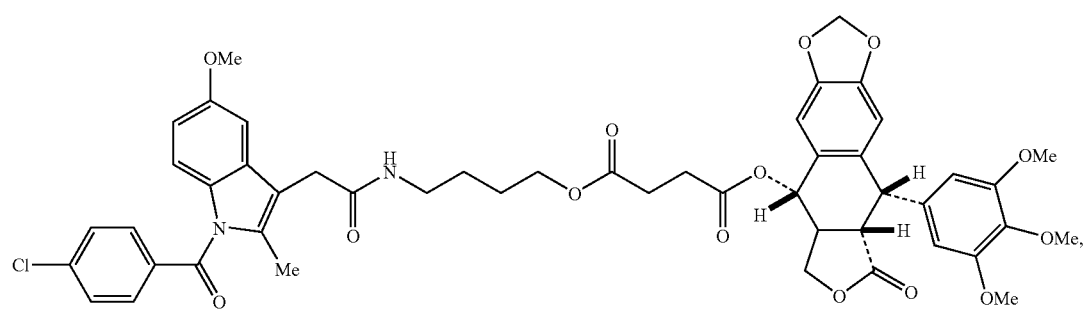
Compound 27q
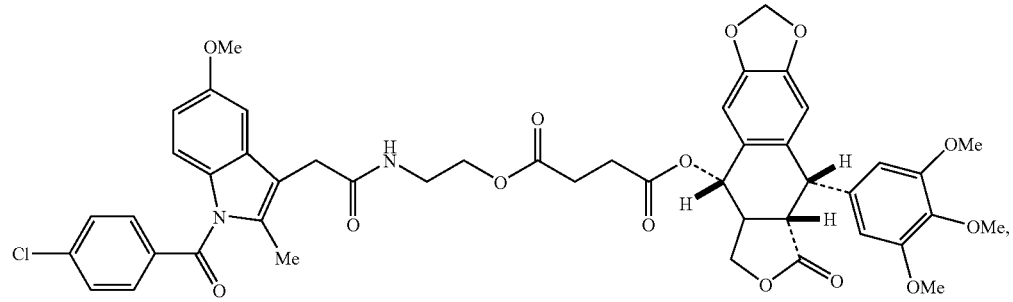

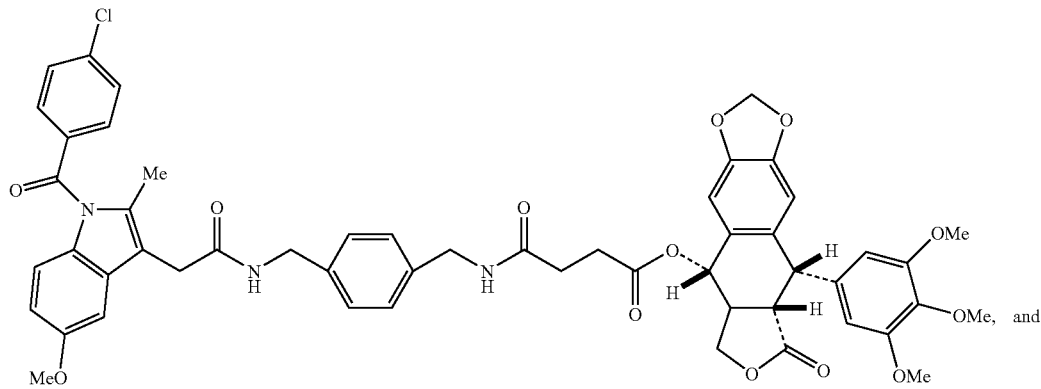

Compound 27r

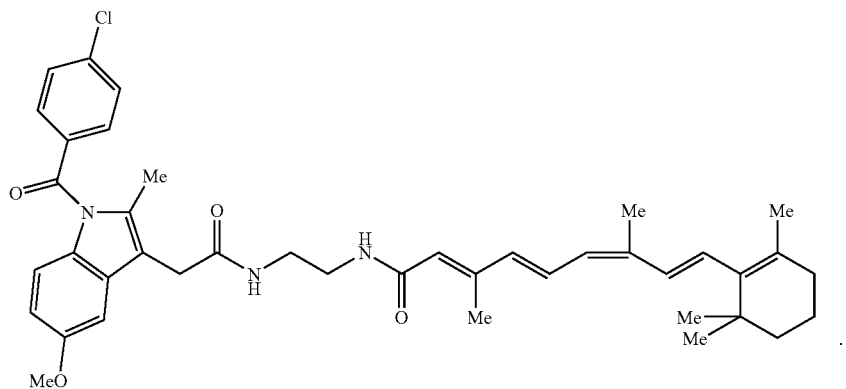

Compound 27s

In some embodiments of the presently disclosed treatment methods, the tether is selected from the group consisting of alkylamide tether, a PEG tether, an alkylpiperazine tether, and phenylene tether. In some embodiments, the alkylamide tether is selected from the group consisting of an alkyldiamide, an alkylamidosulfonamide, an alkylamidothiourea, and alkyldiamidosulfonamide, and an aminoalkyldiamide. In some embodiments, the PEG tether is selected from the group consisting of a PEG4amidoester, a PEG4diamide, and an alkyldiamidoPEG4sulfonamide. In some embodiments, the alkylpiperazine tether is selected from the group consisting of a diamidopiperazine, an alkyldiamidopiperazine, an alkylaminopiperazinylethyl acetamidoether, an alkylaminopiperazinylether ester, and a dialkyldiamidopiperazine.

In some embodiments of the presently disclosed treatment methods, the disorder associated with the COX-2 biological activity comprises a neoplasia or a pre-neoplastic state, and the therapeutic agent is administered to a target cell present in a tissue selected from the group consisting of an inflammatory lesion, a tumor, a pre-neoplastic lesion, a neoplastic cell, a pre-neoplastic cell, and a cancer cell. In some embodiments, the pre-neoplastic lesion is selected from the group consisting of a colon polyp and Barrett's esophagus. In some embodiments, the tumor is selected from the group consisting of a primary tumor, a metastasized tumor, and a carcinoma. In some embodiments, the tumor is selected from the group consisting of a colon adenocarcinoma, an esophageal tumor, a bladder tumor, a breast tumor, a pancreatic tumor, a lung tumor, a gastric tumor, a hepatic tumor, a head and/or neck tumor, a cervical tumor, an endometrial tumor, and a skin tumor. In some embodiments, the target cell overexpresses COX-2. In some embodiments, the presently disclosed treatment methods further comprise treating the subject with one or more additional anti-cancer therapies selected from the group consisting of surgical resection, chemotherapy, radiotherapy, immunotherapy, and combinations thereof.

The therapeutic and/or diagnostic methods and compositions disclosed herein can be employed in therapeutic and/or diagnostic of any subject. In some embodiments, the subject is a mammal. In some embodiments, the mammal is a human.

Accordingly, it is an object of the presently disclosed subject matter to provide methods and compositions for treating, diagnosing, and/or imaging COX-2-expressing cells including, but not limited to neoplastic cells and their normal and/or pre-neoplastic precursors. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter, Drawings, and non-limiting Examples.

DETAILED DESCRIPTION

Figure 1:
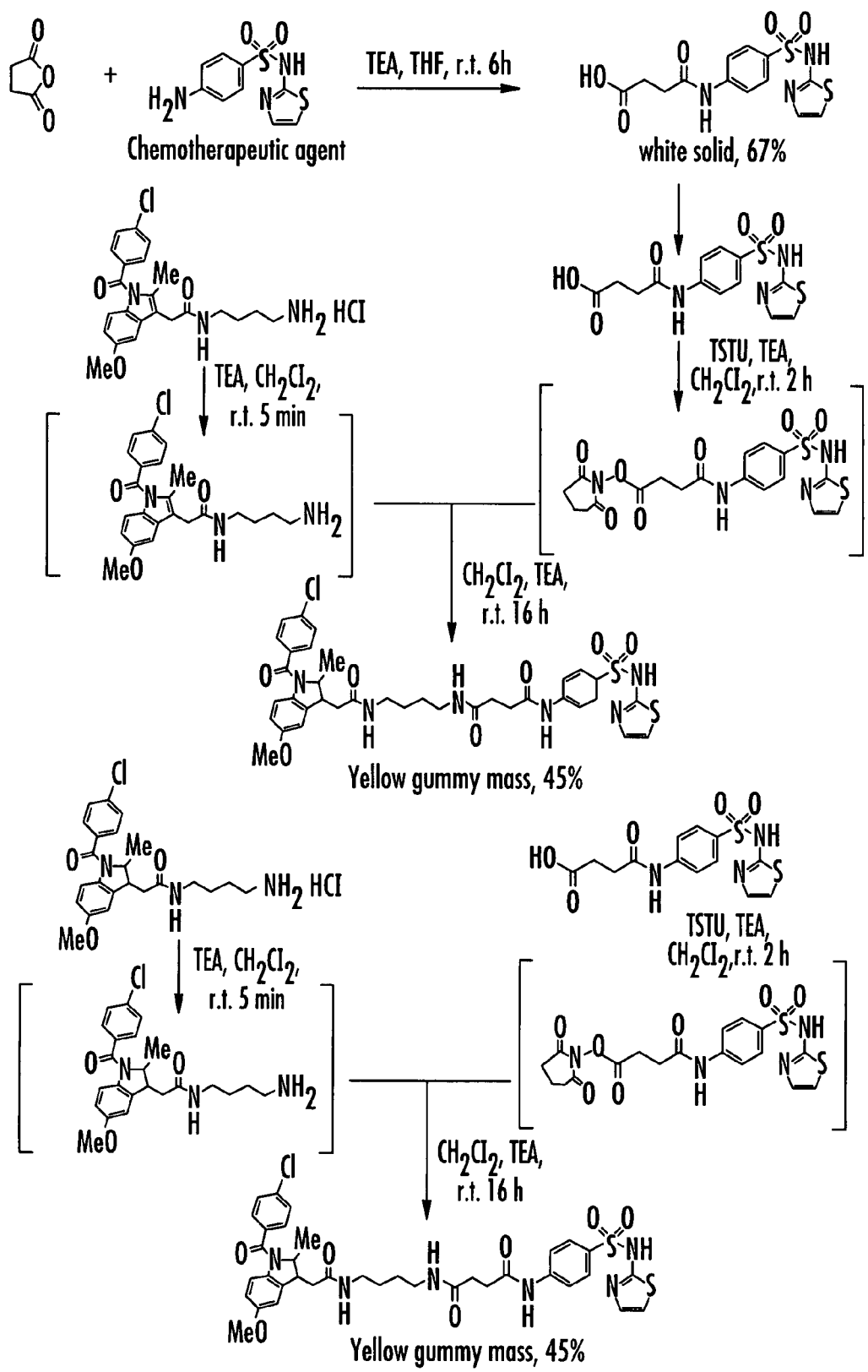
FIG. 1 depicts a synthesis scheme that can be used to produce Compound 27j, an exemplary fluorescent diagnostic agent of the presently disclosed subject matter that comprises a sulfathiazole moiety.
Figure 2:
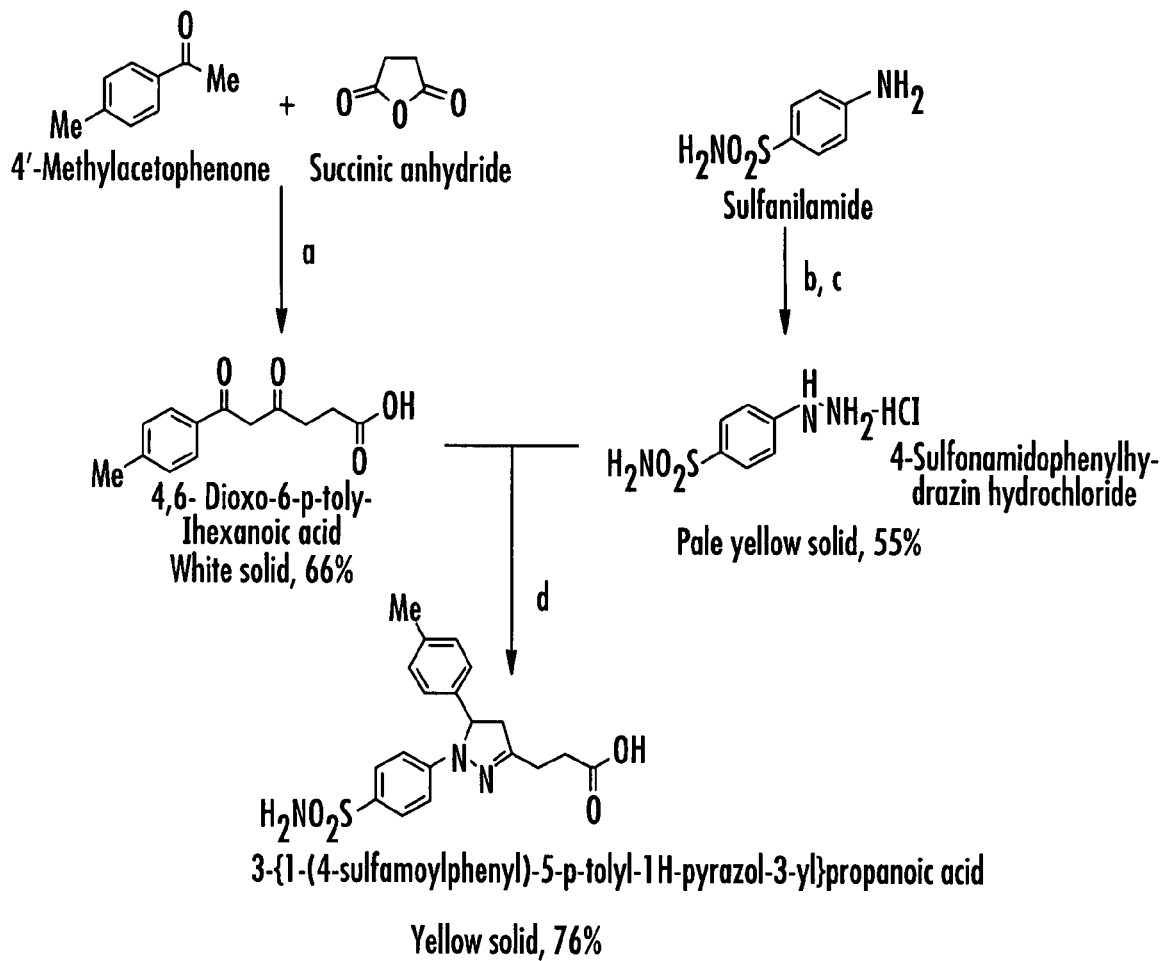
FIG. 2 depicts a synthesis scheme that can be used to produce Compound 30c an exemplary celecoxib analog. Reagents and Conditions: (a) Lithium diisopropylamine (LDA), Tetrahydrofuran (THF), −78° C., 1 hour; (b) Sodium nitrite ($NaNO_2$), Concentrated hydrochloric acid (con. HCl), 0 to 4° C., 30 minutes; (c) Tin(II) chloride ($SnCl_2$), Concentrated hydrochloric acid (con. HCl), 0° C., 4 hours; and (d) Triethylamine (TEA), methanol (MeOH), room temperature (r.t.), 16 hours.
Figure 3:
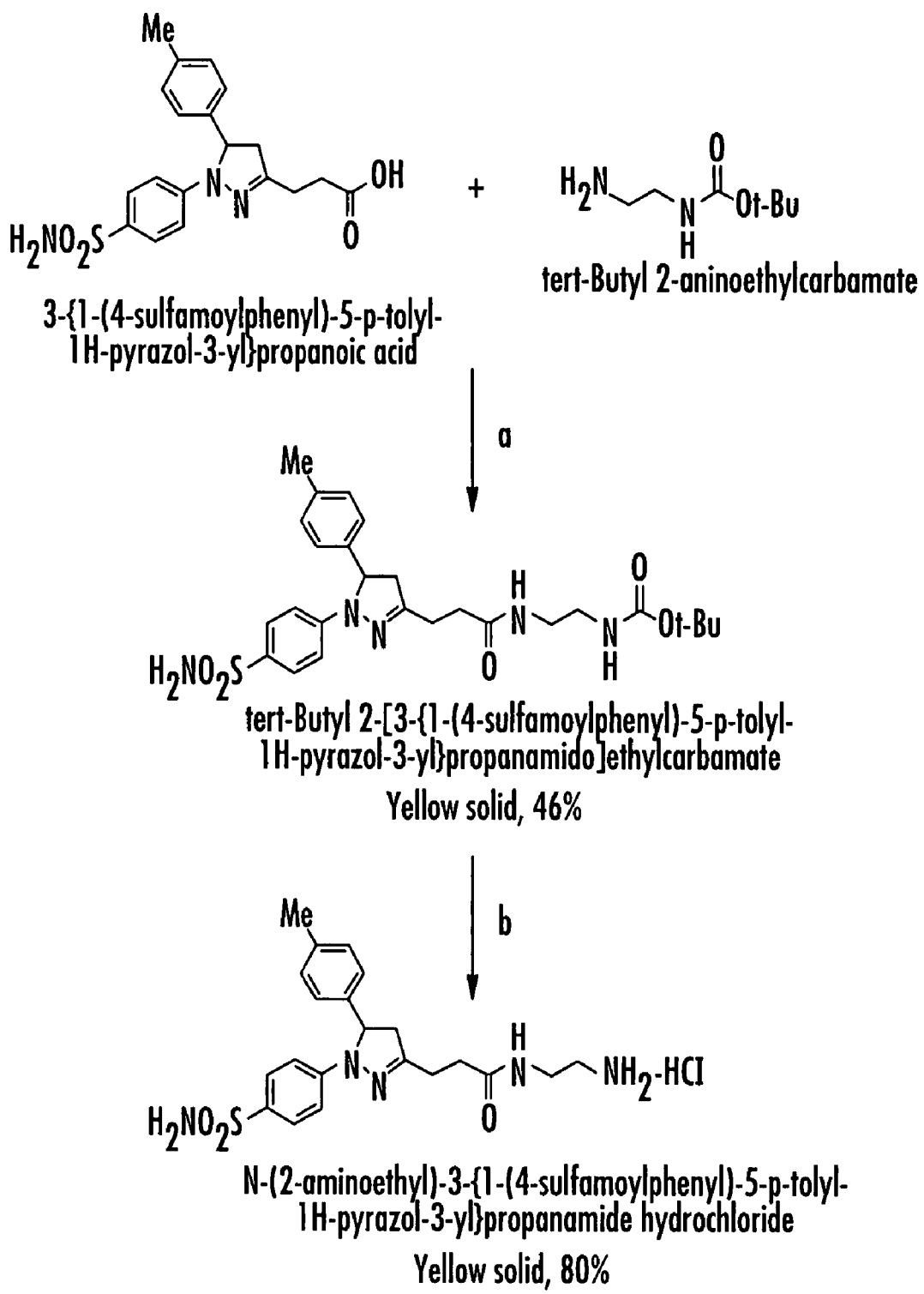
FIG. 3 depicts a synthesis scheme that can be used to produce Compound 30f, an exemplary celecoxib-sulforhodaminyl analog. Reagents and conditions: (a) 1-Ethyl-3-(3Õ-dimethylaminopropyl)carbodiimide hydrochloride (EDCl), 1-hydroxybenzotriazole (HOBt), N,N-diisopropylethylamine (DIPEA), dimethylformamide (DMF), r.t., 16 hours; (b) HCl (gas), dichloromethane, r.t., 2 hours; (c) N,N-diisopropylethylamine (DIPEA), dichloromethane, r.t., 5 minutes; (d) tert-Butyl 1-amino-3,6,9,12-tetraoxapentadecan-15-oate, triethylamine (TEA), dichloromethane, r.t., 16 hours; (e) Trifluoroacetic acid, r.t., 2 hours; (f) 1-ethyl-3-(3'-dimethylaminopropyl)carbodiimide hydrochloride (EDCl), 1-hydroxybenzotriazole (HOBt), N,N-diisopropylethylamine (DIPEA), dichloromethane, r.t, 16 hours.
Figure 3:
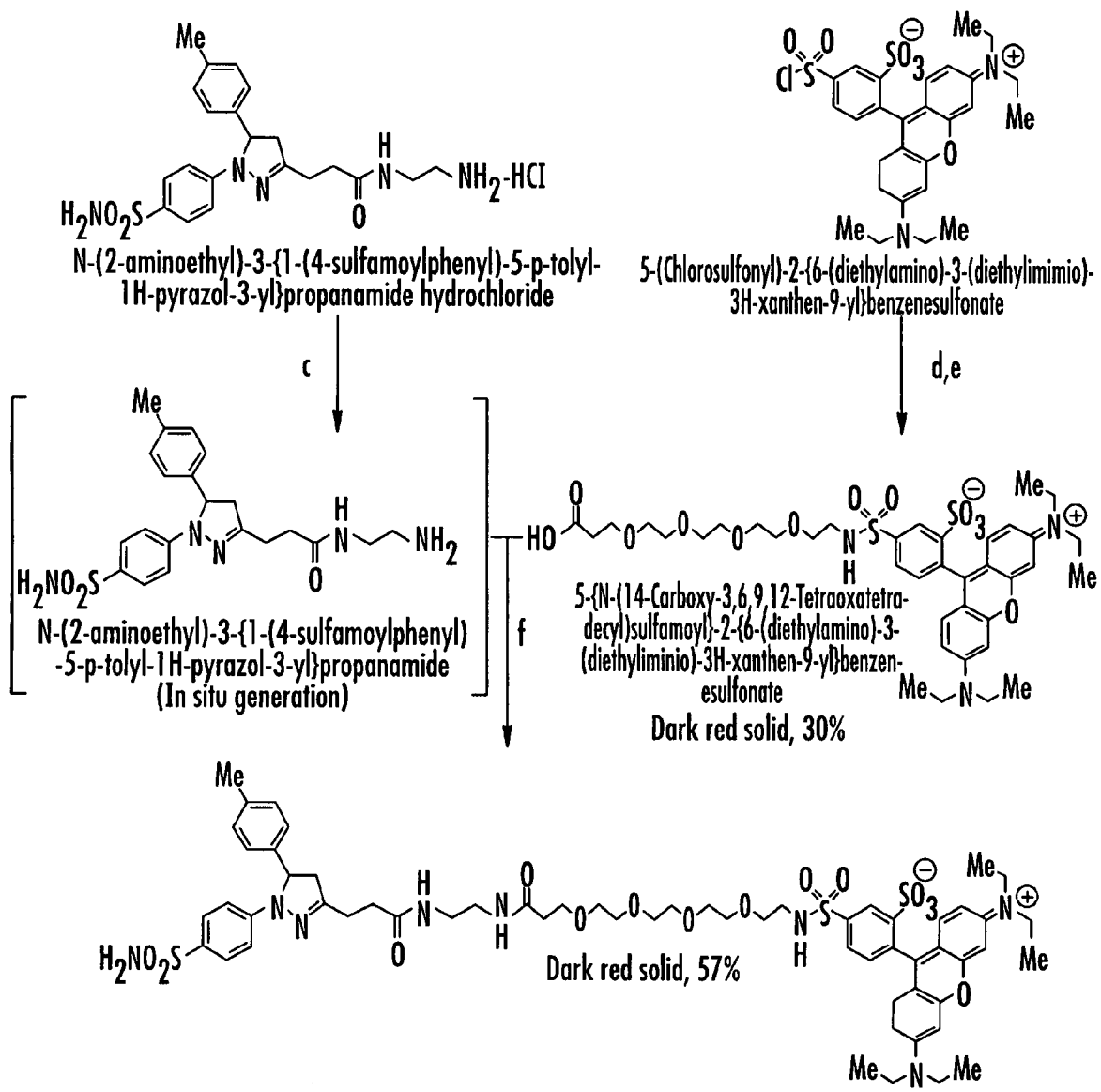

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Unless otherwise defined, all technical and scientific terms used herein have the same meaning as commonly understood by one of ordinary skill in the art to which the presently disclosed subject matter belongs.

All references listed herein, including patents, patent applications, and scientific literature, are incorporated herein by reference in their entireties to the extent that they supplement, explain, provide a background for, or teach methodology, techniques, and/or compositions employed herein.

Following long-standing patent law convention, the terms "a", "an", and "the" refer to "one or more" when used in this application, including the claims, unless the context clearly indicates otherwise. Thus, a reference to "a cell" can include multiple cells; "a tumor" can include multiple tumors, etc.

Throughout the specification and claims, a given chemical formula or name shall encompass all optical and stereoisomers as well as racemic mixtures where such isomers and mixtures exist.

I. General Considerations

As disclosed herein, malignant cells, pre-malignant cells, and other abnormal cells frequently express COX-2, whereas most normal tissues do not. This difference in COX-2 expression provides a biological rationale for developing various interventional methodologies, including, but not limited to the use of selective COX-2 inhibitors to specifically deliver therapeutics and/or diagnostic reagents to these cells.

The presently disclosed subject matter thus provides methods and compositions that can be employed to image neoplastic and pre-neoplastic cells that express COX-2. This provides several benefits, including diagnosing the presence of such cells, and also provides the medical professional with an ability to monitor the response of the cells to anti-tumor therapies such as radiotherapy, chemotherapy, immunotherapy, etc.

The presently disclosed subject matter also provides methods and compositions that can be employed to treat disorders associated with the presence in a subject of neoplastic and/or pre-neoplastic cells and tissues, and other abnormal cells and tissues. For example, the methods and compositions disclosed herein can be employed to enhance the delivery of drugs to COX-2-expressing cells versus normal cells that do not express COX-2. This can yield an improved therapeutic index and can allow higher doses of cytotoxic therapeutics to be administered to a subject.

And finally, given that COX-2 is also overexpressed in various inflammatory conditions, the methods and compositions disclosed herein can also be employed to diagnose and/or treat inflammatory disorders including, but not limited to pancreatitis and inflammatory bowel disease.

II. Therapeutic and/or Diagnostic Agents

The presently disclosed subject matter provides in some embodiments cyclooxygenase-2-selective therapeutic and/or diagnostic agents. In some embodiments, the presently disclosed subject matter provides multicomponent compositions comprising (i) a secondary amide or ester derivative of a carboxylic acid-containing NSAID; (ii) an active agent comprising a detectable moiety and/or a therapeutic moiety; and (iii) a tether that covalently links the first and second components.

II.A. Derivatives of Carboxylic Acid-Containing NSAIDs

In some embodiments, the presently disclosed subject matter provides a non-steroidal anti-inflammatory drug (NSAID), or a derivative thereof, that comprises a carboxylic acid moiety as a starting material. Many NSAIDs contain a carboxylic acid moiety, and as disclosed in Kalgutkar et al. (2000) *Proc Natl Acad Sci USA* 97, 925-930, the carboxylic acid moiety appears to be involved in differences in the selectivity of binding of these NSAIDs between COX-1 and COX-2. Exemplary NSAIDs that comprise a carboxylic acid moiety that can be derivatized include, but are not limited to fenamic acids, indoles, phenylalkanoic acids, phenylacetic acids, pharmaceutically acceptable salts thereof, and combinations thereof. More particularly, NSAIDs that can be derivatized include, but are not limited to 5,8,11,14-eicosatetraynoic acid (ETYA), 6-methoxy-α-methyl-2-naphthylacetic acid, aceclofenac, acelofenac, aceloferac, alcofenac, amfenac, aspirin, benoxaprofen, bromfenac, carprofen, cidanac, clidanac, diclofenac, diflunisal, efenamic acid, etodolac, etodolic acid, fenbufen, fenclofenac, fenclorac, fenoprofen, fleclozic acid, flufenamic acid, flurbiprofen, ibuprofen, idoprofen, indomethacin, indoprofen, isofezolac, ketoprofen, ketorolac, loxoprofen, meclofenamate, meclofenamic acid, mefenamic acid, meloxicam, naproxen, niflumic acid, o-(acetoxyphenyl)hept-2-ynyl sulfide (APHS), orpanoxin, pirprofen, pranoprofen, sulindac, suprofen, tolfenamic acid, tolmetin, zaltoprofen, zomepirac, pharmaceutically acceptable salts thereof, and combinations thereof.

Additionally, it is possible to modify certain NSAIDs that do not contain a carboxylic acid moiety so that they do contain a carboxylic acid moiety that can be modified as disclosed herein. For example, the coxibs are COX-2-selective NSAIDs that, with the exception of lumiracoxib, do not normally contain a carboxylic acid moiety. Exemplary coxibs include, but are not limited to celecoxib, valdecoxib, refecoxib, etoricoxib, parecoxib, and lumiracoxib.

As disclosed herein, various coxibs (e.g., celecoxib) can be modified to contain a carboxylic acid moiety. For example, the trifluoromethyl group of celecoxib can be modified to an alkylcarboxylic acid group to produce a celecoxib analog with the following structural formula:

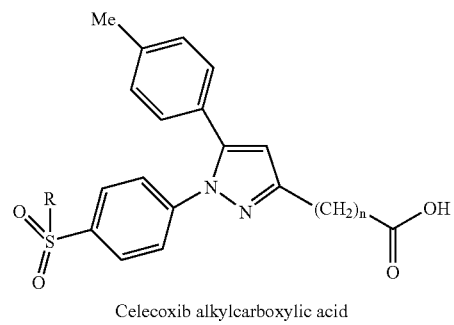

Celecoxib alkylcarboxylic acid wherein R is selected from the group consisting of $CH_3$ and $NH_2$ and n=1-4. Using standard synthetic techniques, the carboxylic acid group can thereafter be modified to an amide or an ester, if desired, to create a celecoxib alkylamide or alkylester. A therapeutic and/or diagnostic moiety can thereafter be complexed to the celecoxib analog using a tether to produce a therapeutic and/or diagnostic agent as disclosed herein. The therapeutic and/or diagnostic agent can have the following general structural formula:

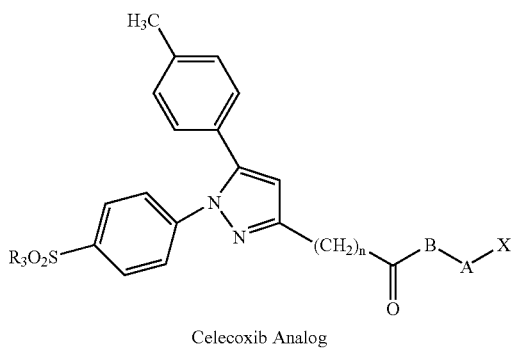

Celecoxib Analog wherein R and n are defined as above; $R_3$ is selected from the group consisting of $CH_3$ and $NH_2$; X comprises an active agent (i.e., a therapeutic moiety and/or a diagnostic moiety); A comprises a tether; and B is O or —NH.

In some embodiments, an NSAID is selected from the group including but not limited to indomethacin, an indolyl amine, and a celecoxib analog, wherein these compounds have the following general formulas:

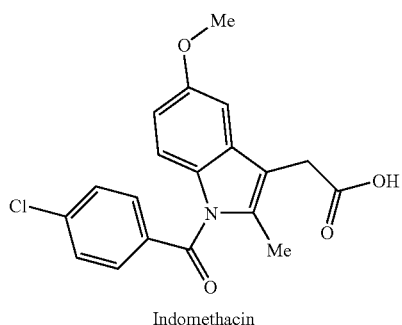

Indomethacin

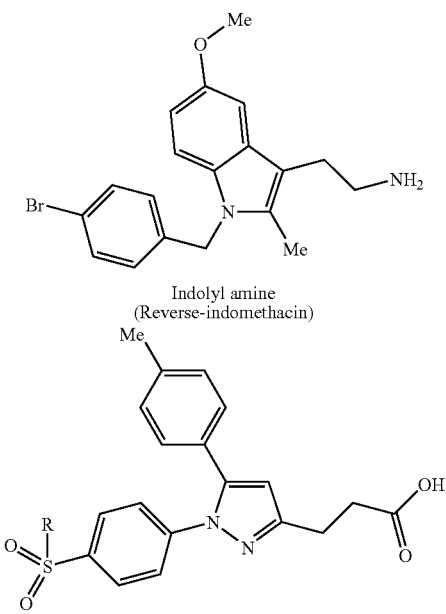

Indolyl amine
(Reverse-indomethacin)

Celecoxib Analogs,
wherein R is $CH_3$ or $NH_2$

These NSAIDs can be further derivatized, such that in some embodiments therapeutic and/or diagnostic agents of the presently disclosed subject matter comprise one of the following general structural formulas:

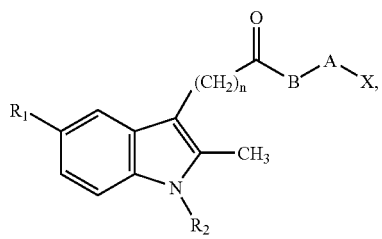

Formula I

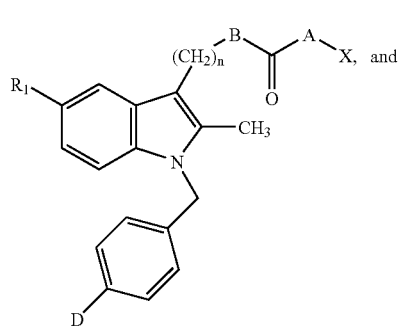

Formula II

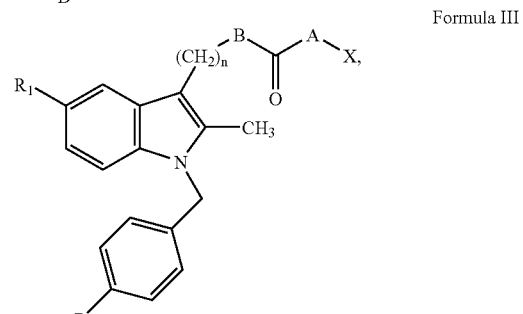

Formula III wherein:
- $R_1$=$C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions thereof, or $R_1$ is halo where halo is chloro, fluoro, bromo, or iodo;
- $R_2$=$C_1$ to $C_6$ alkyl, $C_4$ to $C_8$ aroyl, $C_4$ to $C_8$ aryl, $C_4$ to $C_8$ heterocyclic alkyl or aryl with O, N or S in the ring, $C_4$ to $C_8$ aryl-substituted $C_1$ to $C_6$ alkyl, alkyl-substituted or aryl-substituted $C_4$ to $C_8$ heterocyclic alkyl or aryl with O, N or S in the ring, alkyl-substituted $C_4$ to $C_8$ aroyl, or alkyl-substituted $C_4$ to $C_8$ aryl, or halo-substituted versions thereof;
- $R_3$=$C_1$ to $C_3$ alkyl or branched alkyl, $NH_2$, or a dipolar $N_3$ group;
- X comprises an active agent;
- A comprises a tether;
- B is O or —NH;
- D is halo, $C_1$ to $C_4$ alkyl, branched alkyl, or cycloalkyl; and
- n is 0-4.

Throughout the specification, drawings, and claims, some structural formulas are depicted without including certain methyl groups and/or hydrogens. In the structural formulas, solid lines represent bonds between two atoms, and unless otherwise indicated, between carbon atoms. Thus, bonds that have no atom specifically recited on one end and/or the other have a carbon atom at that and/or the other end. For example, a structural formula depicted as "—O—" represents C—O—C. Given that hydrogens are not explicitly placed in all structural formulas, implicit hydrogens are understood to exist in the structural formulas as necessary. Thus, a structural formula depicted as "—O" can represent $H_3C$—O, as appropriate given the valences of the particular atoms.

As used herein, the term "alkyl" means in some embodiments $C_{1-10}$ inclusive (i.e. carbon chains comprising 1, 2, 3, 4, 5, 6, 7, 8, 9, or 10 carbon atoms); in some embodiments $C_{1-6}$ inclusive (i.e. carbon chains comprising 1, 2, 3, 4, 5, or 6 carbon atoms); and in some embodiments $C_{1-4}$ inclusive (i.e. carbon chains comprising 1, 2, 3, or 4, carbon atoms) linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, ethenyl, propenyl, butenyl, pentenyl, hexenyl, butadienyl, propynyl, butynyl, pentynyl, hexynyl, and allenyl groups.

The alkyl group can be optionally substituted with one or more alkyl group substituents, which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo, and cycloalkyl. In this case, the alkyl can be referred to as a "substituted alkyl". Representative substituted alkyls include, for example, benzyl, trifluoromethyl, and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. Thus, the term "alkyl" can also include esters and amides. "Branched" refers to an alkyl group in which an alkyl group, such as methyl, ethyl, or propyl, is attached to a linear alkyl chain.

The term "aryl" is used herein to refer to an aromatic substituent, which can be a single aromatic ring or multiple aromatic rings that are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine, and benzophenone among others. In particular embodiments, the term "aryl" means a cyclic aromatic comprising about 5 to about 10 carbon atoms, including 5 and 6-membered hydrocarbon and heterocyclic aromatic rings.

An aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl. In this case, the aryl can be referred to as a "substituted aryl". Also, the term "aryl" can also included esters and amides related to the underlying aryl group.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the $—OZ^1$ radical, where $Z^1$ is selected from the group consisting of alkyl, substituted alkyl, cycloalkyl, substituted cycloalkyl, heterocycloalkyl, substituted heterocycloalkyl, silyl groups, and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy, and the like.

The term "amino" is used herein to refer to the group $—NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group can be represented as $N^+ Z^1 Z^2 Z^3$, with the previous definitions applying and $Z^3$ being either H or alkyl.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Aroyl" means an aryl-CO— group wherein aryl is as previously described. Exemplary aroyl groups include benzoyl and 1- and 2-naphthoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Aralkyl" refers to an aryl-alkyl- group wherein aryl and alkyl are as previously described. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl as previously described.

"Dialkylcarbamoyl" refers to a R'RN—CO— group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described herein wherein a carbon or oxygen atom is replaced by a sulfur atom.

The term "sulfate" refers to the —$SO_4$ group.

In some embodiments, the therapeutic and/or diagnostic agents disclosed herein include a component comprising a derivative of a non-steroidal anti-inflammatory drug (NSAID). As used herein, the term "derivative" refers to a structural variant of a compound in which one or more atoms have been changed to yield a new compound containing one or more functional groups that differ from the parent compound. This change can occur by any suitable process, but typically occurs by reacting the NSAID with an intermediate, wherein a group is transferred from the intermediate to the NSAID to create a derivative.

NSAIDs that can be derivatized can intrinsically be COX-2 selective ligands. Alternatively, non-COX-2-selective NSAIDS can be converted into COX-2-selective ligands for use in the methods described herein. Methods for converting non-COX-2-selective NSAIDS into COX-2-selective ligands include the methods generally set forth in Kalgutkar et al. (1998) Science 280, 1268-1270; Kalgutkar et al. (1998) J Med Chem 41, 4800-4818; Kalgutkar et al. (2000) Proc Natl Acad Sci USA 97, 925-930; Kalgutkar et al. (2000) J Med Chem 43, 2860-2870; and U.S. Pat. Nos. 5,475,021; 5,973,191; 6,207,700; 6,284,918; 6,306,890; 6,399,647; and 6,762,182. Each of these references is incorporated by reference herein in its entirety. These methods include, but are not limited to, methods for modifying NSAIDs to make them COX-2-selective, and methods for converting NSAIDs into their respective neutral amide or ester derivatives to make them COX-2 selective. These methods are useful in making NSAID derivatives that covalently bind COX-2, as well as in making NSAID derivatives that non-covalently bind COX-2.

To elaborate, novel approaches have recently been developed that allow the facile conversion of non-selective NSAIDs into highly selective COX-2-binding ligands (Kalgutkar et al. (1998) Science 280, 1268-1270; Kalgutkar et al. (2000) Proc Natl Acad Sci USA 97, 925-930). This is accomplished by conversion of the carboxylic acid functional group, common to most NSAIDs, to a derivative. Utilizing one strategy, it was discovered that several carboxylic acid-containing NSAIDs can be transformed into highly selective COX-2 ligands by converting them into neutral amide or ester derivatives (Kalgutkar et al. (2000) J Med Chem 43, 2860-2870). This strategy has proven effective in the case of the NSAIDs 5,8,11,14-eicosatetraynoic acid (ETYA), meclofenamic acid, ketorolac, and indomethacin. In the cases of ETYA, ketorolac, and meclofenamic acid, their amide derivatives exhibit selective COX-2 inhibitory activity. Several of the most potent inhibitors are haloalkyl or haloaryl amide derivatives, including the p-fluorobenzylamide of ketorolac ($IC_{50}$-COX-2=80 nM; $IC_{50}$-COX-1>65 μM) and the p-fluorophenylamide of indomethacin ($IC_{50}$-COX-2=52 nM; $IC_{50}$-COX-1>66 μM).

A major effort in the development of COX-2-selective ligands as derivatives of NSAIDs has focused on indomethacin as a parent compound. Indomethacin, which is approximately 15-fold more potent a ligand of COX-1 than COX-2, can be converted in a single step to amide or ester derivatives that exhibit COX-2 selectivities of greater than 1300-fold relative to COX-1 (see Kalgutkar et al. (2000) J Med Chem 43, 2860-2870). Both amides and esters of indomethacin are active, and a large number of alkyl and aromatic substituents exhibit potent and selective COX-2 inhibition.

Thus, a derivative of an NSAID comprises in some embodiments an ester moiety or a secondary amide moiety. In some embodiments, a carboxylic acid group of the NSAID as been derivatized to an ester or a secondary amide. In some embodiments, the secondary amide derivative is selected from the group consisting of indomethacin-N-methyl amide, indomethacin-N-ethan-2-ol amide, indomethacin-N-octyl amide, indomethacin-N-nonyl amide, indomethacin-N-(2-methylbenzyl)amide, indomethacin-N-(4-methylbenzyl) amide, indomethacin-N-[(R)-α,4-dimethylbenzyl]amide, indomethacin-N—((S)-α,4-dimethylbenzyl)amide, indomethacin-N-(2-phenethyl)amide, indomethacin-N-(4-fluorophenyl)amide, indomethacin-N-(4-chlorophenyl) amide, indomethacin-N-(4-acetamidophenyl)amide, indomethacin-N-(4-methylmercapto)phenyl amide, indomethacin-N-(3-methylmercaptophenyl)amide, indomethacin-N-(4-methoxyphenyl)amide, indomethacin-N-(3-ethoxyphenyl)amide, indomethacin-N-(3,4,5-trimethoxyphenyl)amide, indomethacin-N-(3-pyridyl)amide, indomethacin-N-5-[(2-chloro)pyridyl]amide, indomethacin-N-5-[(1-ethyl)pyrazolo]amide, indomethacin-N-(3-chloropropyl)amide, indomethacin-N-methoxycarbonylmethyl amide, indomethacin-N-2-(2-L-methoxycarbonylethyl) amide, indomethacin-N-2-(2-D-methoxycarbonylethyl) amide, indomethacin-N-(4-methoxycarbonylbenzyl)amide, indomethacin-N-(4-methoxycarbonylmethylphenyl)amide, indomethacin-N-(2-pyrazinyl)amide, indomethacin-N-2-(4-methylthiazolyl)amide, indomethacin-N-(4-biphenyl)amide, and combinations thereof.

II.B. Tethers

The NSAID moiety and the active agent (e.g., the diagnostic and/or therapeutic agent) can be attached to each other via a tether. As used herein, the term "tether" refers to any molecule that can be employed for linking a diagnostic and/or therapeutic agent to an NSAID moiety. Any tether can be employed, provided that the combination of the tether and the diagnostic and/or therapeutic agent does not destroy the ability of the composition to selectively bind to COX-2. An exemplary tether comprises $C_4$ to $C_{10}$ alkyl, cycloalkyl, or functionalized alkyl.

In some embodiments, the tether is selected from the group consisting of an alkylamide tether, a polyethylene glycol (PEG) tether, an alkylpiperazone tether, and a 4-(amidomethyl)anilide tether. As used herein, the phrase "alkylamide tether" refers to a tether comprising an amide moiety to which the NSAID moiety is attached. Representative alkylamide tethers include, but are not limited to, the following:

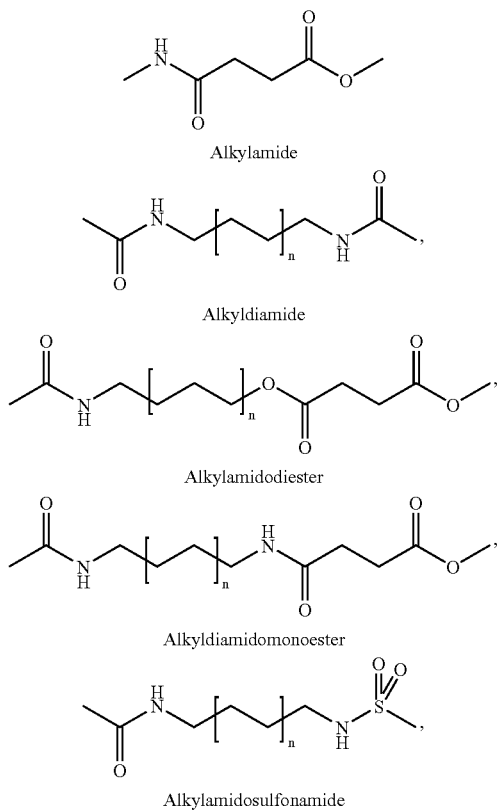

-continued

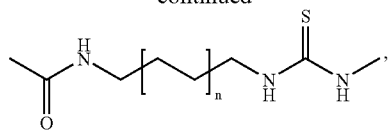

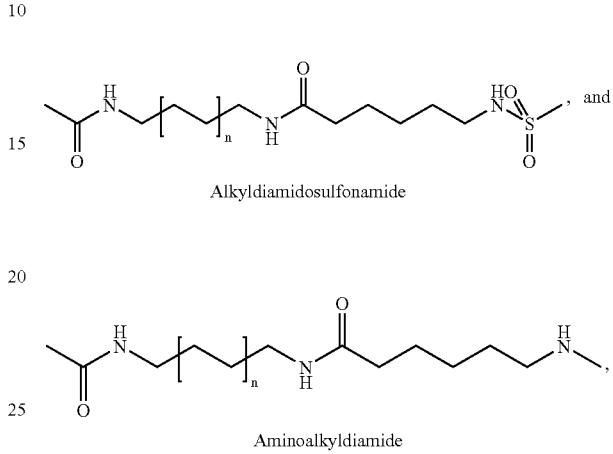

wherein an NSAID moiety or derivative thereof is linked to one end of the tether, an active agent (e.g., a therapeutic and/or diagnostic moiety) is linked to the other of the tether, and m=0-3.

As used herein, the phrase "PEG tether" refers to a tether comprising an amide moiety to which the NSAID moiety is attached to the carbonyl carbon and a polyethylene glycol (PEG) moiety is attached to the amide nitrogen. Representative PEG tethers include, but are not limited to, the following:

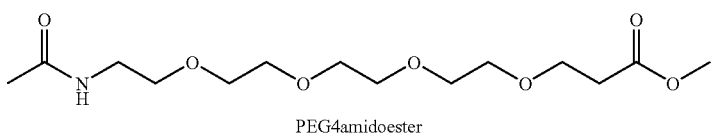

PEG4amidoester

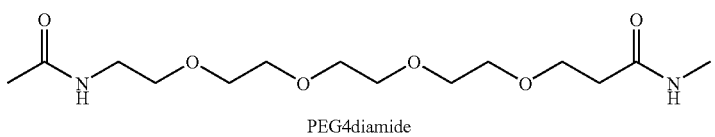

PEG4diamide

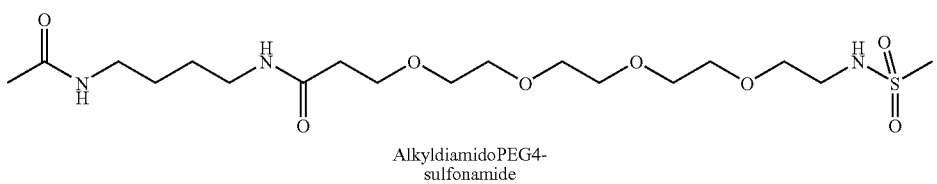

AlkyldiamidoPEG4-sulfonamide wherein an NSAID moiety or derivative thereof is linked to one end of the tether and an active agent (e.g., a therapeutic and/or diagnostic moiety) is linked to the other of the tether As used herein, the phrase "alkylpiperazine tether" refers to a tether comprising a piperazine group. Representative alkylpiperazine tethers include, but are not limited to, the following:

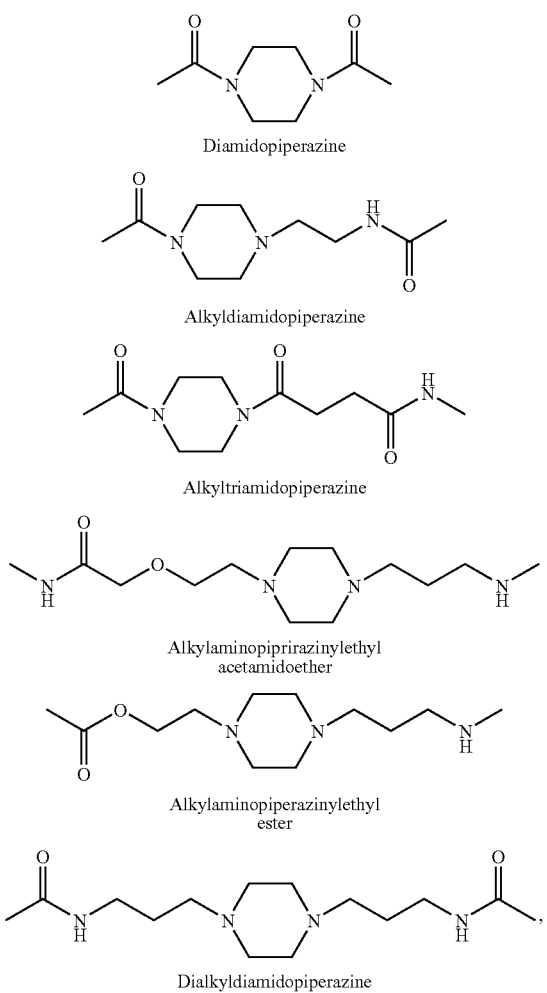

wherein an NSAID moiety or derivative thereof is linked to one end of the tether and an active agent (e.g., a therapeutic and/or diagnostic moiety) is linked to the other of the tether.

In some embodiments, the phrase "phenylene tether" refers to a tether with a phenylene group. Representative phenylene tethers include, but are not limited to, the following:

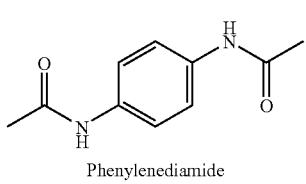

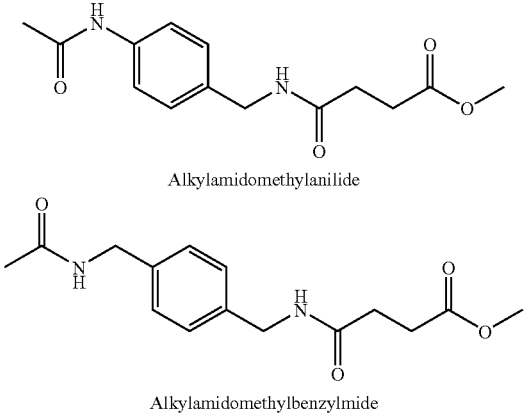

wherein an NSAID moiety or derivative thereof is linked to one end of the tether and an active agent (e.g., a therapeutic and/or diagnostic moiety) is linked to the other of the tether.

Figure 16:
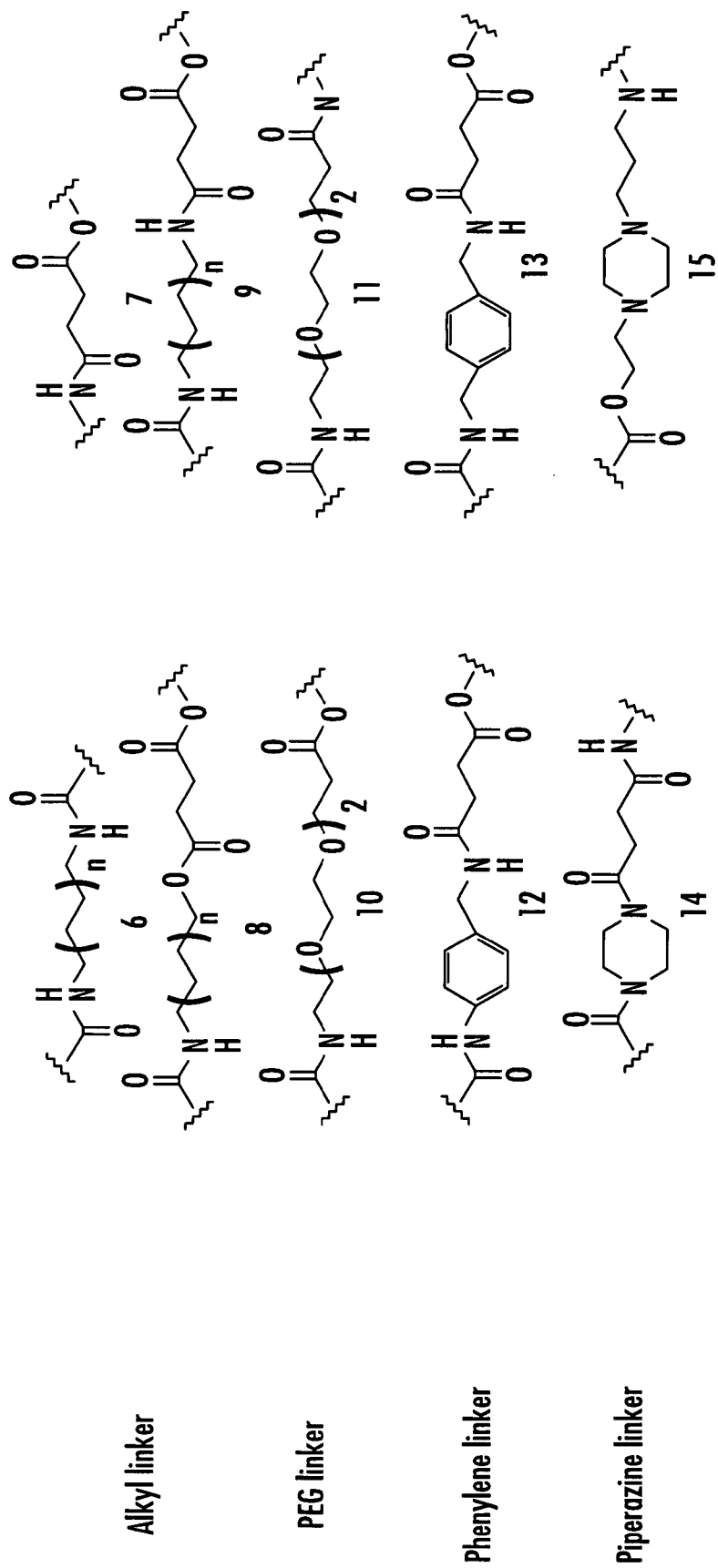
FIG. 16 depicts the structures of representative tethers that can be employed to generate the compositions of the presently disclosed subject matter.

Representative tethers include those depicted in FIG. 16.

II.C. Active Agents

The therapeutic and/or diagnostic agents of the presently disclosed subject matter comprise an active agent comprising a therapeutic moiety and/or a diagnostic moiety. As used herein, the phrase "active agent" thus refers to a component of the presently disclosed therapeutic and/or diagnostic agents that provides a therapeutic benefit to a subject and/or permits the medical professional to visualize a cell or tissue in which the therapeutic and/or diagnostic agents of the presently disclosed subject matter accumulate.

II.C.1. Therapeutic Moieties

Figure 17:
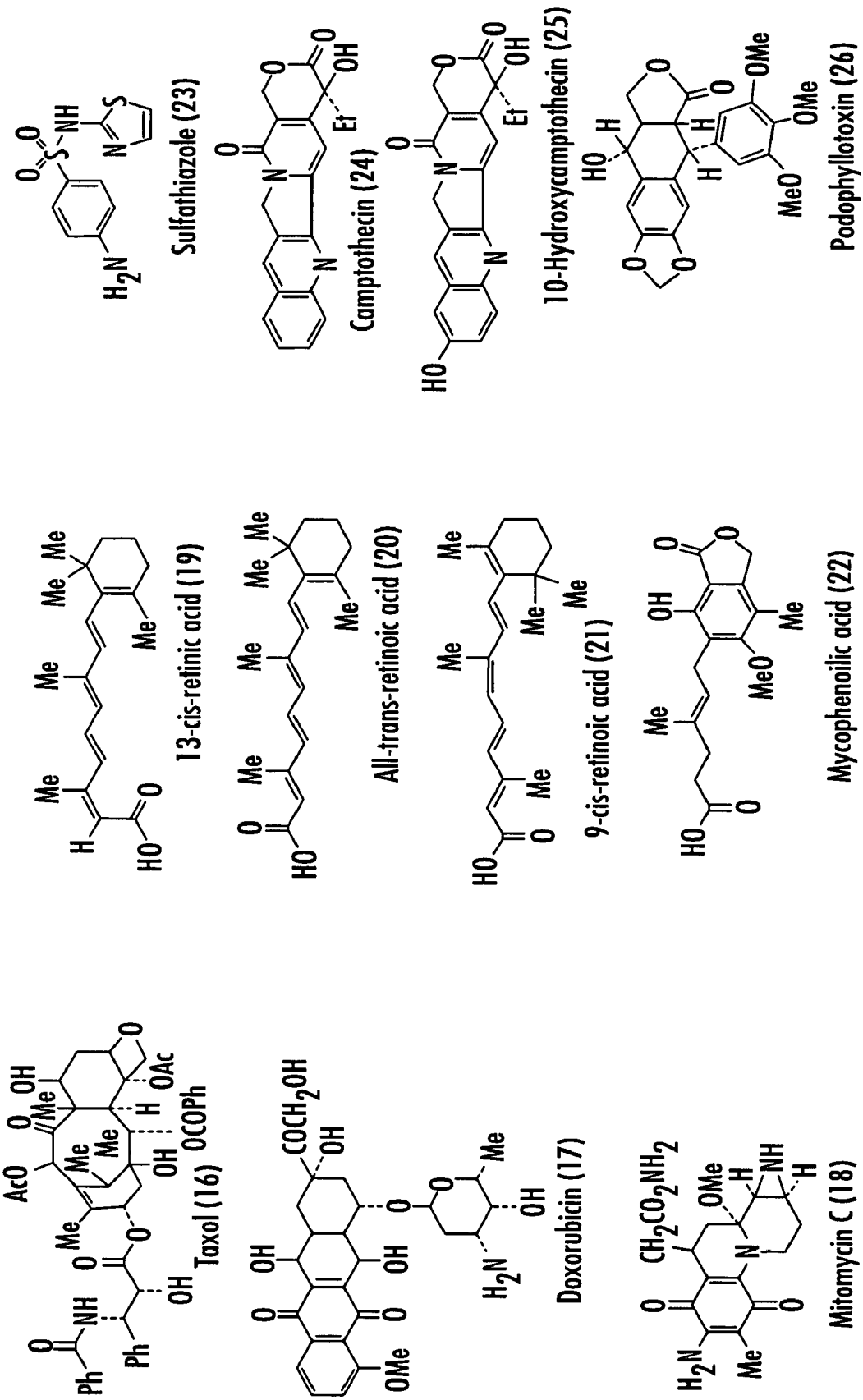
FIG. 17 depicts the structures of representative active agents of the presently disclosed subject matter that can be tethered to secondary amide or ester derivatives of carboxylic acid-containing non-steroidal anti-inflammatory drugs (NSAIDs) to generate the compositions of the presently disclosed subject matter.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, and sulfadiethoxane. Representative therapeutic and/or diagnostic agents of the presently disclosed subject matter that comprise these chemotherapeutics include, but are not limited to the Indo-Taxol analog Compound 27a; Indo-Retinoic Acid analogs Compounds 27g, 27h, and 27s; and the Indo-Sulfathiazole analogs Compounds 27j and 27k. See also FIG. 17 for additional representative therapeutic agents.

II.C.2. Detectable Moieties

In some embodiments, an active agent comprises a detectable moiety. In some embodiments, a detectable moiety comprises a fluorophore. Any fluorophore can be employed with the tethers and COX-2-selective moieties of the presently disclosed subject matter, provided that the combination of COX-2-selective moiety, tether, and fluorophore retains COX-2 selectivity and is detectable after administration to a subject. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the Alexa Fluor dye series includes at least 19 different dyes that are characterized by different emission spectra. These dyes include Alexa Fluors 350, 405, 430, 488, 500, 514, 532, 546, 555, 568, 594, 610, 633, 635, 647, 660, 680, 700, and 750 (available from Invitrogen Corp., Carlsbad, Calif., United States of America), and the choice of which dye to employ can be made by the skilled artisan after consideration of the instant specification based on criteria including, but not limited to the chemical compositions of the specific Alexa Fluors, the tether to be employed, and the chemical structure of the derivative of the NSAID, whether multiple detectable moieties are to be employed and the emission spectra of each, etc.

Non-limiting examples of diagnostic agents that employ these detectable moieties include the Dansyl analogs Compounds 27x, 27y, and 27z; the Dabsyl analog Compound 27aa; the Coumarin analogs Compounds 27cc, 27ee, 27ff, and 27gg; the Cinnamyl analog Compound 27hh; the Indo-NBD analog Compound 27ii; the Fluoresceinyl analogs Compounds 27ll, 27mm, and 27nn; the Nile Blue analog Compound 27uu; the Carboxyrhodaminyl (ROX) analogs Compounds 27vv, 27aaa, 27eee, 27ggg, and 27hhh; and the Sulforhodaminyl analogs Compounds 27iii, 27jjj, 27kkk. Representative fluorescent celecoxib derivatives include, but are not limited to the Sulforhodaminyl analog Compound 30f.

In some embodiments, a detectable moiety comprises a cyanine dye. Non-limiting examples of cyanine dyes that can be tethered to COX-2-selective moieties of the presently disclosed subject matter include the succinimide esters Cy5, Cy5.5, and Cy7, supplied by Amersham Biosciences (Piscataway, N.J., United States of America). Representative Cyanine dye analogs include, but are not limited to the analog referred to herein as Compound 27ooo.

In some embodiments, a detectable moiety comprises a near infrared (NIR) dye. Non-limiting examples of near infrared dyes that can be tethered to COX-2-selective moieties of the presently disclosed subject matter include NIR641, NIR664, NIT7000, and NIT782. Non-limiting examples of diagnostic agents that employ these detectable moieties include the analogs referred to herein as Compounds 27ppp, 27qqq, and 27ttt.

II.D. COX-2-Selective Compositions

The therapeutic and/or diagnostic agents disclosed herein are COX-2-selective. As used herein, the phrase "COX-2-selective" refers to a molecule that exhibits selective binding to a COX-2 polypeptide. As used herein, "selective binding" means a preferential binding of one molecule for another in a mixture of molecules. Typically, the binding of a ligand to a target molecule can be considered selective if the binding affinity is about $1 \times 10^2$ $M^{-1}$ to about $1 \times 10^6$ $M^{-1}$ or greater. In some embodiments, COX-2-selective therapeutic and/or diagnostic agent binds covalently to a COX-2 polypeptide. In some embodiments, a COX-2-selective therapeutic and/or diagnostic agent binds non-covalently to a COX-2 polypeptide Those skilled in the art will appreciate that an evaluation of the selectivity and efficacy of binding of the NSAID derivative to the COX-2 enzyme, e.g., after the derivative is synthesized, can be desirable. Methods of screening selective COX-2 inhibitors for activity can be carried out in vitro and/or in intact cells, and are known in the art. See e.g., Kalgutkar et al. (1998) *Science* 280, 1268-1270; Kalgutkar et al. (1998) *J Med Chem* 41, 4800-4818; Kalgutkar et al. (2000) *Proc Natl Acad Sci USA* 97, 925-930; Kalgutkar et al. (2000) *J Med Chem* 43, 2860-2870; and Kalgutkar et al. (2002) *Med Chem Lett* 12, 521-524. One example of an in vitro screening method takes advantage of the fact that both human and murine recombinant COX-2 can be expressed and isolated in pure form from an Sf9 cell expression system. Briefly, typical assays involve the incubation of COX-1 or COX-2 in a reaction mixture containing 100 mM Tris-HCl, pH 8.0, 500 µM phenol and $^{14}$C-arachidonic acid for 30 seconds at 37° C. COX-1, which is not readily obtained in pure form from similar expression systems, can be purified from ovine seminal vesicles by standard procedures. Alternatively, membrane preparations from outdated human platelets can provide a source of human COX-1. The NSAID derivative(s) that is being screened for activity is added as a stock solution in dimethyl sulfoxide (DMSO) either concomitantly with the addition of arachidonic acid (to test for competitive inhibition) or for various periods of time prior to the addition of arachidonic acid (to test for time-dependent inhibition). The reaction is stopped by the addition of of ethanol/methanol/1 M citrate, pH 4.0 (30:4:1). The extracted products are separated by thin layer chromatography (TLC), which allows quantitation of total product formation as well as assessment of product distribution. This assay is useful to define $IC_{50}$ values for inhibition of either enzyme, and to determine time-dependency of inhibition. It also provides information concerning changes in products formed as a result of inhibition. A representative assay is set forth in EXAMPLE 3.

While the TLC assay described above provides considerable information, it is labor-intensive for screening large numbers of candidate NSAID derivatives. Accordingly, as an alternative, a simplified assay can be used. Incubation conditions can be essentially as described above, except all candidate derivatives are first screened at a concentration of 10 µM with a preincubation time of 30 minutes. The substrate need not be radiolabeled, and the reaction can be stopped by the addition of 2 μL of formic acid. Product formation can be quantitated by enzyme-linked immunosorbent assay (ELISA) using commercially available kits. Compounds found to demonstrate potency and selectivity against COX-2 can optionally be further evaluated by the TLC assay. Other in vitro assay methods for screening NSAID derivatives for activity (e.g., selectivity for the COX-2 enzyme) can also be used by the skilled artisan.

As will be appreciated by the skilled artisan, activity in purified enzyme preparations as described above does not guarantee that an NSAID derivative will be effective in intact cells. Thus, NSAID derivatives that are identified as potentially useful in the methods described herein can be further tested using, for example, the RAW264.7 murine macrophage cell line. These cells are readily available (for example, from the American Type Culture Collection (ATCC), Manassas, Va., United States of America) and are easily cultured in large numbers. They normally express low levels of COX-1 and very low to undetectable levels of COX-2. Upon exposure to bacterial lipopolysaccharide (LPS), however, COX-2 levels increase dramatically over the ensuing 24 hour period, and the cells produce $PGD_2$ and $PGE_2$ from endogenous arachidonic acid stores (generally, ~1 nmol/$10^7$ cells total PG formation). After LPS exposure, the addition of exogenous arachidonic acid results in the formation of additional $PGD_2$ and $PGE_2$ as a result of metabolism by the newly synthesized COX-2.

This system provides a number of approaches for testing the inhibitory potency of COX-2-selective ligands (e.g., inhibitors). In general, following LPS activation, cells can be treated for 30 minutes with the desired concentrations of candidate derivative(s) in DMSO. $^{14}$C-arachidonic acid can be added, and the cells can be incubated for 15 minutes at 37° C. Product formation can be assessed following extraction and TLC separation of the culture medium. Alternatively, the effects of candidate derivatives on PG synthesis from endogenous arachidonic acid can be assessed by incubating cells with desired concentrations of candidate derivatives 30 minutes prior to LPS exposure. Following a 24-hour incubation, medium can be collected and extracted, and the amount of $PGD_2$ and/or $PGE_2$ can be assayed by gas chromatography-mass spectrometry, liquid chromatography-mass spectrometry, or ELISA. The latter method can prove to be particularly useful, since NSAID derivatives are often found to be more potent when assayed for activity using endogenous arachidonic acid as opposed to exogenously supplied substrate.

The RAW264.7 assay is but one example of a cell-based assay for screening the activity of NSAID derivatives; upon a review of the present disclosure the skilled artisan will appreciate that assays using alternative cell lines and methodologies can be used.

III. Methods for Synthesizing COX-2-Selective Therapeutic and/or Diagnostic Agents The presently disclosed subject matter also provides methods for synthesizing a therapeutic and/or diagnostic agent. In some embodiments, the methods comprise (a) providing a non-steroidal anti-inflammatory drug (NSAID), or a derivative thereof, comprising a carboxylic acid moiety; (b) derivatizing the carboxylic acid moiety to a secondary amide or ester; and (c) complexing an active agent to the secondary amide or ester, wherein (i) the active agent comprises a therapeutic moiety, a diagnostic moiety, or both a therapeutic moiety and a diagnostic moiety; (ii) the active agent is complexed to the derivative of the NSAID via a tether; and (iii) the therapeutic and/or diagnostic agent selectively binds to cyclooxygenase-2 (COX-2).

Any synthesis scheme can be employed for complexing a secondary amide or ester derivative of an NSAID to a therapeutic moiety, a diagnostic moiety, or both a therapeutic moiety and a diagnostic moiety, and one of ordinary skill in the art will understand what synthesis schemes can be employed based on the selection of specific NSAID derivatives, specific therapeutic and/or diagnostic moieties, and if desired, specific tethers.

Figure 4:
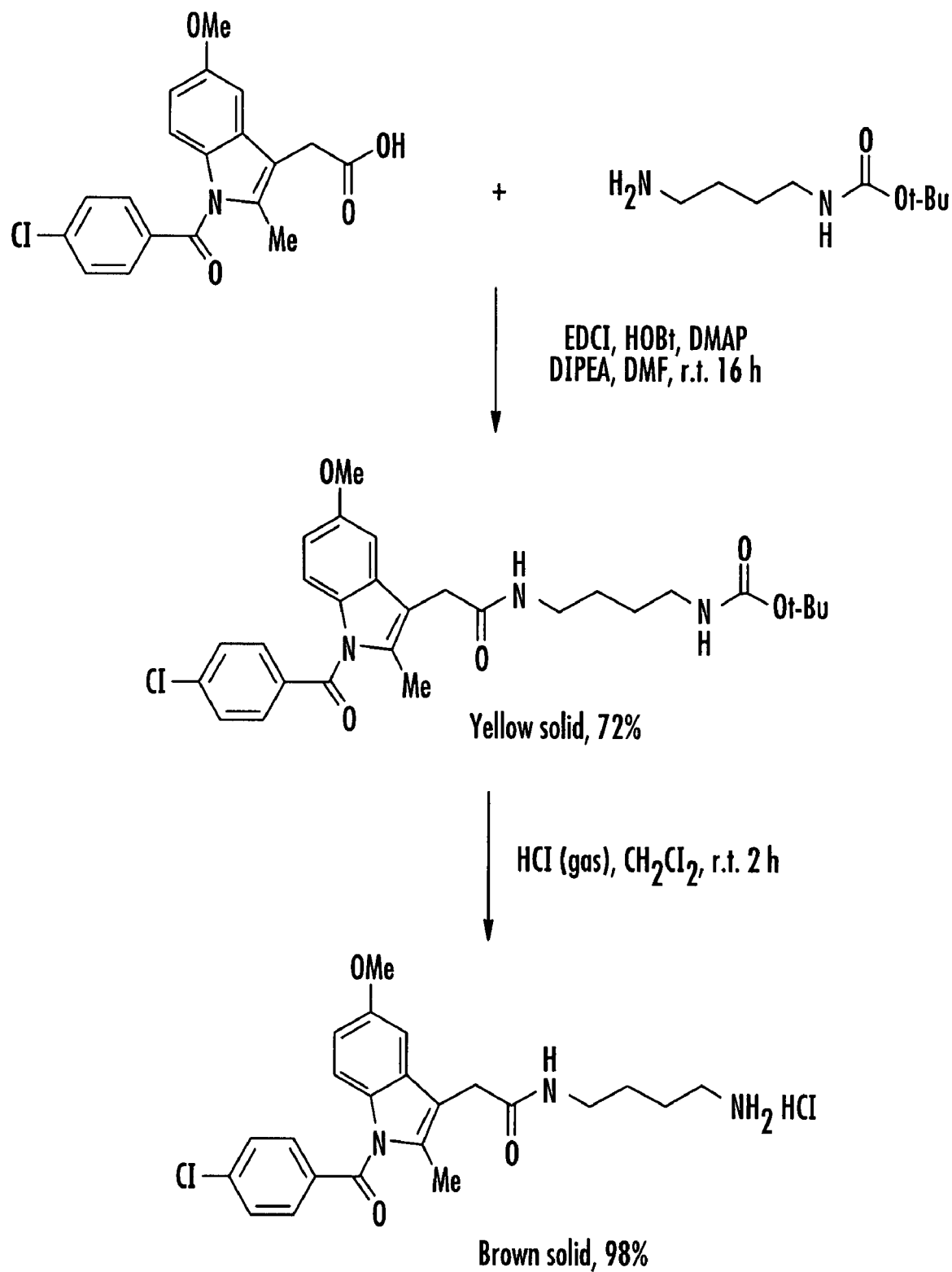
FIG. 4 depicts a synthesis scheme that can be used to produce Compound 27z, an exemplary fluorescent diagnostic agent of the presently disclosed subject matter that comprises a dansyl moiety.
Figure 4:
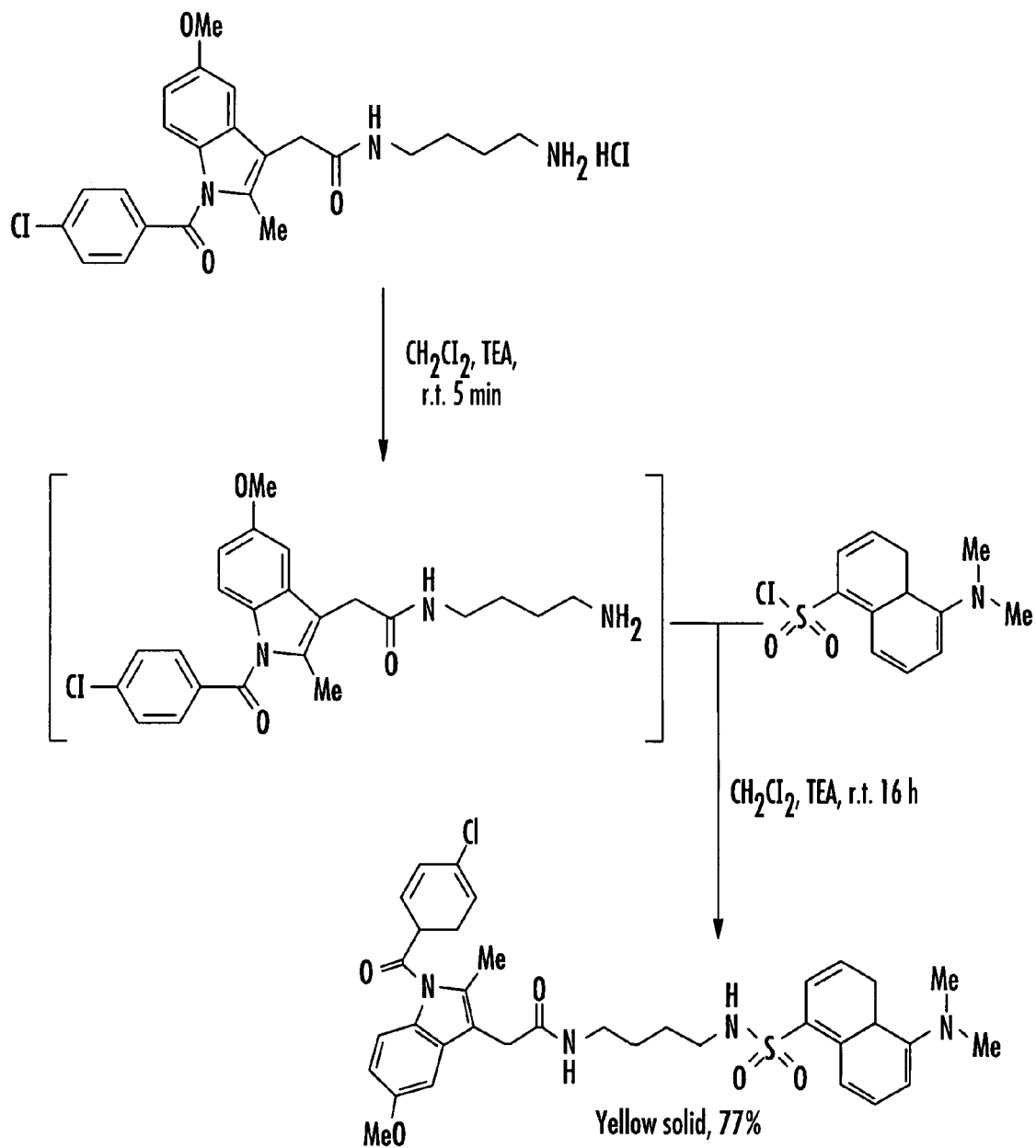
Figure 5:
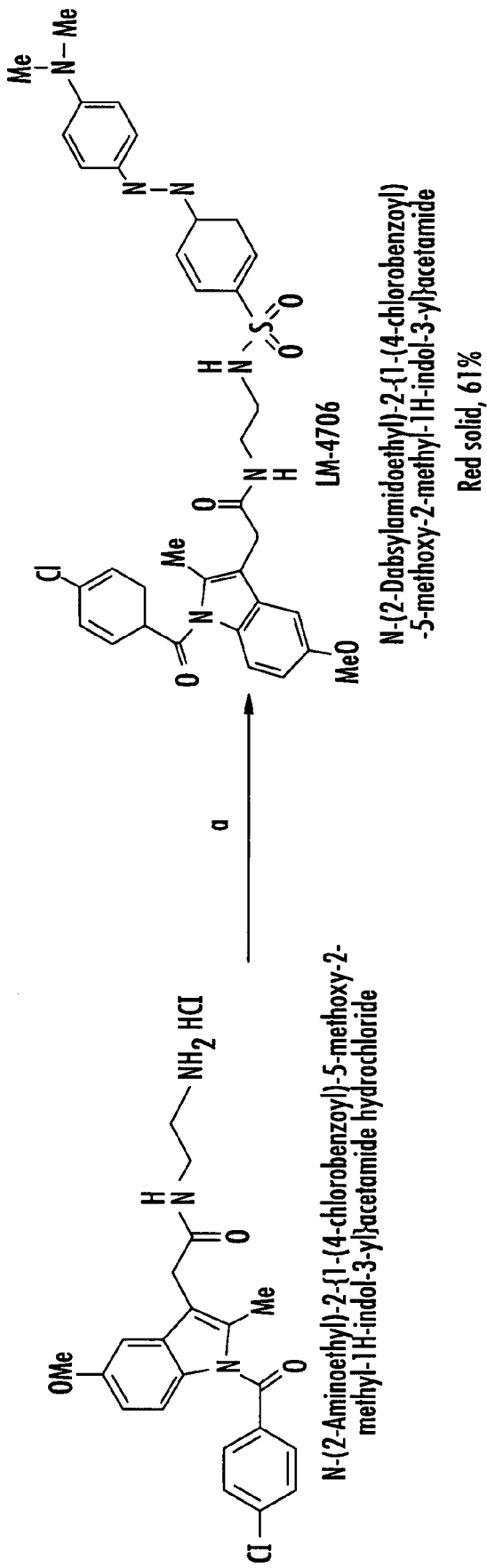
FIG. 5 depicts a synthesis scheme that can be used to produce Compound 27aa, an exemplary fluorescent diagnostic agent of the presently disclosed subject matter that comprises a dabsyl moiety. Reagents and conditions: (a) Dabsyl chloride, triethylamine (TEA), dichloromethane, r.t., 16 hours.
Figure 6:
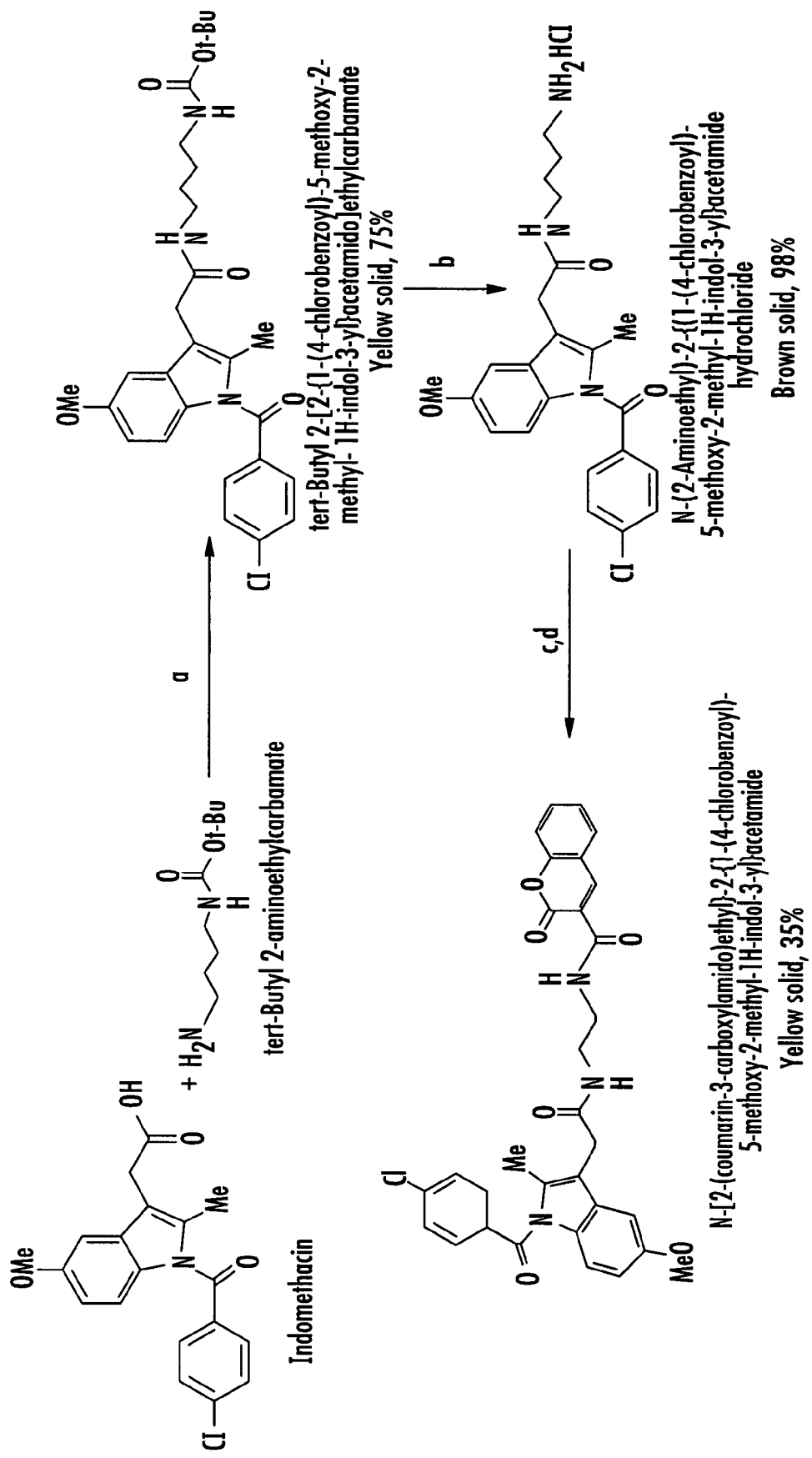
FIG. 6 depicts a synthesis scheme that can be used to produce Compound 27cc, an exemplary fluorescent diagnostic agent of the presently disclosed subject matter that comprises a coumarinyl moiety. Reagents and conditions: (a) 1-Ethyl-3-(3'-dimethylaminopropyl)carbodiimide hydrochloride (EDCl), 1-hydroxybenzotriazole (HOBt), N,N-diisopropylethylamine (DIPEA), dimethylformamide (DMF), r.t, 16 hours; (b) HCl (gas), dichloromethane, r.t., 2 hours; (c) N,N-diisopropylethylamine (DIPEA), dichloromethane, r.t., 5 minutes; (d) Coumarin-3-carboxylic acid, 1-Ethyl-3-(3'-dimethylaminopropyl)carbodiimide hydrochloride (EDCl), 1-hydroxybenzotriazole (HOBt), N,Ndiisopropylethylamine (DIPEA), dichloromethane, r.t, 16 hours.
Figure 7:
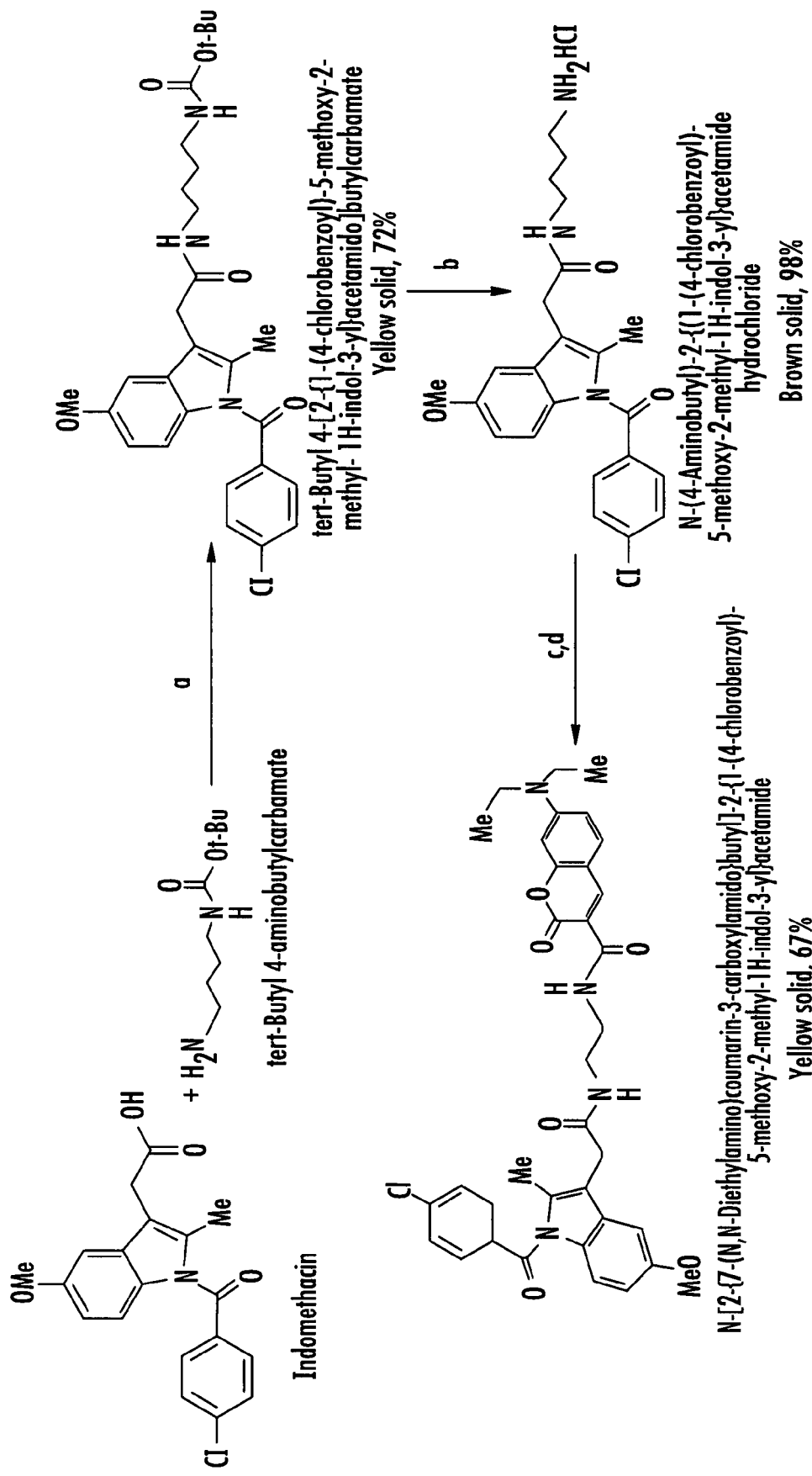
FIG. 7 depicts a synthesis scheme that can be used to produce Compound 27ff, an exemplary fluorescent diagnostic agent of the presently disclosed subject matter that comprises a coumarinyl moiety. Reagents and conditions: (a) 1-Ethyl-3-(3'-dimethylaminopropyl)carbodiimide hydrochloride (EDCl), 1-hydroxybenzotriazole (HOBt), N,N-diisopropylethylamine (DIPEA), dimethylformamide (DMF), r.t, 16 hours; (b) HCl (gas), dichloromethane, r.t., 2 hours; (c) Triethylamine (TEA), dimethyl sulfoxide (DMSO), r.t., 5 minutes; (d) 7-(N,N-Diethylamino)coumarin-3-carboxylic acid succinimidyl ester, triethylamine (TEA), dimethyl sulfoxide (DMSO), r.t, 16 hours.
Figure 8:
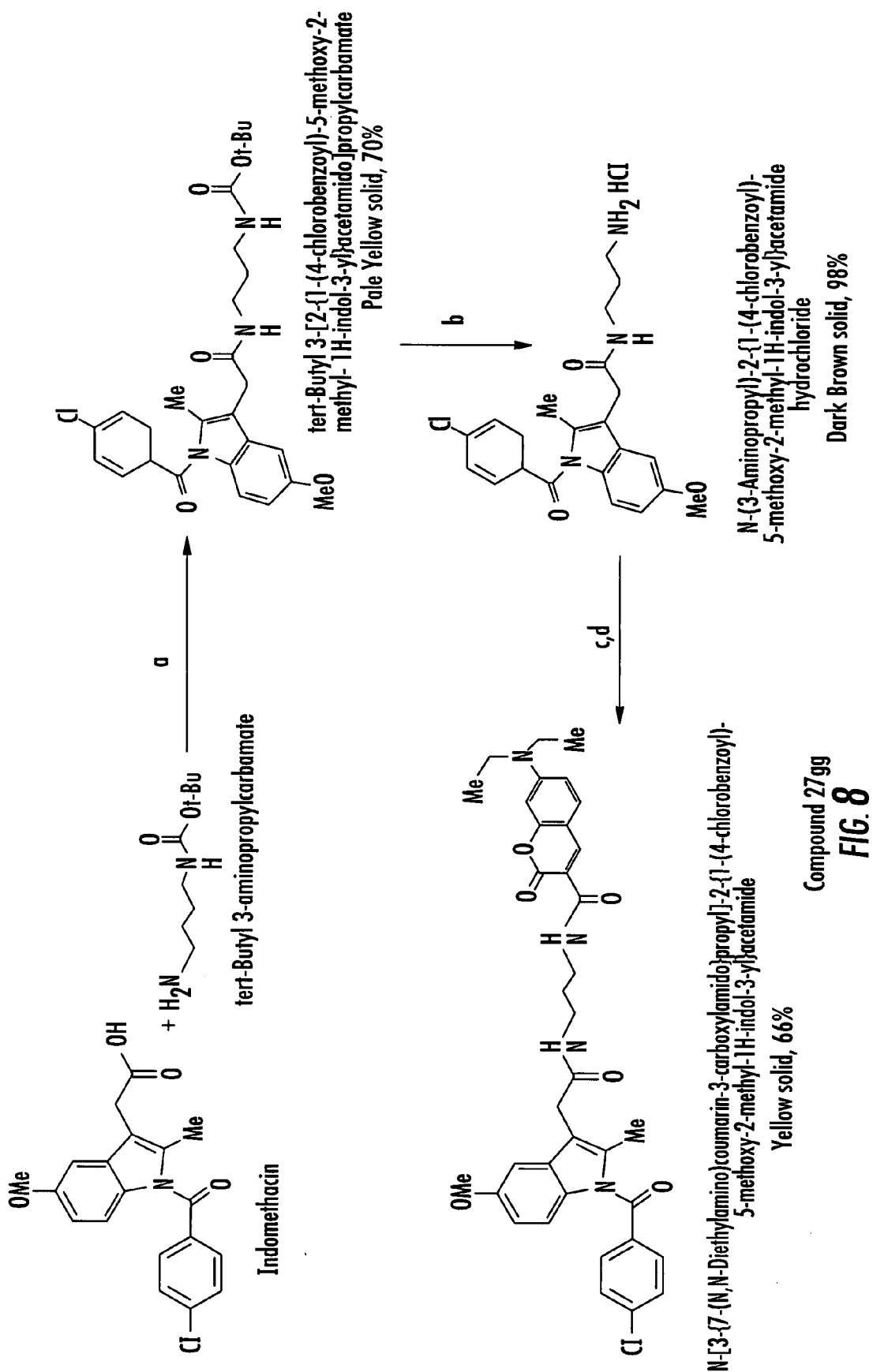
FIG. 8 depicts a synthesis scheme that can be used to produce Compound 27gg, an exemplary fluorescent diagnostic agent of the presently disclosed subject matter that comprises a coumarinyl moiety. Reagents and conditions: (a) 1-Ethyl-3-(3'-dimethylaminopropyl)carbodiimide hydrochloride (EDCl), 1-hydroxybenzotriazole (HOBt), N,N-diisopropylethylamine (DIPEA), dimethylformamide (DMF), r.t, 16 hours; (b) HCl (gas), dichloromethane, r.t., 2 hours; (c) Triethylamine (TEA), dimethyl sulfoxide (DMSO), r.t., 5 minutes; (d) 7-(N,N-Diethylamino)coumarin-3-carboxylic acid succinimidyl ester, triethylamine (TEA), dimethyl sulfoxide (DMSO), r.t, 16 hours.
Figure 9:
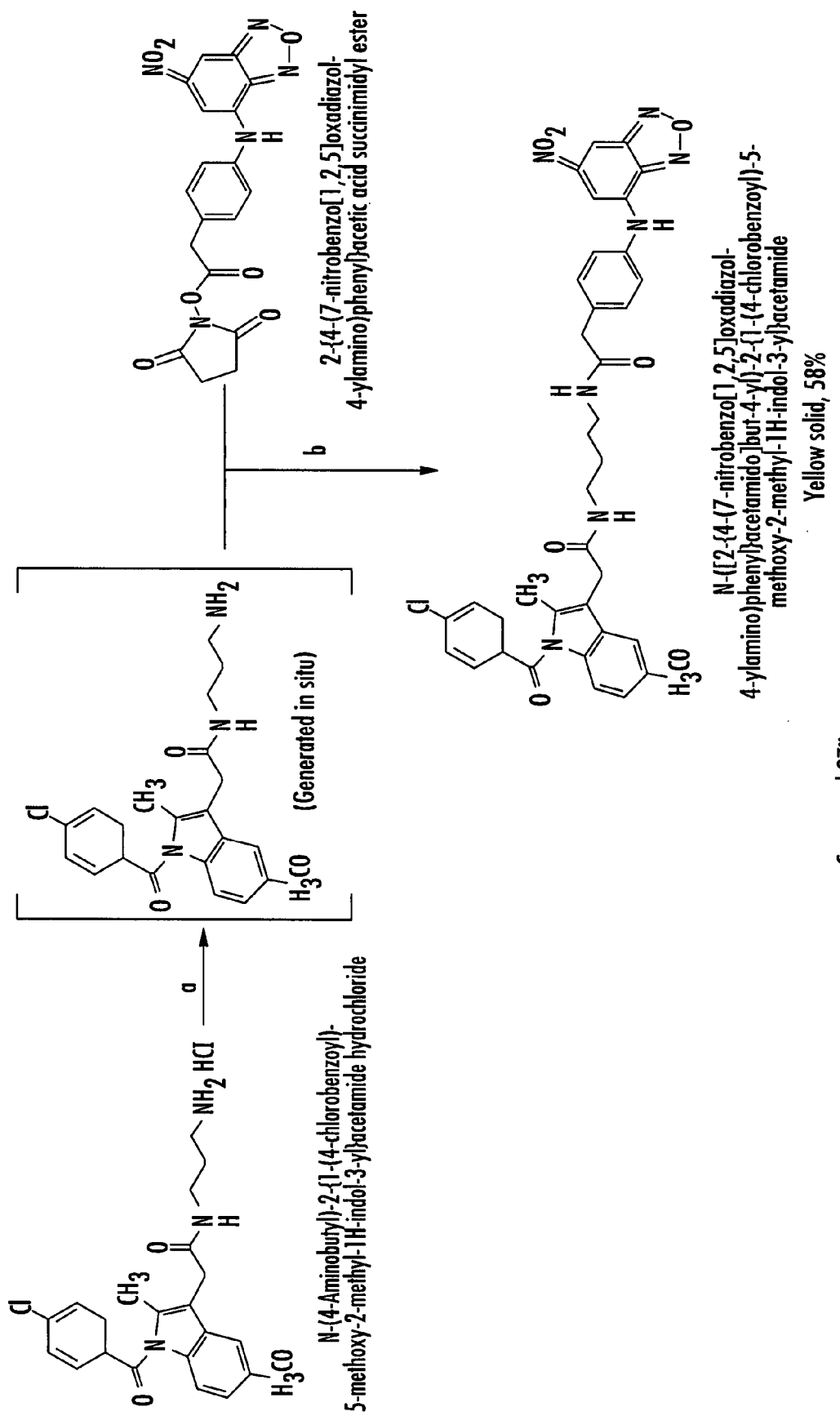
FIG. 9 depicts a synthesis scheme that can be used to produce Compound 27ii, an exemplary fluorescent diagnostic agent of the presently disclosed subject matter that comprises an nitrobenzodiazolamine (NBD) moiety. Reagents and conditions: (a) Triethylamine (TEA), dimethyl sulfoxide (DMSO), r.t., 5 minutes; (b) Triethylamine (TEA), dimethyl sulfoxide (DMSO), r.t, 16 hours.
Figure 10:
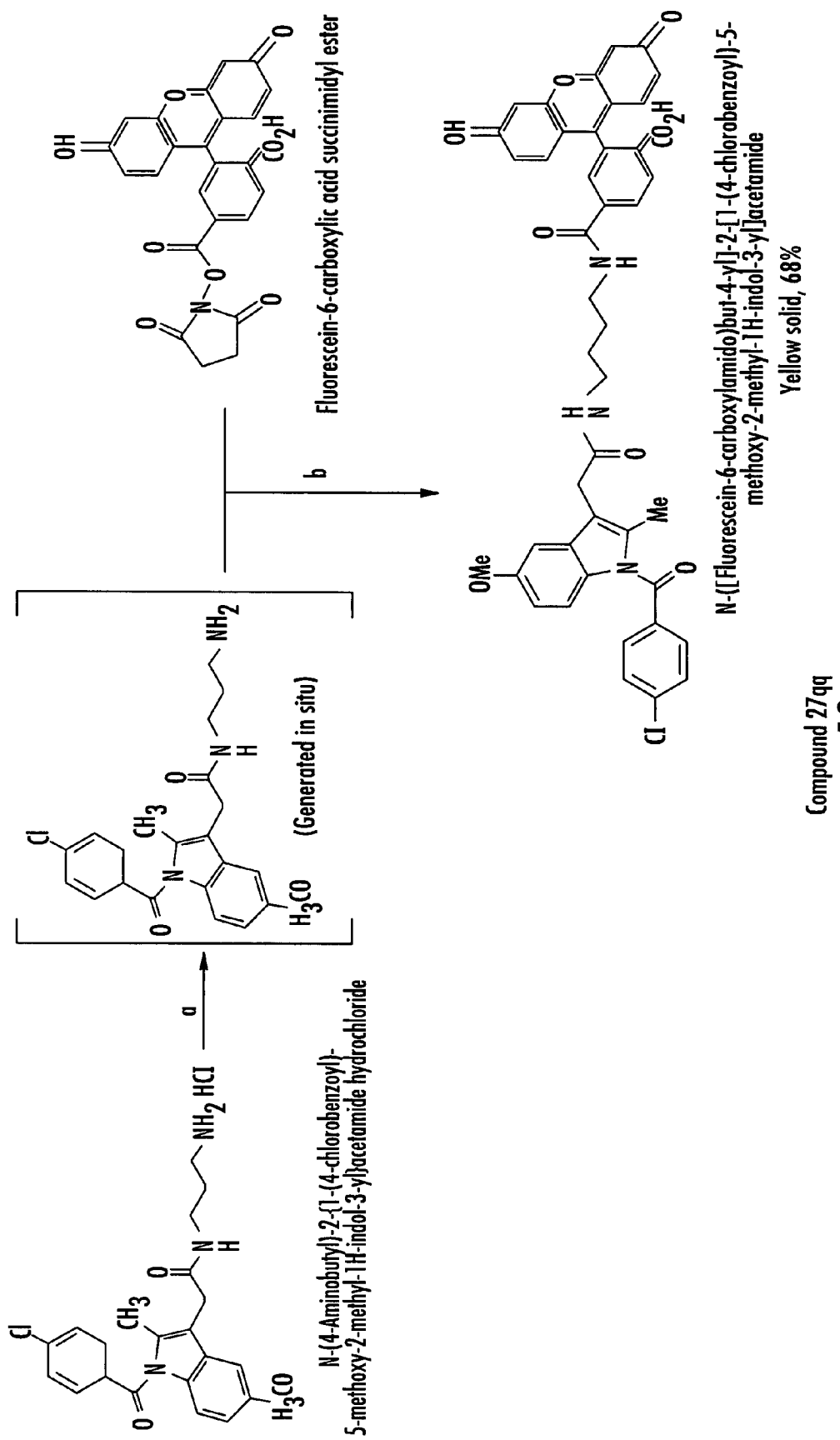
FIG. 10 depicts a synthesis scheme that can be used to produce Compound 27qq, an exemplary fluorescent diagnostic agent of the presently disclosed subject matter that comprises a fluoresceinyl moiety. Reagents and conditions: (a) Triethylamine (TEA), dimethyl sulfoxide (DMSO), r.t., 5 minutes; (b) Triethylamine (TEA), dimethyl sulfoxide (DMSO), r.t., 16 hours.
Figure 11:
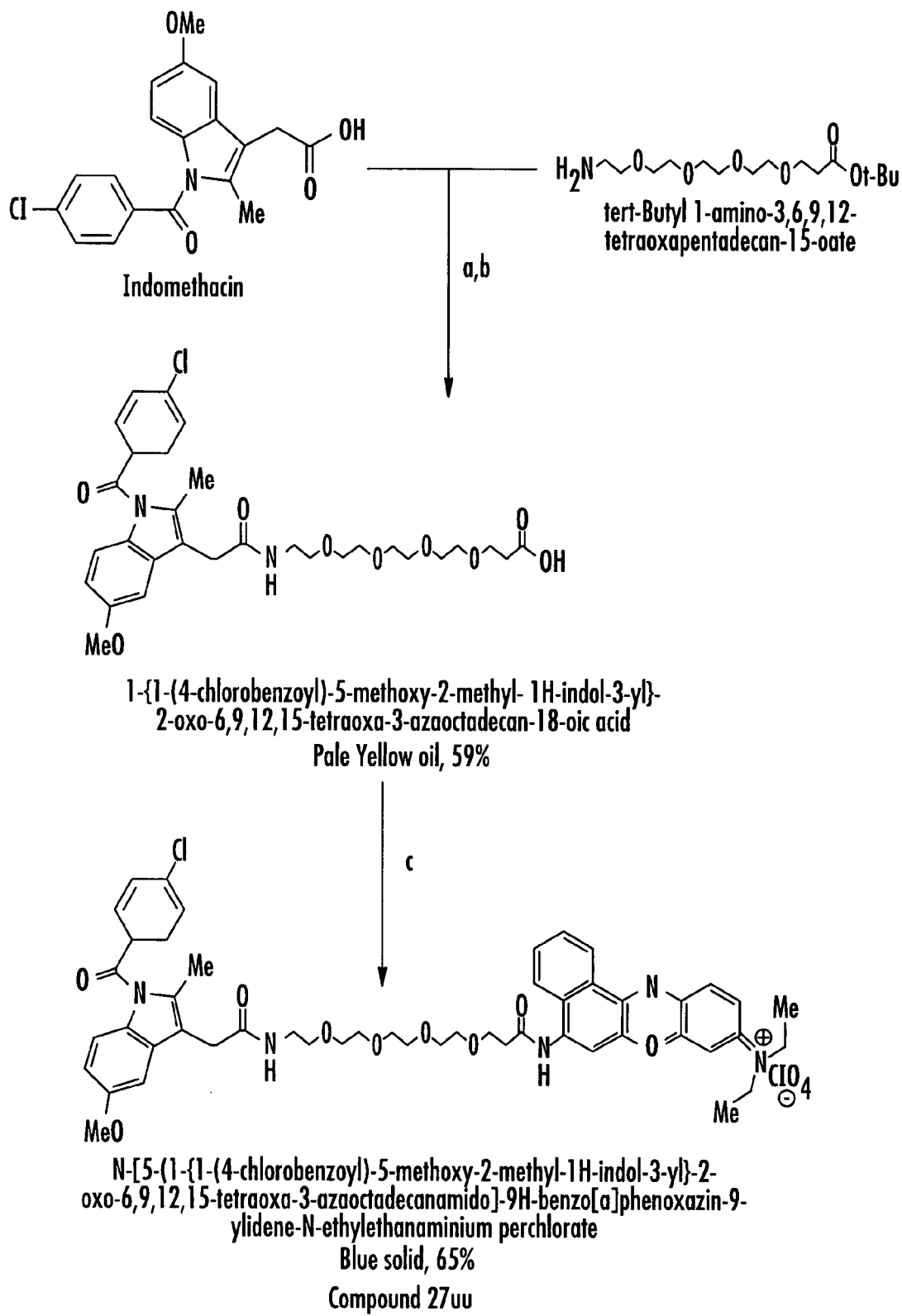
FIG. 11 depicts a synthesis scheme that can be used to produce Compound 27uu, an exemplary fluorescent diagnostic agent of the presently disclosed subject matter that comprises a Nile Blue moiety. Reagents and conditions: (a) 1-Ethyl-3-(3'-dimethylaminopropyl)carbodiimide hydrochloride (EDCl), 1-hydroxybenzotriazole (HOBt), N,N-diisopropylethylamine (DIPEA), dichloromethane, r.t, 16 hours; (b) Trifluoroacetic acid, r.t., 2 hours; (c) 1-Ethyl-3-(3'-dimethylaminopropyl)carbodiimide hydrochloride(EDCl), 1-hydroxybenzotriazole (HOBt), N,N-diisopropylethylamine (DIPEA), dichloromethane, r.t, 16 hours.

Representative synthesis schemes are discussed in more detail hereinbelow in the EXAMPLES and are presented in FIGS. 1-15. It is understood that the representative schemes are non-limiting, and further that the scheme depicted in FIG. 1 as being applicable for synthesizing Indo-sulfathiazole analog Compound 27j can also be employed with modifications that would be apparent to one of ordinary skill in the art after review of the instant specification for synthesizing other NSAID-sulfathiazole analogs. Similarly, the scheme depicted in FIG. 4 as applicable, for example, for synthesizing Indo-Dansyl analog Compound 27z is equally applicable for synthesizing any of the other Indo-Dansyl analogs disclosed herein with minor modifications that would be apparent to one of ordinary skill in the art. This scheme, for example, is also understood to be applicable to synthesizing other NSAID-Dansyl analogs, also by employing minor modifications of the disclosed scheme that would be apparent to one of ordinary skill in the art.

Figure 12:
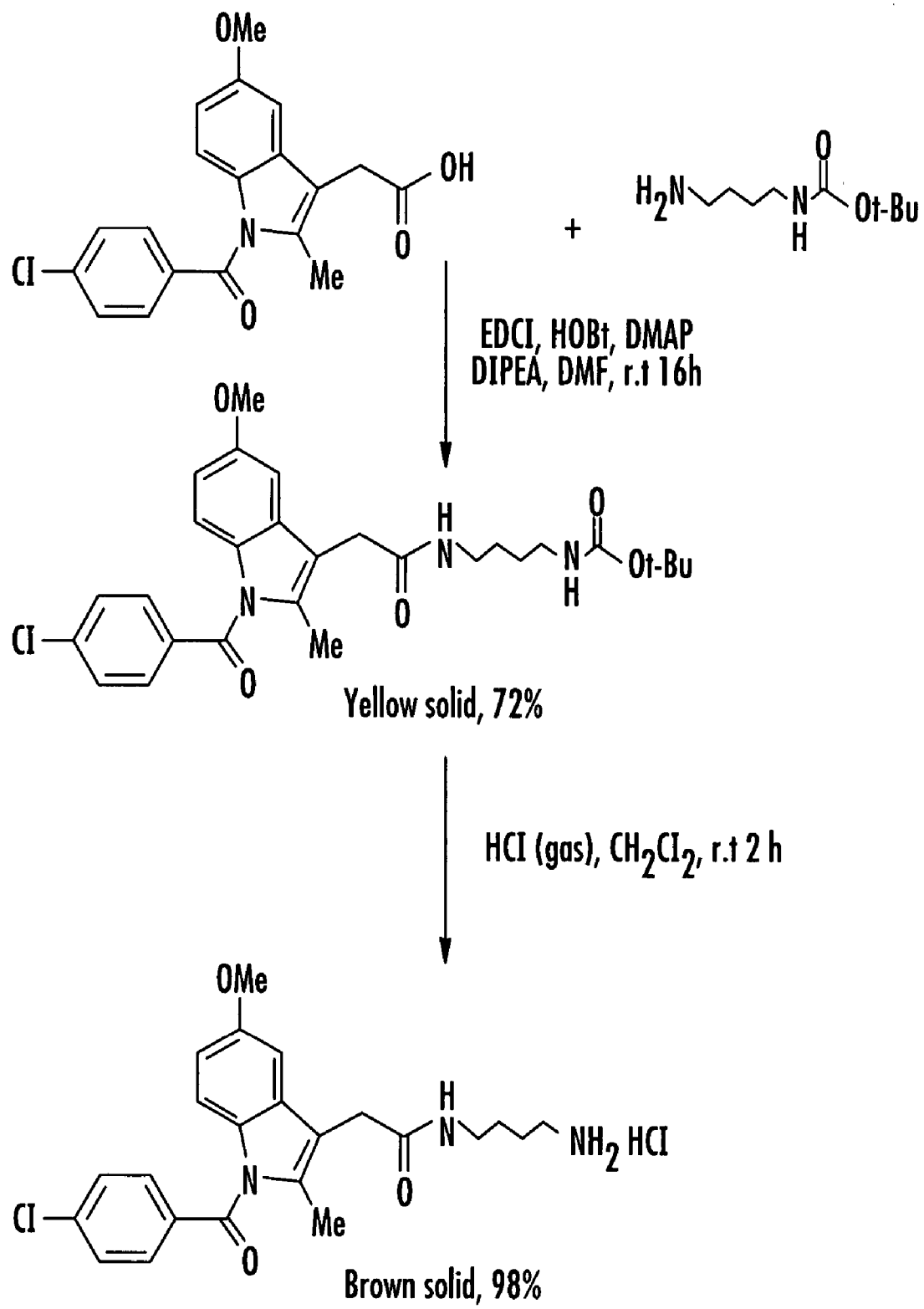
FIG. 12 depicts a synthesis scheme that can be used to produce Compound 27vv, an exemplary fluorescent diagnostic agent of the presently disclosed subject matter that comprises a ROX moiety.
Figure 12:
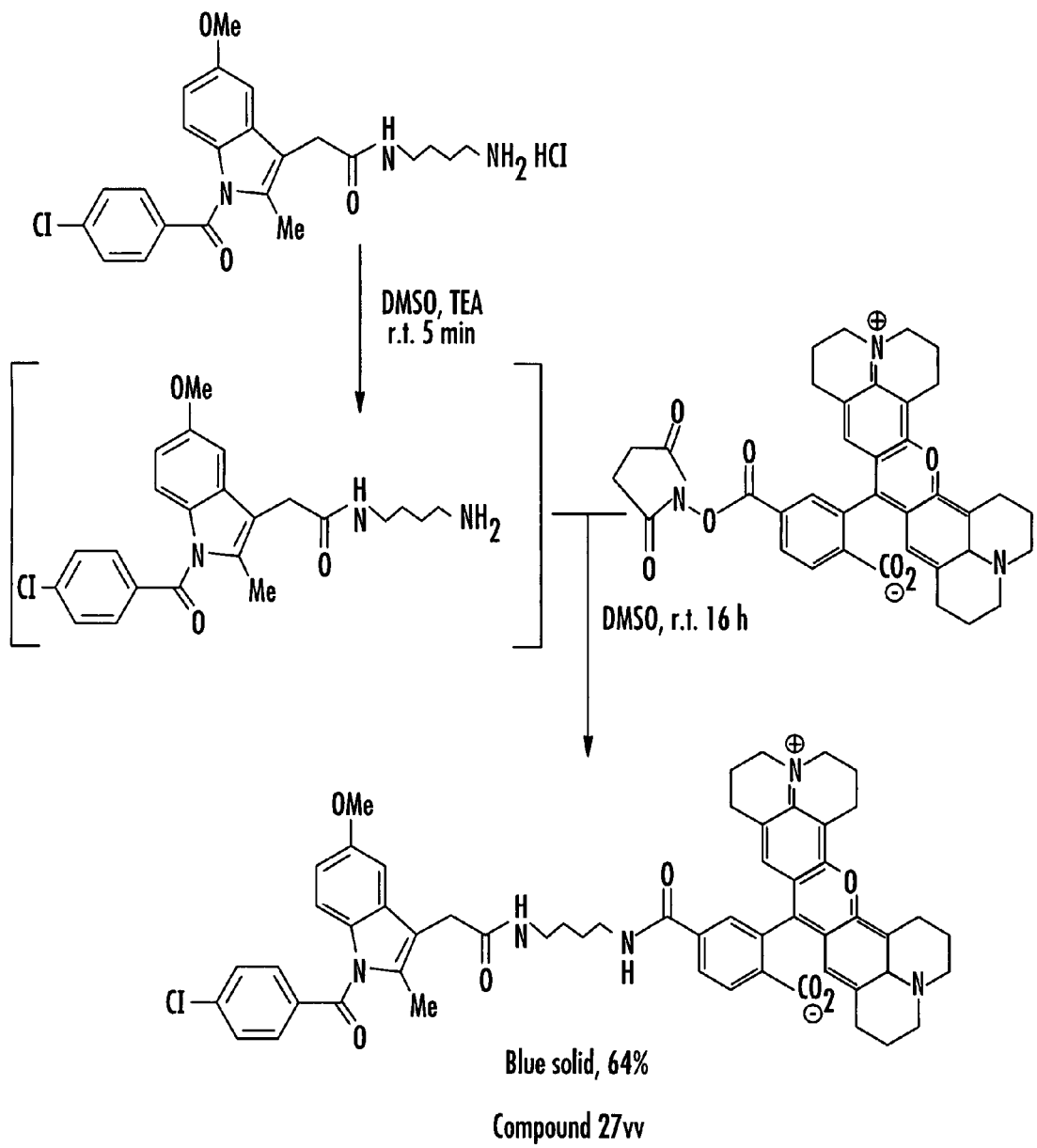
Figure 13:
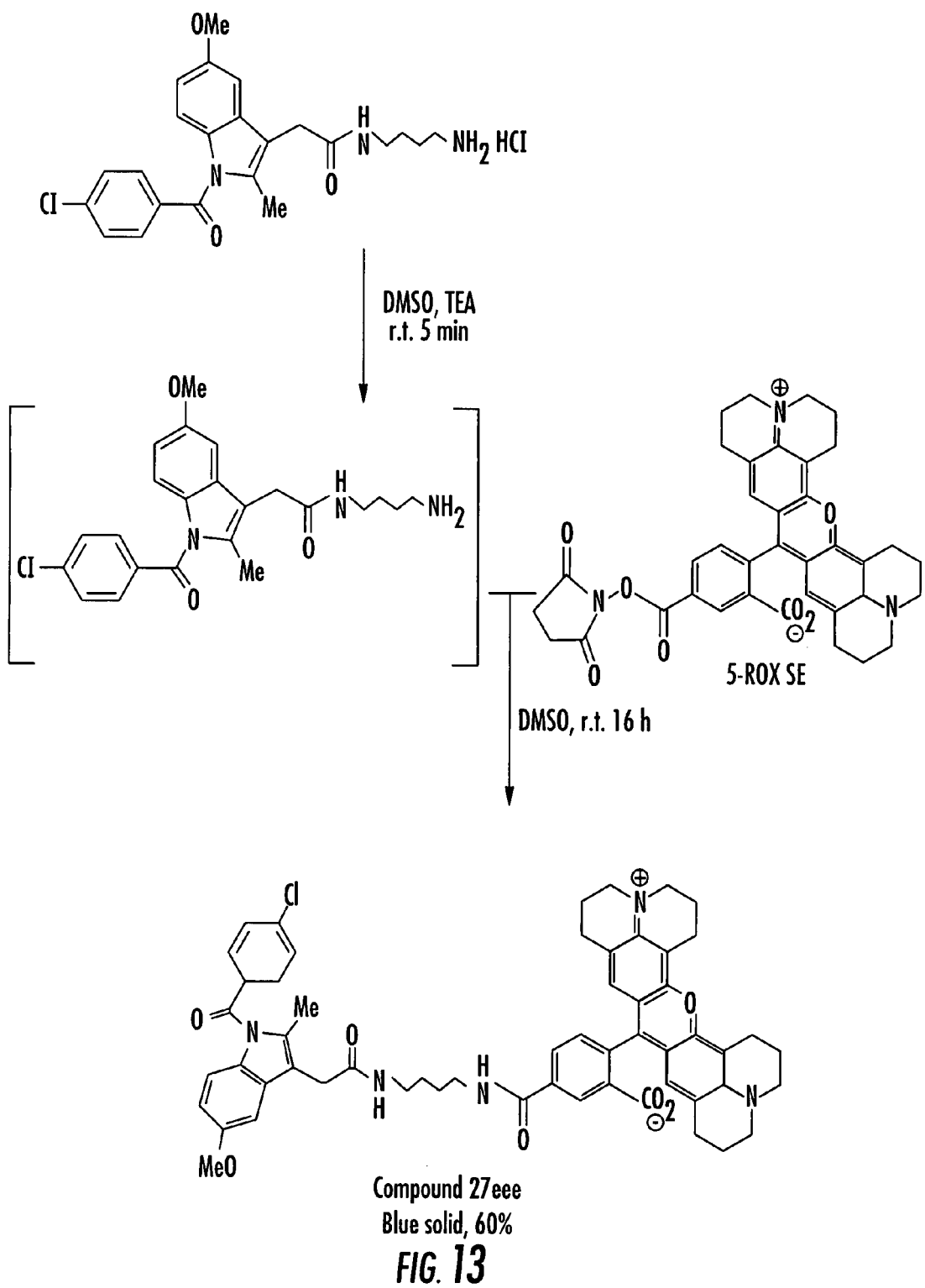
FIG. 13 depicts a synthesis scheme that can be used to produce Compound 27eee, an exemplary fluorescent diagnostic agent of the presently disclosed subject matter that comprises another ROX moiety.
Figure 14:
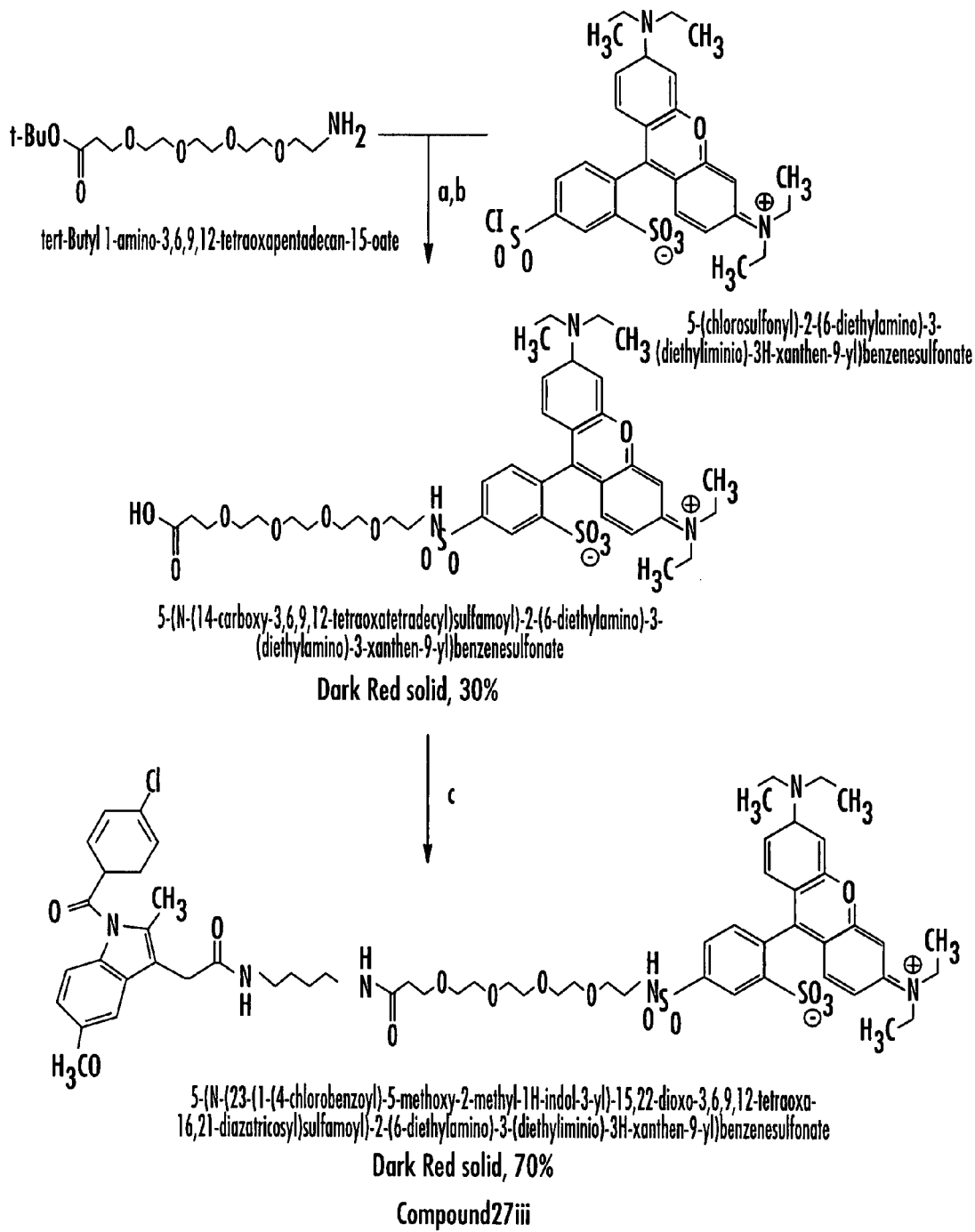
FIG. 14 depicts a synthesis scheme that can be used to produce Compound 27iii, an exemplary fluorescent diagnostic agent of the presently disclosed subject matter that comprises a sulforhodaminyl moiety. Reagents and conditions: (a) Triethylamine (TAE), dichloromethane, R.t., 16 hours; (b) Trfluoroacetic acid (TFA), r.t., 2 hours; (c) N-(4-aminobutyl)-2-[1-(4-chlorobenzoyl)-5-methoxy-2-methyl-1H-indol-3-yl]acetamide hydrochloride, O—(N-succinimidyl)-1,1,3,3-tetramethyluronium tetrafluoroborate (TSTU), triethylamine (TEA), r.t., 16 hours.
Figure 15:
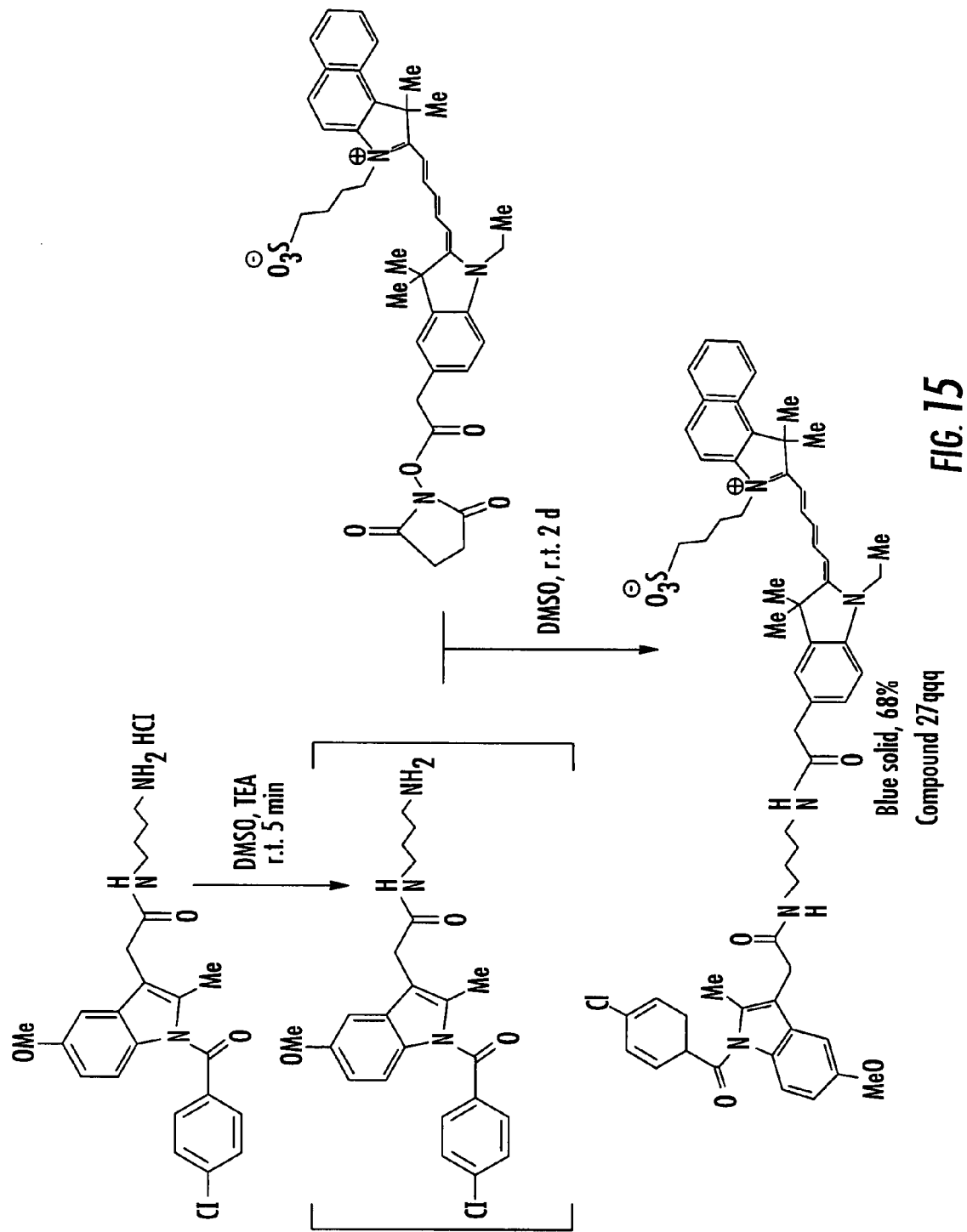
FIG. 15 depicts a synthesis scheme that can be used to produce Compound 27qqq, an exemplary fluorescent diagnostic agent of the presently disclosed subject matter that comprises an NIR dye moiety.

Similarly, the schemes depicted in FIGS. 12 and 13 as being applicable for synthesizing Indo-carboxyrhodaminyl analogs 27vv and 27eee can also be employed with modifications that would be apparent to one of ordinary skill in the art after review of the instant specification for synthesizing other NSAID-carboxyrhodaminyl analogs, and the scheme depicted in the scheme depicted in FIG. 15 as being applicable for synthesizing Indo-NIR analog Compound 27qqq can also be employed with modifications that would be apparent to one of ordinary skill in the art after review of the instant specification for synthesizing other NSAID-NIR analogs.

IV. Methods of Using the Disclosed Therapeutic and/or Diagnostic Agents

IV.A. Diagnosis and Imaging Methods

The presently disclosed subject matter also provides methods for imaging a target cell in a subject. In some embodiments, the method comprises (a) administering to the subject a diagnostic agent under conditions sufficient for contacting the diagnostic agent with the target cell, wherein the diagnostic agent comprises a detectable moiety linked (e.g., covalently linked) via a tether to a derivative of a non-steroidal anti-inflammatory drug (NSAID), and further wherein the diagnostic agent selectively binds to COX-2 expressed by the target cell; and (b) detecting the detectable moiety. In some embodiments, the presently disclosed methods employ a diagnostic agent as disclosed herein.

Representative diagnostic agents of the presently disclosed subject matter include, but are not limited to diagnostic agents having the following structural formulas:
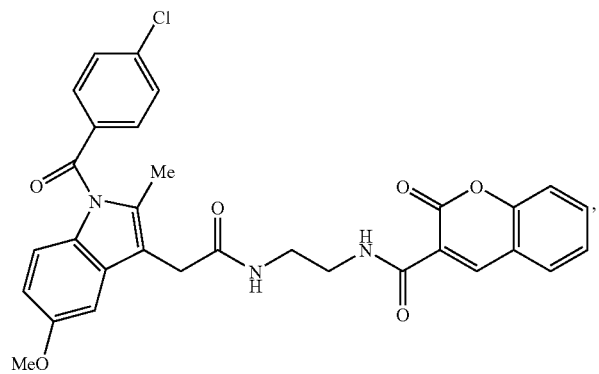
Compound 27cc
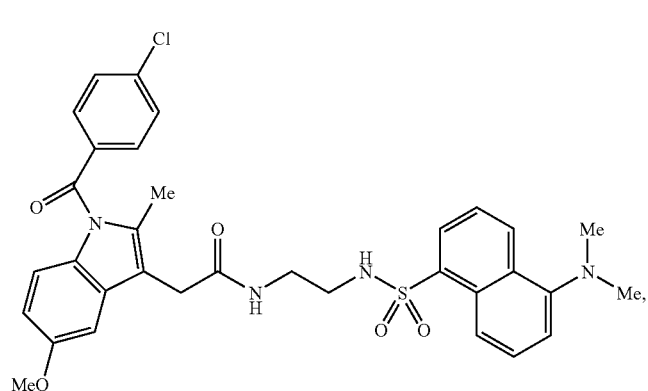
Compound 27x
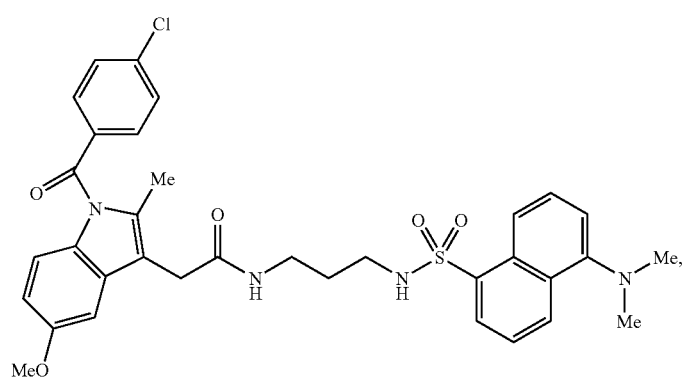
Compound 27y
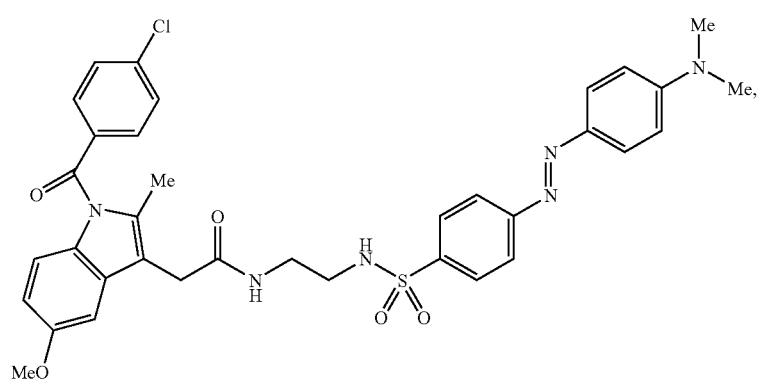
Compound 27aa Compound 27z
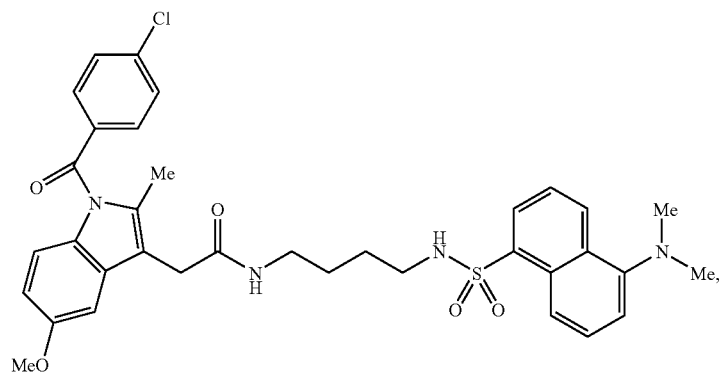
Compound 27iii
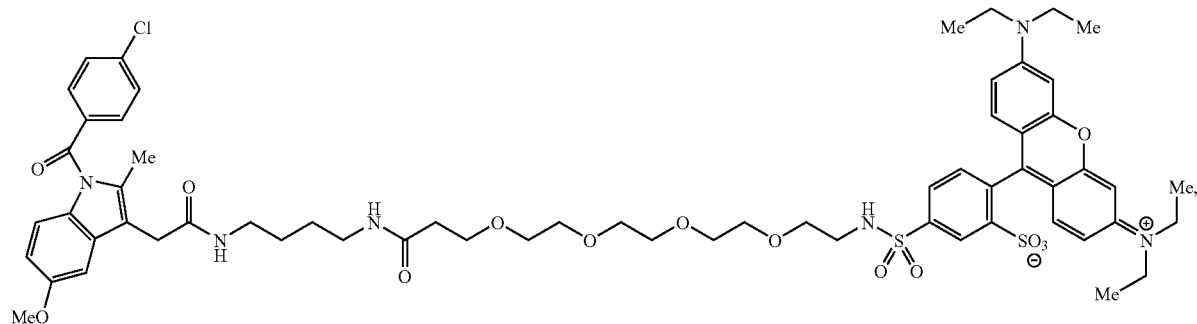
Compound 27ii
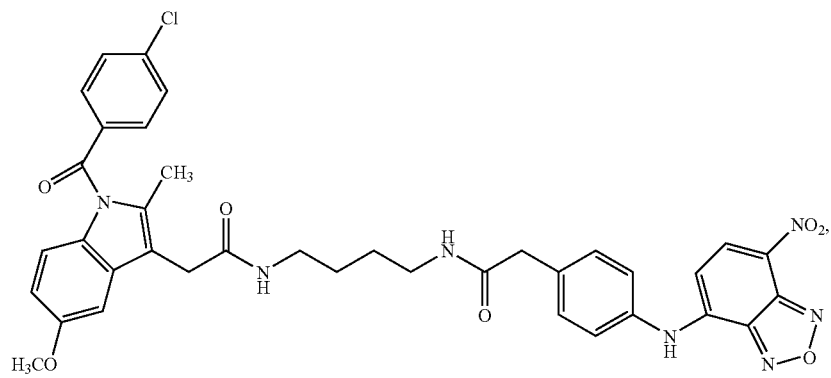
Compound 27uu
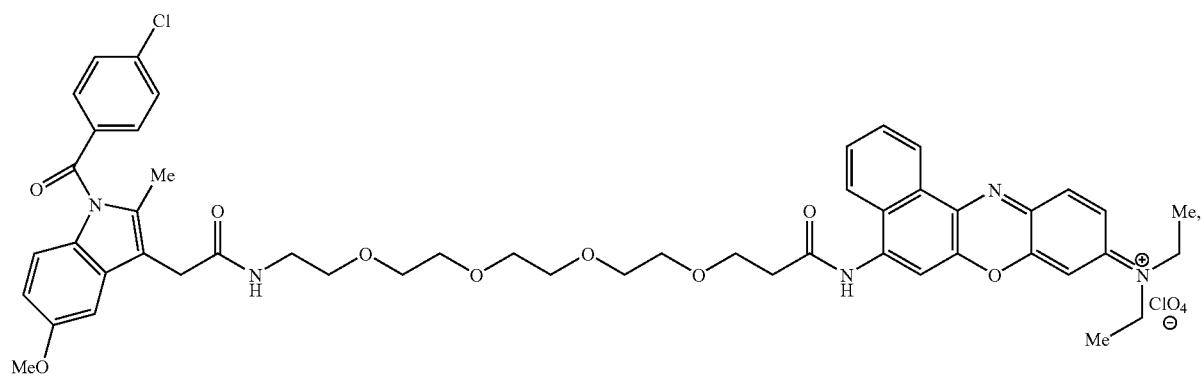

-continued
Compound 27pp
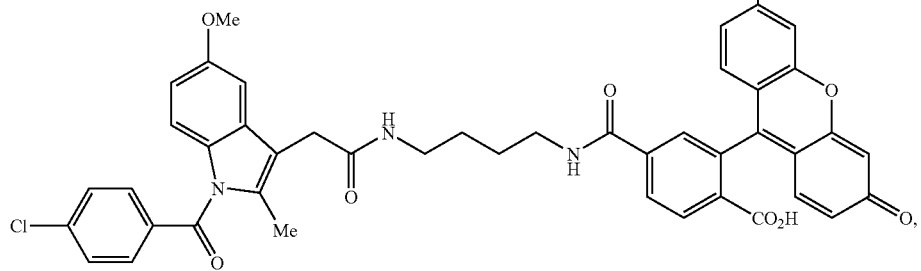
Compound 27qqq
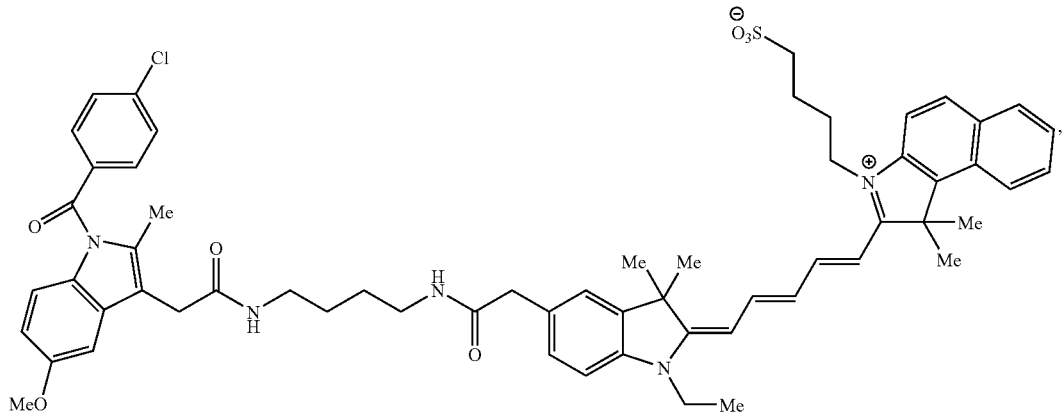
Compound 27ttt
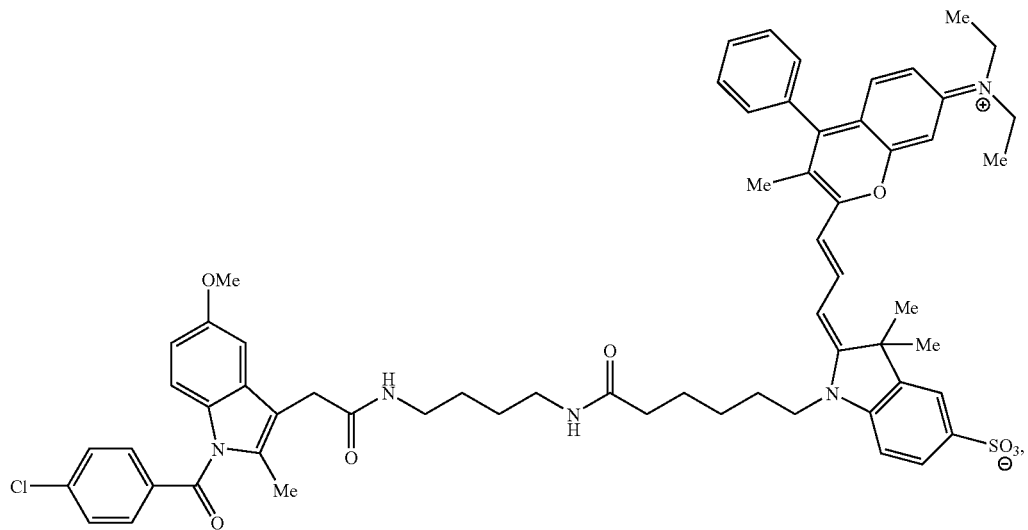

-continued
Compound 27vv
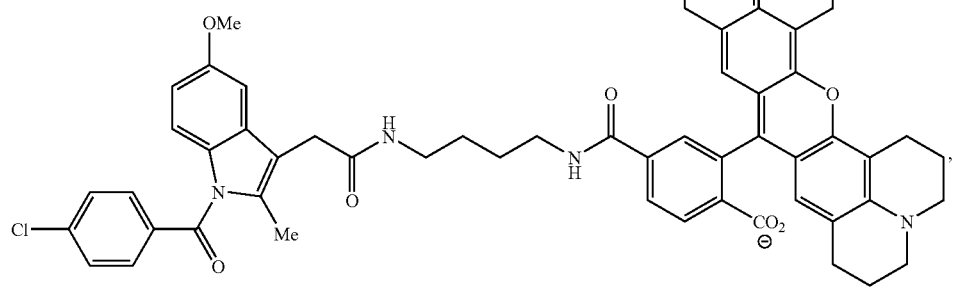
Compound 27eee
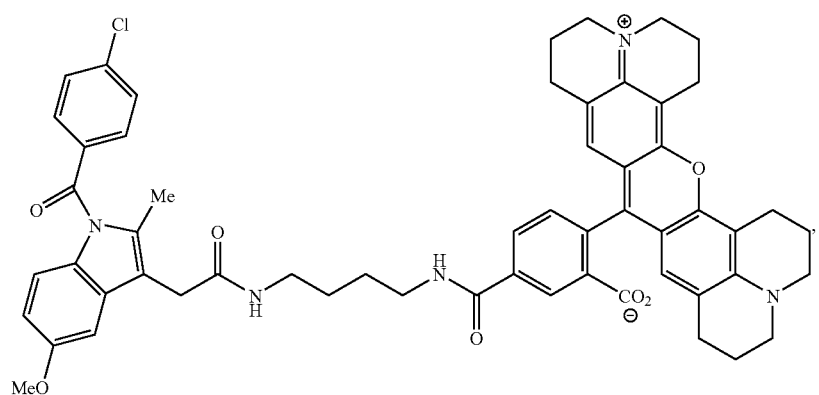
Compound 27ff
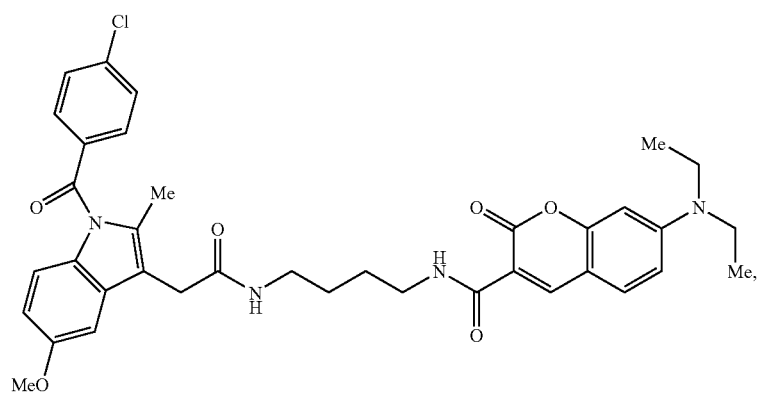
Compound 27gg
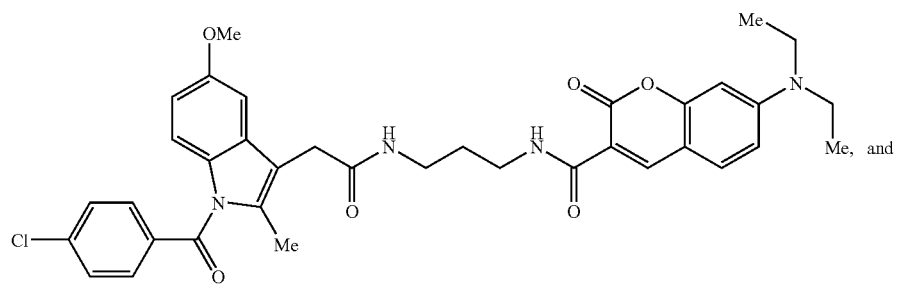

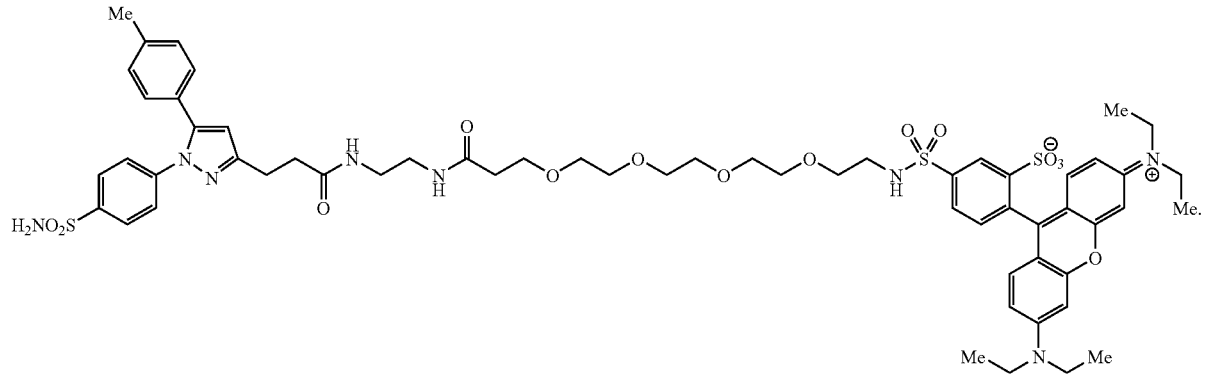

Compound 30f

The term "target cell" refers to any cell or group of cells present in a subject. This term thus includes single cells and populations of cells. As such, the term includes, but is not limited to, cell populations comprising glands and organs such as skin, liver, heart, kidney, brain, pancreas, lung, stomach, and reproductive organs. It also includes, but is not limited to, mixed cell populations such as bone marrow. Further, it includes but is not limited to such abnormal cells as neoplastic or tumor cells, whether individually or as a part of solid or metastatic tumors. The term "target cell" as used herein additionally refers to an intended site for accumulation of a therapeutic and/or diagnostic agent as described herein following administration to a subject. In some embodiments, the methods of the presently disclosed subject matter employ a target cell that is part of a tumor. In some embodiments, the target cell is present in a tissue selected from the group consisting of an inflammatory lesion and a tumor, and/or is a neoplastic cell, a pre-neoplastic cell, or a cancer cell. In some embodiments, the tumor is selected from the group consisting of a primary tumor, a metastasized tumor, and a carcinoma. In some embodiments, the tumor is selected from the group consisting of a colon adenocarcinoma, an esophageal tumor, a bladder tumor, a breast tumor, a pancreatic tumor, a lung tumor, a gastric tumor, a hepatic tumor, a head and/or neck tumor, a cervical tumor, an endometrial tumor, and a skin tumor. In some embodiments, the inflammatory lesion is selected from the group consisting of a colon polyp and Barrett's esophagus.

As used herein, the term "cancer" encompasses cancers in all forms, including polyps, neoplastic cells, and pre-neoplastic cells.

As used herein, the term "neoplastic" is intended to refer to its ordinary meaning, namely aberrant growth characterized by abnormally rapid cellular proliferation. In general, the term "neoplastic" encompasses growth that can be either benign or malignant, or a combination of the two.

The term "tumor" as used herein encompasses both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant tumors, including radioresistant variants of any of the tumors listed above.

In some embodiments, the tumor is selected from the group consisting of a primary tumor, a metastasized tumor, and a carcinoma.

The methods and compositions of the presently claimed subject matter are useful for imaging of a target tissue in any subject. Thus, the term "subject" as used herein includes any vertebrate species, for example, warm-blooded vertebrates such as mammals and birds. More particularly, the methods of the presently disclosed subject matter are provided for the therapeutic and/or diagnostic treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants and livestock (such as cattle, oxen, sheep, giraffes, deer, goats, bison, and camels), and horses. Also provided is the treatment of birds, including those kinds of birds that are endangered or kept in zoos, as well as fowl, and more particularly domesticated fowl or poultry, such as turkeys, chickens, ducks, geese, guinea fowl, and the like, as they are also of economic importance to humans. In some embodiments, the subject is a mammal. In some embodiments, the mammal is a human.

IV.B. Therapeutic Methods
IV.B.1. Generally

The presently disclosed subject matter also provides methods for treating a disorder associated with a cyclooxygenase-2 (COX-2) biological activity in a subject. As used herein, the phrase "disorder associated with a cyclooxygenase-2 (COX-2) biological activity" refers to any medical condition at least one consequence of which is caused by or results from a biological activity of a COX-2 enzyme in a cell in the subject. It is understood that a consequence that is caused by or results from a COX-2 biological activity need not be caused by or result from a COX-2 biological activity directly, but can also be caused by or result from downstream effects of a COX-2 biological activity. Therefore, the phrase "a disorder associated with a COX-2 biological activity" encompasses any disorder in which a biological activity of COX-2 has any medically relevant consequence in the subject. Exemplary disorders associated with a COX-2 biological activity include, but are not limited to neoplasias and/or pre-neoplastic states (e.g., tumors, pre-neoplastic lesions, neoplastic cells, pre-neoplastic cells, and cancer cells) and inflammatory states. In some embodiments, a disorder associated with a COX-2 biological activity comprises a disorder that a medical professional would believe would be beneficially treated with a COX-2-selective inhibitor (even if the COX-2-selective inhibitor might have otherwise undesirable side effects).

In some embodiments, the methods comprise administering to the subject a therapeutically effective amount of a therapeutic agent comprising a therapeutic moiety and a derivative of a non-steroidal anti-inflammatory drug (NSAID), wherein (i) the therapeutic moiety and the derivative of a non-steroidal anti-inflammatory drug (NSAID) are linked (e.g., covalently linked) to each other via a tether; and (ii) the therapeutic agent selectively binds COX-2. Exemplary therapeutic agents of the presently disclosed subject matter include, but are not limited to analogs comprising the therapeutic active agents disclosed herein, and also those having the structural formulas depicted in Tables 1 and 2. In some embodiments, the methods employ a therapeutic agent having one of the following structural formulas:

Compound 27a

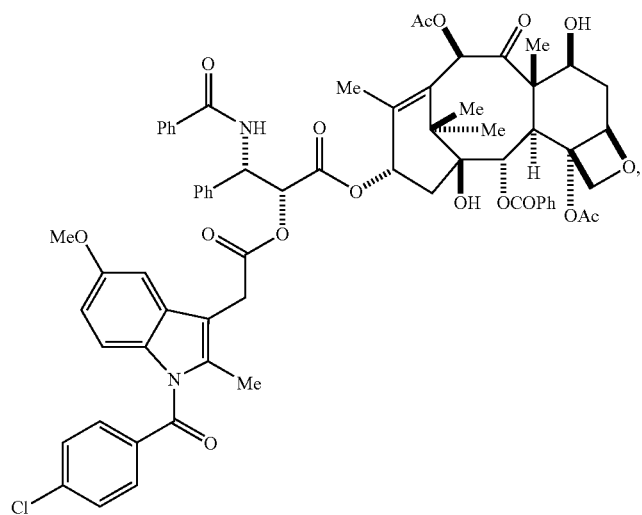

Compound 27c

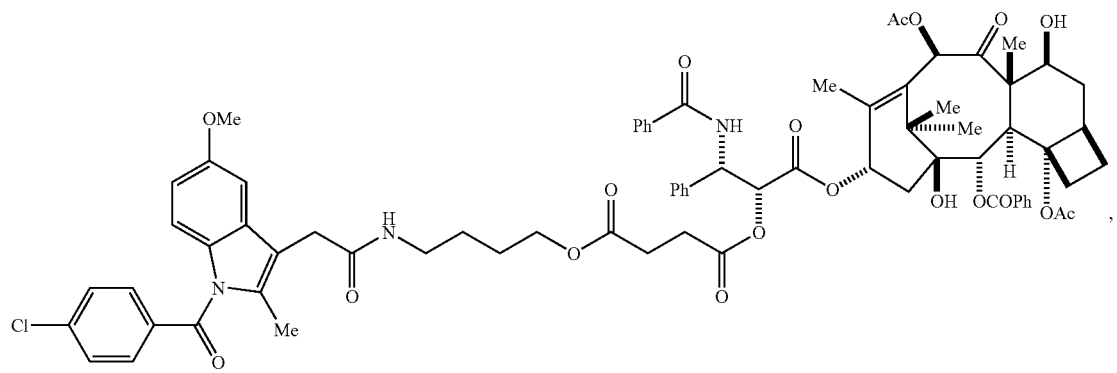

-continued
Compound 27d
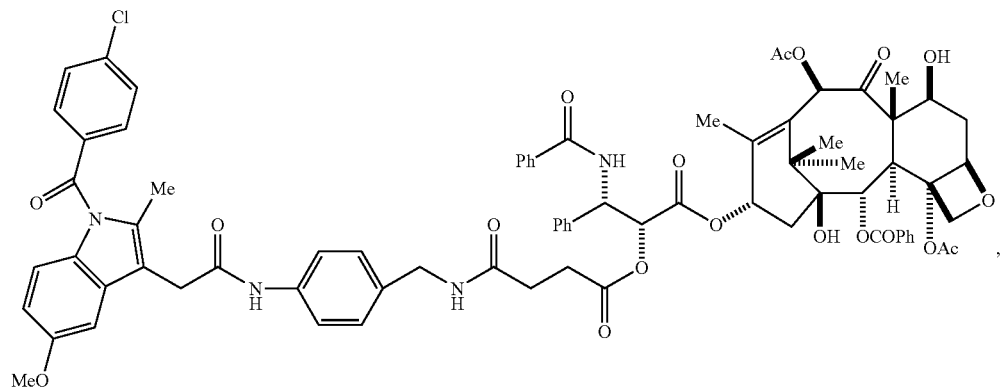
Compound 27g
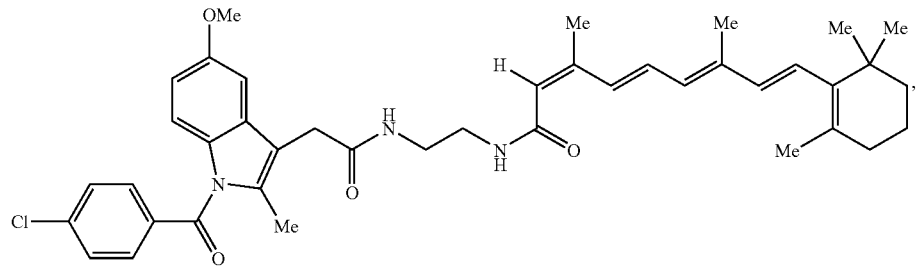
Compound 27h
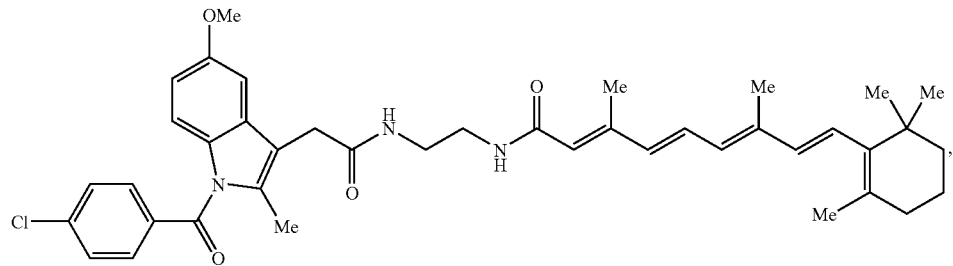
Compound 27i
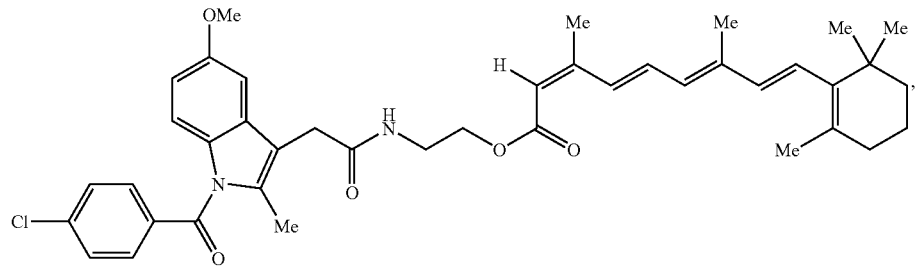
Compound 27j
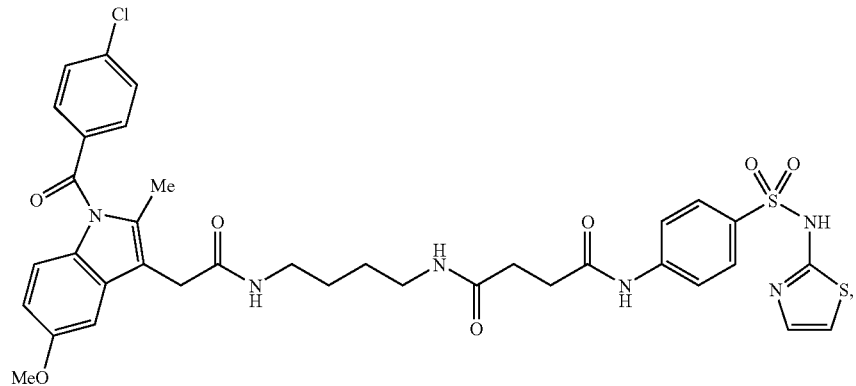

-continued
Compound 27n
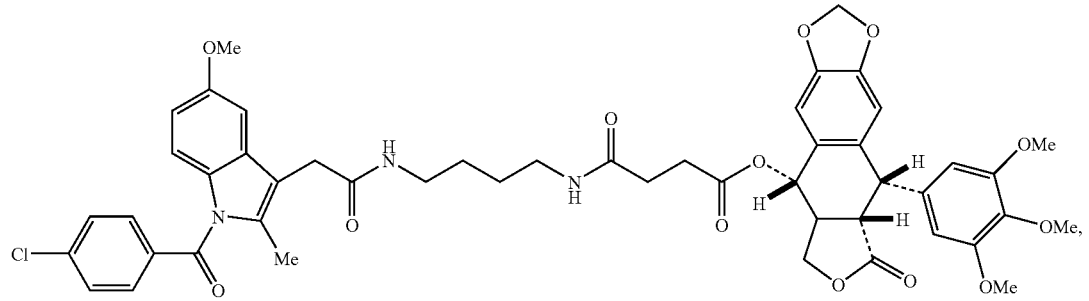
Compound 27o
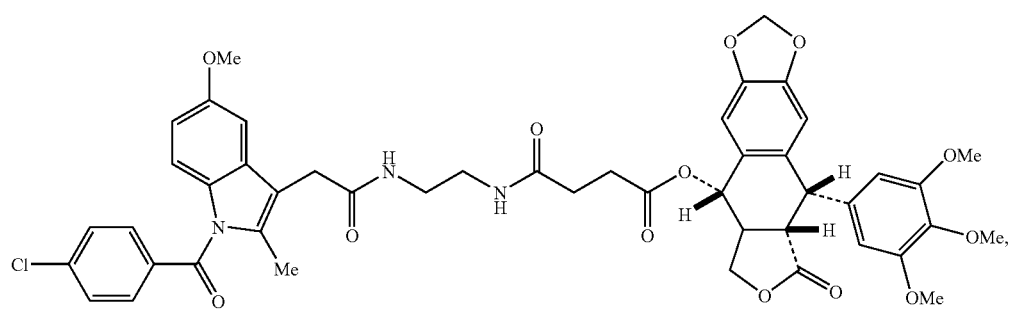
Compound 27p
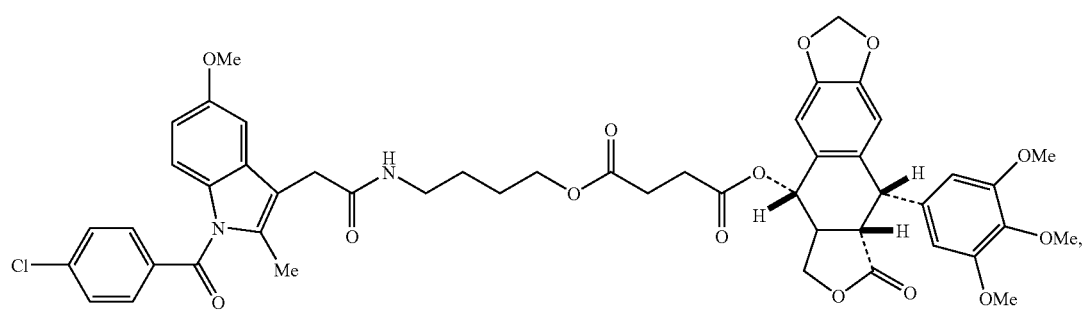
Compound 27q
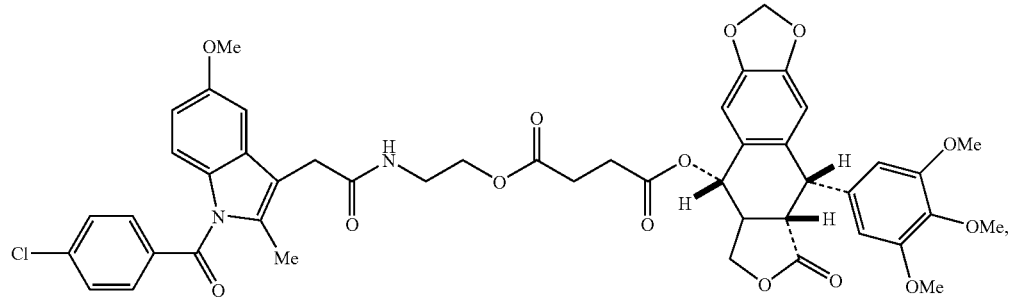

-continued

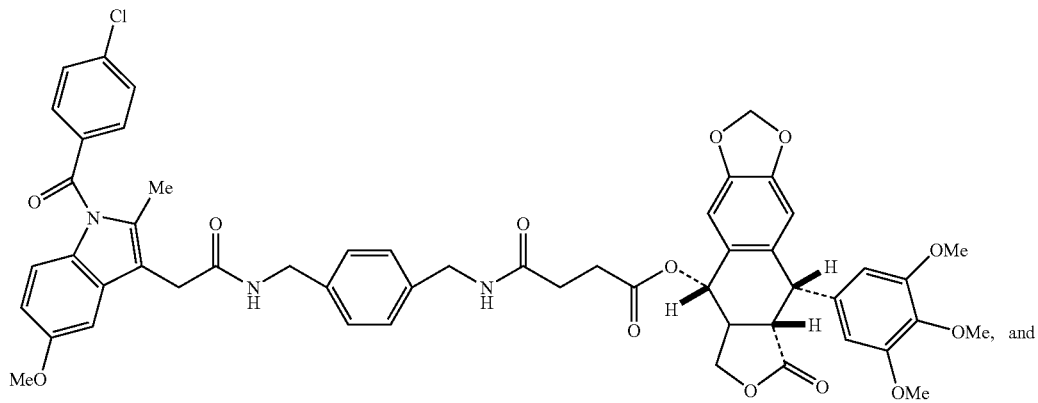
Compound 27r

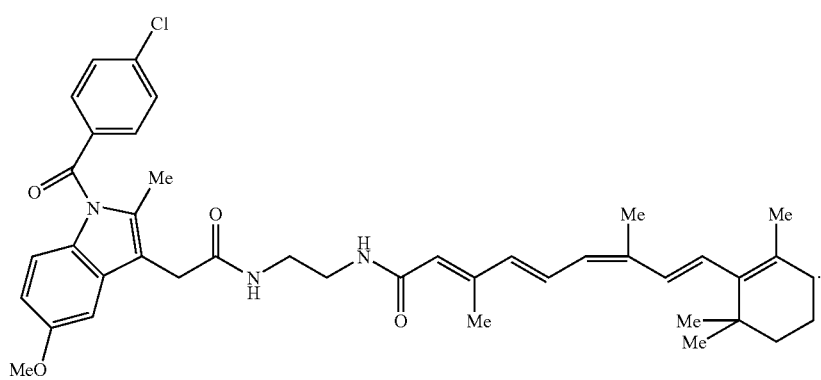
Compound 27s

It is noted that consistent with the presently disclosed subject matter, a therapeutic and/or diagnostic agent as disclosed herein can have a beneficial therapeutic effect that does not result from an activity of the active when the therapeutic and/or diagnostic agent is administered to a subject. For example, in some embodiments the therapeutic and/or diagnostic agent of the presently disclosed subject matter is also a COX-2-selective inhibitor, and as such provides a therapeutic effect in a subject that has a disorder associated with an undesirable COX-2 biological activity. As such, the therapeutic and/or diagnostic agents disclosed herein can provide a beneficial therapeutic effect to a subject that is in some embodiments a combination of the benefit provided by the active agent (i.e., the chemotherapeutic) as well as the benefit provided by the binding of the therapeutic and/or diagnostic agent to COX-2 (and in some embodiments, the inhibition of the COX-2 enzyme that results) in the subject. In some embodiments, the overall therapeutic benefit comprises a cumulative, additive, or synergistic effect of the COX-2 binding and the activity of the therapeutic moiety.

IV.B.2. Adjunct Therapies

The presently disclosed methods and compositions can also be employed in conjunction with other therapies typically employed to treat the relevant disorder associated with COX-2 biological activity. As used herein, the phrase "combination therapy" refers to any treatment wherein the methods and compositions disclosed herein are used in combination with another therapy including, but not limited to radiation therapy (radiotherapy), chemotherapy, surgical therapy (e.g., resection), immunotherapy, photodynamic therapy, and combinations thereof.

In some embodiments, the methods and compositions disclosed herein are employed in a combination therapy with radiation treatment. For such treatment of a tumor, the tumor is irradiated concurrent with, or subsequent to, administration of a composition as disclosed herein. In some embodiments, the tumor is irradiated daily for 2 weeks to 7 weeks (for a total of 10 treatments to 35 treatments). Alternatively, tumors can be irradiated with brachytherapy utilizing high dose rate or low dose rate brachytherapy internal emitters.

The duration for administration of a composition as disclosed herein comprises in some embodiments a period of several months coincident with radiotherapy, but in some embodiments can extend to a period of 1 year to 3 years as needed to effect tumor control. A composition as disclosed herein can be administered about one hour before each fraction of radiation. Alternatively, a composition can be administered prior to an initial radiation treatment and then at desired intervals during the course of radiation treatment (e.g., weekly, monthly, or as required). An initial administration of a composition (e.g., a sustained release drug carrier) can comprise administering the composition to a tumor during placement of a brachytherapy after-loading device.

Subtherapeutic or therapeutic doses of radiation can be used for treatment of a radiosensitized tumor as disclosed herein. In some embodiments, a subtherapeutic or minimally therapeutic dose (when administered alone) of ionizing radiation is used. For example, the dose of radiation can comprise in some embodiments at least about 2 Gy ionizing radiation, in some embodiments about 2 Gy to about 6 Gy ionizing radiation, and in some embodiments about 2 Gy to about 3 Gy ionizing radiation. When radiosurgery is used, representative doses of radiation include about 10 Gy to about 20 Gy administered as a single dose during radiosurgery or about 7 Gy administered daily for 3 days (about 21 Gy total). When high dose rate brachytherapy is used, a representative radiation dose comprises about 7 Gy daily for 3 days (about 21 Gy total). For low dose rate brachytherapy, radiation doses typically comprise about 12 Gy administered twice over the course of 1 month. $^{125}$I seeds can be implanted into a tumor can be used to deliver very high doses of about 110 Gy to about 140 Gy in a single administration.

Radiation can be localized to a tumor using conformal irradiation, brachytherapy, stereotactic irradiation, or intensity modulated radiation therapy (IMRT). The threshold dose for treatment can thereby be exceeded in the target tissue but avoided in surrounding normal tissues. For treatment of a subject having two or more tumors, local irradiation enables differential drug administration and/or radiotherapy at each of the two or more tumors. Alternatively, whole body irradiation can be used, as permitted by the low doses of radiation required following radiosensitization of the tumor.

Radiation can also comprise administration of internal emitters, for example $^{131}$I for treatment of thyroid cancer, NETASTRON™ and QUADRAGEN® pharmaceutical compositions (Cytogen Corp., Princeton, N.J., United States of America) for treatment of bone metastases, $^{32}$P for treatment of ovarian cancer. Other internal emitters include $^{125}$I, iridium, and cesium. Internal emitters can be encapsulated for administration or can be loaded into a brachytherapy device.

Radiotherapy methods suitable for use in the practice of presently disclosed subject matter would be known to those of skill in the art after consideration of the instant specification.

IV.C. Formulation

In some embodiments, a therapeutic and/or diagnostic agent of the presently disclosed subject matter comprises a pharmaceutical composition that includes a pharmaceutically acceptable carrier. Suitable formulations include aqueous and non-aqueous sterile injection solutions that can contain antioxidants, buffers, bacteriostats, bactericidal antibiotics, and solutes that render the formulation isotonic with the bodily fluids of the subject; and aqueous and non-aqueous sterile suspensions, which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in some embodiments in the range of 0.1 to 10 mg/ml, in some embodiments about 2.0 mg/ml; and/or mannitol or another sugar, in some embodiments in the range of 10 to 100 mg/ml, in some embodiments about 30 mg/ml; and/or phosphate-buffered saline (PBS). Any other agents conventional in the art having regard to the type of formulation in question can be used.

The methods and compositions of the presently disclosed subject matter can be used with additional adjuvants or biological response modifiers including, but not limited to the cytokines IFN-α, IFN-γ, IL-2, IL-4, IL-6, TNF, or other cytokine affecting immune cells.

The methods and compositions of the presently disclosed subject matter can also be employed in combination with a potentiator. A "potentiator" can be any material that improves or increases the efficacy of a pharmaceutical composition and/or acts on the immune system. Exemplary potentiators are triprolidine and its cis-isomer, which can be used in combination with chemotherapeutic agents. Triprolidine is described in U.S. Pat. No. 5,114,951. Other potentiators are procodazole 1H-Benzimidazole-2-propanoic acid; [β-(2-benzimidazole) propionic acid; 2-(2-carboxyethyl)benzimidazole; propazol) Procodazole is a non-specific active immunoprotective agent against viral and bacterial infections and can be used with the compositions disclosed herein. Potentiators can improve the efficacy of the disclosed compositions and can be used in a safe and effective amount.

IV.D. Administration

Suitable methods for administration of a therapeutic and/or diagnostic agent of the presently disclosed subject matter include, but are not limited to peroral, intravenous, intraperitoneal, inhalation, intravascular, subcutaneous, and intratumoral administration. In some embodiments, intravascular administration is employed. For delivery of compositions to pulmonary pathways, compositions can be administered as an aerosol or coarse spray.

For diagnostic applications, a detectable amount of a composition of the presently disclosed subject matter is administered to a subject. A "detectable amount", as used herein to refer to a diagnostic agent, refers to a dose of such a composition that the presence of the composition can be determined in vivo or in vitro. A detectable amount can vary according to a variety of factors including, but not limited to chemical features of the conjugate being labeled, the detectable label, labeling methods, the method of imaging and parameters related thereto, metabolism of the labeled conjugate in the subject, the stability of the label (e.g., the half-life of a radionuclide label), the time elapsed following administration of the conjugate prior to imaging, the route of administration, the physical condition and prior medical history of the subject, and the size and longevity of the tumor or suspected tumor. Thus, a detectable amount can vary and is optimally tailored to a particular application. After study of the present disclosure, and in particular the Examples, it is within the skill of one in the art to determine such a detectable amount.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for Examples 1 and 2

HPLC-UV analysis was performed on a Waters 2695 Separation Module in-line with a Waters 2487 Dual Wavelength Absorbance detector (Waters Corp. Milford, Mass., United States of America). Mass spectrometric analyses were performed on a Thermo-Electron Surveyor (Thermo Scientific, Waltham, Mass., United States of America) pump and autosampler operated in-line with a Quantum triple quadrupole instrument in ESI positive or negative ion mode. Silica gel column chromatography was performed using Sorbent silica gel standard grade, porosity 60 Å, particle size 32-63 µm (230×450 mesh), surface area 500-600 m$^2$/g, bulk density 0.4 g/mL, pH range 6.5-7.5. All other reagents, purchased from the Aldrich Chemical Company (Milwaukee, Wis., United States of America), were used without further purification.

$^1$H NMR was taken on a Bruker AV-I console operating at 400.13 MHz. 13C NMR was taken on a Bruker DRX console operating at 500.13 MHz (Bruker BioSpin Corp., Billerica, Mass., United States of America). $^1$H COSY experiments were acquired using a 9.4 T Oxford magnet equipped with a Bruker AV-I console operating at 400.13 MHz. Experimental conditions included 2048×512 data matrix, 13 ppm sweep width, recycle delay of 1.5 seconds and 4 scans per increment. The data was processed using squared sinebell window function, symmetrized, and displayed in magnitude mode.

$^{13}$C direct detection, HSQC and HMBC NMR experiments were acquired using an 11.7 T Oxford magnet equipped with a Bruker DRX console operating at 500.13 MHz. Experimental parameters for $^{13}$C direct detection experiments (acquired with $^1$H decoupling during the acquisition) included 32K data points, 230 ppm sweep width, a 20° pulse tip-angle, a recycle delay of 2 seconds and 20,000 scans. Multiplicity-edited HSQC experiments were acquired using a 2048×256 data matrix, a J(C—H) value of 145 Hz which resulted in a multiplicity selection delay of 34 ms, a recycle delay of 1.5 seconds and 16 scans per increment along with GARP decoupling on $^{13}$C during the acquisition time (150 ms). The data was processed using a p/2 shifted squared sine window function and displayed with CH/CH$_3$ signals phased positive and CH$_2$ signals phased negative. $J_1$(C—H) filtered HMBC experiments were acquired using a 2048×256 data matrix, a J(C—H) value of 9 Hz for detection of long range couplings resulting in an evolution delay of 55 ms, $J_1$(C—H) filter delay of 145 Hz (34 ms) for the suppression of one-bond couplings, a recycle delay of 1.5 seconds and 128 scans per increment. The HMBC data was processed using a p/2 shifted squared sine window function and displayed in magnitude mode.

Example 1

Synthesis of Representative Therapeutic Analogs

Compound 27i: an Indo-Sulfathiazole Analog: Compound 27j was synthesized by the method outlined in FIG. 1. Briefly, Compound 27j was synthesized by first complexing succinic anhydride with sulfathiazole by reacting these compounds at room temperature for 6 hours in tetrahydrofuran (THF) in the presence of triethylamine (TEA) to produce succinylsulfathiazole as a white solid (67% yield). The succinylsulfathiazole was then reacted for 2 hours at room temperature with O—(N-succinimidyl)-1,1,3,3-tetramethyluronium tetrafluoroborate (TSTU) in dichloromethane in the presence of TEA to produce the corresponding succinimidyl ester, which was reacted with 1-(4-aminobutyl)-2-{1-(4-chlorobenzoyl)-5-methoxy-2-methyl-1H-indol-3-yl}acetamide in dichloromethane in the presence of TEA at room temperature for 16 hours to produce Compound 27j as a yellow gummy mass (45% yield). Compound 27j was characterized by NMR, two-dimensional NMR, and mass spectroscopy.

Compound 30c: a Celecoxib Analog: Compound 30c, 3-[1-{p-(Sulfonamido)phenyl}-5-p-tolyl-1H-pyrazol-3-yl] propanoic acid., was synthesized by the method depicted in FIG. 2. Briefly, 4'-methylacetophenone and succinnic hydride were reacted in the presence of lithium diisopropanolamine (LDA) and tetrahydrofuran (THF) for 1 hour at −78° C. to produce p-tolyl-4,6-dioxohexanoic acid as a white solid (66% yield). Also sulfanilamide has reacted with sodium nitrite (NaNO$_2$) and concentrated hydrochloric acid at 0-4° C. for 30 minutes, after which tin(II) chloride (SnCl$_2$) was added and the reaction allowed to continue for an additional 4 hours at 0° C. to produce 4-sulfonamidophenylhydrazine hydrochloride as a pale yellow solid (55% yield). The 4,6,dioxo-6-p-tolylhexanoic acid and the 4-sulfonamidophenylhydrazine hydrochloride were then complexed for 16 hours at room temperature in the presence of triethanolamine (TEA) in methanol to produce Compound 30c as a yellow solid (76% yield).

Compound 30f: a Celecox-Sulforhodamine Analog: Compound 30f was synthesized by the method outlined in FIG. 3. Briefly, Compound 30c as synthesized as set forth hereinabove. Compound 30c was then complexed with tert-butyl 2-aminoethylcarbamate for 16 hours at room temperature in the presence of 1-ethyl-3-(3'-dimethylaminopropyl)carbodiimide hydrochloride (EDCl), 1-hydroxybenzotriazole (HOBt), and N,N-diisopropylethylamine (DIPEA) in mimethylformamide (DMF) to produce tert-butyl 2-[3-{1-(4-sulfamoylphenyl)-5-p-tolyl-1H-pyrazol-3-yl}propanamido] ethylcarbamate as a yellow solid (46% yield). This product was then dissolved in dichloromethane and treated with HCl (gas) for 2 hours at room temperature, producing N-(2-aminoethyl)-3-{1-(4-sulfamoylphenyl)-5-p-tolyl-1H-pyrazol-3-yl}propanamide hydrochloride as a yellow solid (80% yield).

N-(2-aminoethyl)-3-{1-(4-sulfamoylphenyl)-5-p-tolyl-1H-pyrazol-3-yl}propanamide hydrochloride was reacted with N,N-diisopropylethylamine (DIPEA) in dichloromethane for 5 minutes at room temperature to produce N-(2-aminoethyl)-3-{1-(4-sulfamoylphenyl)-5-p-tolyl-1H-pyrazol-3-yl}propanamide which was then reacted with 5-(N-(14-carboxy-3,6,9,12-tetraoxatetradecyl)sulfamoyl)-2-(6-(diethylamino)-3-(diethyliminio)-3H-xanthen-9-yl)benzenesulfonate (produced as disclosed hereinabove with respect to Compound 27iii) in the presence of 1-ethyl-3-(3'-dimethylaminopropyl)carbodiimide hydrochloride (EDCl), 1-hydroxybenzotriazole (HOBt), and N,N-diisopropylethylamine (DIPEA) in dichloromethane at room temperature to produce Compound 30f as a dark red solid (57% yield).

Taxol is one of the most important and promising anticancer drug currently in the clinic. Taxol has antitubulin-assembly activity. It is being used for the treatment of breast, lung, ovarian, head, and neck cancers for more than a decade. Taxol has three secondary hydroxyl groups and the exocyclic hydroxyl group is less hindered for derivatization. Taxol was reacted with indomethacin to synthesize INDO-Taxol conjugate Compound 27a (see Table 1). The coupling reaction was carried out using EDC in presence of a catalytic amount of DMAP. This ester was tested to check the inhibitory activity against purified COX-2 or COX-1. Although this compound did not inhibit either COX isozyme related compounds, Compounds 27c and 27q selectively inhibited COX-2 (Table 1). The reason for this failure could be due to the lack of the space at the entrance of the active site to accommodate the bulky taxol moiety.

Structures and inhibitory profiles for additional representative therapeutic analogs are presented in Table 2 below.

TABLE 1

Structures and Inhibitory Profiles of Representative Therapeutic Agents

| Cmpnd No. | Tether (T) | Active Agent (Q) | IC$_{50}$ (nM)$^a$ COX-1 | COX-2 |
|---|---|---|---|---|
| 27 | (core structure: 5-methoxy-2-methyl-1-(4-chlorobenzoyl)indole with 3-CH$_2$-T-Q) | | | |
| 27a | -C(O)O- linker | Taxol | >4000 | >4000 |
| 27b | amide-NH-CH$_2$CH$_2$-(OCH$_2$CH$_2$)$_2$-O-C(O)- | Taxol | >4000 | >4000 |
| 27c | amide-NH-(CH$_2$CH$_2$O)$_n$-C(O)CH$_2$CH$_2$C(O)O-, n=1 | Taxol | >4000 | 2200 |
| 27d | amide-NH-C$_6$H$_4$-CH$_2$NH-C(O)CH$_2$CH$_2$C(O)O- | Taxol | >4000 | 254 |
| 27e | amide-NH-CH$_2$CH$_2$-(OCH$_2$CH$_2$)$_2$-O-C(O)- | Doxorubicin | >4000 | >4000 |
| 27f | amide-NH-CH$_2$CH$_2$-(OCH$_2$CH$_2$)$_2$-C(O)N- | Mitomycin C | >4000 | >4000 |
| 27g | amide-NH-(CH$_2$)$_n$-NHC(O)-, n=0 | 13-cis-Retinoic acid | >4000 | 454 |
| 27h | amide-NH-(CH$_2$)$_n$-NHC(O)-, n=0 | All-trans-Retinoic acid | >4000 | 107 |

TABLE 1-continued
Structures and Inhibitory Profiles of Representative Therapeutic Agents
| Cmpnd No. | Tether (T) | Active Agent (Q) | IC$_{50}$ (nM)[a] COX-1 | COX-2 |
|---|---|---|---|---|
| 27i | 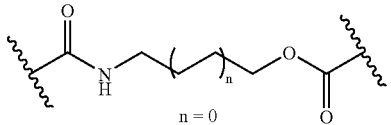 n = 0 | 13-cis-Retinoic acid | >4000 | 107 |
| 27j | 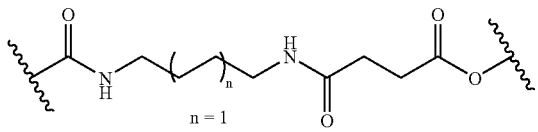 n = 1 | Sulfathiazole | >4000 | 960 |
| 27k | 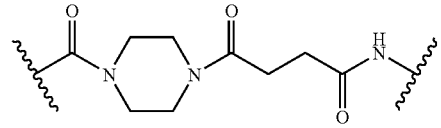 | Sulfathiazole | >4000 | >4000 |
| 27l | 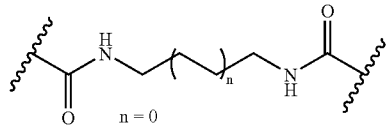 n = 0 | Micophenolic acid | >4000 | >4000 |
| 27m | 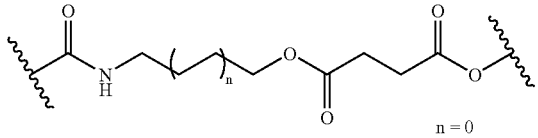 n = 0 | Camptothecin | >4000 | >4000 |
| 27n | 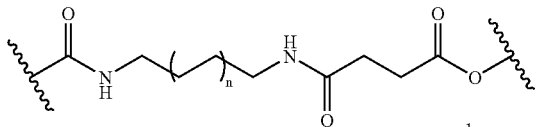 n = 1 | Podophyllotoxin | >4000 | 295 |
| 27o | 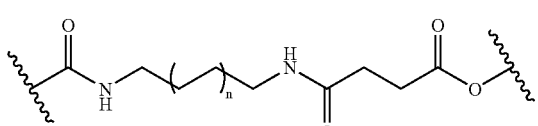 n = 0 | Podophyllotoxin | >4000 | 475 |
| 27p | 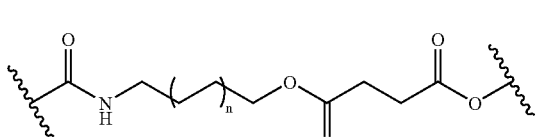 n = 1 | Podophyllotoxin | >4000 | 147 |
| 27q | 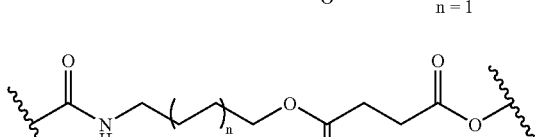 n = 0 | Podophyllotoxin | >4000 | 254 |

TABLE 1-continued

Structures and Inhibitory Profiles of Representative Therapeutic Agents

| Cmpnd No. | Tether (T) | Active Agent (Q) | IC$_{50}$ (nM)$^a$ COX-1 | COX-2 |
|---|---|---|---|---|
| 27r | (structure) | Podophyllotoxin | >4000 | 187 |
| 28 | (structure with 5-methoxy-1-(4-bromobenzyl)-2-methylindole-3-ethylamine-T-Q) | | | |
| 28a | (structure) | Podophyllotoxin | >4000 | >4000 |
| 29 | (structure: 1-(4-methylsulfonylphenyl)-5-(4-methylphenyl)pyrazole-3-ethyl-T-Q) | | | |
| 29a | (structure, n = 0) | Podophyllotoxin | >4000 | >4000 |
| 30 | (structure: 1-(4-sulfamoylphenyl)-5-(4-methylphenyl)pyrazole-3-ethyl-T-Q) | | | |

TABLE 1-continued

Structures and Inhibitory Profiles of Representative Therapeutic Agents

| Cmpnd No. | Tether (T) | Active Agent (Q) | IC$_{50}$ (nM)[a] | |
|---|---|---|---|---|
| | | | COX-1 | COX-2 |
| 30a | (structure, n = 0) | Podophyllotoxin | >4000 | >4000 |

[a] Assayed against purified enzymes

TABLE 2

Structures and Inhibitory Profiles of Additional Therapeutic Agents

| Cmpnd No. | | IC$_{50}$ (nM)* | | IC$_{50}$ (nM)** | |
|---|---|---|---|---|---|
| | | COX-2 | COX-1 | COX-2 | COX-1 |

Retinoic Acid Analog

| 27s | (structure) | 388 | >25000 | n.d. | n.d. |

Sulfadimethoxane Analog

| 27u | (structure) | 148 | 80 | n.d. | n.d. |

TABLE 2-continued

Structures and Inhibitory Profiles of Additional Therapeutic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 |
|---|---|---|---|---|---|
| | Perphenazine Analog | | | | |
| 27v | | 387 | >25000 | n.d. | n.d. |
| | Piperazine Analog | | | | |
| 27w | | >25000 | 1300 | n.d. | n.d. |
| | Celecoxib Analogs | | | | |
| 29b | | 2800 | >25000 | n.d. | n.d. |
| 29c | | >25000 | >25000 | n.d. | n.d. |

TABLE 2-continued

Structures and Inhibitory Profiles of Additional Therapeutic Agents

| Cmpnd No. | Structure | IC$_{50}$ (nM)* | | IC$_{50}$ (nM)** | |
|---|---|---|---|---|---|
| | | COX-2 | COX-1 | COX-2 | COX-1 |
| 29d | | >25000 | >25000 | n.d. | n.d. |
| 29e | | >25000 | >25000 | n.d. | n.d. |
| 29f | | >25000 | >25000 | n.d. | n.d. |
| 30b | | 920 | >25000 | 110 (M) | >5000 (M) |
| 30c | | 8900 | >25000 | 1400 (M) | >5000 (M) |

TABLE 2-continued

Structures and Inhibitory Profiles of Additional Therapeutic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 |
|---|---|---|---|---|---|
| 30d | [Structure: pyrazole with 4-methylphenyl, 4-sulfamoylphenyl (H$_2$NO$_2$S), and carboxylic acid (OH) groups] | >25000 | >25000 | n.d. | n.d. |
| 31 | [Structure: pyrazole with 4-methylphenyl, 4-(N,N-dimethylsulfamoyl)phenyl ((Me)$_2$NO$_2$S), and methyl ester (OMe) groups] | >25000 | >25000 | n.d. | n.d. |

*Assayed against purified enzymes;
**Assayed in a macrophage assay (M) or a cell viability assay (C);
n.d.: not determined Example 2

Synthesis of Representative Diagnostic Analogs

Compound 27z: a Fluorescent Indo-Dansyl Analog: Compound 27z was synthesized by the method outlined in FIG. 4. Briefly, indomethacin was complexed with N-BOC butanediamine for 16 hours at room temperature in the presence of 1-ethyl-3-(3'-dimethylaminopropyl)carbodiimide hydrochloride (EDCl), 1-hydroxybenzotriazole (HOBt), dimethylaminopyridine (DMAP), N,N'-diisopropylethylamine (DIPEA), and N,N-dimethylformamide (DMF). A yellow solid corresponding to a percent yield of 72% was obtained. This solid was then dissolved in dichloromethane and treated with HCl (gas) for 2 hours at room temperature, producing N-(4-aminobutyl)-2-[1-(4-chlorobenzoyl)-5-methoxy-2-methyl-1H-indol-3-yl]acetamide hydrochloride as a brown solid (98% yield), which was reacted with triethylamine (TEA) in dichloromethane for 5 minutes at room temperature prior to the addition of dansyl chloride. Dansyl chloride was then added, and the reaction was allowed to continue for 16 hours at room temperature, which produced Compound 27z as a yellow solid in a yield of 77%. Compound 27z was characterized by NMR and mass spectroscopy (MS).

Other Indo-Dansyl analogs, including Compound 27x and Compound 27y were synthesized using similar strategies by varying the length of the alkyl chain.

Compound 27aa: a Fluorescent Indo-Dabsyl Analog: Compound 27aa, N-(2-Dabsylaminoethyl)-2-{1-(4-chlorobenzoyl)-5-methoxy-2-methyl-1H-indol-3-yl}acetamide was synthesized by the method depicted in FIG. 5. Briefly, indomethacin was complexed with tert-Butyl-2-aminoethyl-carbamate for 16 hours at room temperature in the presence of 1-ethyl-3-(3'-dimethylaminopropyl)carbodiimide hydrochloride (EDCl), 1-hydroxybenzotriazole (HOBt), N,N-diisopropylethylamine (DIPEA), and N,N-dimethylformamide (DMF). A yellow solid of tert-Butyl 2-[2-{1-(4-chlorobenzoyl)-5-methoxy-2-methyl-1H-indol-3-yl}acetamido]ethylcarbamate was produced at 75% yield. This product was then dissolved in dichloromethane and treated with HCl (gas) for 2 hours at room temperature, producing N-(2-Aminoethyl)-2-{1-(4-chlorobenzoyl)-5-methoxy-2-methyl-1H-indol-3-yl}acetamide hydrochloride as a brown solid with a yield of 98%, which was reacted with triethylamine (TEA) in dichloromethane for 5 minutes at room temperature prior to the addition of dabsyl chloride. Dabsyl chloride was then added, and the reaction was allowed to continue for 16 hours at room temperature, which produced Compound 27aa as a red solid in a yield of 61%.

Compound 27cc: a Fluorescent Indo-Coumarinyl Analog: Compound 27cc, N-{2-(Coumarin-3-carboxylamido)ethyl}-2-{1-(4-chlorobenzoyl)-5-methoxy-2-methyl-1H-indol-3-yl}acetamide, was synthesized by the method depicted in FIG. 6. Briefly, indomethacin was complexed with tert-Butyl-2-aminoethylcarbamate for 16 hours at room temperature in the presence of 1-ethyl-3-(3'-dimethylaminopropyl)carbodiimide hydrochloride (EDCl), 1-hydroxybenzotriazole (HOBt), N,N-diisopropylethylamine (DIPEA), and N,N-dimethylformamide (DMF). A yellow solid of tert-Butyl 2-[2-{1-(4-chlorobenzoyl)-5-methoxy-2-methyl-1H-indol-3-yl}acetamido]ethylcarbamate was produced as a yellow solid at 75% yield. This product was then dissolved in dichloromethane and treated with HCl (gas) for 2 hours at room temperature, producing N-(2-Aminoethyl)-2-{1-(4-chlorobenzoyl)-5-methoxy-2-methyl-1H-indol-3-yl}acetamide hydrochloride as a brown solid with a yield of 98%, which was reacted with N,N-diisopropylethylamine (DIPEA) in dichloromethane for 5 minutes at room temperature prior to the addition of Coumarin-3-carboxylic acid, 1-ethyl-3-(3'-dimethylaminopropyl)carbodiimide hydrochloride (EDCl), 1-hydroxybenzotriazole (HOBt), and N,N-diisopropylethylamine (DIPEA) in dichloromethane. The reaction proceeded for 16 hours at room temperature and produced Compound 27cc as a yellow solid (35% yield).

Compound 27ff: an Indo-Coumarinyl Analog: Compound 27ff, N-[2-{7-(N,N-Diethylamino)coumarin-3-carboxylamido}butyl]-2-{1-(4-chlorobenzoyl)-5-methoxy-2-methyl-1H-indol-3-yl}acetamide was synthesized by the method depicted in FIG. 7. Briefly, indomethacin was complexed with tert-Butyl-4-aminobutylcarbamate for 16 hours at room temperature in the presence of 1-ethyl-3-(3'-dimethylaminopropyl)carbodiimide hydrochloride (EDCl), 1-hydroxybenzotriazole (HOBt), N,N-diisopropylethylamine (DIPEA), and N,N-dimethylformamide (DMF). tert-Butyl 4-[2-{1-(4-chlorobenzoyl)-5-methoxy-2-methyl-1H-indol-3-yl}acetamido]ethylcarbamate was produced as a yellow solid at 72% yield. This product was then dissolved in dichloromethane and treated with HCl (gas) for 2 hours at room temperature, producing N-(4-aminobutyl)-2-{1-(4-chlorobenzoyl)-5-methoxy-2-methyl-1H-indol-3-yl}acetamide hydrochloride as a brown solid with a yield of 98%, which was reacted with triethylamine (TEA) in dimethyl sulfoxide (DMSO) for 5 minutes at room temperature prior to the addition of 7-(N,N-Diethylamino)coumarin-3-carboxylic acid succinimidyl ester. The reaction proceeded for 16 hours at room temperature and produced Compound 27ff as a yellow solid (67% yield).

Compound 27gg: an Indo-Coumarinyl Analog: Compound 27gg, N-[3-{7-(N,N-Diethylamino)coumarin-3-carboxylamido}butyl]-2-{1-(4-chlorobenzoyl)-5-methoxy-2-methyl-1H-indol-3-yl}acetamide was synthesized by the method depicted in FIG. 8. Briefly, indomethacin was complexed with tert-Butyl-3-aminopropylcarbamate for 16 hours at room temperature in the presence of 1-ethyl-3-(3'-dimethylaminopropyl)carbodiimide hydrochloride (EDCl), 1-hydroxybenzotriazole (HOBt), N,N-diisopropylethylamine (DIPEA), and N,N-dimethylformamide (DMF). tert-Butyl 3-[2-{1-(4-chlorobenzoyl)-5-methoxy-2-methyl-1H-indol-3-yl}acetamido]propylcarbamate was produced as a pale yellow solid at 70% yield. This product was then dissolved in dichloromethane and treated with HCl (gas) for 2 hours at room temperature, producing N-(4-qminobutyl)-2-{1-(4-chlorobenzoyl)-5-methoxy-2-methyl-1H-indol-3-yl}acetamide hydrochloride as a brown solid with a yield of 98%, which was reacted with triethylamine (TEA) in dimethyl sulfoxide (DMSO) for 5 minutes at room temperature prior to the addition of 7-(N,N-Diethylamino)coumarin-3-carboxylic acid succinimidyl ester. The reaction proceeded for 16 hours at room temperature and produced Compound 27gg as a yellow solid (66% yield).

Compound 27ii: an Indo-NBD Analog: Compound 27ii, N-([2-{4-(7-nitrobenzo[1,2,5]oxadiazol-4-ylamino) phenyl}acetamido]but-4-yl)-2-{1-(4-chloro benzoyl)-5-methoxy-2-methyl-1H-indol-3-yl]acetamide was synthesized by the method depicted in FIG. 9. Briefly, indomethacin was complexed with tert-Butyl-4-aminobutylcarbamate for 16 hours at room temperature in the presence of 1-ethyl-3-(3'-dimethylaminopropyl)carbodiimide hydrochloride (EDCl), 1-hydroxybenzotriazole (HOBt), N,N-diisopropylethylamine (DIPEA), and N,N-dimethylformamide (DMF).

tert-Butyl 4-[2-{1-(4-chlorobenzoyl)-5-methoxy-2-methyl-1H-indol-3-yl}acetamido]ethylcarbamate was produced as a yellow solid at 72% yield. This product was then dissolved in dichloromethane and treated with HCl (gas) for 2 hours at room temperature, producing N-(4-aminobutyl)-2-{1-(4-chlorobenzoyl)-5-methoxy-2-methyl-1H-indol-3-yl}acetamide hydrochloride as a brown solid with a yield of 98%. The product was reacted with triethylamine (TEA) in dimethyl sulfoxide (DMSO) for 5 minutes at room temperature, and 2-{4-(7-nitrobenzo[1,2,5]oxadiazol-4-ylamino) phenyl}acetic acid succinimidyl ester was added. The reaction was allowed to continue for 16 hours at room temperature, producing Compound 27ii as a yellow solid (58% yield).

Compound 27qq: a Fluorescent Indo-Fluoresceinyl Analog: Compound 27qq, N-[(Fluorescein-6-carboxylamido) but-4-yl]-2-[1-(4-chlorobenzoyl)-5-methoxy-2-methyl-1H-indol-3-yl)acetamide was synthesized by the method outlined in FIG. 10. Briefly, Briefly, N-(4-aminobutyl)-2-[1-(4-chlorobenzoyl)-5-methoxy-2-methyl-1H-indol-3-yl]acetamide hydrochloride was reacted with dimethyl sulfoxide (DMSO) and triethylamine (TEA) for 5 minutes at room temperature. Fluorescein-6-carboxylic acid succinimidyl ester was added and the reaction was allowed to continue for 16 hours at room temperature. Compound 27qq was produced as a yellow solid (68% yield)

Compound 27uu: a Fluorescent Indo-Nile Blue Analog: Compound 27uu, N-[5-)1-{1-(4-chlorobenzoyl)-5-methoxy-2-methyl-1H-indol-3-yl}-2-6,9,12,15-tetraoxa-3-azaoctadecanamido]-9H-benzo[a]penoxazin-9-ylidene)-N-ethylethanaminium perchlorate, was synthesized by the method depicted in FIG. 11. Briefly, indomethacin was complexed with ter-butyl 1-amino-3,6,9,12-tetraoxapentadecan-15-oate for 16 hours at room temperature in the presence of 1-ethyl-3-(3'-dimethylaminopropyl)carbodiimide hydrochloride (EDCl), 1-hydroxybenzotriazole (HOBt), and N,N-diisopropylethylamine (DIPEA) in dichloromethane, after which trifluoroacetic acid was added and the reaction continued for 2 hours at room temperature. A pale yellow oil was produced at 59% yield. This pale yellow oil was reacted for 16 hours at room temperature with 1-ethyl-3-(3'-dimethylaminopropyl) carbodiimide hydrochloride (EDCl), 1-hydroxybenzotriazole (HOBt), and N,N-diisopropylethylamine (DIPEA) in dichloromethane to produce Compound 27uu as a blue solid (65% yield).

Compound 27vv: an Indo-6-ROX Analog: Compound 27vv was synthesized by the method outlined in FIG. 12. Briefly, N-(4-aminobutyl)-2-[1-(4-chlorobenzoyl)-5-methoxy-2-methyl-1H-indol-3-yl]acetamide hydrochloride was produced from indomethacin and tert-butyl 4-aminobutylcarbamate as described hereinabove. The 1-(4-aminobutyl)-2-{1-(4-chlorobenzoyl)-5-methoxy-2-methyl-1H-indol-3-yl}acetamide hydrochloride was reacted with dimethyl sulfoxide (DMSO) and triethylamine (TEA) for 5 minutes at room temperature, and the product of this reaction was then complexed with 6-carboxy-X-rhodamine succinimidyl ester (6-ROX SE) for 16 hours at room temperature in DMSO. Compound 27vv was produced as a blue solid (64% yield). Compound 27vv was characterized by NMR, two-dimensional NMR, and mass spectroscopy.

Compound 27eee: an Indo-5-ROX Analog: Compound 27eee was synthesized by the method outlined in FIG. 13. Briefly, Compound 27eee was synthesized using the same strategy as Compound 27vv, except that 6-carboxy-X-rhodamine succinimidyl ester (6-ROX SE) was substituted by 5-carboxy-X-rhodamine succinimidyl ester (5-ROX SE).

Compound 27eee was produced as a blue solid (60% yield). Compound 27eee was characterized by NMR, two-dimensional NMR, and mass spectroscopy.

Compound 27iii: a Fluorescent Indo-Sulforhodaminyl Analog: Compound 27iii, 5-(N-(23-(1-(4-chlorobenoyl)-5-methoxy-2-methyl-1H-indol-3-yl)-15,22-dioxo-3,6,9,12-tetraoxa-16,21-diazatricosyl)sulfamoyl)-2-(6-(diethylamino)-3-(diethyliminio)-3H-xanthen-9-yl)benzenesulfonate, was synthesized by the method outlined in FIG. 14. Briefly, ter-butyl 1-amino-3,6,9,12-tetraoxapentadecan-15-oate was reacted at room temperature for 16 hours with 5-(chlorosulfonyl)-2-(6-(diethylamino)-3-(diethyliminio)-3H-xanthen-9-yl)benzenesulfonate in the presence of triethylamine (TEA) and dichloromethane, after which trifluoroacetic acid was added and the reaction allowed to continue for 2 hours at room temperature to produce 5-(N-(14-carboxy-3,6,9,12-tetraoxatetradecyl)sulfamoyl)-2-(6-(diethylamino)-3-(diethyliminio)-3H-xanthen-9-yl)benzenesulfonate as a dark red solid with 30% yield. The dark red solid was then reacted for 16 hours at room temperature with N-(4-Aminobutyl)-2-{1-(4-chlorobenzoyl)-5-methoxy-2-methyl-1H-indol-3-yl}acetamide hydrochloride in the presence of O—(N-succinimidyl)-1,1,3,3-tetramethyluronium tetrafluoroborate (TSTU) and triethylamine (TEA) to produce Compound 27iii as a dark red solid (70% yield).

Compound 27qqq: an Indo-NIR Dye Analog: Compound 27qqq was synthesized by the method outlined in FIG. 15. Briefly, N-(4-aminobutyl)-2-[1-(4-chlorobenzoyl)-5-methoxy-2-methyl-1H-indol-3-yl]acetamide hydrochloride was reacted with dimethyl sulfoxide (DMSO) and triethylamine (TEA) for 5 minutes at room temperature. The product of this reaction was then complexed with NIR664 succinimidyl ester by incubation at room temperature for 2 days in DMSO to produce Compound 27qqq as a blue solid (68% yield). A similar strategy employing an NIR700 succinimidyl ester was employed to produce Compound 27ttt. Compound 27qqq was characterized by NMR and mass spectroscopy.

A poly ethylene glycol (PEG4) tether (linker 10, FIG. 16) was added between INDO and Taxol moieties to generate Compound 27b. This molecule showed a sleight inhibition (25%) for COX-2 with no inhibition for COX-1. However, the INDOPEG4-acid was a non-selective COX inhibitor having an $IC_{50}$ of 4 µM for COX-1.

When PEG-4 linker was replaced by linker 8 (FIG. 16), a monoamido-diester conjugate, Compound 27c, was formed, which inhibited COX-2 selectively ($IC_{50}$ COX-2=2.2 µM) with an insufficient potency. However, the INDO-alkanol was a highly potent and selective COX-2 inhibitor and the corresponding succinyl-derivative was a potent non-selective COX-inhibitor. The potency was dramatically increased with Compound 27d where a phenylelenediamido-monoester linker was used between indomethacin and taxol. This compound showed highly potent and selective inhibition of COX-2 with an $IC_{50}$ at 254 nM concentration. The Compound 27d was synthesized from the reaction of indomethacin with 4-{(N-BOC)aminomethyl}aniline in the presence of ethyl-1-{3-(dimethylamino)propyl}-3-ethylcarbodiimide (EDCl) followed by treatment with HCl (gas) to give the corresponding INDO-phenylenamidomethylamine hydrochloride salts. This INDO-phenylenamidomethylamine hydrochloride was reacted with succinic anhydride to form the corresponding succinyl-derivative, which was esterified with taxol to give the target Compound 27d.

Conjugation of indomethacin with doxorubicin or mitomycin C using a PEG4 linker gave conjugates Compounds 27e and 27f. Unfortunately, they showed little inhibitory activity against COX enzymes.

Retinoic acids are ligands for retinoic acid receptor and act as a transcription factor to regulate the growth and differentiation of normal and malignant cells. The 13-cis-retinoic acid is being used to treat severe acne. It is also been used in the prevention of certain skin cancers. Therefore, it was decided to conjugate 13-cis-retinoic acid and all-trans retinoic acid with indomethacin using ethylenediamide linkage.

The conjugate chemistry afforded Compounds 27g and 27h. Interestingly, both the compounds inhibited COX-2 in a highly selective fashion. The 13-cis-retinoic acid conjugate Compound 27g showed inhibitory activity against COX-2 with an $IC_{50}$ at 454 nM concentration. A dramatic increase in potency was observed with all-trans-retinoic acid conjugate Compound 27h, which inhibited COX-2 in a highly selective manner with an $IC_{50}$ of 107 nM. The reaction of indomethacin with mono BOC-protected ethylenediamine in the presence of ethyl-1-[3-(dimethylamino)propyl]-3-ethylcarbodiamide (EDCl) followed by treatment with HCl (gas) gave the corresponding INDO-amidoethylamine hydrochloride salts, which was treated with DIPEA followed by a coupling reaction with 13-cis-retinoic acid using EDCl, HOBt, and DIPEA to give the target Compound 27g in 65% yield. The all-trans-retinoic acid conjugate Compound 27h was synthesized in a similar manner. In addition, 13-cis retinoic acid conjugate Compound 27i having an amidoester linkage was synthesized, which inhibited COX-2 selectively (COX-2 $IC_{50}$=107 nM).

An in vitro metabolism study was performed with Compound 27i using 1483 HNSCC cells to check the enzymatic (esterase) hydrolysis of the conjugate and identify metabolites up to 24 hours (h). Using a C-12 RP-HPLC, the disappearance of the parent conjugate Compound 27i was assayed ($t_{1/2}$=5.5 hour; Compound 27i remained 25% up to 24 hours). As expected, the concentration of alcohol was gradually increased up to 75% at 24 hours.

In addition, INDO-sulfathiazole conjugate Compound 27j, also described in EXAMPLE 1 containing a triamide linker was synthesized, which showed selective COX-2 inhibition (COX-2 $IC_{50}$=960 nM). This compound was synthesized from the reaction of succinyl sulfathiazole and INDO-amidobutylamine using TSTU coupling reagent. Succinyl sulfathiazole was synthesized from the reaction of sulfathiazole and succinic anhydride using TEA as a base. Unfortunately, the piperazine tethered conjugate Compound 27k showed no COX inhibitory activity. Both mycophenolic acid conjugate Compound 27l and camptothecin conjugate Compound 27m showed slight inhibition for COX-2 with no inhibition for COX-1.

Podophyllotoxin is a topoisomerse II inhibitor. Etoposide or teniposide are the derivatives of podophyllotoxin and used in the clinic for the treatment of lung cancer, testicular cancer, lymhoma, non-lymphocytic leukemia, glioblasma, etc. Accordingly, podophyllotoxin was selected for conjugation with indomethacin, reverse-indomethacin, and celecoxib analogs. Podophyllotoxin conjugated reverse-indomethacin (Compound 28a) or carboxyl derivatives of celecoxib (Compounds 29a and 30a) were found to be inactive against COX isozymes. However, when podophyllotoxin was conjugated with indomethacin through a diamido-ester linkage to form Compound 27n, COX-2 selective COX-2 inhibition was observed (COX-2 $IC_{50}$=295 nM). A decrease of potency was estimated with the conjugate Compound 27o when the conjugate was formed with a two-carbon shorter linker (COX-2 $IC_{50}$=475 nM).

The potency was recovered with Compound 27p upon incorporation of an n-butylamido-diester linkage between INDO and podophyllotoxin (Compound 27p, COX-2

IC$_{50}$=147 nM). A slight decrease of potency was observed with the conjugate Compound 27q, where a chain that was two carbons shorter was employed, which showed selective COX-2 IC$_{50}$ at 254 nM concentration. Interestingly, replacement of n-butylamido-diester linkage (of Compound 27p) with diamidophenylene-monoester gave Compound 27r, which inhibited COX-2 with a high potency and selectivity (COX-2 IC$_{50}$ of 187 nM) comparable to Compound 27p.

In conclusion, indomethacin, rev-indomethacin, and carboxyl-celecoxibs were conjugated with taxol, doxorubicin, mitomycin C, retinoic acids, mycophenolic acid, sulfathioazole, camptothecin, and podophyllotoxin using alkyl, PEG, aryl, or piperazine tethers containing amido/ester linkages. A SAR-study identified Compounds 27i (COX-2 IC$_{50}$ at 107 nM), 27p (COX-2 IC$_{50}$ at 147 nM), 27r (COX-2 IC$_{50}$ at 187 nM), 27d (COX-2 IC$_{50}$ at 254 nM) and 27q (COX-2 IC$_{50}$ at 254 nM) as particularly promising compounds of the series. In an in vitro metabolism study of Compound 27i with 1483 HNSCC cells, selectively hydrolyzed products were characterized by RP-HPLC analysis.

3-[1-{p-(methanesulfonyl)phenyl}-5-p-tolyl-1H-pyrazol-3-yl]propanoic acid (Compound 27e). 3-[1-{p-(methanesulfonyl)phenyl}-5-p-tolyl-1H-pyrazol-3-yl]propanoic acid (Compound 27e) was synthesized essentially as described in Murry et al. (1991) *Synthesis* 1, 18-20. Briefly, p-methanesulfonylphenyl hydrazine hydrochloride (10 mmol) was added to a stirred solution of p-tolyl-4,6-dioxohexanoic acid (10 mmol) in MeOH (75 mL), followed by the addition of TEA (10 mmol) and stirred for 16 h at 25° C. The mixture was then concentrated in vacuo to a residue, which was partitioned between Et2O (75 mL) and 5% aq HCl (75 mL). The ether layer was separated, washed with 5% aq HCl (2×20 mL), and brine (20 mL), dried (Na2SO4, 500 mg), filtered and concentrated to a residue. The crude residue was purified using a silica gel gravity column chromatography (35:7:1 CHCl$_3$:MeOH:NH$_4$OH) to give 3-[1-{p-(methanesulfonyl)phenyl}-5-p-tolyl-1H-pyrazol-3-yl]propanoic acid as a yellow solid (Compound 27e; 76%). $^1$H NMR (500 MHz, CDCl3) δ 2.36 [s, 3H, CH$_3$ (tolyl)], 2.78 (t, J=7.9 Hz, 2H, CH$_2$), 3.00-3.08 (m, 5H, SO$_2$CH$_3$ and CH$_2$), 6.33 (s, C=CH), 7.05 (d, J=8.5 Hz, 2H, p-tolyl H-3, H-5), 7.12 (d, J=8.5 Hz, 2H, p-tolyl H-2, H-6), 7.45 [d, J=8.8 Hz, 2H, p-(methanesulfonyl)phenyl H-2, H-6], 7.85 (d, J=8.8 Hz, 2H, p-(methanesulfonyl)phenyl H-3, H-5), 12.15 (s, 1H, CO$_2$H. Mass (ESI) (M+1) calcd for C$_{20}$H$_{20}$N$_2$O$_4$S 385.11; found 385.00.

3-[1-{p-(Sulfonamido)phenyl}-5-p-tolyl-1H-pyrazol-3-yl]propanoic acid (Compound 30c). A mixture of p-tolyl-4,6-dioxohexanoic acid (20 mmol), p-(sulfonamido)phenyl hydrazine hydrochloride (20 mmol), and TEA (20 mmol) in MeOH (150 mL) was stirred at 25° C. for 16 h. The mixture was then concentrated in vacuo to a residue, which was partitioned between Et$_2$O (150 mL) and 5% aq HCl (150 mL). The ether layer was separated, washed with 5% aq HCl (2×40 mL), and brine (40 mL), dried (Na$_2$SO$_4$, 1 g), filtered and concentrated to a residue. The crude residue was purified using a silica gel gravity column chromatography (35:7:1 CHCl$_3$:MeOH:NH$_4$OH) to give 3-[1-{p-(sulfonamido)phenyl}-5-p-tolyl-1H-pyrazol-3-yl]propanoic acid (Compound 30c) as a yellow solid (70%). $^1$H NMR (500 MHz, DMSO-d6) δ 2.30 [s, 3H, CH$_3$ (tolyl)], 2.65 (t, J=8.0 Hz, 2H, CH$_2$), 2.87 (t, J=8.0 Hz, 2H, CH$_2$), 6.47 (s, C=CH), 7.10 (d, J=8.6 Hz, 2H, p-tolyl H-3, H-5), 7.20 (d, J=8.6 Hz, 2H, p-tolyl H-2, H-6), 7.37 [d, J=8.9 Hz, 2H, p-(sulfonamido)phenyl H-2, H-6], 7.42 (s, 2H, SO$_2$NH$_2$), 7.75 (d, J=8.9 Hz, 2H, p-(sulfonamido)phenyl H-3, H-5), 10.42 (s, 1H, CO$_2$H). Mass (ESI) (M−1) calcd for C$_{19}$H$_{19}$N$_3$O$_4$S 384.11; found 384.28.

N-(4-Hydroxybutyl)-2-{1-(4-chlorobenzoyl)-5-methoxy-2-methyl-1H-indol-3-yl}acetamide. To a stirred solution of indomethacin (3.57 g, 10 mmol) in DMF was added 4-hydroxybutylamine (4.64 g), HOBt (2.02 g, 15 mmol), DIPEA (3.88 g, 30 mmol), EDCl (2.10 g, 11 mmol) at 25° C. The resultant solution was stirred for 16 h at 25° C. Removal of solvent in vacuo afforded a residue, where 100 mL water was added and extracted with EtOAc (3×75 mL). Combined organic layers were dried over Na$_2$SO$_4$. Solvent was evaporated completely and the obtained mass was dissolved in CH$_2$Cl$_2$ (40 mL), then HCl (gas) was bubbled for 2 h at 25° C. Removal of solvent in vacuo afforded a yellow residue, where n-hexane was added (20 mL) and stirred for 30 min to a make good slurry, which was filtered to afford the desired N-(4-hydroxybutyl)-2-[1-(4-chlorobenzoyl)-5-methoxy-2-methyl-1H-indol-3-yl]acetamide as yellow solid (2.5 g, 70%). $^1$H NMR (500 MHz, DMSO-d6) δ 1.44-1.52 (m, 2H, CCH$_2$CC), 1.53-1.59 (m, 2H, CCCH$_2$C), 2.23 (s, 3H, CH$_3$), 3.03-3.08 (m, 2H, CH$_2$CCC), 3.52 (s, 2H, CH$_2$CO), 3.75 (s, 3H, OCH$_3$), 3.77-3.78 (m, 2H, CCCCH$_2$), 4.53 (br s, 1H, OH), 6.684 (dd, J=9, 2.4 Hz, 1H, indolyl H-6), 6.916 (d, J=9 Hz, 1H, indolyl H-7), 7.144 (d, J=2.4 Hz, 1H, indolyl H-4), 7.64 (d, J=8.7 Hz, 2H, p-chlorobenzoyl H-3, H-5), 7.67 (d, J=8.7 Hz, 2H, p-chlorobenzoyl H-2, H-6), 8.24 (br s, 1H, NHCO). Mass (ESI) (M+Na) calcd for C$_{23}$H$_{25}$ClN$_2$O$_4$Na 451.15; found 451.04.

Succinylpodophyllotoxin. Succinic anhydride (0.9 g) was added to a solution of podophyllotoxin (207.2 mg, 0.5 mmol) in pyridine (12 mL). The resultant reaction mixture was stirred for 16 h at 25° C. Removal of solvent in vacuo afforded a residue. The crude residue was purified using a silica gel gravity column chromatography (35:7:1 CHCl$_3$:MeOH:NH$_4$OH) to give succinylpodophyllotoxin as white solid (198.5 mg, 80%) $^1$H NMR (500 MHz, DMSO-d6) δ 2.10 (d, J=5.4 Hz, 1H, H-4), 2.32 (dd, J=12.6, 4.8 Hz, 1H, H-2), 2.53 (m, 1H, H-3), 3.52 (s, 3H, OMe H-4'), 3.65 (dd, J=10.5, 7.5 Hz, 2H, H-11), 3.82 (s, 6H, two OMe groups, H-3' and H-5'), 4.15 (t, J=7.9 Hz, 2H, CH2), 4.26 (t, J=7.9 Hz, 2H, CH2), 4.51 (d, J=5.4 Hz, 1H, H-1), 5.89 (s, 2H, OCH$_2$), 6.00 (s, 2H, H-2', H-6'), 6.67 (s, 1H, H-8), 6.94 (s, 1H, H-5), 12.15 (s, 1H, CO$_2$H). Mass (ESI) (M−1) calcd for C$_{26}$H$_{26}$N$_2$O$_{11}$ 513.15; found 512.93.

Compound 27P. To a stirred solution succinylpodophyllotoxin (51 mg, 0.1 mmol) in CH$_2$Cl$_2$ was added EDCl (25 mg, 0.13 mmol) and DMAP (2 mg) at 25° C. followed by N-(4-hydroxybutyl)-2-[1-(4-chlorobenzoyl)-5-methoxy-2-methyl-1H-indol-3-yl]acetamide (43 mg, 0.1 mmol). The resultant solution was stirred for 16 h at 25° C. Removal of solvent in vacuo afforded a residue, which was purified using a silica gel gravity column chromatography (35:7:1 CHCl$_3$:MeOH:NH$_4$OH) to give the target conjugate Compound 27p in (27 mg) 55% yield. $^1$H NMR (500 MHz, DMSO-d6) δ 1.42-1.47 (m, 2H, CCH$_2$CC), 1.50-1.55 (m, 2H, CCCH$_2$C), 2.12 (d, J=5.4 Hz, 1H, podoH-4), 2.24 (s, 3H, CH3), 2.34 (dd, J=12.6, 4.8 Hz, 1H, podoH-2), 2.51 (m, 1H, podoH-3), 3.05-3.09 (m, 2H, CH$_2$CCC), 3.57 (s, 3H, podo-OMe (H-4')), 3.66 (dd, J=10.5, 7.5 Hz, 2H, podoH-11), 3.75 (s, 2H, CH$_2$CO), 3.79 (s, 3H, OCH$_3$), 3.84 (s, 6H, two podo-OMe groups, (H-3' and H-5')), 3.79 (s, 3H, OCH$_3$), 4.17 (t, J=7.9 Hz, 2H, succinylCH$_2$), 4.22 (t, J=7.9 Hz, 2H, succinylCH$_2$), 4.23-4.33 (m, 2H, CCCCH$_2$), 4.55 (d, J=5.4 Hz, 1H, podoH-1), 5.99 (s, 2H, podo-OCH$_2$O), 6.12 (s, 2H, podoH-2', podoH-6'), 6.57 (s, 1H, podoH-8), 6.67 (dd, J=9, 2.4 Hz, 1H, indolyl H-6), 6.85 (s, 1H, podoH-5), 6.92 (d, J=9 Hz, 1H, indolyl H-7), 7.15 (d, J=2.4 Hz, 1H, indolyl H-4), 7.64 (d, J=8.8 Hz, 2H, p-chlorobenzoyl H-3, H-5), 7.87 (d, J=8.8 Hz, 2H, p-chlorobenzoyl H-2, H-6), 8.54 (m, 1H, NHCO). Mass (ESI) (M+Na) calcd for C$_{49}$H$_{49}$ClN$_2$O$_{14}$ 947.29; found 947.27.

Structures, inhibitory profiles, and fluorescence data for representative diagnostic agents are presented in Table 3 below.

TABLE 3

Structures, Inhibitory Profiles, and Fluorescence Data for Representative Diagnostic Agents

| Cmpnd No. | Structure | $IC_{50}$ (nM)* COX-2 | $IC_{50}$ (nM)* COX-1 | $IC_{50}$ (nM)** COX-2 | $IC_{50}$ (nM)** COX-1 | Fluor.*** $\lambda_{ex}$ $\lambda_{em}$ |
|---|---|---|---|---|---|---|
| | Dansyl Analogs | | | | | |
| 27x | | 66 | >25000 | 30 | >1000 | 355 nm 493 nM |
| 27y | | 75 | >25000 | 40 | >1000 | 343 nm 497 nm |
| 27z | | 67 | >25000 | 60 | >1000 | 324 nm 504 nm |

TABLE 3-continued

Structures, Inhibitory Profiles, and Fluorescence Data for Representative Diagnostic Agents

| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |

Dabsyl Analogs

| 27aa | | 80 | >25000 | 180 | >2500 | 390 nm 450 nm |
| 27bb | | 134 | 214 | n.d. | n.d. | n.d. |

Coumarinyl Analogs

| 27cc | | 789 | >25000 | 100 | >25000 | 340 nm 405 nm |

TABLE 3-continued

Structures, Inhibitory Profiles, and Fluorescence Data for Representative Diagnostic Agents

| Cmpnd No. | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|
| 27dd | >25000 | >25000 | n.d. | n.d. | n.d. |
| 27ee | 600 | >25000 | n.d. | n.d. | n.d. |
| 27ff | 31 | >25000 | n.d. | n.d. | n.d. |
| 27gg | 53 | >25000 | n.d. | n.d. | n.d. |

TABLE 3-continued
Structures, Inhibitory Profiles, and Fluorescence Data for Representative Diagnostic Agents
| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |
| 28b | 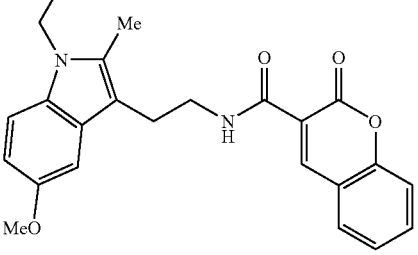 | >25000 | >25000 | n.d. | n.d. | n.d. |
Cinnamyl Analog
| 27hh | 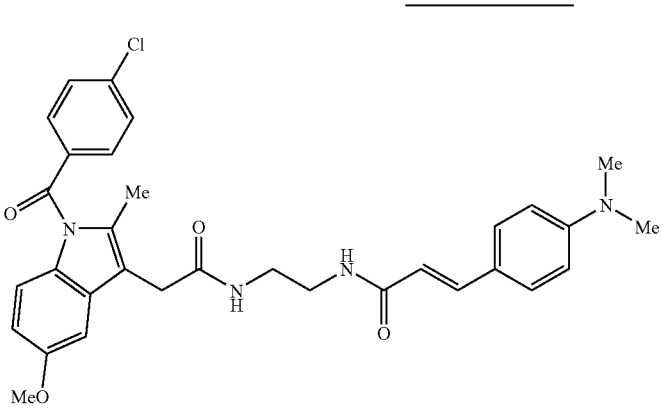 | 510 | >25000 | n.d. | n.d. | n.d. |
NBD Analogs
| 27ii | 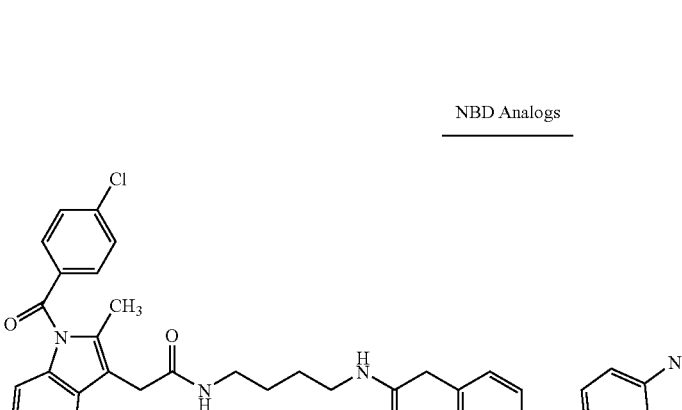 | 500 | >25000 | 570 | >10000 | 492 nm 605 nm |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 28c | | >25000 | >25000 | n.d. | n.d. | n.d. |

Fluoresceinyl Analogs

| 27jj | | >25000 | 5351 | n.d. | n.d. | n.d. |
| 27kk | | >25000 | >25000 | n.d. | n.d. | n.d. |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27ll | | 3100 | >25000 | n.d. | n.d. | n.d. |
| 27mm | | 3200 | 22500 | n.d. | n.d. | n.d. |
| 27nn | | 2900 | 10400 | n.d. | n.d. | n.d. |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27oo | | >25000 | >25000 | n.d. | n.d. | n.d. |
| 27pp | | >25000 | >25000 | n.d. | n.d. | n.d. |

TABLE 3-continued

Structures, Inhibitory Profiles, and Fluorescence Data for Representative Diagnostic Agents

| Cmpnd No. | | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27qq | [structure] | >25000 | >25000 | 188 | >5000 | n.d. |
| 27rr | [structure] | >25000 | >25000 | n.d. | n.d. | n.d. |
| 27ss | [structure] | >25000 | >25000 | n.d. | n.d. | n.d. |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27tt | | >25000 | >25000 | n.d. | n.d. | n.d. |
| 28d | | >25000 | >25000 | n.d. | n.d. | n.d. |

TABLE 3-continued
Structures, Inhibitory Profiles, and Fluorescence Data for Representative Diagnostic Agents
| Cmpnd No. | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|
| Nile Blue Analogs | | | | | |
| 27uu | 1700 | >25000 | 85 | >25000 | 618 nm 670 nm |
| 29g | >25000 | >25000 | n.d. | n.d. | n.d. |
| Carboxyrhodaminyl Analogs | | | | | |
| 27vv | 3500 | >25000 | 360 | >5000 | 581 nm 603 nm |
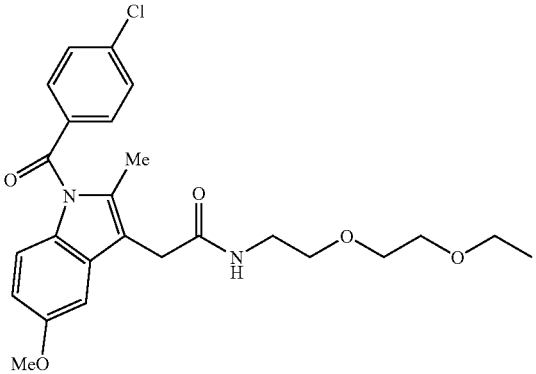
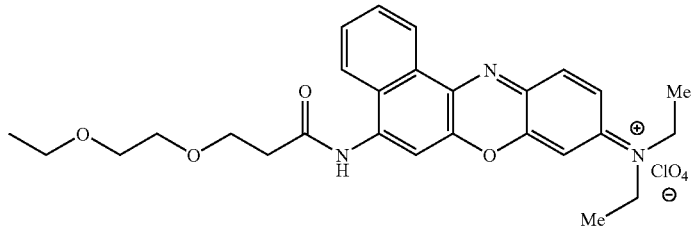
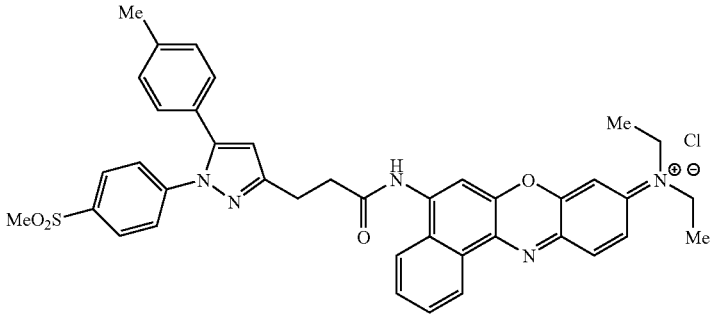
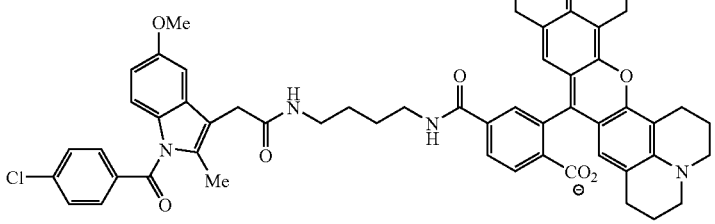

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27ww | | >25000 | >25000 | n.d. | n.d. | n.d. |
| 27xx | | >25000 | >25000 | n.d. | n.d. | n.d. |
| 27yy | | >25000 | >25000 | n.d. | n.d. | n.d. |

TABLE 3-continued

Structures, Inhibitory Profiles, and Fluorescence Data for Representative Diagnostic Agents

| Cmpnd No. | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|
| 27zz | >25000 | >25000 | n.d. | n.d. | n.d. |
| 27aaa | 3900 | >25000 | n.d. | n.d. | n.d. |
| 27bbb | >25000 | >25000 | n.d. | n.d. | n.d. |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27ccc | | >25000 | >25000 | n.d. | n.d. | n.d. |
| 27ddd | | >25000 | 1800 | n.d. | n.d. | n.d. |

TABLE 3-continued
Structures, Inhibitory Profiles, and Fluorescence Data for Representative Diagnostic Agents
| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |
| 27eee[1] | 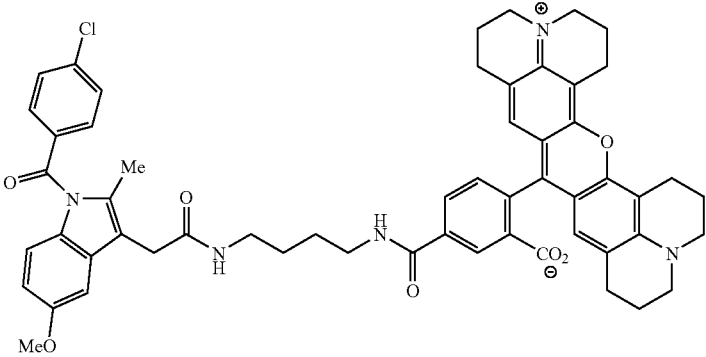 | 700 | >25000 | 320 | >5000 | n.d. |
| 27fff | 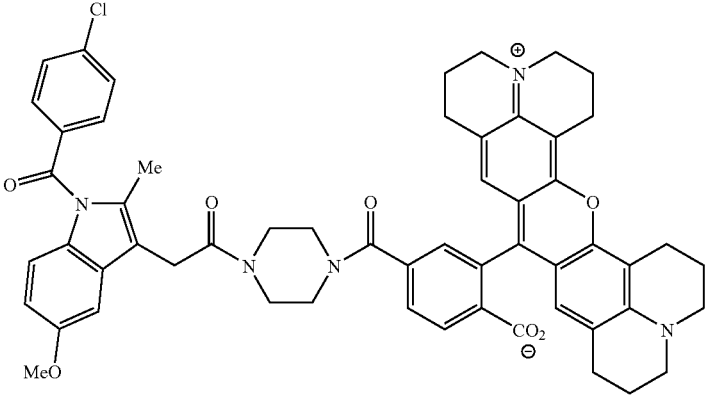 | >25000 | >25000 | n.d. | n.d. | n.d. |
| 27ggg | 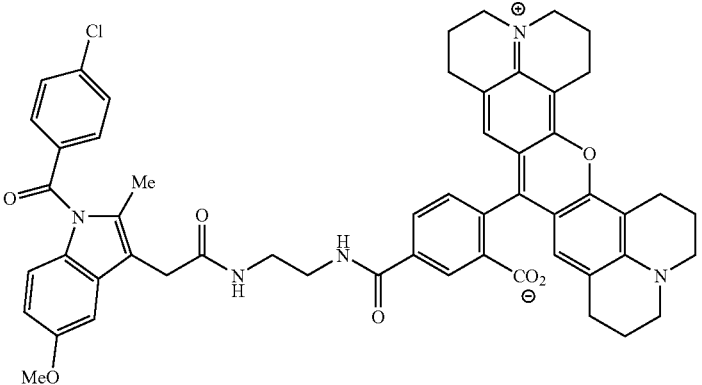 | 2800 | 500 | n.d. | n.d. | n.d. |

TABLE 3-continued

Structures, Inhibitory Profiles, and Fluorescence Data for Representative Diagnostic Agents

| Cmpnd No. | IC$_{50}$ (nM)* | | IC$_{50}$ (nM)** | | Fluor.*** $\lambda_{ex}$ $\lambda_{em}$ |
|---|---|---|---|---|---|
| | COX-2 | COX-1 | COX-2 | COX-1 | |
| 27hhh | 1300 | 5800 | n.d. | n.d. | n.d. |
| 28e | >25000 | >25000 | n.d. | n.d. | n.d. |
| 28f | >25000 | >25000 | n.d. | n.d. | n.d. |
| 29h | >25000 | >25000 | n.d. | n.d. | n.d. |

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 30e | | >25000 | >25000 | n.d. | n.d. | n.d. |
| 32 | | >25000 | >25000 | n.d. | n.d. | n.d. |

Sulforhodaminyl Analogs

| | | | | | | |
|---|---|---|---|---|---|---|
| 27iii | | 160 | >25000 | 2000 | >5000 | 571 nm 293 nm |

TABLE 3-continued
Structures, Inhibitory Profiles, and Fluorescence Data for Representative Diagnostic Agents
| Cmpnd No. | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|
| 27jjj | 1200 | >25000 | n.d. | n.d. | n.d. |
| 27kkk | 1100 | >25000 | n.d. | n.d. | n.d. |
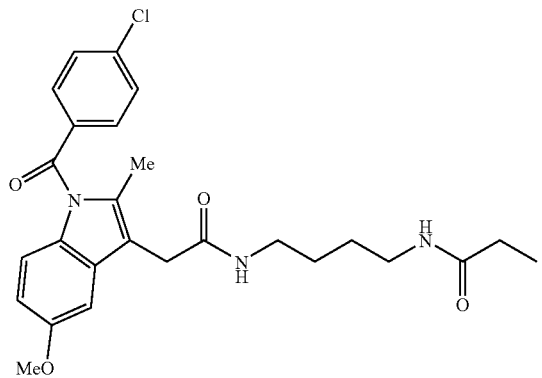
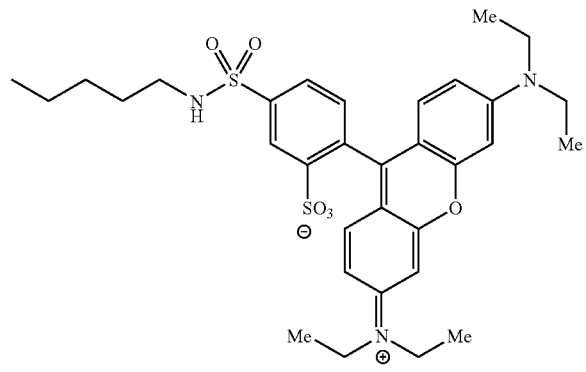
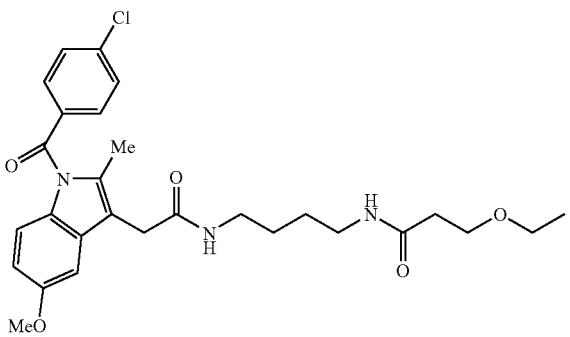
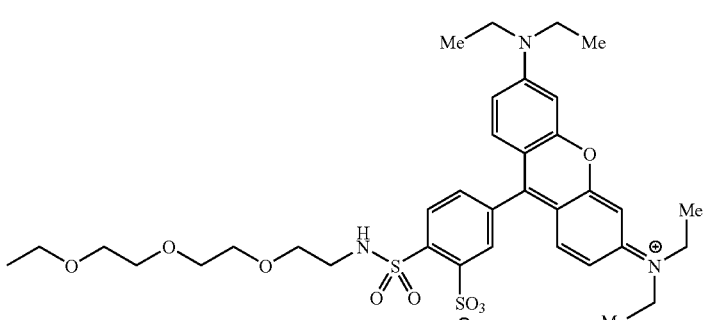

TABLE 3-continued

Structures, Inhibitory Profiles, and Fluorescence Data for Representative Diagnostic Agents

| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |
| 27lll | | >25000 | >25000 | n.d. | n.d. | n.d. |
| 30f | | 25000 | >25000 | 500 (M) | >5000 (M) | n.d. |
| | Alexa Fluor Analog | | | | | |
| 27mmm | | >25000 | >25000 | n.d. | n.d. | n.d. |

TABLE 3-continued

Structures, Inhibitory Profiles, and Fluorescence Data for Representative Diagnostic Agents

| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |

Cy Analogs

| 27nnn | >25000 | >25000 | n.d. | n.d. | n.d. |
|---|---|---|---|---|---|

| 27ooo | 1400 | >25000 | n.d. | n.d. | n.d. |
|---|---|---|---|---|---|

TABLE 3-continued
Structures, Inhibitory Profiles, and Fluorescence Data for Representative Diagnostic Agents
| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |
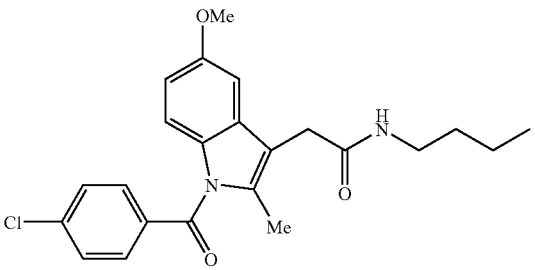
NIR Analogs
| 27ppp | 500 | 3400 | n.d. | n.d. | n.d. |
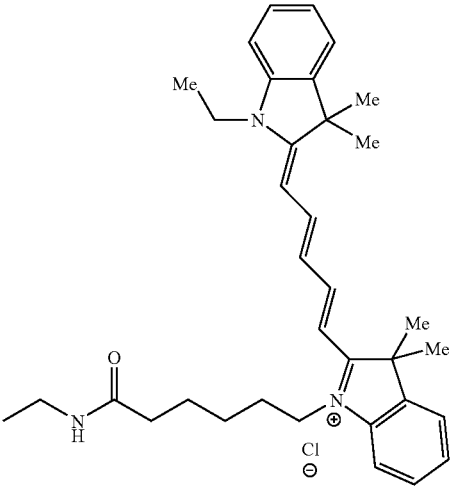

TABLE 3-continued

Structures, Inhibitory Profiles, and Fluorescence Data for Representative Diagnostic Agents

| Cmpnd No. | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|
| 27qqq | 500 | >25000 | n.d. | n.d. | n.d. |
| 27rrr | >25000 | >25000 | n.d. | nd. | n.d. |

TABLE 3-continued
Structures, Inhibitory Profiles, and Fluorescence Data for Representative Diagnostic Agents
| Cmpnd No. | | IC$_{50}$ (nM)* | | IC$_{50}$ (nM)** | | Fluor.*** $\lambda_{ex}$ $\lambda_{em}$ |
|---|---|---|---|---|---|---|
| | | COX-2 | COX-1 | COX-2 | COX-1 | |
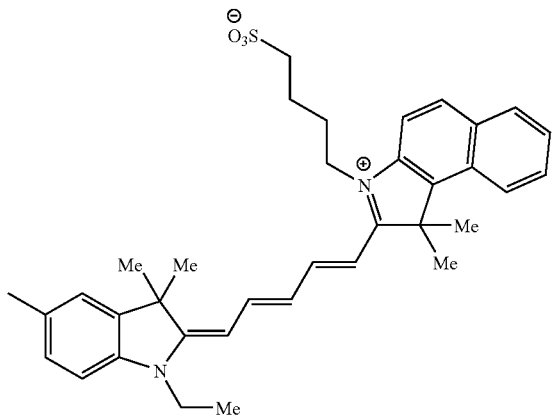
| 27sss | >25000 | >25000 | n.d. | n.d. | n.d. |
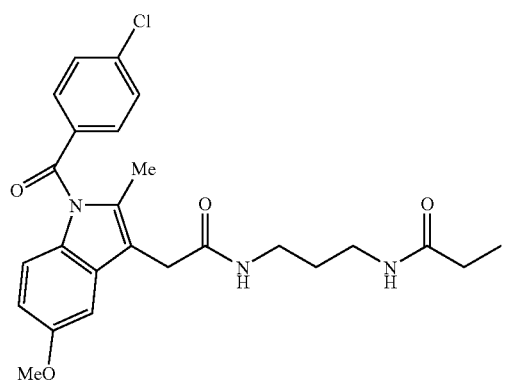
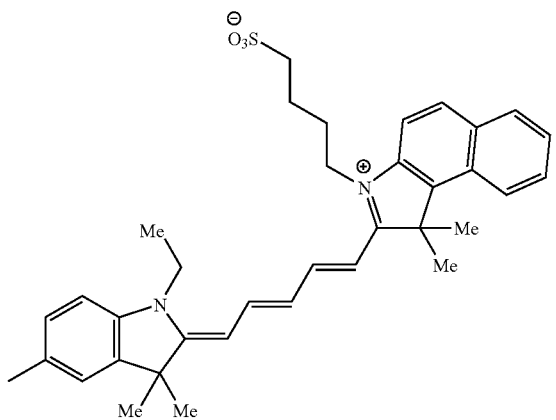

TABLE 3-continued

Structures, Inhibitory Profiles, and Fluorescence Data for Representative Diagnostic Agents

| Cmpnd No. | Structure | IC$_{50}$ (nM)* COX-2 | IC$_{50}$ (nM)* COX-1 | IC$_{50}$ (nM)** COX-2 | IC$_{50}$ (nM)** COX-1 | Fluor.*** $\lambda_{ex}$ $\lambda_{em}$ |
|---|---|---|---|---|---|---|
| 27ttt | | 1000 | >25000 | 890 | >5000 | 710 nm 731 nm |
| 27uuu | | >25000 | >25000 | n.d. | n.d. | n.d. |

TABLE 3-continued

Structures, Inhibitory Profiles, and Fluorescence Data for Representative Diagnostic Agents

| Cmpnd No. | IC$_{50}$ (nM)* | | IC$_{50}$ (nM)** | | Fluor.*** $\lambda_{ex}$ $\lambda_{em}$ |
|---|---|---|---|---|---|
| | COX-2 | COX-1 | COX-2 | COX-1 | |
| 27vvv | 3000 | 3000 | n.d. | n.d. | n.d. |

*Assayed against purified enzymes;
**Assayed in a macrophage assay;
***Fluorescence in buffer;
n.d.: not determined.
(1)also had an COX-2 IC$_{50}$ in 1483 Cells of 92 nM.

Example 3

IC$_{50}$ Determinations Using Purified Enzymes

Cyclooxygenase activity of ovine COX-1 (44 nM) or human COX-2 (130 nM) was assayed by TLC. Reaction mixtures of 200 μL consisted of hematin-reconstituted protein in 100 mM Tris-HCl, pH 8.0, 500 μM phenol, and [1-$^{14}$C]-arachidonic acid (50 μM, ~55-57 mCi/mmol; PerkinElmer Life And Analytical Sciences, Inc., Wellesley, Mass., United States of America). For the time-dependent inhibition assay, hematin-reconstituted protein was preincubated at room temperature for 17 minutes and then at 37° C. for 3 minutes with varying concentrations of the presently disclosed compositions in DMSO followed by the addition of [1-$^{14}$C]-arachidonic acid (50 μM) for 30 seconds at 37° C. Reactions were terminated by solvent extraction in Et$_2$O/CH$_3$OH/1 M citrate, pH 4.0 (30:4:1). The phases were separated by centrifugation at 2000 g for 5 minutes and the organic phase was spotted on a 20×20 cm TLC plate (Lieselgel 60, EMD Chemicals, Inc., Gibbstown, N.J., United States of America). The plate was developed in EtOAc/CH$_2$Cl$_2$/glacial AcOH (75:25:1) at 4° C. Radiolabeled prostanoid products were quantitatively determined with a radioactivity scanner available from Bioscan, Inc. (Washington, D.C., United States of America). The percentage of total products observed at different concentrations of the presently disclosed compositions was divided by the percentage of products observed for protein samples preincubated for the same amount of time with DMSO.

Example 4

In Vitro Cell Imaging Assays with Representative Indo-ROX Analogs

RAW264.7 cells (a line established from a tumor induced in a mouse by Abelson murine leukemia virus and available from the American Type Culture Collection, Manassas, Va., United States of America) were grown overnight on 35 mm culture dishes (MatTek Corp., Ashland, Mass., United States of America) with glass coverslips in Dulbecco's Modified Eagle Medium (DMEM) plus 10% heat-inactivated fetal bovine serum (FBS). Platings of cells were done in order to reach 30% confluency the next day. After overnight growth, the growth medium was replaced with 2 ml serum-free DMEM per dish. Individual dishes then received 200 ng/ml LPS plus 10 units/ml murine IFNγ (Roche Applied Science, Indianapolis, Ind., United States of America) for 6 hours to induce COX-2. After 6 hours, certain dishes were treated with 200 nM Compound 27vv (IC$_{50}$=360 nM) or 200 nM Compound 27ww, which differs from Compound 27vv in that the latter has a tether that is shorter by 2 methylenes, for 30 minutes at 37° C. After 30 minutes, the cells were washed briefly three times in medium and incubated in Hank's balanced salt solution (HBSS)/Tyrode's for 60 minutes at 37° C. After 60 minutes, the HBSS/Tyrode's was removed and fresh HBSS/Tyrode's was added. The cells were immediately imaged using a Zeiss Axiovert 25 Microscope (propidium iodide filter/2-3 sec exposure/gain of 2).

LPS activation enhanced imaging of RAW264.7 cells by Compound 27vv, whereas pretreatment with indomethacin (20 μM) reduced the fluorescent signal. No fluorescence above background was observed with Compound 27ww.

A second experimental design employed HEK293 cells (a cell line generated by transformation of human embryonic kidney cell cultures with adenovirus) that had been transformed with an expression construct encoding a constitutively active human COX-2. For imaging experiments, cells were also plated on 35 mm culture dishes (MatTek Corp., Ashland, Mass., United States of America) with glass coverslips and grown to 70% confluency in DMEM plus 20% FBS. When the appropriate confluency was reached (approximately 48 hours after plating), the medium was replaced with DMEM/1% FBS and exposed to 200 nM Compound 27vv or Compound 27ww as described hereinabove. After 30 minutes, the cells were washed briefly 3 times and incubated in DMEM/10% FBS for 60 minutes at 37° C. After 60 minutes, the medium was removed and the cells were washed with HBSS/Tyrode's. After the second wash, fresh HBSS/Tyrode's was added and the cells were immediately imaged using a Zeiss Axiovert 25 Microscope (propidium iodide filter/3 sec exposure/gain of 3). Exposure to Compound 27vv resulted in clearly observable fluorescent staining of COX-2-transformed HEK293 cells, which was also reduced by indomethacin (20 μM) pretreatment.

Similar experiments to the above were performed with Compounds 27eee (IC$_{50}$ in RAW 264.7 cells=320 nM) and 28f with RAW264.7 cells and with HEK/COX-2 cells, and Compound 27eee provided good specific staining that was also reducible by pretreatment with indomethacin.

Additionally, 1483 Head/Neck Squamous Cell Carcinoma Cells (Sacks et al. (1988) *Cancer Res* 48, 2858-2866), which express COX-2, were treated at 70% confluency on 35 mm dishes with 200 nM Compound 27eee (IC$_{50}$ in 1483 cells=92 nM), or Compound 28f and imaged using a Zeiss Axiovert 25 Microscope (propidium iodide filter/2 sec exposure/gain of 2). Compound 27eee provided good specific staining that was also reducible by pretreatment with indomethacin in this cell line as well.

Discussion of Example 4

From these in vitro experiments, several following conclusions can be drawn. First, LPS-activated RAW264.7 cells show consistent fluorescent signals over control cells when treated with Compound 27vv or Compound 27eee. The fluorescence is attenuated by pre-incubating the cells with indomethacin. Second, HEK293 cells that overexpress COX-2 show fluorescence above the level observed in control HEK293 cells when treated with Compound 27vv or with Compound 27eee. This fluorescence is also reduced by pretreatment with indomethacin. Third, 1483 cells show considerable fluorescence with Compound 27eee, and the signal can be attenuated with indomethacin pre-treatment. Fourth, control compounds Compound 27ww (similar to Compound 27vv, but with a tether shortened by 2 carbons) and Compound 28f (similar to Compound 27eee but with a tether shortened by 2 carbons) show minimal fluorescence in these in vitro assays. And finally, auto-fluorescence of the cells does not contribute to the detected fluorescence signal with the rhodamine-based compositions.

Example 5

In Vivo Imaging of Nude Mice with Liver Metastases of SW620 Cells

Nude mice with liver tumors from SW620 cells (a human colorectal adenocarcinoma cell line that expresses a low level of COX-2 and that is available from ATCC) were obtained from Dr. Ray DuBois of the Vanderbilt-Ingram Cancer Center of Vanderbilt University (Nashville, Tenn., United States of America). Mice were obtained about 8-10 weeks after metastasis of the cells from the spleen. Control mice and mice bearing and tumor metastases were anesthetized and injected intraperitoneally (i.p.) with 5 mg/kg Compound 27vv. Images of injected mice were captured by a XENOGEN® IVIS® Imaging System (Xenogen Corp., Alameda, Calif., United States of America) using a Cy5.5 filter or a DsRed filter (1 second exposure/f2/high resolution/1.5 cm depth). Animals were imaged at 30 minutes and at 3-4 hours post-injection, and liver-specific imaging was provided by Compound 27vv. At 5 hours post-injection, mice were euthanized and liver tumors were imaged by fluorescence microscopy. Similar to the in vivo results, cells present in livers tumors strongly fluoresced.

In parallel experiments, nude mice were xenografted with a subcutaneous injection on a lateral side of $1 \times 10^6$. HCA7 colorectal adenocarcinoma cells (Marsh et al. (1993) *J Pathol* 170:441-450). Control mice (i.e., nude mice that did not have tumors) were also treated with 5 mg/ml or 2 mg/ml Compound 27vv and imaged. Images taken demonstrated strong tumor-specific fluorescence both in vivo and after removal of tumor masses.

Additionally, the presence of intact Compound 27vv in tumors and normal tissues were examined by high performance liquid chromatography (HPLC) and mass spectroscopy (MS). Tumors and other tissues were collected from treated mice and immediately frozen on dry ice. Tissues were homogenized in Tris buffer (pH=7.4) and proteins precipitated with acetonitrile (ACN). Protein pellets were collected by centrifugation and dried before reconstitution in Tris buffer pH 7.4 plus 10% methanol. Proteins were purified by reverse-phase solid=phase extraction (RP-SPE) and analyzed by HPLC-UV using the conditions set forth in Table 4:

TABLE 4

Conditions for HPLC-UV

| Solutions | A: water |
| | B: acetonitrile |
| Column | Phenomenex Synergi Fusion (Phenomenex Inc., Torrance, California, United States of America); 15 × 0.46 cm w C18 guard @ 40° C. |
| Gradient elution | 50% B at t = 0 |
| | 50% B at t = 1 min |
| | 10% B at t = 7.5 min |
| | 10% B at t = 9.5 min |
| | 50% B at t = 10 min |
| Flow | 1.3 mL/min |
| UV Detection | 581 nm |

A standard curve was generated for Compound 27vv between 1 and 15 nmoles. Linear regression analysis generated an equation for the resulting line of y=311624x+85461 ($R^2$=0.9956). Various normal and tumor samples were then analyzed and the amounts of Compound 27vv present in the samples were determined. These results are summarized in Table 5.

TABLE 5

Amounts of Compound 27vv Present in Tissue Samples Calculated Against the Standard Curve

| Sample Description | Compound 27vv Peak Area | Mass (g) | nmol 4751 | Compound 27vv nmol/g |
|---|---|---|---|---|
| Mouse 1 - normal liver lobe 2 | | 0.41 | | |
| Mouse 1 - kidney | | 0.27 | | |
| Mouse 2 - normal liver lobe 2 | | 0.32 | | |
| Mouse 1 - extremely small tumor | | 0.01 | | |
| Mouse 1 - small isolated tumor | | 0.54 | | |
| Mouse 1 - giant tumor C | 15577128 | 0.67 | 4.7 | 41.1 |
| Mouse 2 - normal kidney | | 0.28 | | |
| Mouse 2 - tissue between the lobes | 10777 | 0.14 | | <Std. A |
| Mouse 1 - giant tumor B | 660489 | 0.63 | 1.8 | 15.3 |
| Mouse 1 - giant tumor A | 1127131 | 0.73 | 3.3 | 31.1 |
| Mouse 1 - giant tumor D | 145324 | 0.74 | 0.2 | 0.9 |
| Mouse 1 - normal liver lobe 1 | | 0.52 | | |
| Mouse 2 - normal liver lobe | 19921 | 0.70 | | <Std. A |
| Mouse 2 - small tumor | 19025 | 0.07 | | <Std. A |

The putative Compound 27vv peak in the tumor samples was collected and analyzed by LCMS in order to verify its identity.

No brightly fluorescent areas were observed in any liver lobe in the control mice by either in vivo or ex vivo examination. Mice bearing liver metastases of SW620 cells, however, showed increased fluorescent signal during in vivo imaging, and also after excised livers were imaged by fluorescence microscopy. Additionally, HPLC and MS analyses confirmed the presence of intact Compound 27vv in the SW620 tumors at 5 hours post-injection. In parallel assays, the level of Compound 27vv in normal liver tissue was below the limit of detection.

It will be understood that various details of the described subject matter can be changed without departing from the scope of the described subject matter. Furthermore, the foregoing description is for the purpose of illustration only, and not for the purpose of limitation.

What is claimed is:

1. A cyclooxygenase-2-selective therapeutic and/or diagnostic agent of the following structural formula:

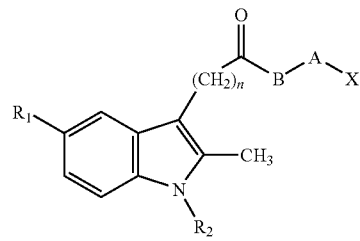

wherein:
R$_1$=C$_1$ to C$_6$ alkoxy, C$_1$ to C$_6$ branched alkoxy, or halo-substituted versions thereof;
R$_2$=benzoyl or halo-substituted benzoyl;
X is an active agent selected from the group consisting of a chemotherapeutic agent; a fluorophore selected from the group consisting of dansyl chloride, dabsyl chloride, nitrobenzodiazolamine (NBD), fluorescein and derivatives thereof, rhodamine and derivatives thereof; a cyanine dye; and a near infrared (NIR) dye; and A is an alkylamide tether selected from the group consisting of an alkyldiamide tether, an alkylamidodiester tether, an alkyldiamidomonoester tether, an alkylamidosulfonamide tether, an alkylamidothiourea tether, an alkyldiamidosulfonamide tether, and an aminoalkyldiamide tether;

B is —NH; and n is 1.

2. The therapeutic and/or diagnostic agent of claim 1, wherein the chemotherapeutic is selected from the group consisting of taxol, retinoic acid and derivatives thereof, doxorubicin, sulfathiazole, sulfadimethoxane, mitomycin C, retinoic acid or derivative thereof, camptothecin and derivatives thereof, podophyllotoxin, and mycophenolic acid.

3. The therapeutic and/or diagnostic agent of claim 2, wherein the therapeutic agent is selected from the group consisting of:

Compound 27g

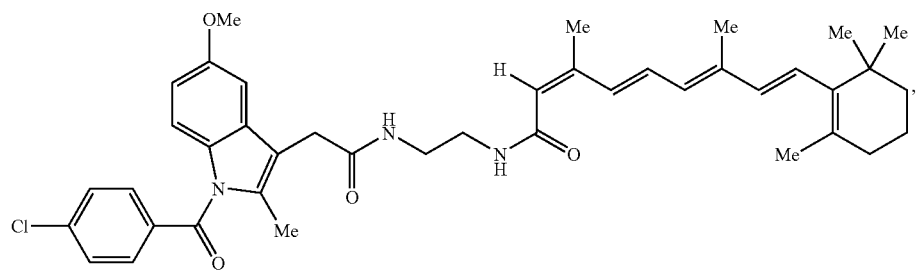

Compound 27h

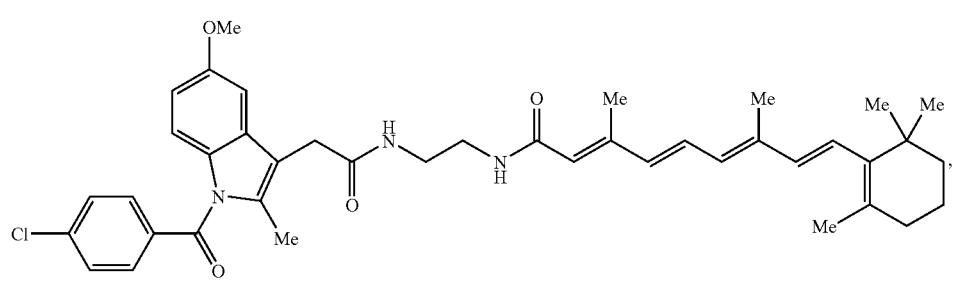

Compound 27j

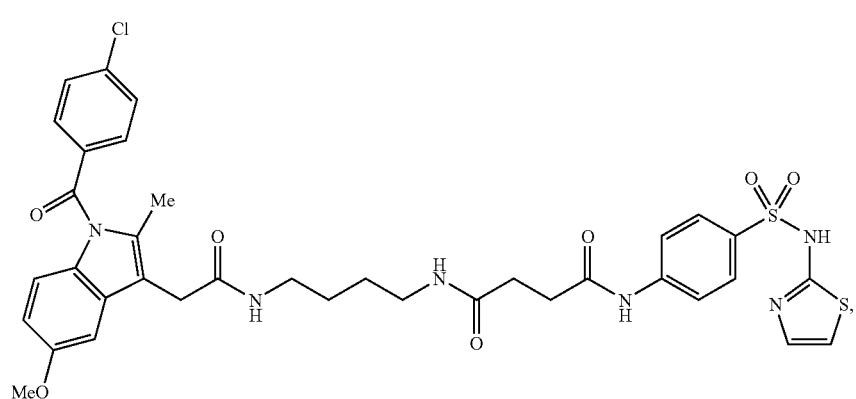

Compound 27n

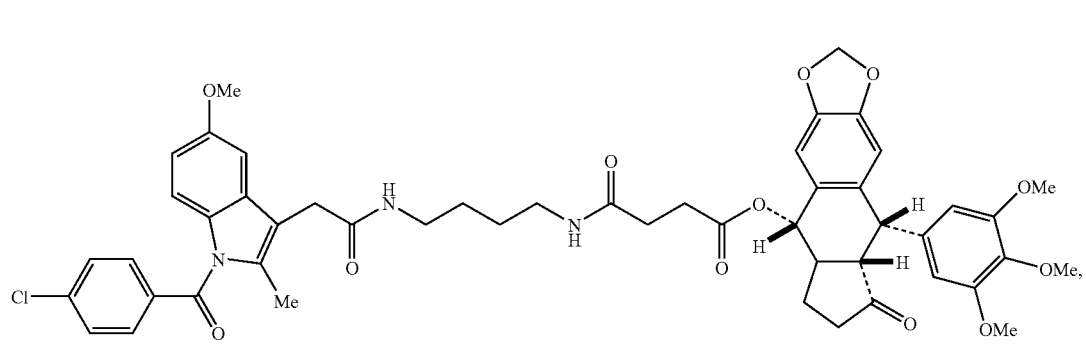

-continued

Compound 27o

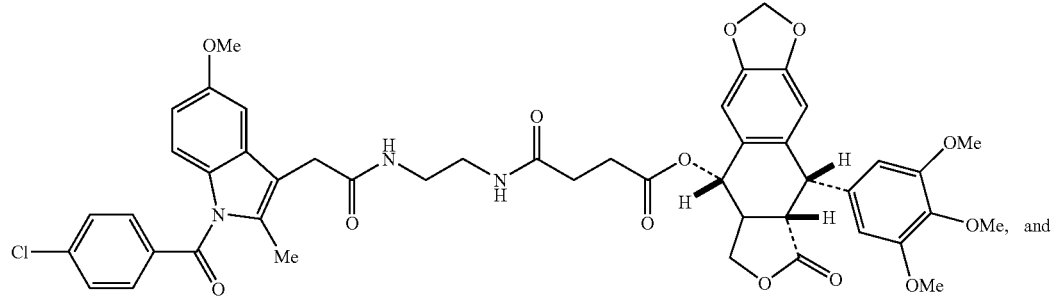

Compound 27s

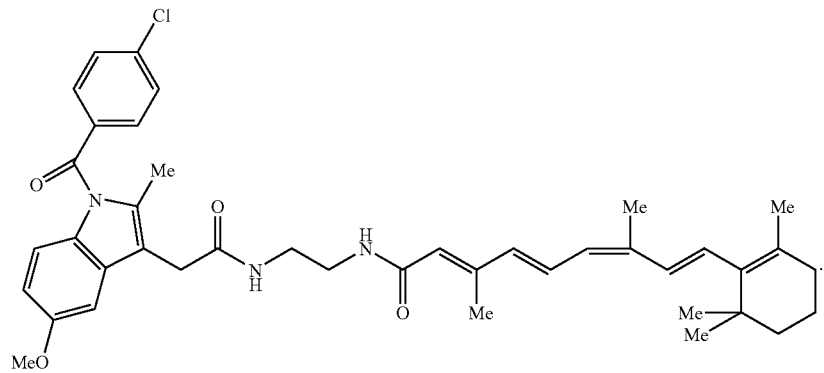

4. The therapeutic and/or diagnostic agent of claim 1, wherein the active agent is a fluorophore is selected from the group consisting of dansyl chloride, dabsyl chloride, nitrobenzodiazolamine (NBD), fluorescein and derivatives thereof, rhodamine and derivatives thereof, Nile Blue, an Alexa Fluor and derivatives thereof, and combinations thereof.

5. The therapeutic and/or diagnostic agent of claim 4, wherein the therapeutic and/or diagnostic agent is selected from the group consisting of:

Compound 27x

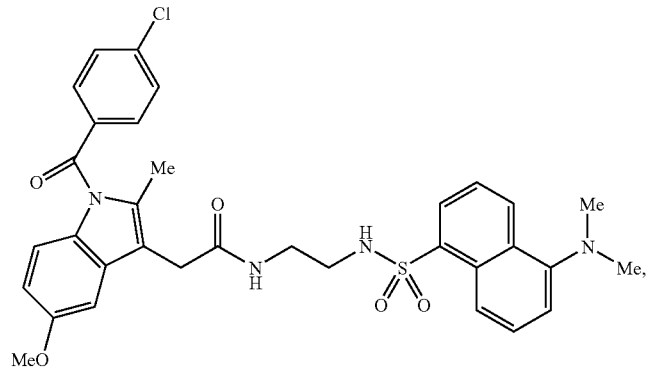

-continued
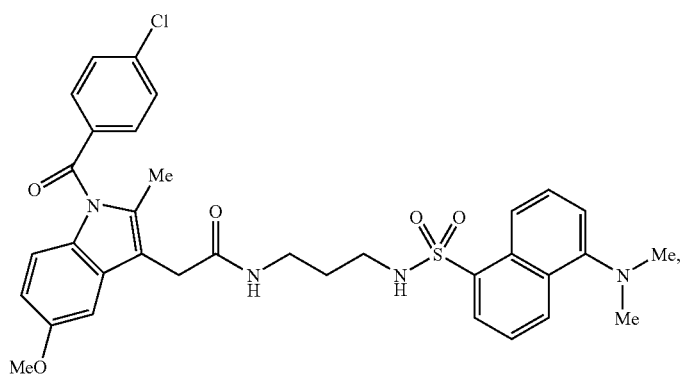
Compound 27y
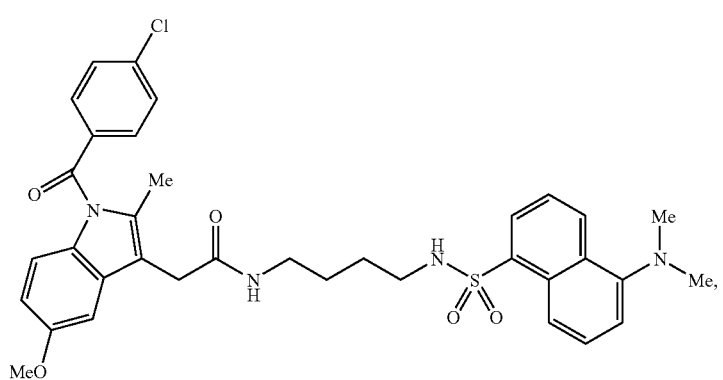
Compound 27z
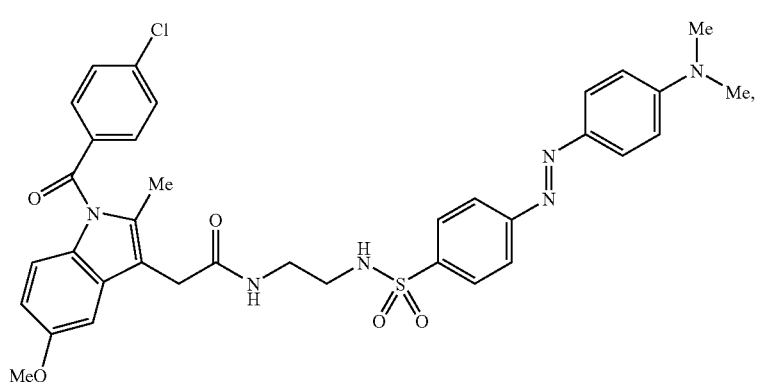
Compound 27aa
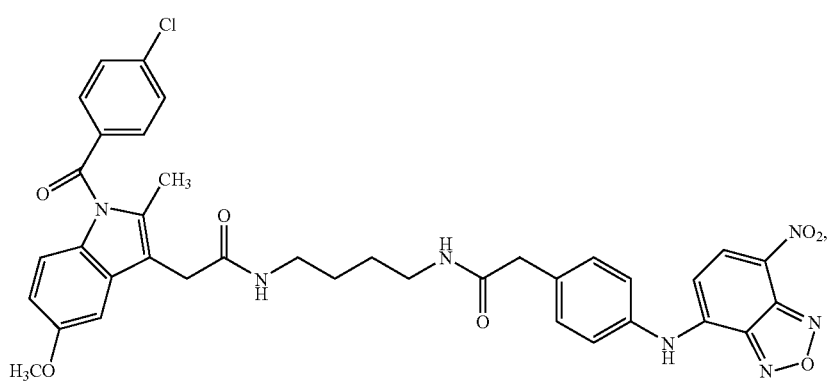
Compound 27ii Compound 27qq
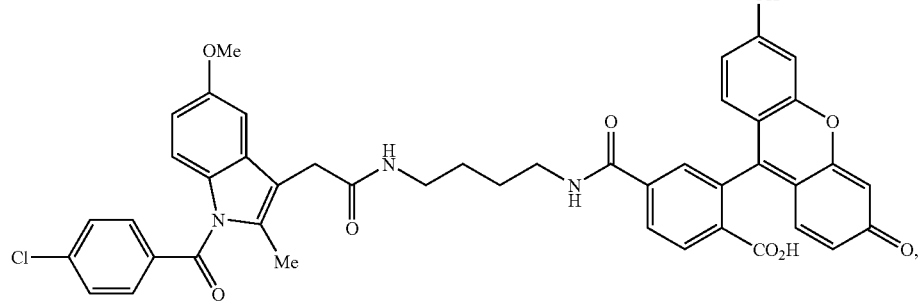
Compound 27vv
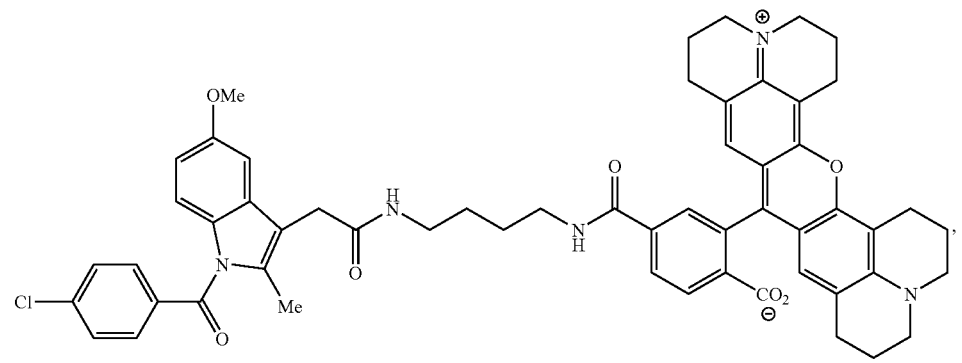
Compound 27eee
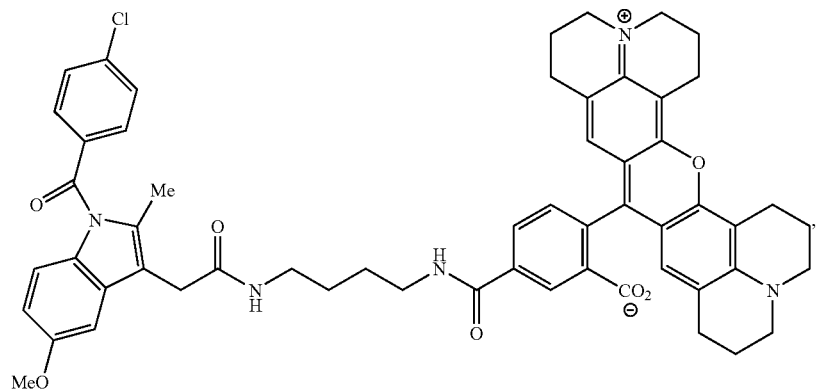
Compound 27qqq
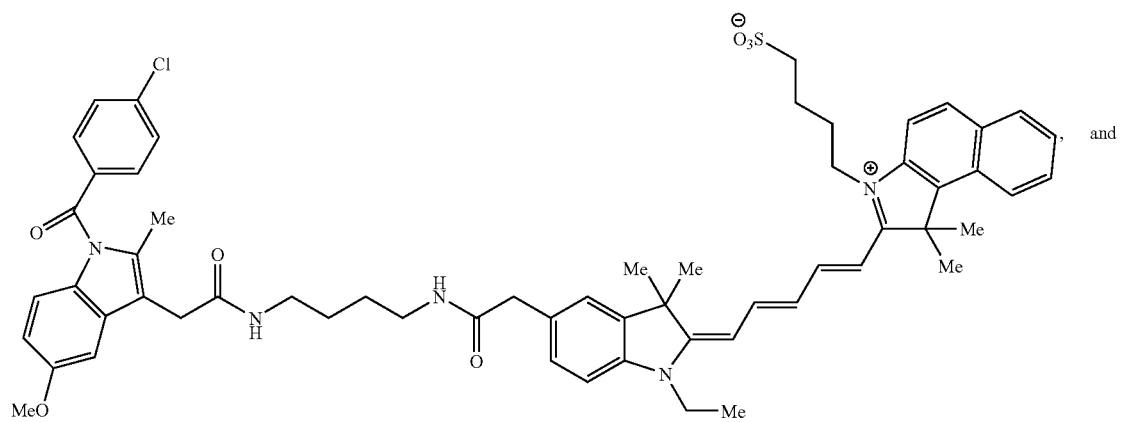
and

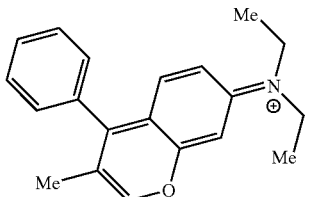
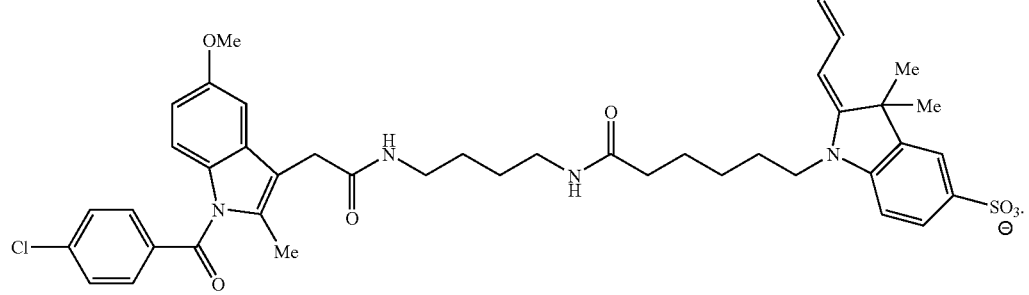
6. The therapeutic and/or diagnostic agent of claim 5, wherein the therapeutic and/or diagnostic agent is selected from the group consisting of:
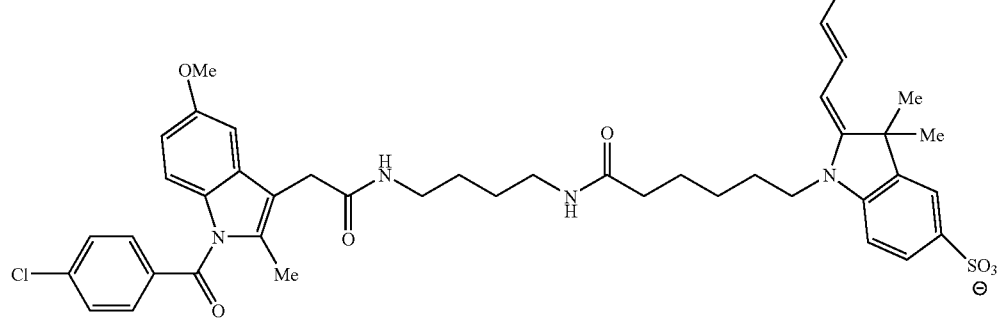
and
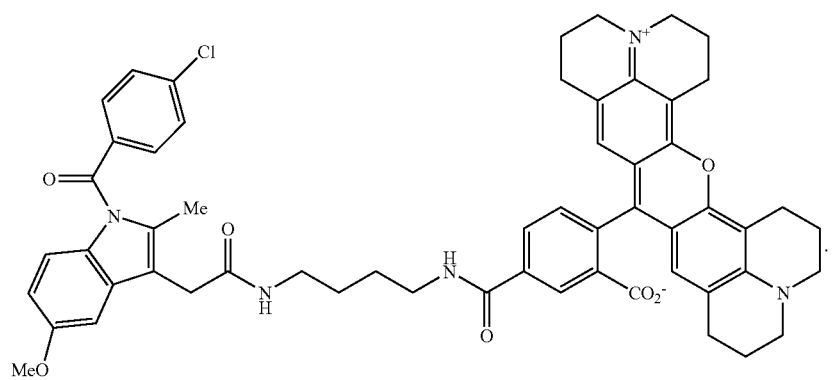

7. The therapeutic and/or diagnostic agent of claim 4, wherein the rhodamine and derivatives thereof are selected from the group consisting of 5-carboxy-X-rhodamine and 6-carboxy-X-rhodamine.

8. The therapeutic and/or diagnostic agent of claim 1, wherein the cyanine dye is selected from the group consisting of Cy5, Cy5.5, and Cy7.

9. The therapeutic and/or diagnostic agent of claim 1, wherein the NIR dye is selected from the group consisting of NIR641, NIR664, NIR700, and NIR782.

10. A method for synthesizing a therapeutic and/or diagnostic agent, the method comprising:

(a) providing a non-steroidal anti-inflammatory drug (NSAID), or a derivative thereof, comprising the following formula:

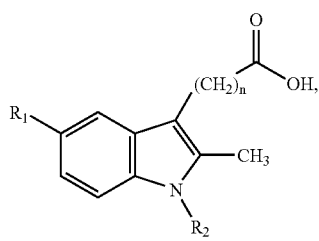

Formula I wherein:

$R_1 = C_1$ to $C_6$ alkoxy, $C_1$ to $C_6$ branched alkoxy, or halo-substituted versions thereof;
$R_2$=benzoyl or halo-substituted benzoyl;
n is 1

(b) derivatizing the carboxylic acid moiety to a secondary amide or an ester; and (c) complexing an active agent to the secondary amide or the ester to produce a therapeutic and/or diagnostic agent having the following structure:

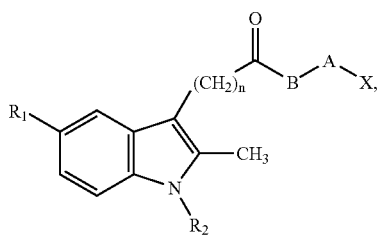

Formula I wherein:

(i) X is an active agent selected from the group consisting of a chemotherapeutic agent; a fluorophore selected from the group consisting of dansyl chloride, dansyl chloride, nitrobenzodiazolamine (NBD), fluorescein and derivatives thereof, rhodamine and derivatives thereof; a cyanine dye; and a near infrared (NIR) dye;

(ii) A is an alkylamide tether selected from the group consisting of an alkyldiamide tether, an alkylamidodiester tether, an alkyldiamidomonoester tether, an alkylamidosulfonamide tether, an alkylamidothiourea tether, an alkyldiamidosulfonamide tether, and an aminoalkyldiamide tether;

(iii) B —NH; and (iv) the therapeutic and/or diagnostic agent selectively binds to cyclooxygenase-2 (COX-2).

11. The method of claim 10, wherein the active agent is a chemotherapeutic.

12. The method of claim 11, wherein the chemotherapeutic is selected from the group consisting of taxol, retinoic acid and derivatives thereof, doxorubicin, sulfathiazole, sulfadimethoxane, mitomycin C, retinoic acid or derivative thereof, camptothecin and derivatives thereof, podophyllotoxin, and mycophenolic acid.

13. The method of claim 12, wherein the therapeutic and/or diagnostic agent is selected from the group consisting of:

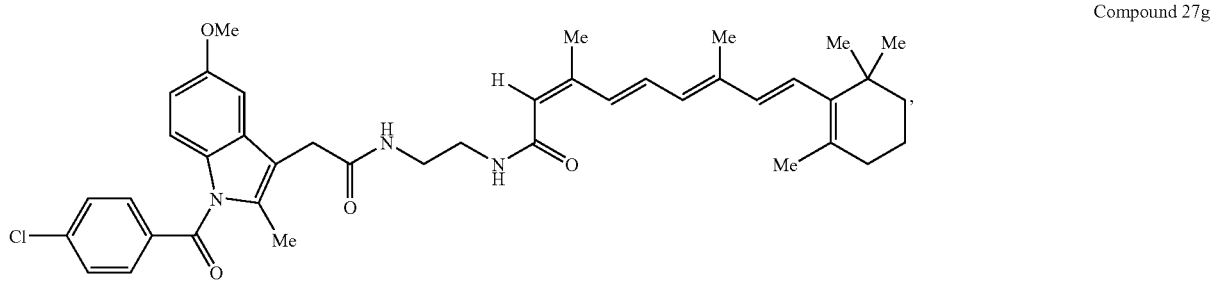

Compound 27g

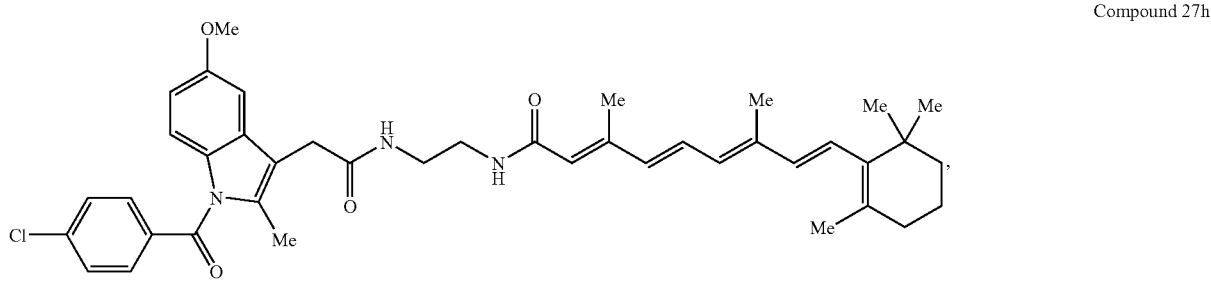

Compound 27h

-continued
Compound 27j
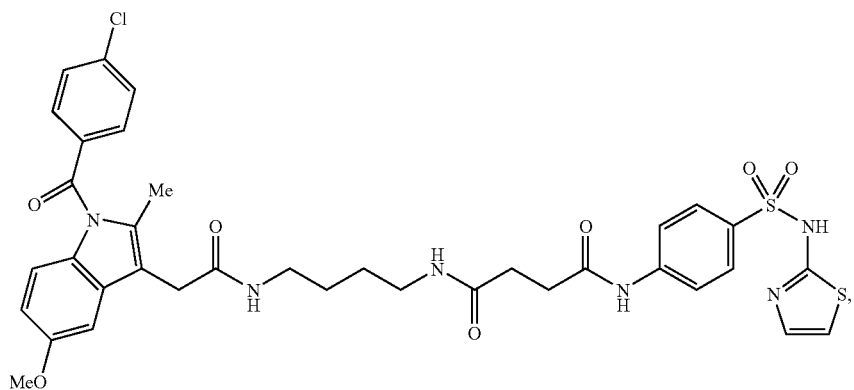
Compound 27n
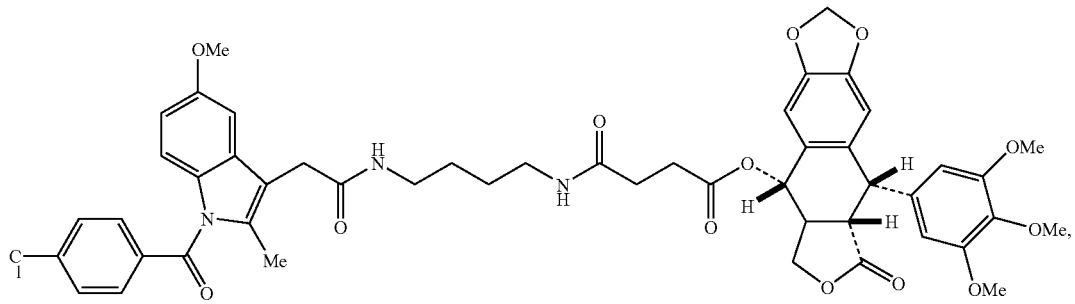
Compound 27o
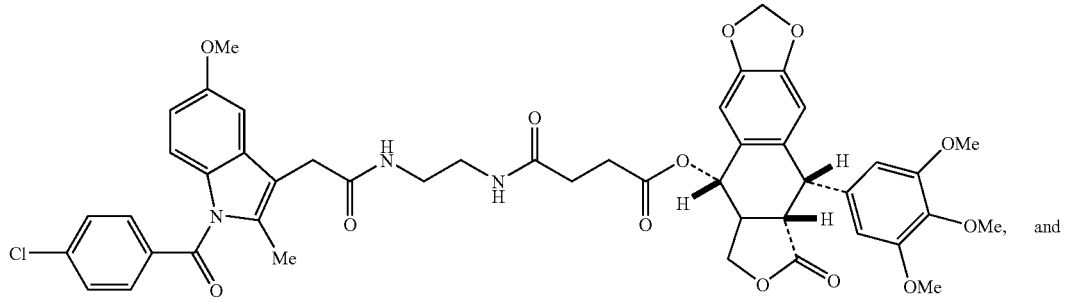
27s
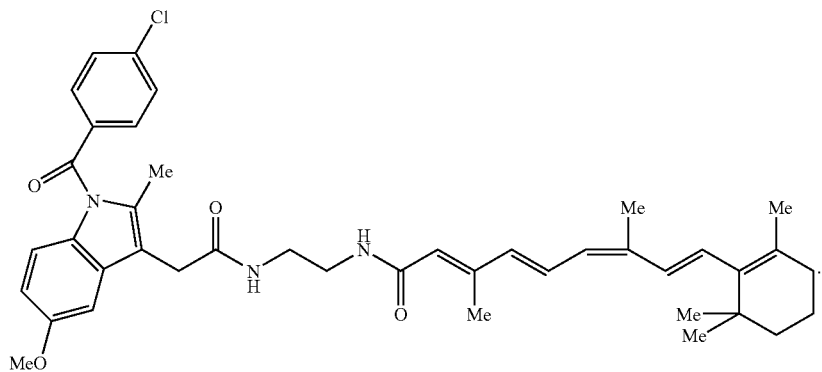

14. The method of claim 10, wherein the active agent is a fluorophore selected from the group consisting of dansyl chloride, dabsyl chloride, nitrobenzodiazolamine (NBD), fluorescein and derivatives thereof, rhodamine and derivatives thereof; a cyanine dye; and a near infrared (NIR) dye.

15. The method of claim 14, wherein the fluorophore is selected from the group consisting of dansyl chloride, dabsyl chloride, nitrobenzodiazolamine (NBD), fluorescein and derivatives thereof, rhodamine and derivatives thereof, and Nile Blue.

16. The method of claim 15, wherein the therapeutic and/or diagnostic agent is selected from the group consisting of:

Compound 27x

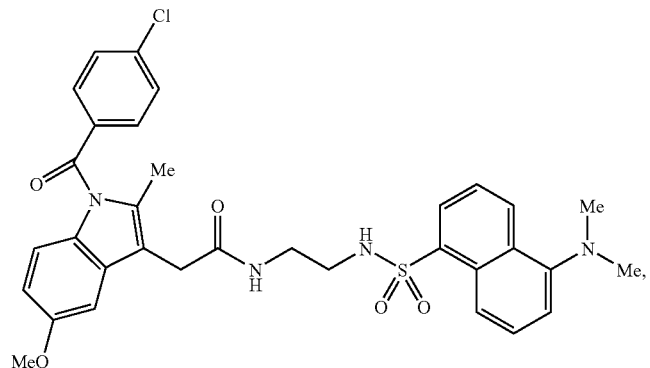

Compound 27y

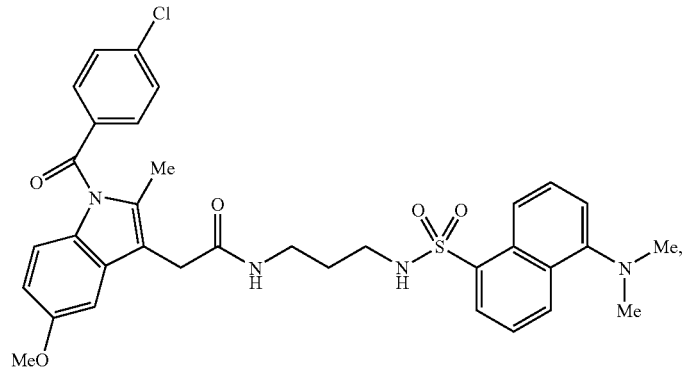

Compound 27z

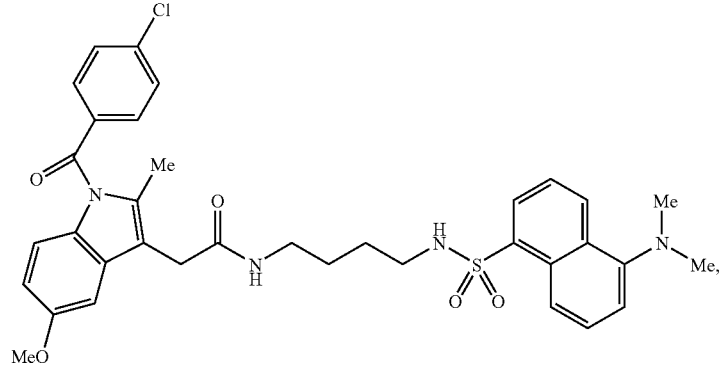

Compound 27aa

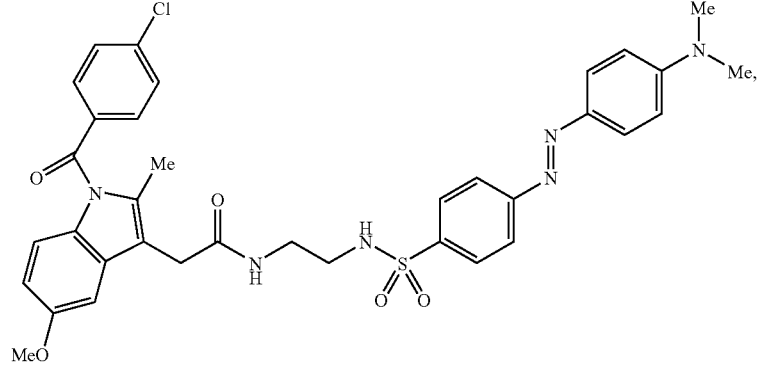

-continued
Compound 27ii
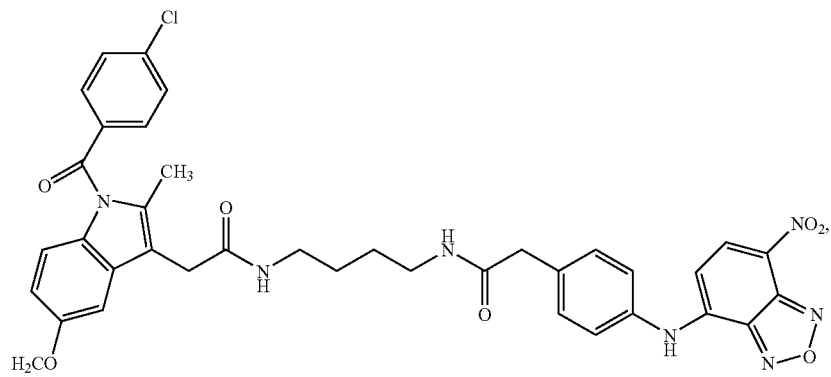
Compound 27qq
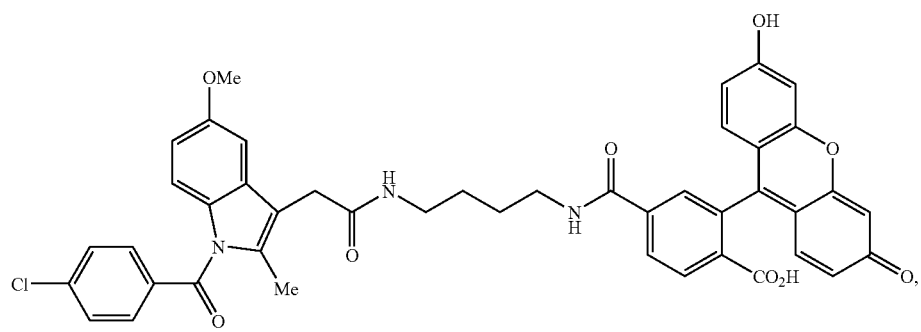
Compound 27vv
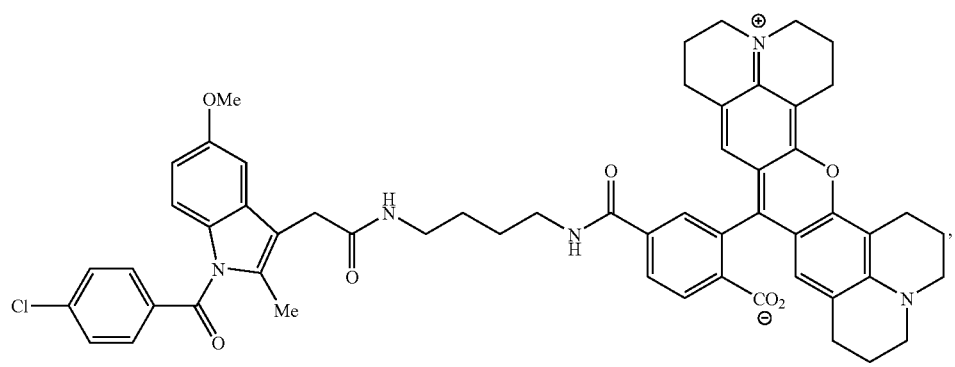
Compound 27eee
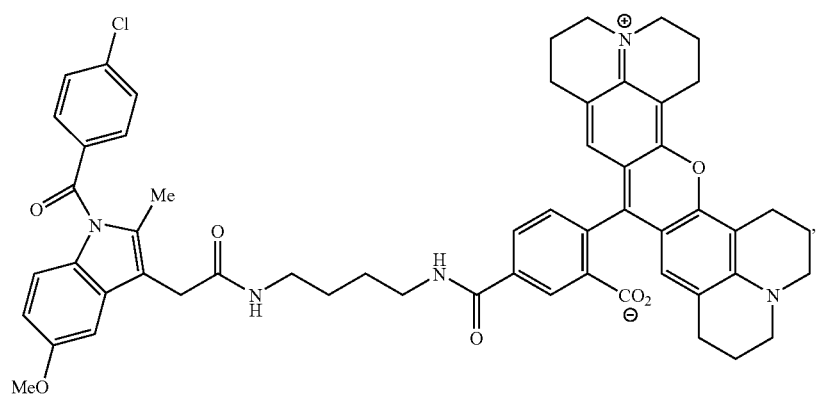

-continued

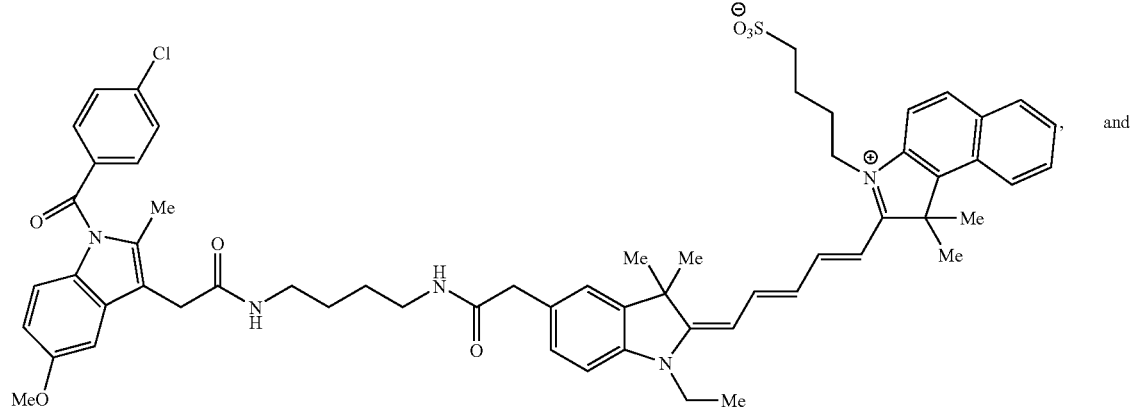

Compound 27qqq

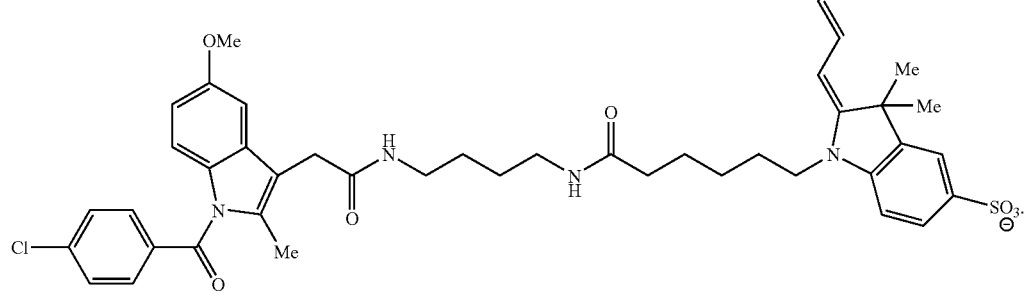

Compound 27ttt

17. The method of claim 15, wherein the rhodamine and derivatives thereof are selected from the group consisting of 5-carboxy-X-rhodamine and 6-carboxy-X-rhodamine.

18. The method of claim 14, wherein the cyanine dye is selected from the group consisting of Cy5, Cy5.5, and Cy7.

19. The method of claim 14, wherein the NIR dye is selected from the group consisting of NIR641, NIR664, NIR700, and NIR782.

20. The therapeutic and/or diagnostic agent of claim 1, wherein the therapeutic and/or diagnostic agent is selected from the group consisting of:

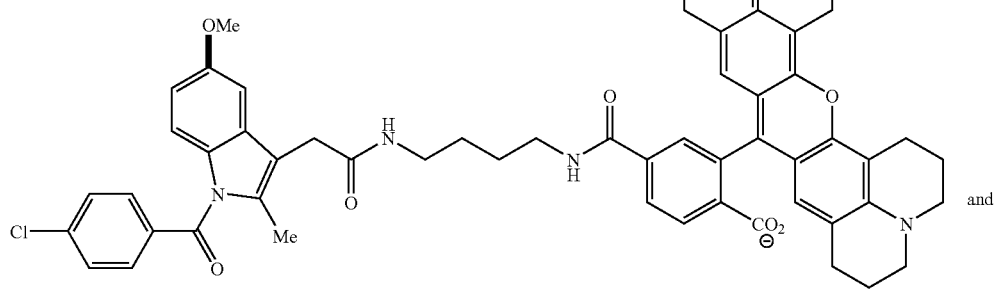

Compound 27vv

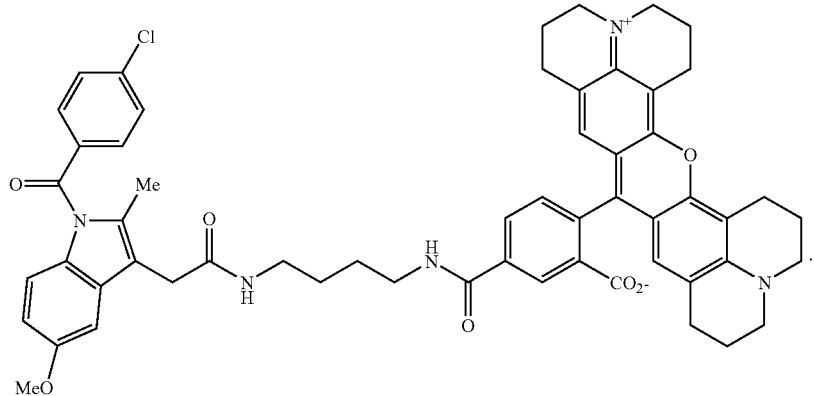
Compound 27eee
21. The method of claim 10, wherein the therapeutic and/or diagnostic agent is selected from the group consisting of:
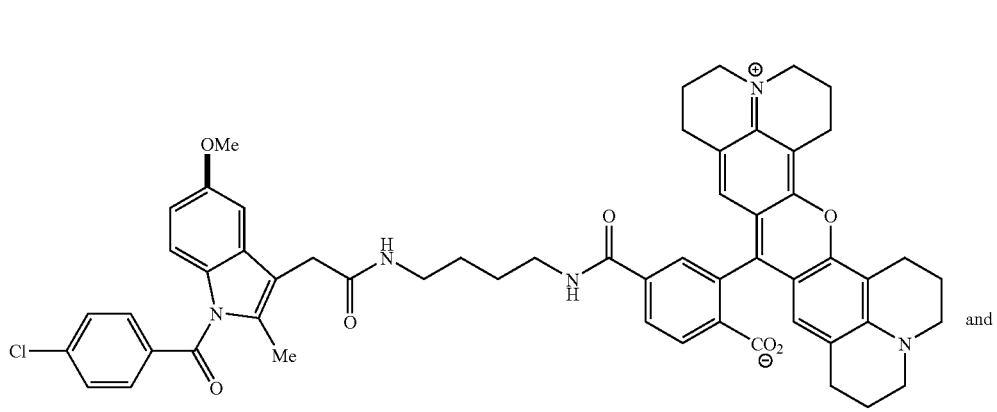
Compound 27vv
and
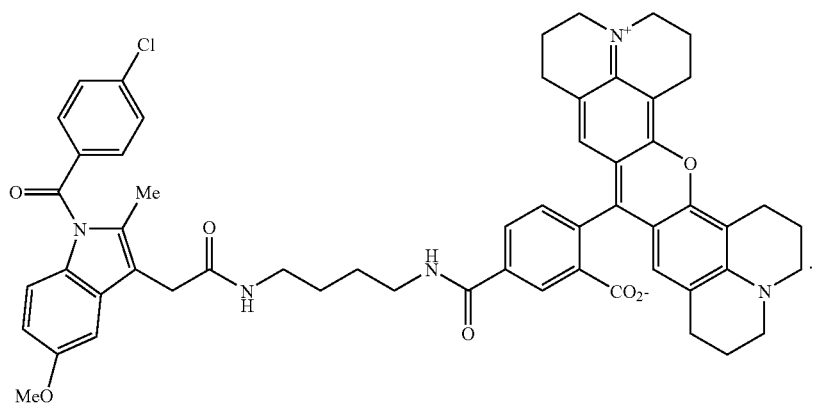
Compound 27eee
* * * * *

UNITED STATES PATENT AND TRADEMARK OFFICE
CERTIFICATE OF CORRECTION

| | | |
|---|---|---|
| PATENT NO. | : 7,736,624 B2 | Page 1 of 1 |
| APPLICATION NO. | : 11/820481 | |
| DATED | : June 15, 2010 | |
| INVENTOR(S) | : Marnett et al. | |

It is certified that error appears in the above-identified patent and that said Letters Patent is hereby corrected as shown below:

On title page, add item 73:

--Assignee: Vanderbilt University--

Signed and Sealed this
Fifteenth Day of March, 2011

David J. Kappos
*Director of the United States Patent and Trademark Office*